(12) United States Patent
Zhang et al.

(10) Patent No.: US 8,513,229 B2
(45) Date of Patent: Aug. 20, 2013

(54) 4-AZETIDINYL-1-PHENYL-CYCLOHEXANE ANTAGONISTS OF CCR2

(75) Inventors: Xuqing Zhang, Audubon, PA (US); Heather Rae Hufnagel, Glenmoore, PA (US); Cuifen Hou, Spring House, PA (US); Dana L. Johnson, Upper Black Eddy, PA (US); Zhihua Sui, Spring House, PA (US)

(73) Assignee: Janssen Pharmaceutica NV (BE)

( * ) Notice: Subject to any disclaimer, the term of this patent is extended or adjusted under 35 U.S.C. 154(b) by 86 days.

(21) Appl. No.: 13/280,690

(22) Filed: Oct. 25, 2011

(65) Prior Publication Data

US 2012/0040960 A1    Feb. 16, 2012

Related U.S. Application Data

(63) Continuation of application No. 12/761,080, filed on Apr. 15, 2010, now abandoned.

(60) Provisional application No. 61/170,307, filed on Apr. 17, 2009.

(51) Int. Cl.
*A61K 31/397* (2006.01)
*C07D 205/00* (2006.01)

(52) U.S. Cl.
USPC .................................. 514/210.01; 548/953

(58) Field of Classification Search
USPC .................................. 514/210.01; 548/953
See application file for complete search history.

(56) References Cited

U.S. PATENT DOCUMENTS

| | | |
|---|---|---|
| 6,245,799 B1 | 6/2001 | Asselin et al. |
| 6,255,315 B1 | 7/2001 | Patane et al. |
| 2003/0004151 A1 | 1/2003 | Cherney et al. |
| 2006/0069123 A1 | 3/2006 | Xia et al. |
| 2006/0135502 A1 | 6/2006 | Cherney et al. |
| 2006/0252751 A1 | 11/2006 | Xue et al. |
| 2010/0144695 A1 | 6/2010 | Zhang et al. |
| 2010/0267668 A1 | 10/2010 | Zhang et al. |
| 2010/0267688 A1 | 10/2010 | Zhang et al. |
| 2010/0267689 A1 | 10/2010 | Zhang et al. |

FOREIGN PATENT DOCUMENTS

| | | |
|---|---|---|
| EP | 1201239 | 5/2002 |
| WO | 9857641 | 12/1998 |
| WO | 01/34598 | 5/2001 |
| WO | WO 2004/050024 | 6/2004 |
| WO | 2005/060665 | 7/2005 |
| WO | WO 2006/073592 | 7/2006 |
| WO | 2007/003965 | 1/2007 |
| WO | WO 2007/053498 | 5/2007 |
| WO | WO 2007/130712 | 11/2007 |
| WO | 2010/068663 | 6/2010 |
| WO | 2010/121011 | 10/2010 |
| WO | 2010/121036 | 10/2010 |
| WO | 2010/121046 | 10/2010 |

OTHER PUBLICATIONS

Han, Targeted Prodrug Design to Optimize Drug Delivery, 2000, AAPS Pharmsci, vol. 2 (1), p. 1-11.*
Barnes, New Drugs for Asthma, 2004, Nature Reviews: Drug Discovery, vol. 3, p. 831-844.*
Horuk, Chemokine receptor antagonists: overcoming developmental hurdles, 2009, Nature Reviews: Drug Discovery, vol. 8, p. 23-33.*
Kang, CCR2 antagonism improves insulin resistance, lipid metabolism, and diabetic nephropathy in type 2 diabetic mice, 2010, Kidney Internation, vol. 78, p. 883-894.*
Palmqvist, Chemokines and their receptors as potential targets for the treatment of asthma, 2007, British Journal of Pharmacology, vol. 151, p. 725-736.*
Tamura, Inhibition of CCR2 Ameloiorates Insulin Resistance and Hepatic Steatosis in db/db Mice, 2008, Arterioscler Thromb Vasc Biol, p. 2195-2201.*
Bundgaard, et al., "Design of Prodrugs: Bioreversible Derivatives for Various Functional Groups and Chemical Entities", Elsevier Science Publishers, 1985, pp. 1-4, Chapter 1.
Bryn, et al., "Hydrates and Solvates", Solid State Chemistry of Drugs, 2nd Edition, 1999, pp. 232-247, Chapter 10, Polymorphs.
Dawson, et al, "Targeting Monocyte Chemoattractant Protein-1 Signalling in Disease", Expert Opin. Ther. Targets, 2003, vol. 7(1), pp. 35-48.
Seebach, et al, "Safe One-Pot Carbon-Carbon Bond Formation with Lithiated Nitrosamines Including Denitrosation by Sequential Reduction with Lithium a Aluminium Hydride and Raney-Nickel", Synthesis, 1979, vol. 6, pp. 423-424.
Gdaniec, et al., "Conformation and Stereodynamics of N,N-Dinitroso-2,4,6,8- tetraaryl-1-3,7-diazabicyclo [3.3.1] nonanes", J. Org. Chem., 1997 vol. 62, pp. 5619-5622.
Abdel-Magid, et al., "Reductive Amination of Aldehydes and Ketones with Sodium Triacetoxyborohydride. Studies on Direct and Indirect Reductive Amination Procedures", J. Org. Chem, 1996, vol. 61, pp. 3849-3862.

(Continued)

*Primary Examiner* — Golam M M Shameem
*Assistant Examiner* — Karen Cheng
(74) *Attorney, Agent, or Firm* — Mary A. Appollina

(57) ABSTRACT

The present invention comprises compounds of Formula (I):

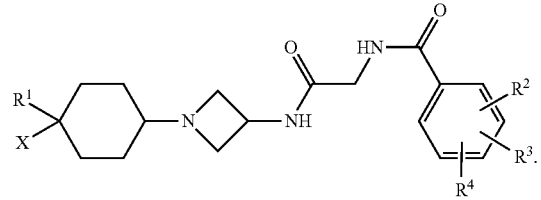

Formula (I)

wherein: X, $R^1$, $R^2$, $R^3$, and $R^4$ are as defined in the specification. The invention also comprises a method of preventing, treating or ameliorating a syndrome, disorder or disease, wherein said syndrome, disorder or disease is type II diabetes, obesity and asthma. The invention also comprises a method of inhibiting CCR2 activity in a mammal by administration of a therapeutically effective amount of at least one compound of Formula (I).

13 Claims, No Drawings

(56) References Cited

OTHER PUBLICATIONS

Chan, et al., "1,5-BIS (Trimethylsiloxy)-1,5-Dimethoxy-1-4-Pentadienes. Cyclopropance Synthesis Via Intramolecular Coupling", Tetrahedron Letters, 1982 vol. 23, No. 8, pp. 799-802.
Rollins, "Monocyte chemoattractant protein 1: a potential regulator of monocyte recruitment in inflammatory disease", 89Mol. Med. Today, 1996 vol. 2, pp. 198.
Das, B. et al. "A Highly Chemoselective Boc Protection of Amines using Sulfonic-Acid-Functionalized Silica As an Efficient Heterogeneous Recyclable Catalyst", Tetrahedron Lett. 2006, 47, 7551-7556.
Ingersoll, A. W. et. al., "Hippuric Acid", Organic Syntheses 1932, XII, vol. 12. pp. 40.
Xia M, Sui Z, "Recent Developments in CCR2 Antagonists", *Expert Opin. Ther. Patents*, 2009, 19(3), 295-303.
ISR , PCT/US2010/031265, dated Jun. 1, 2010.
International Search Report, PCT/US2010/031255, Oct. 18, 2011.
International Search Report, PCT/US2009/067307, Aug. 2, 2010.
International Search Report, PCT/US2011/062593, Mar. 28, 2012.
International Search Report, PCT/US2011/039724, Jul. 19, 2011.
International Search Report, PCT/US2011/040610, Aug. 29, 2011.
International Search Report, PCT/US2010/031212, Oct. 18, 2011.
Silva, A., et al., "Advances in Prodrug Design", Mini Rev. Med. Chem 2005 vol. 5, pp. 893-914.
Lanter, et al., "The discovery of Novel Cyclohexylamide CCR2 Antagonists", Bioorganic & Medicinal Chemistry Letters, Pergamon; 2011, vol. 21, No. 24, pp. 7496-7501.
Vippagunta, S., "Crystalline solids" Advanced Drug Delivery, Rev 2001, vol. 48, pp. 3-26.
Morissette, et al., "High-throughput Crystallization: Polymorphs, Salts, Co-Crystals and Solvates of Pharmaceutical Solids", Advanced Drug Delivery Reviews, 2004, vol. 56, pp. 275-300.
Thornber, "Isosterism and Molecular Modification in Drug Design", Royal Society of Chemistry 1979, pp. 563-580.
Golub, et al., "Molecular Classification of Cancer: Class Discovery and Class Prediction by Gene Expression Monitoring", Science, 1999, vol. 286, pp. 531-537.
Lala, et al, "Role of Nitric Oxide in Tumor Progression: Lessons from Experimental Tumors", Cancer and Metastasis Reviews, 1998, vol. 17(1), pp. 91-106.
Havlioglu, et al., "Slit Proteins, Potential Endogenous Modulators of Inflammation", Journal of Neuro Virology, vol. 8, 2002, pp. 486-495.
Banker, et al., "Modern Pharmaceutics", Third Edition, Revised and Expanded, 1996, pp. 451-596.
Wolf, et al., "Some consideration for Prodrug Design, Burger's Medicinal Chemistry and Drug Discovery", 5th Edition, vol. 1: Principles and Practice, 1995, pp. 975-977.
Damasio, "Alzheimer's Disease and Related Dementias" Cecil textbook of Medicine, 20th Edition, vol. 2, pp. 1996, pp. 1992-1996.
Simone,"Oncology: Introduction", Cecil textbook of Medicine, 20th Edistion, vol. 1, 1996, pp. 1004-1010.
Gura, et al., "Systems for Identifying New Drugs Are Often Faulty", Science, vol. 278, 1997, pp. 1041-1042.
Johnson, et al., "Relationships Between Drug Activity in NCI Preclinical in Vitro and in Vivo Models and Early Clinical Trials" Britsh Journal of Cancer, vol. 84(10): 2001, pp. 1424-1431.
Ulrich, et al., "Crystallization", Kirk-Othmer Encyclopedia of Chemical Technology, 2002.
West, et al., Solid Solutions, Solid State Chemistry and it's Applications, 1988, pp. 358 &365.

\* cited by examiner

4-AZETIDINYL-1-PHENYL-CYCLOHEXANE ANTAGONISTS OF CCR2

CROSS-REFERENCE TO RELATED APPLICATIONS

This application is a continuation of U.S. Ser. No. 12/761,080 filed Apr. 15, 2010, now abandoned which claims priority from U.S. Provisional Application Ser. No. 61/170,307 filed Apr. 17, 2009, the contents of each of which are hereby incorporated by reference in their entirety.

FIELD OF THE INVENTION

The invention is directed to substituted dipiperidine compounds, which are antagonists to the chemoattractant cytokine receptor 2 (CCR2), pharmaceutical compositions, and methods for use thereof. More particularly, the CCR2 antagonists are substituted piperidyl acrylamide compounds useful for preventing, treating or ameliorating a CCR2 mediated syndrome, disorder or disease.

BACKGROUND OF THE INVENTION

CCR2 is a member of the GPCR family of receptors, as are all known chemokine receptors, and are expressed by monocytes and memory T-lymphocytes. The CCR2 signaling cascade involves activation of phospholipases (PLCβ2), protein kinases (PKC), and lipid kinases (PI-3 kinase).

Chemoattractant cytokines (i.e., chemokines) are relatively small proteins (8-10 kD), which stimulate the migration of cells. The chemokine family is divided into four subfamilies based on the number of amino acid residues between the first and second highly conserved cysteines.

Monocyte chemotactic protein-1 (MCP-1) is a member of the CC chemokine subfamily (wherein CC represents the subfamily having adjacent first and second cysteines) and binds to the cell-surface chemokine receptor 2 (CCR2). MCP-1 is a potent chemotactic factor, which, after binding to CCR2, mediates monocyte and lymphocyte migration (i.e., chemotaxis) toward a site of inflammation. MCP-1 is also expressed by cardiac muscle cells, blood vessel endothelial cells, fibroblasts, chondrocytes, smooth muscle cells, mesangial cells, alveolar cells, T-lymphocytes, marcophages, and the like.

After monocytes enter the inflammatory tissue and differentiate into macrophages, monocyte differentiation provides a secondary source of several proinflammatory modulators, including tumor necrosis factor-α (TNF-α), interleukin-1 (IL-1), IL-8 (a member of the CXC chemokine subfamily, wherein CXC represents one amino acid residue between the first and second cysteines), IL-12, arachidonic acid metabolites (e.g., $PGE_2$ and $LTB_4$), oxygen-derived free radicals, matrix metalloproteinases, and complement components.

Animal model studies of chronic inflammatory diseases have demonstrated that inhibition of binding between MCP-1 and CCR2 by an antagonist suppresses the inflammatory response. The interaction between MCP-1 and CCR2 has been implicated (see Rollins B J, Monocyte chemoattractant protein 1: a potential regulator of monocyte recruitment in inflammatory disease, *Mol. Med. Today*, 1996, 2:198; and Dawson J, et al., Targeting monocyte chemoattractant protein-1 signaling in disease, *Expert Opin. Ther. Targets*, 2003 Feb. 7 (1):35-48) in inflammatory disease pathologies such as psoriasis, uveitis, atherosclerosis, rheumatoid arthritis (RA), multiple sclerosis, Crohn's Disease, nephritis, organ allograft rejection, fibroid lung, renal insufficiency, type II diabetes and diabetic complications, diabetic nephropathy, diabetic retinopathy, diabetic retinitis, diabetic microangiopathy, tuberculosis, sarcoidosis, invasive staphyloccocia, inflammation after cataract surgery, allergic rhinitis, allergic conjunctivitis, chronic urticaria, Chronic Obstructive Pulmonary Disease (COPD), allergic asthma, periodontal diseases, periodonitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, and stomach. Monocyte migration is inhibited by MCP-1 antagonists (either antibodies or soluble, inactive fragments of MCP-1), which have been shown to inhibit the development of arthritis, asthma, and uveitis. Both MCP-1 and CCR2 knockout (KO) mice have demonstrated that monocyte infiltration into inflammatory lesions is significantly decreased. In addition, such KO mice are resistant to the development of experimental allergic encephalomyelitis (EAE, a model of human MS), cockroach allergen-induced asthma, atherosclerosis, and uveitis. Rheumatoid arthritis and Crohn's Disease patients have improved during treatment with TNF-α antagonists (e.g., monoclonal antibodies and soluble receptors) at dose levels correlated with decreases in MCP-1 expression and the number of infiltrating macrophages.

MCP-1 has been implicated in the pathogenesis of seasonal and chronic allergic rhinitis, having been found in the nasal mucosa of most patients with dust mite allergies. MCP-1 has also been found to induce histamine release from basophils in vitro. During allergic conditions, both allergens and histamines have been shown to trigger (i.e., to up-regulate) the expression of MCP-1 and other chemokines in the nasal mucosa of people with allergic rhinitis, suggesting the presence of a positive feedback loop in such patients. There remains a need for small molecule CCR2 antagonists for preventing, treating or ameliorating a CCR2 mediated inflammatory syndrome, disorder or disease resulting from MCP-1 induced monocyte and lymphocyte migration to a site of inflammation. All documents cited herein are incorporated by reference.

SUMMARY OF THE INVENTION

The present invention comprises compounds of Formula (I).

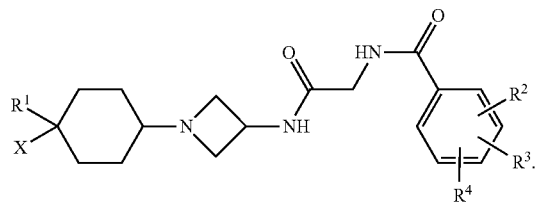

Formula (I)

wherein:
X is $NH_2$, F, H, SH, $S(O)CH_3$, $SCH_3$, $SO_2CH_3$, or OH;
$R^1$ is phenyl optionally substituted with one or two substituents, one of which is selected from the group consisting of: $OC_{(1-4)}alkyl$, $SC_{(1-4)}alkyl$, $SOC_{(1-4)}alkyl$, $SO_2C_{(1-4)}alkyl$, —$OSO_2NH_2$, —$SO_2NHC_{(1-4)}alkyl$, —$OSO_2NH_2$, —$SO_2NH_2$, $N(C_{(1-4)}alkyl)_2$, $NH_2$, $NHC_{(1-4)}alkyl$, $NHSO_2$ $C_{(1-4)}$alkyl, $N(SO_2CH_3)_2$, OH, $OC_{(1-4)}$alkyl$CO_2C_{(1-4)}$alkyl, $OC_{(1-4)}$alkyl$CO_2H$, $OCH_2CH_2N(C_{(1-4)}$alkyl$)_2$, F, Cl, $CH_2CN$, CN, $C_{(1-4)}$alkyl, $NHCO_2H$, $NHCO_2C_{(1-4)}$alkyl, $NHCOC_{(1-4)}$alkyl, —C≡CH, $CONH_2$, $NHCONH_2$, $NHCONHC_{(1-4)}$alkyl, $CONHC_{(1-4)}$alkyl, $CH_2CONHC_{(1-4)}$alkyl, $C_{(1-4)}$alkyl$CONH_2$, $C_{(1-4)}$alkyl$CO_2C_{(1-4)}$alkyl, $C_{(1-4)}$alkyl$CO_2H$, $CO_2H$, $CH_2C(NH)NH_2$, $CO_2C_{(1-4)}$alkyl, $CF_3$, $OCHF_2$, $CHF_2$, $OCF_3$, $OCH_2CF_3$, cycloalkyl, heterocyclyl, phenoxy, phenyl, $CH_2$phenyl, $CH_2$heteroaryl, and heteroaryl; and the second substituent, if present, is selected from the group consisting of F, $C_{(2-4)}$alkyl and $OCH_3$, or said phenyl may be substituted on two adjacent carbon atoms to form a fused bicyclic system, selected from the group consisting of benzothiazolyl, benzooxazolyl, benzofuranyl, indolyl, quinolinyl, isoquinolinyl, benzo[b]thiophenyl, 3H-benzothiazol-2-onyl, 3H-benzooxazol-2-onyl, 1,3-dihydro-benzoimidazol-2-onyl, 1-methyl-1H-benzoimidazolyl, benzo[1,3]dioxolyl, 2,3-dihydro-benzofuranyl, 2,3-dihydro-benzo[1,4]dioxinyl, wherein said 3H-benzooxazol-2-onyl, 1,3-dihydro-benzoimidazol-2-onyl, and 1-methyl-1H-benzoimidazolyl, are optionally substituted on any nitrogen atom with $C_{(1-4)}$alkyl;

$R^2$ is H, $C_{(1-4)}$alkyl, $NH_2$, $NO_2$, $NHCH_2CH_2OH$, $N(C_{(1-4)}$alkyl$)_2$, $N(SO_2CH_3)_2$, $NHCONHC_{(1-4)}$alkyl, CN, F, Cl, Br, $CF_3$, cycloalkyl, heterocyclyl, $OCF_3$, $OCF_2H$, $CF_2H$, or $OC_{(1-4)}$alkyl;

$R^3$ is F, Cl, $CF_3$, or $OC_{(1-4)}$alkyl; alternatively, $R^2$ and $R^3$ may be taken together with their attached phenyl to form a benzo[1,3]dioxolyl, 2,3-dihydro-benzofuranyl, or 2,3-dihydro-benzo[1,4]dioxinyl group;

$R^4$ is H, $OC_{(1-4)}$alkyl, or F;

and solvates, hydrates, tautomers, prodrugs, and pharmaceutically acceptable salts thereof.

DETAILED DESCRIPTION OF THE INVENTION

The present invention comprises compounds of Formula (I):

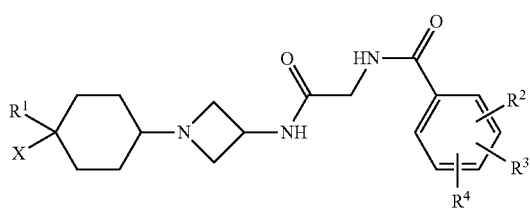

Formula (I)

wherein X, $R^1$, $R^2$, $R^3$ and $R^4$ are as described above;
and solvates, hydrates, tautomers, prodrugs, and pharmaceutically acceptable salts thereof.

Another embodiment of the invention comprises the compounds of Formula (Ia):

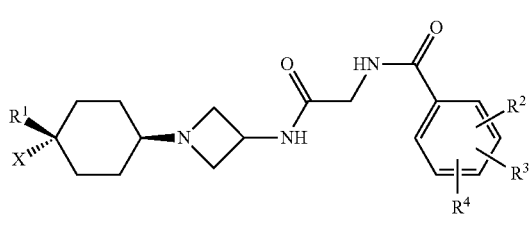

Formula (Ia)

wherein X, $R^1$, $R^2$, $R^3$ and $R^4$ are as defined above for Formula (I);
and solvates, hydrates, tautomers, prodrugs, and pharmaceutically acceptable salts thereof.

Another embodiment of the invention comprises compounds of Formula (I) and/or Formula (Ia) wherein:
X is $NH_2$, F, H, or OH;
$R^1$ is phenyl optionally substituted with one or two substituents, one of which is selected from the group consisting of: $OC_{(1-4)}$alkyl, $SC_{(1-4)}$alkyl, $SOC_{(1-4)}$alkyl, $SO_2C_{(1-4)}$alkyl, —$OSO_2NH_2$, —$SO_2NHC_{(1-4)}$alkyl, —$OSO_2NH_2$, —$SO_2NH_2$, $N(C_{(1-4)}$alkyl$)_2$, $NH_2$, $NHC_{(1-4)}$alkyl, $NHSO_2C_{(1-4)}$alkyl, $N(SO_2CH_3)_2$, OH, $OCH_2CO_2C_{(1-4)}$alkyl, $OCH_2CO_2H$, $OCH_2CH_2N(CH_3)_2$, F, Cl, $CH_2CN$, CN, $C_{(1-4)}$alkyl, $NHCO_2H$, $NHCO_2C_{(1-4)}$alkyl, $NHCOC_{(1-4)}$alkyl, —C≡CH, $CONH_2$, $NHCONH_2$, $NHCONHC_{(1-4)}$alkyl, $CONHC_{(1-4)}$alkyl, $CH_2CONHC_{(1-4)}$alkyl, $CH_2CONH_2$, $CH_2CO_2C_{(1-4)}$alkyl, $CH_2CO_2H$, $CO_2H$, $CH_2C(NH)NH_2$, $CO_2C_{(1-4)}$alkyl, $CF_3$, $OCHF_2$, $CHF_2$, $OCF_3$, cyclopentyl, cyclohexyl, morpholinyl, piperazinyl, piperidinyl, phenoxy, $CH_2$phenyl, phenyl, $CH_2$pyridyl, pyridyl, pyrrolidinyl, $CH_2$tetrazolyl, and tetrazolyl; and the second substituent, if present, is selected from the group consisting of F, $CH_2CH_3$ and $OCH_3$, or said phenyl may be substituted on two adjacent carbon atoms to form a fused bicyclic system, selected from the group consisting of 3H-benzothiazol-2-onyl, 3H-benzooxazol-2-onyl, 1,3-dihydro-benzoimidazol-2-onyl, 1-methyl-1H-benzoimidazolyl, benzo[1,3]dioxolyl, 2,3-dihydro-benzofuranyl, 2,3-dihydro-benzo[1,4]dioxinyl, wherein said 3H-benzooxazol-2-onyl, 1,3-dihydro-benzoimidazol-2-onyl, and 1-methyl-1H-benzoimidazolyl, are optionally substituted on any nitrogen atom with $C_{(1-4)}$alkyl;

$R^2$ is H, $C_{(1-4)}$alkyl, $NH_2$, $NO_2$, $NHCH_2CH_2OH$, $N(C_{(1-4)}$alkyl$)_2$, $N(SO_2CH_3)_2$, $NHCONHC_{(1-4)}$alkyl, CN, F, Cl, Br, $CF_3$, pyridinyl, pyrrolidinyl, $OCF_3$, $OCF_2H$, $CF_2H$, or $OC_{(1-4)}$alkyl;

$R^3$ is F, Cl, $CF_3$, or $OC_{(1-4)}$alkyl; alternatively, $R^2$ and $R^3$ may be taken together with their attached phenyl to form a benzo[1,3]dioxolyl group;

$R^4$ is H, $OCH_3$, or F;

and solvates, hydrates, tautomers, prodrugs, and pharmaceutically acceptable salts thereof.

Another embodiment of the invention comprises compounds of Formula (I) and/or Formula (Ia) wherein:
X is $NH_2$, F, H, or OH;
$R^1$ is phenyl optionally substituted with one or two substituents, one of which is selected from the group consisting of: $OC_{(1-4)}$alkyl, $SC_{(1-4)}$alkyl, $SO_2CH_3$, $N(C_{(1-4)}$alkyl$)_2$, $NH_2$, $NHSO_2C_{(1-4)}$alkyl, $N(SO_2CH_3)_2$, OH, F, Cl, $CH_2CN$, CN, $C_{(1-4)}$alkyl, $NHCO_2C(CH_3)_3$, $OCH_2CO_2C_{(1-4)}$alkyl, $OCH_2CO_2H$, $OCH_2CH_2N(CH_3)_2$, —C≡CH, $CONH_2$, $CO_2H$, $CO_2C_{(1-4)}$alkyl, $CH_2CO_2H$, $CH_2CO_2C_{(1-4)}$alkyl, $CH_2C(NH)NH_2$, $CH_2CONH_2$, pyrrolidinyl, $CH_2$tetrazolyl, and tetrazolyl; and the second substituent, if present, is selected from the group consisting of F, $CH_2CH_3$ and $OCH_3$, or said phenyl may be substituted on two adjacent carbon atoms to form a fused bicyclic system, selected from the group consisting of 3H-benzooxazol-2-onyl, 1,3-dihydro-benzoimidazol-2-onyl, 1-methyl-1H-benzoimidazolyl, benzo[1,3]dioxolyl, 2,3-dihydro-benzofuranyl, 2,3-dihydro-benzo[1,4]dioxinyl, wherein said 3H-benzothiazol-2-onyl, 3H-benzooxazol-2-onyl, 1,3-dihydro-benzoimidazol-2-onyl, and 1-methyl-1H-benzoimidazolyl, are optionally substituted on any nitrogen atom with $C_{(1-4)}$alkyl;

$R^2$ is H, $NH_2$, $NO_2$, $NHCH_2CH_2OH$, $N(CH_3)_2$, $N(SO_2CH_3)_2$, $NHCONHC_{(1-4)}$alkyl, CN, F, Cl, Br, $CF_3$, pyridinyl, pyrrolidinyl, or $OCH_3$;

$R^3$ is F, Cl, $CF_3$, or $OCH_3$; alternatively, $R^2$ and $R^3$ may be taken together with their attached phenyl to form a benzo[1,3]dioxolyl group;

$R^4$ is H, or F;

and solvates, hydrates, tautomers, prodrugs, and pharmaceutically acceptable salts thereof.

Another embodiment of the invention comprises compounds of Formula (I) and/or Formula (Ia) wherein:

X is $NH_2$, F, H, or OH;

$R^1$ is phenyl optionally substituted with one substituent selected from the group consisting of: $OC_{(1-4)}$alkyl, $SC_{(1-4)}$alkyl, $SO_2CH_3$, $N(C_{(1-4)}alkyl)_2$, $NH_2$, $NHSO_2C_{(1-4)}$alkyl, $N(SO_2CH_3)_2$, OH, F, Cl, $CH_2CN$, CN, $C_{(1-4)}$alkyl, $NHCO_2C(CH_3)_3$, $OCH_2CO_2C_{(1-4)}$alkyl, $OCH_2CO_2H$, $OCH_2CH_2N(CH_3)_2$, —C≡CH, $CONH_2$, $CO_2H$, $CO_2C_{(1-4)}$alkyl, $CH_2CO_2H$, $CH_2CO_2C_{(1-4)}$alkyl, $CH_2C(NH)NH_2$, $CH_2CONH_2$, pyrrolidinyl, $CH_2$tetrazolyl, and tetrazolyl; or said phenyl may be substituted with one $OCH_3$ group and one F, or said phenyl may be substituted on two adjacent carbon atoms to form a fused bicyclic system, selected from the group consisting of 3H-benzothiazol-2-onyl, 3H-benzooxazol-2-onyl, 1,3-dihydro-benzoimidazol-2-onyl, 1-methyl-1H-benzoimidazolyl, benzo[1,3]dioxolyl, 2,3-dihydro-benzofuranyl, 2,3-dihydro-benzo[1,4]dioxinyl, wherein said 3H-benzooxazol-2-onyl, 1,3-dihydro-benzoimidazol-2-onyl, and 1-methyl-1H-benzoimidazolyl, are optionally substituted on any nitrogen atom with $C_{(1-4)}$alkyl.

$R^2$ is H, $NH_2$, $NO_2$, $NHCH_2CH_2OH$, $N(CH_3)_2$, $N(SO_2CH_3)_2$, $NHCONHC_{(1-4)}$alkyl, CN, F, Cl, Br, $CF_3$, pyridinyl, pyrrolidinyl, or $OCH_3$;

$R^3$ is F, Cl, $CF_3$, or $OCH_3$; alternatively, $R^2$ and $R^3$ may be taken together with their attached phenyl to form a benzo[1,3]dioxolyl group;

$R^4$ is H, or F;

and solvates, hydrates, tautomers, prodrugs, and pharmaceutically acceptable salts thereof.

Another embodiment of the invention comprises compounds of Formula (I) and/or Formula (Ia) wherein:

X is $NH_2$, F, H, or OH;

$R^1$ is phenyl,

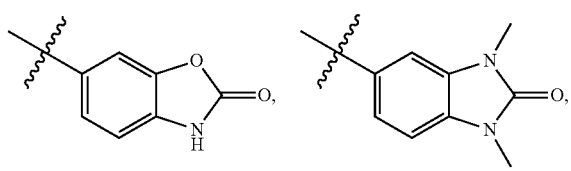

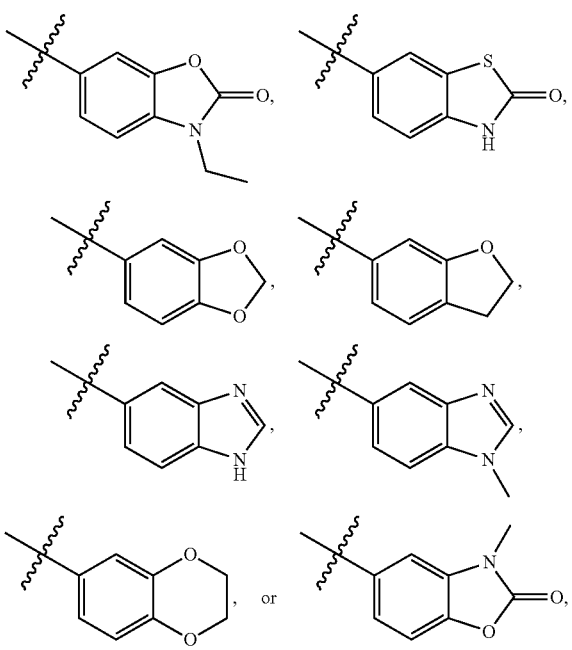

wherein said phenyl is optionally substituted with one substituent selected from the group consisting of: $OCH_3$, $SCH_3$, $SO_2CH_3$, $N(CH_3)_2$, $NH_2$, $NHSO_2CH_3$, $N(SO_2CH_3)_2$, OH, F, Cl, $CH_2CN$, CN, $CH_3$, $NHCO_2C(CH_3)_3$, $OCH_2CO_2CH_3$, $OCH_2CO_2H$, $OCH_2CH_2N(CH_3)_2$, —C≡CH, $CH_2CH_3$, $CONH_2$, $CO_2H$, $CO_2CH_3$, $CO_2CH_2CH_3$, $CH_2CO_2H$, $CH_2CO_2CH_2CH_3$, $CH_2C(NH)NH_2$, $CH_2CONH_2$, pyrrolidinyl, $CH_2$tetrazolyl and tetrazolyl; or said phenyl may be substituted with one $OCH_3$ group and one F;

$R^2$ is H, F, Br, $CF_3$, $NO_2$, $NH_2$, $NHCH_2CH_2OH$, $N(CH_3)_2$, $N(SO_2CH_3)_2$, $NHCONHC_{(1-4)}$alkyl, pyrrolidinyl, pyridinyl, $OCH_3$;

$R^3$ is $CF_3$;

$R^4$ is H;

and solvates, hydrates, tautomers, prodrugs, and pharmaceutically acceptable salts thereof.

Another embodiment of the invention is a compound which is selected from the group consisting of:

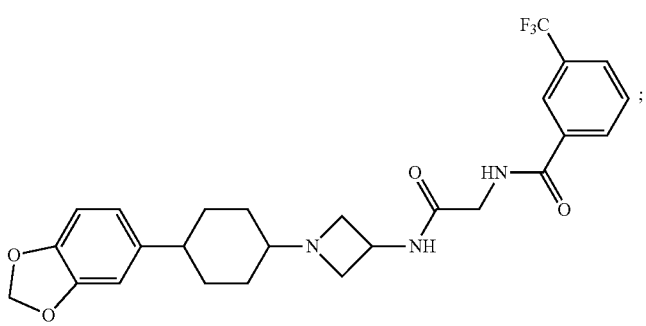

-continued
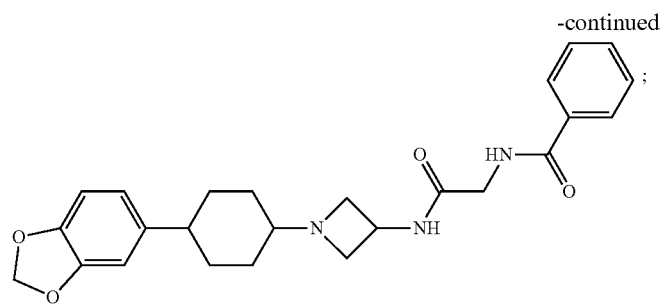
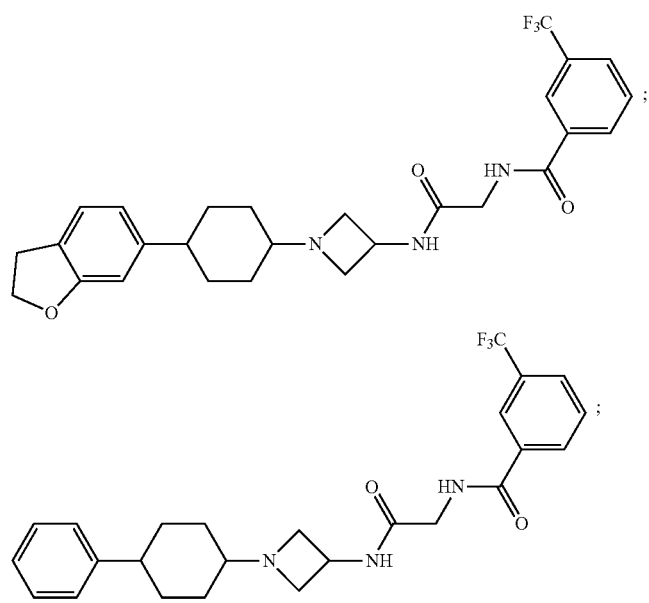
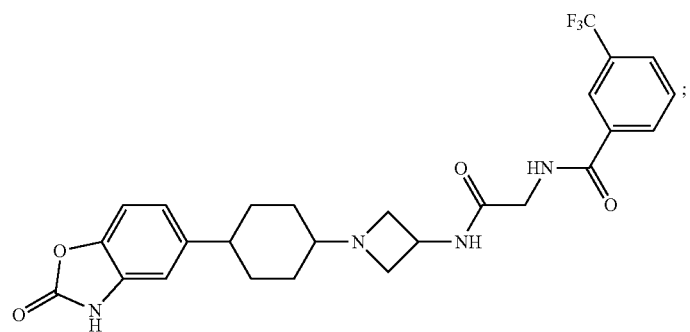
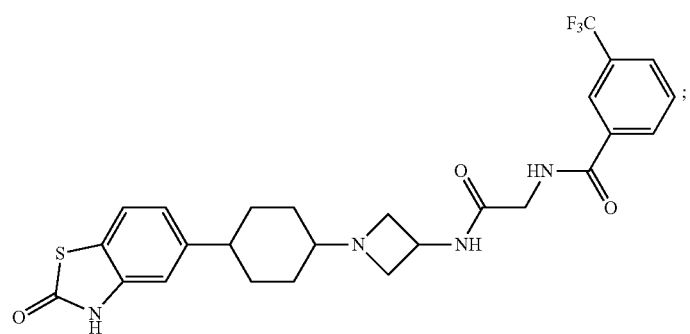

-continued
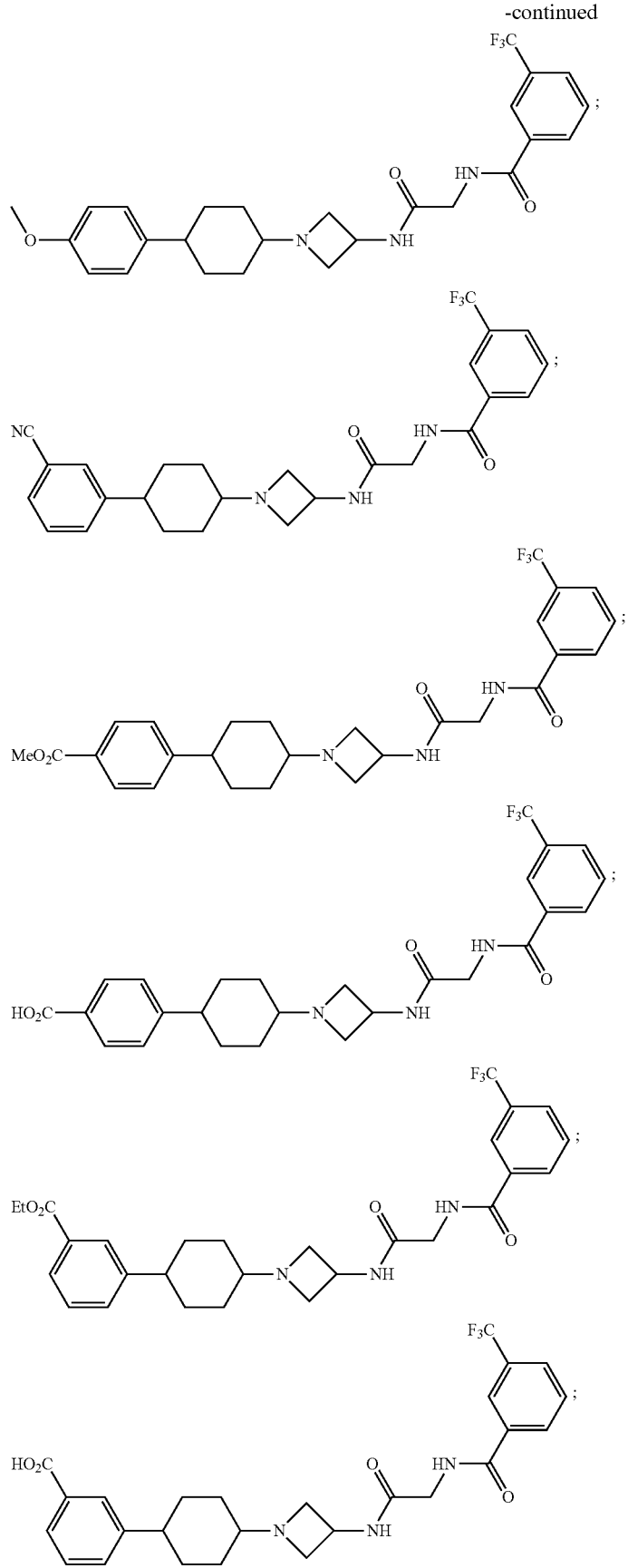

-continued
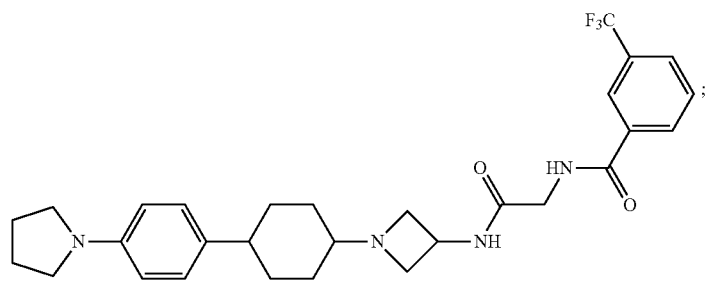
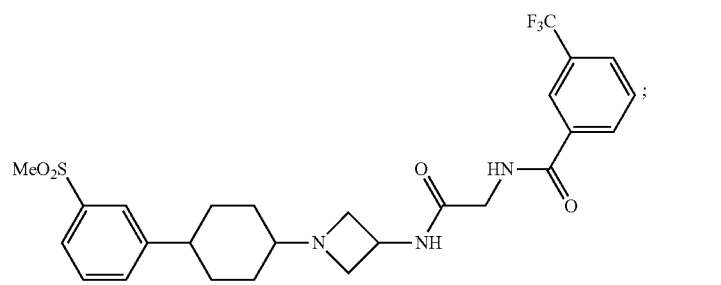
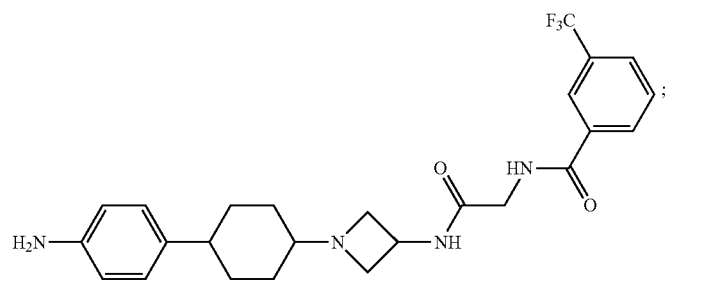
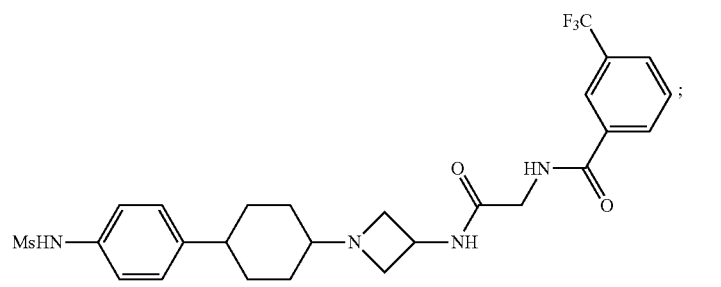
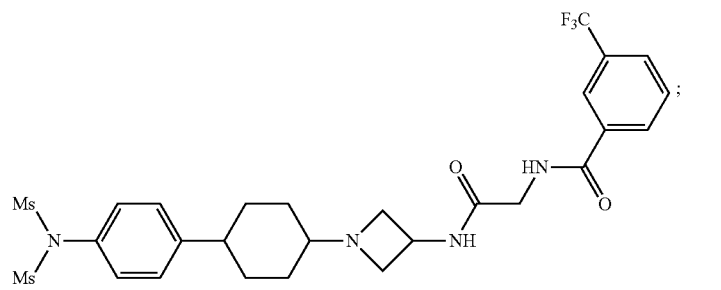
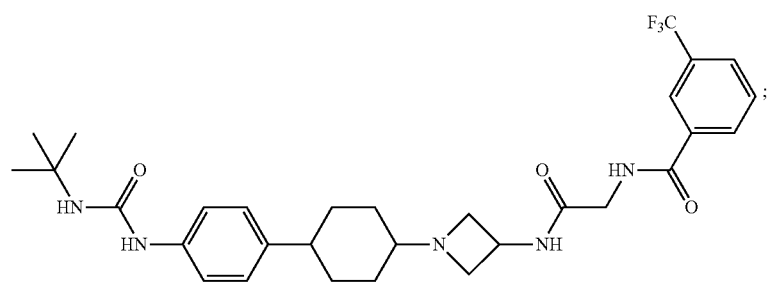

-continued
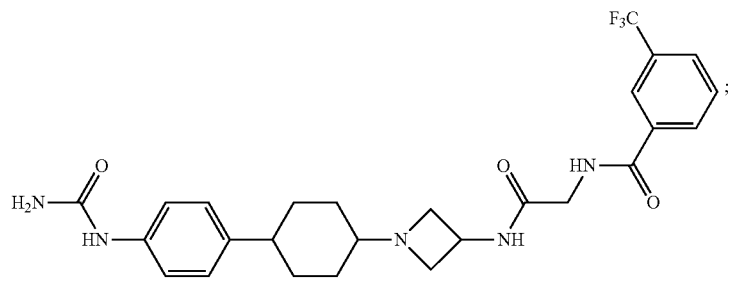
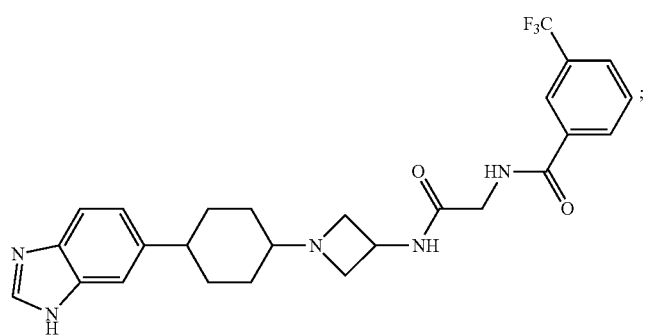
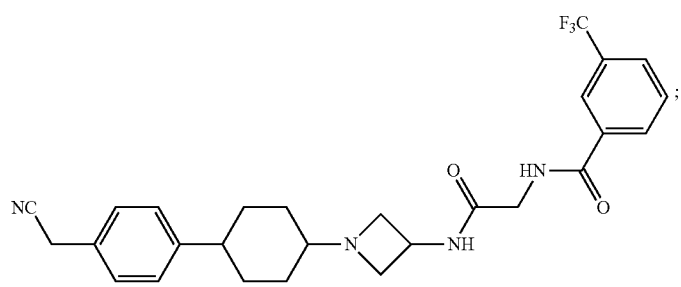
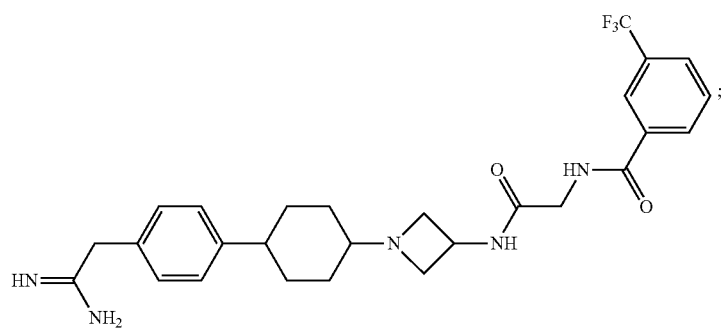
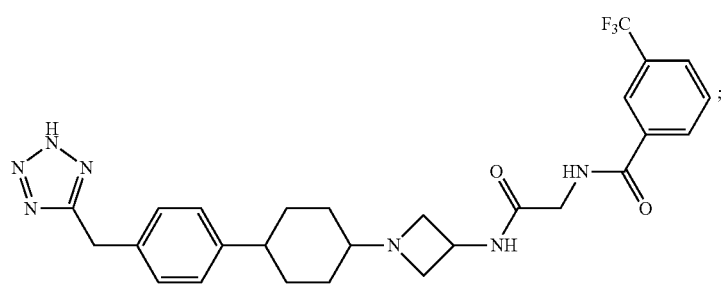

-continued
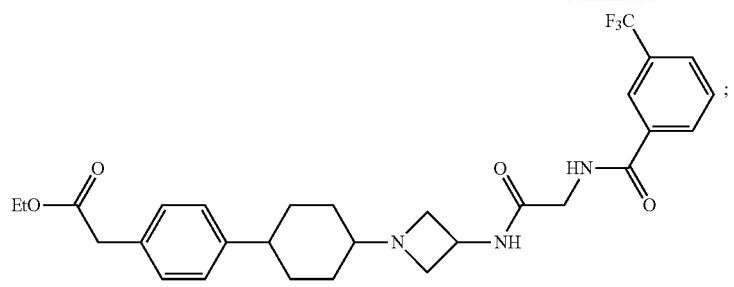
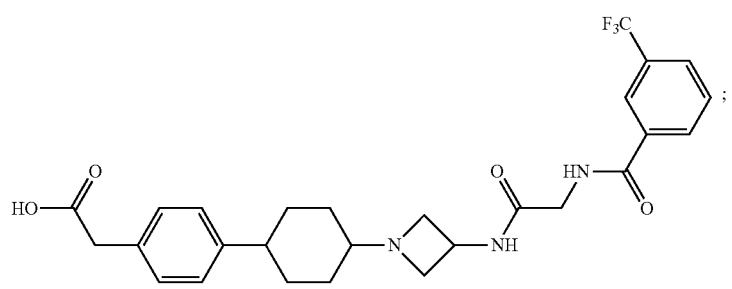
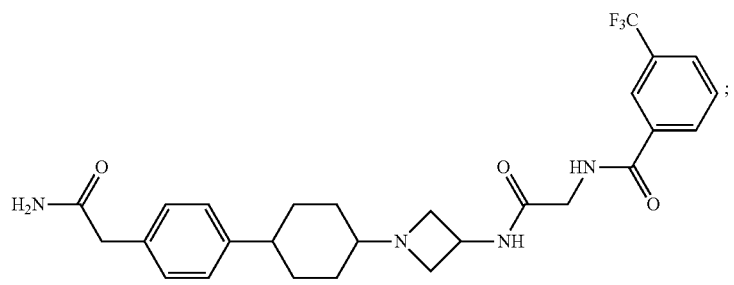
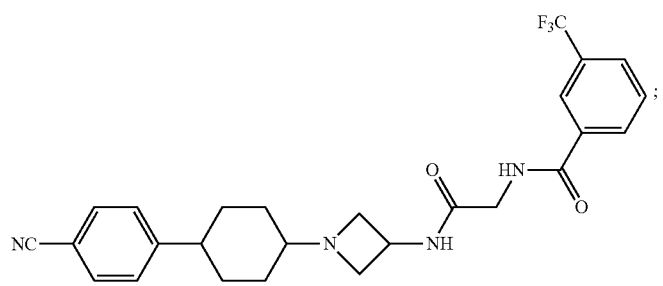
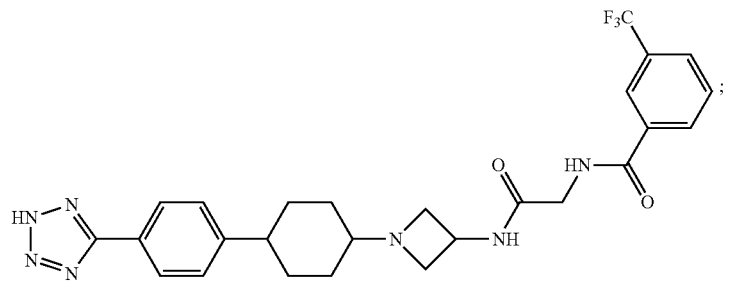

-continued
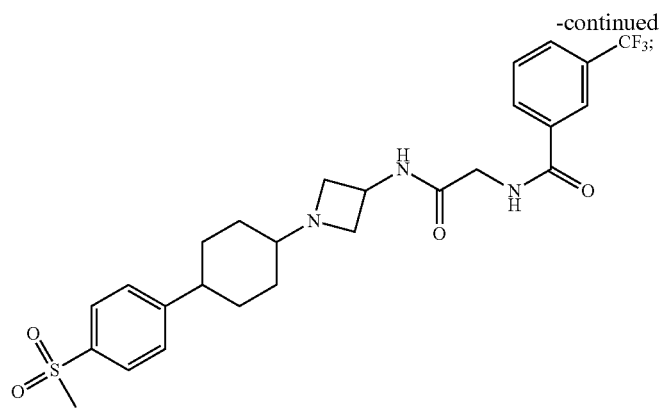
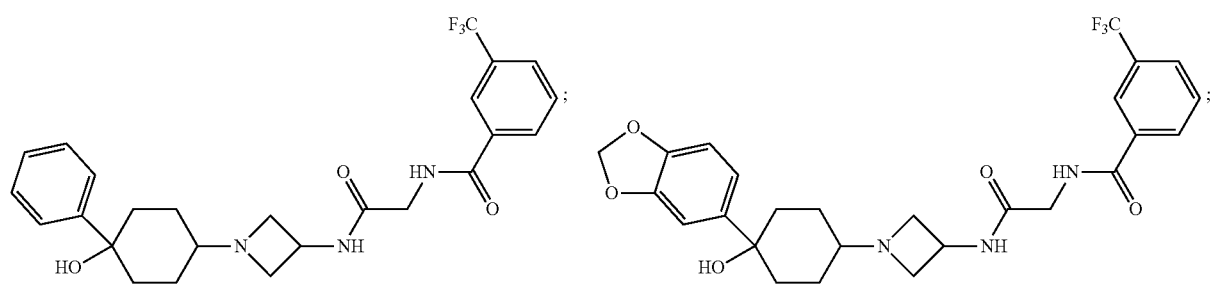
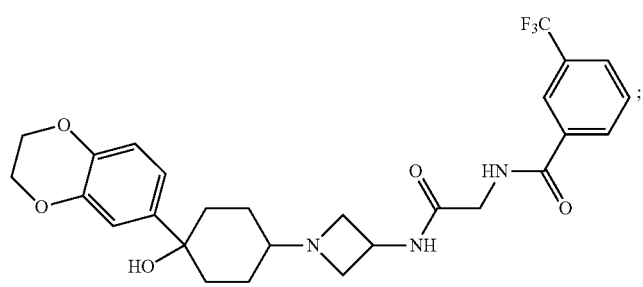 [SMILES: COc1cccc(C2(N)CCC(N3CC(NC(=O)CNC(=O)c4cccc(C(F)(F)F)c4)C3)CC2)c1]
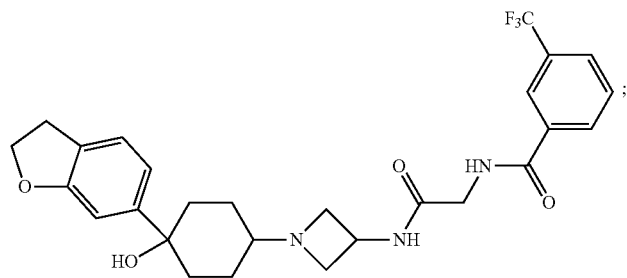
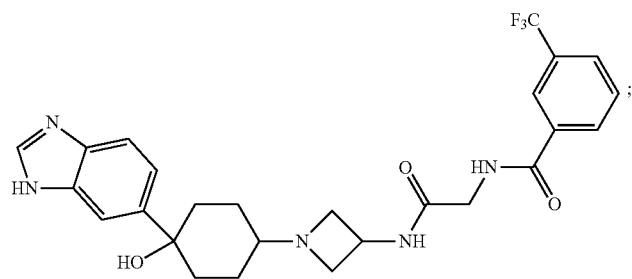

-continued
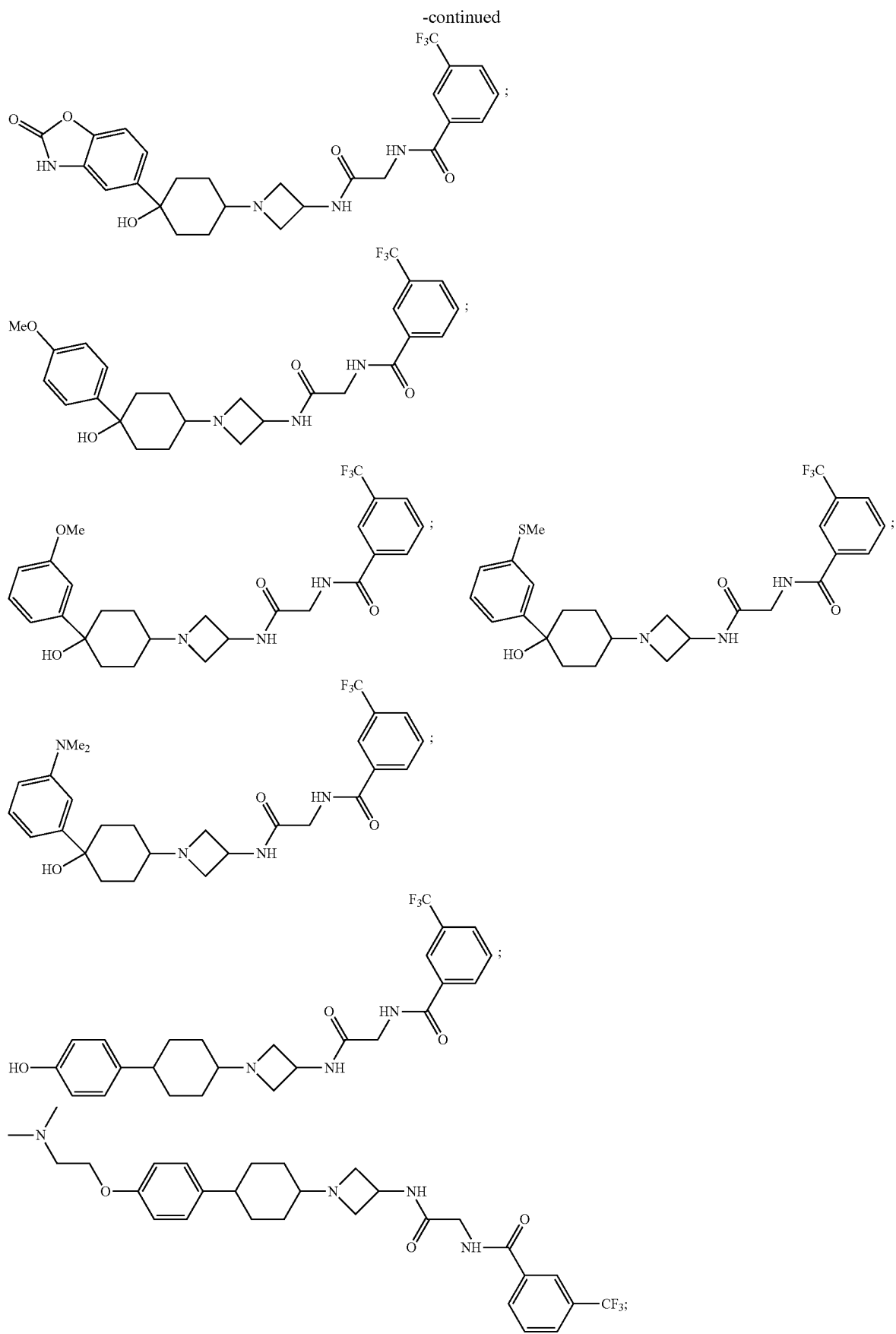

-continued
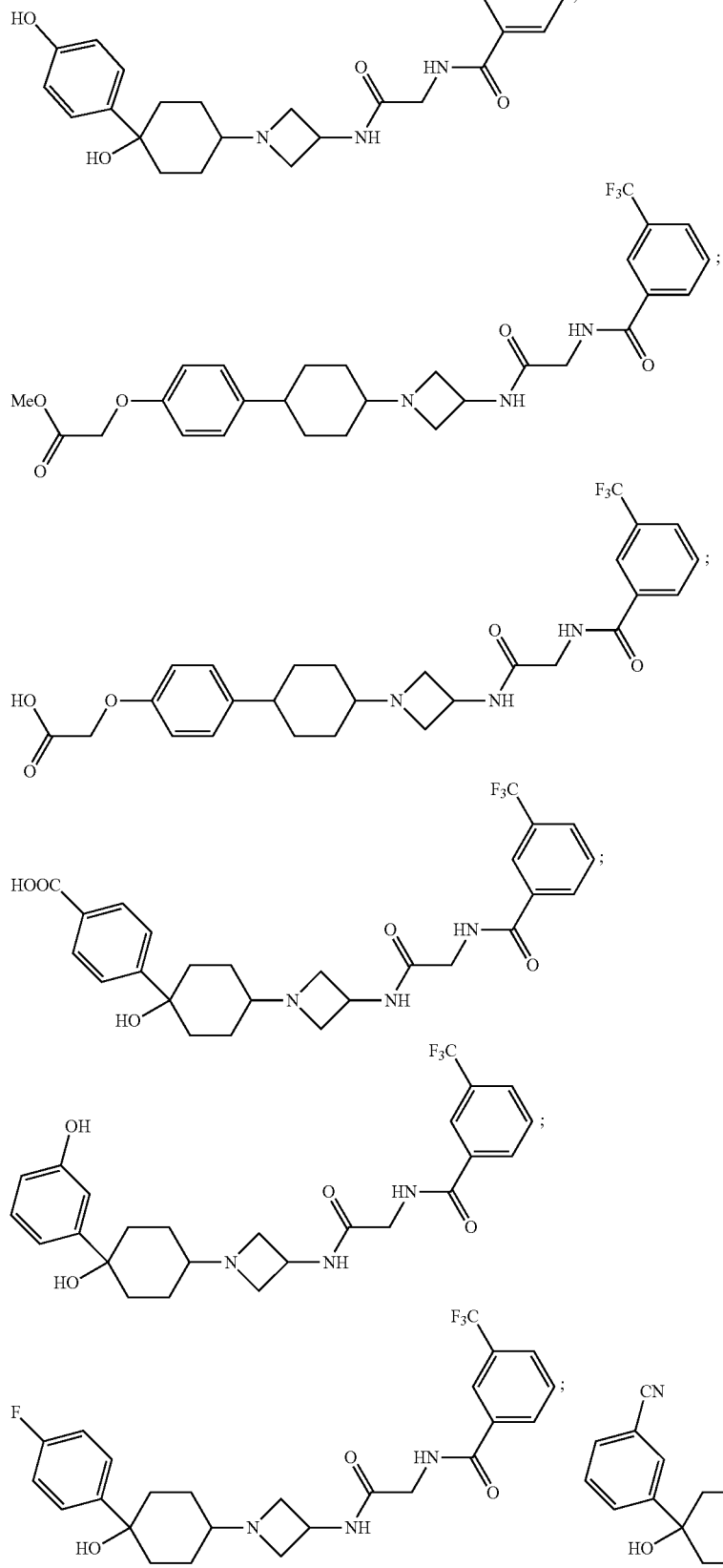

-continued
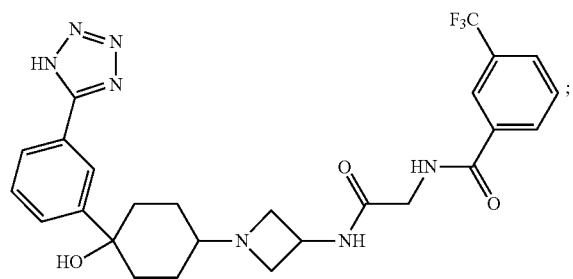
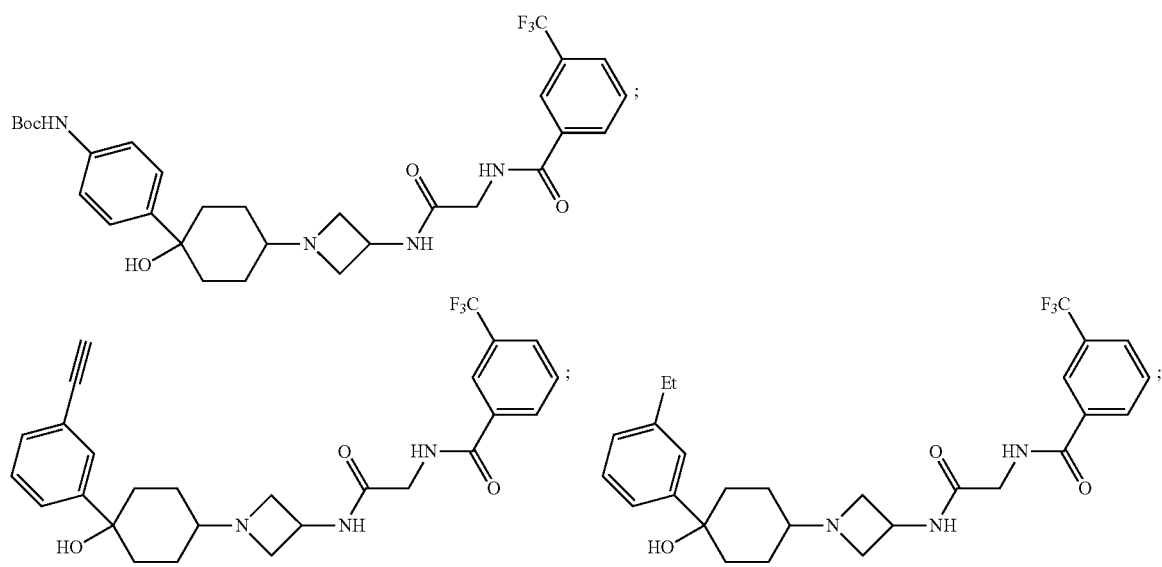
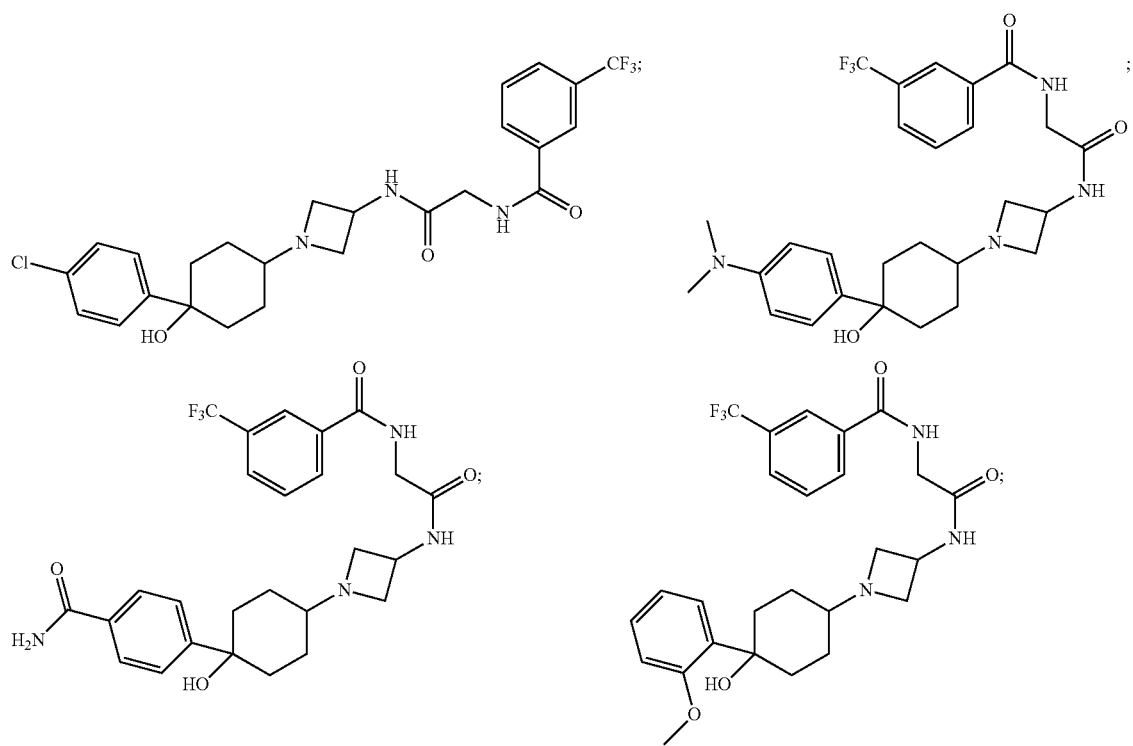

-continued
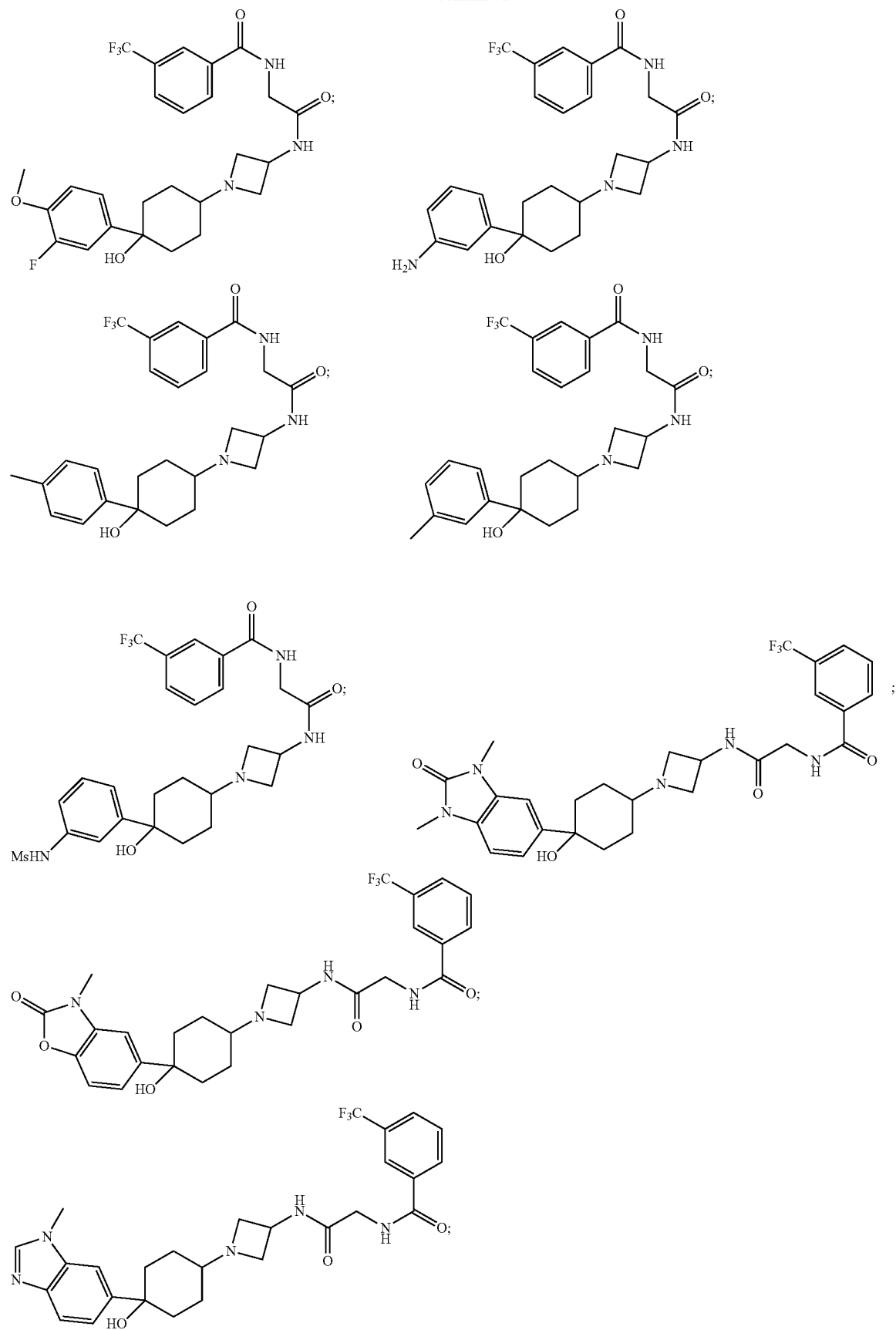

-continued
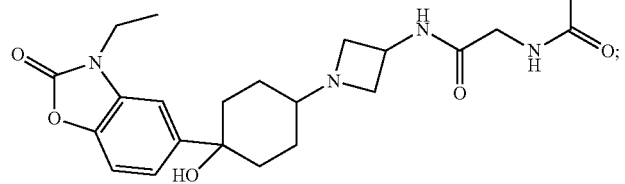
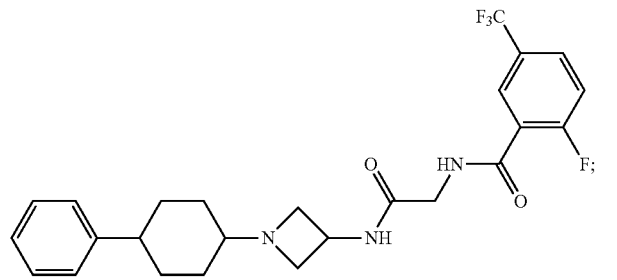
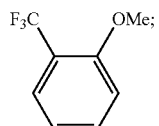
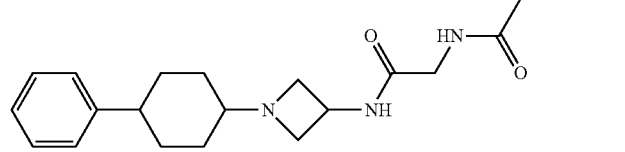
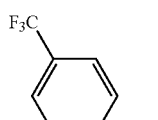
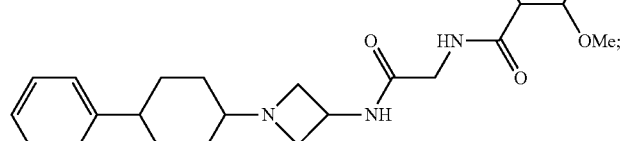
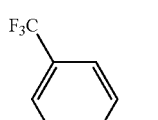
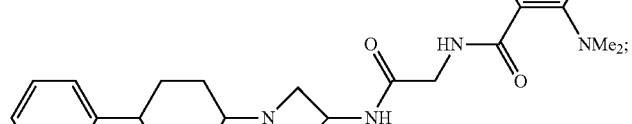
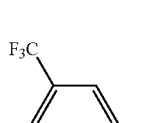
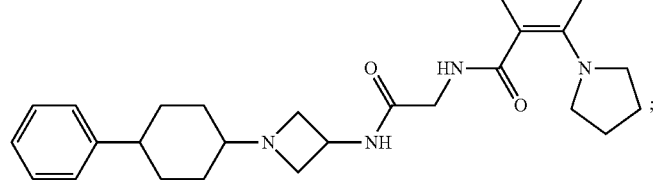

-continued
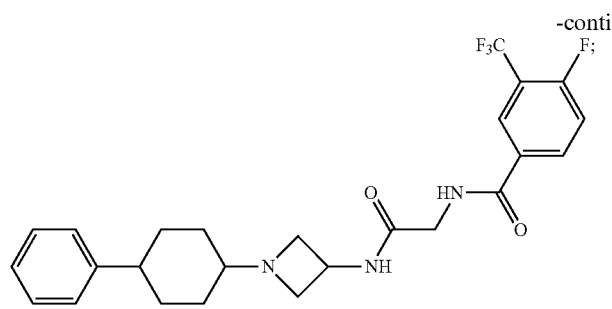
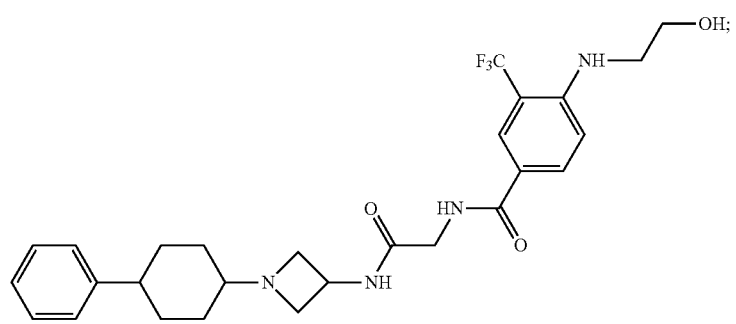
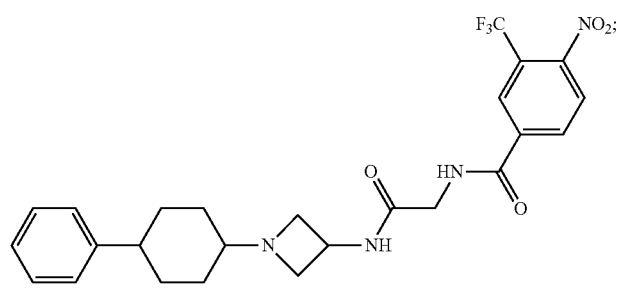
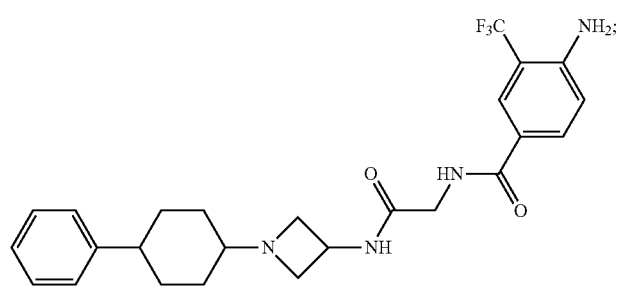
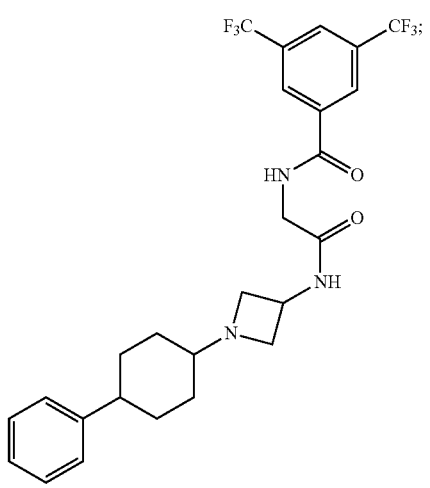

31
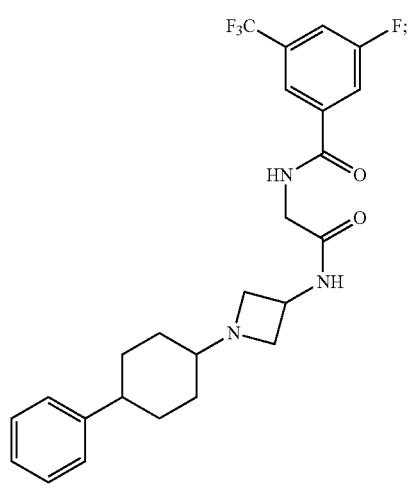
-continued
32
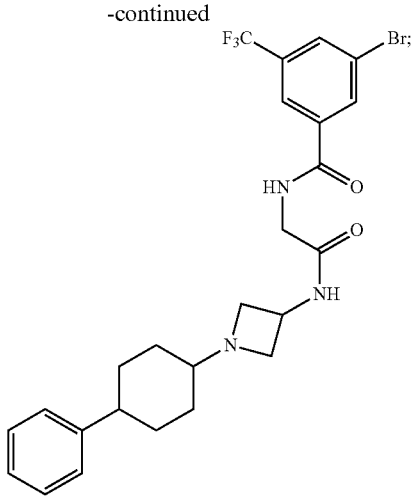
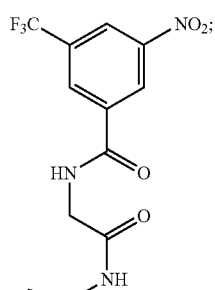
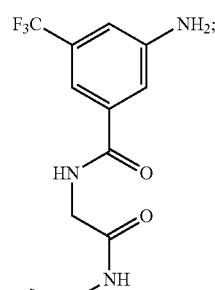
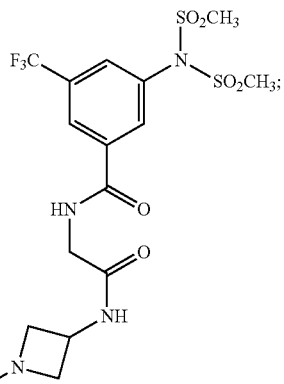
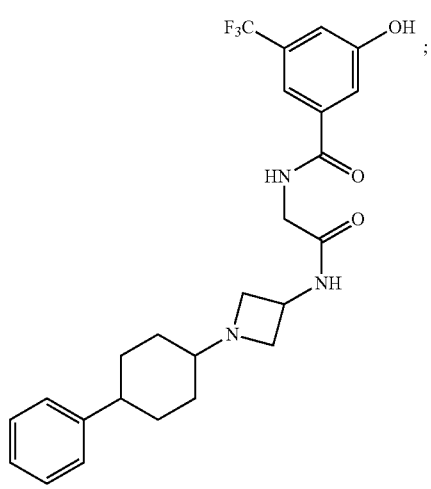

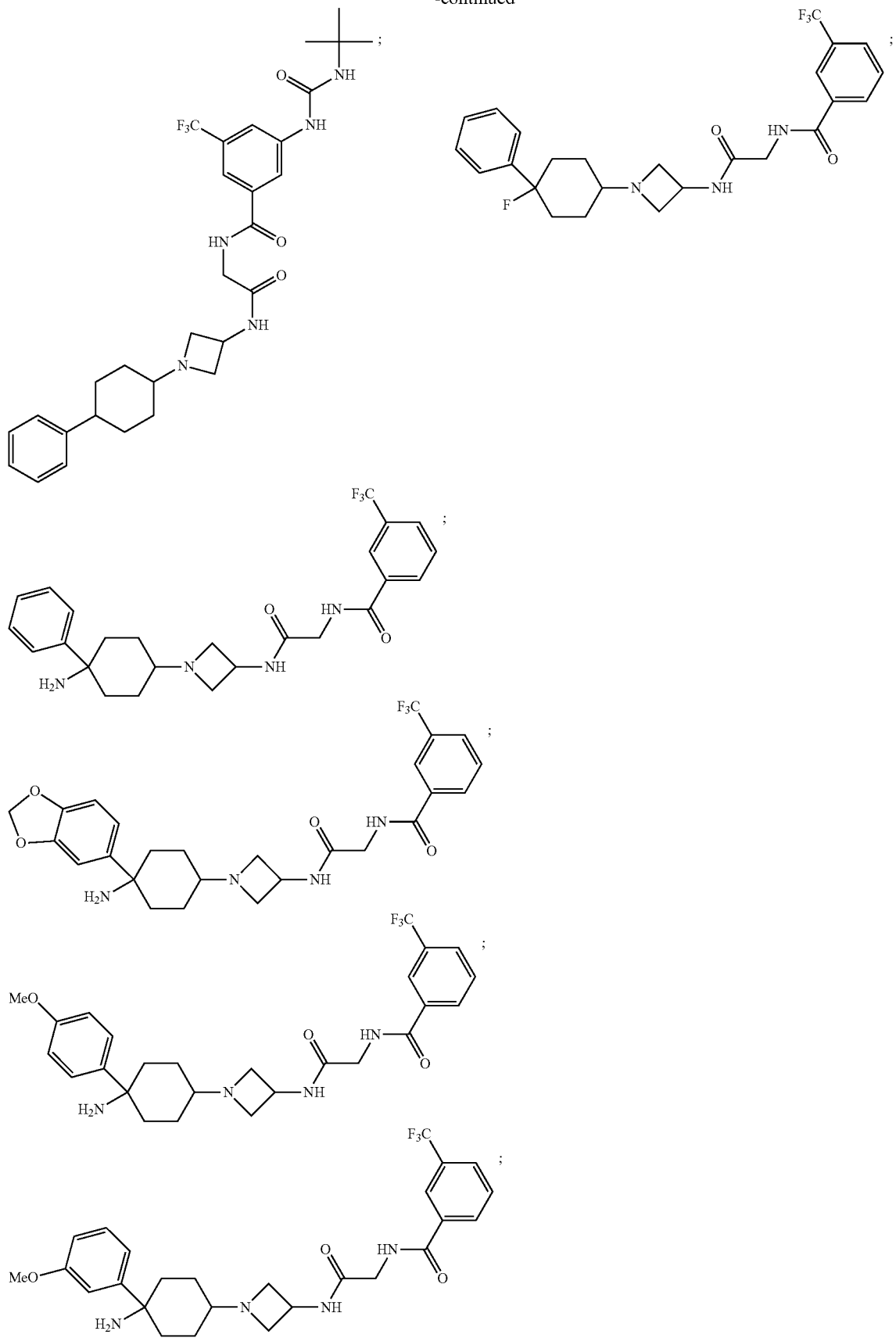

and solvates, hydrates, tautomers, prodrugs, and pharmaceutically acceptable salts thereof.
Another embodiment of the invention is a compound which is compound selected from the group consisting of:
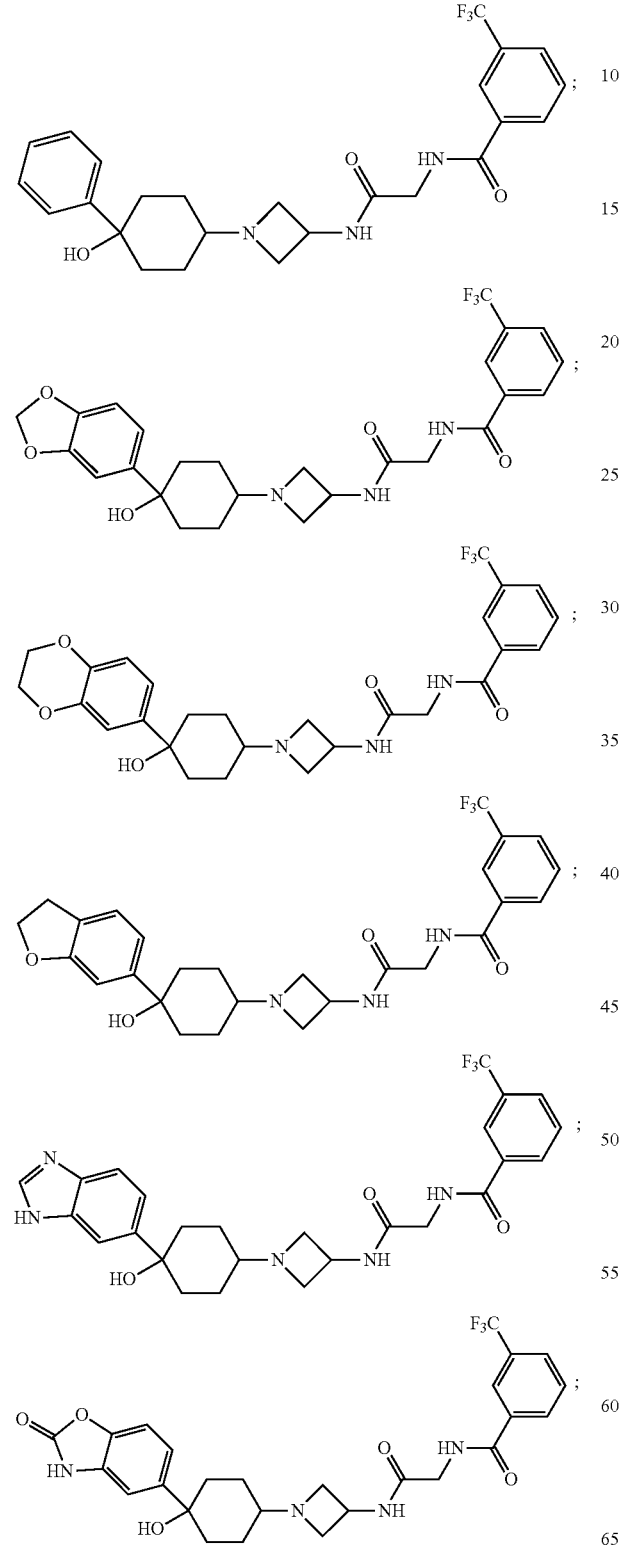
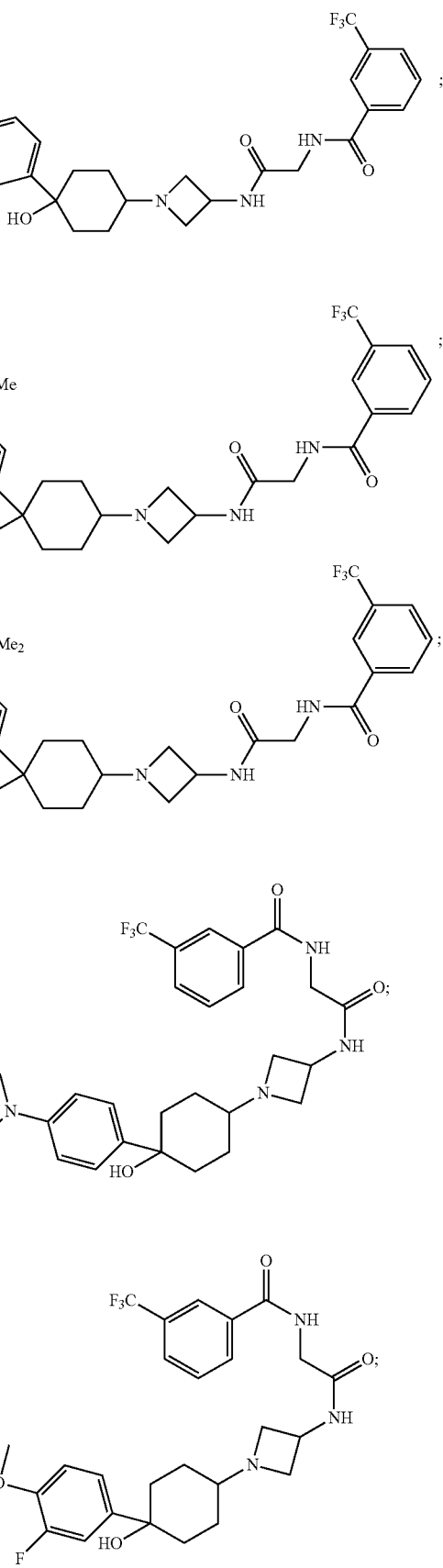

-continued
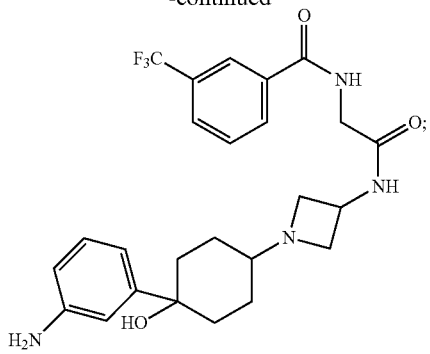
and solvates, hydrates, tautomers, prodrugs, and pharmaceutically acceptable salts thereof.
Another embodiment of the invention is a compound which is
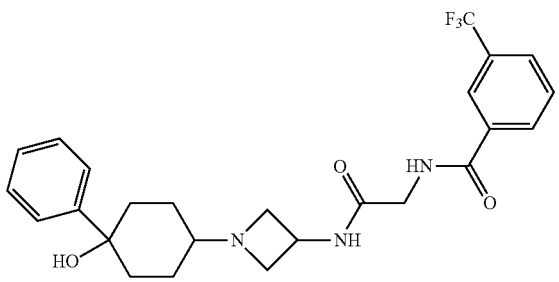 [SMILES: O=C(CNC(=O)c1cccc(C(F)(F)F)c1)NC1CN(C2CCC(O)(c3ccccc3)CC2)C1]
and solvates, hydrates, tautomers, prodrugs, and pharmaceutically acceptable salts thereof.
Another embodiment of the invention is a compound selected from the group consisting of:
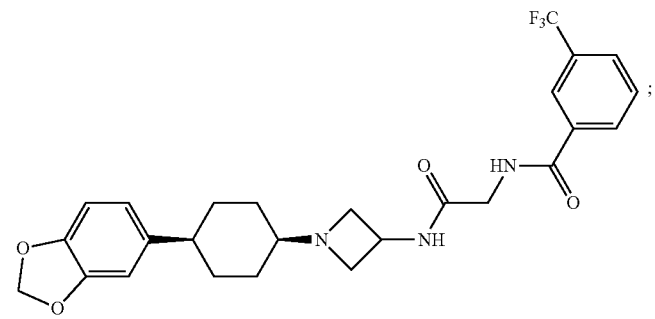
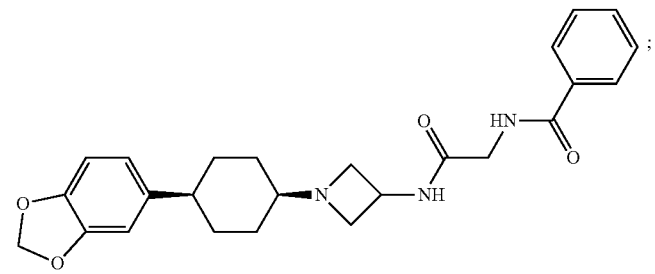
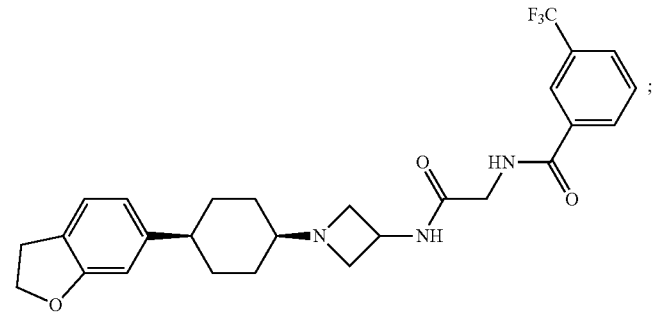
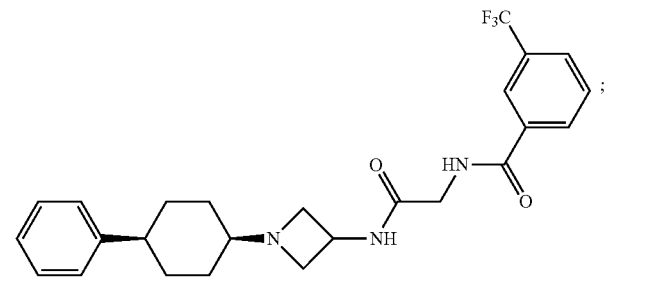

-continued
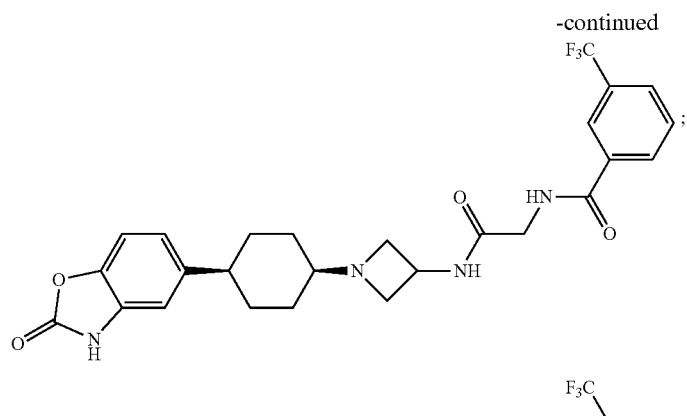
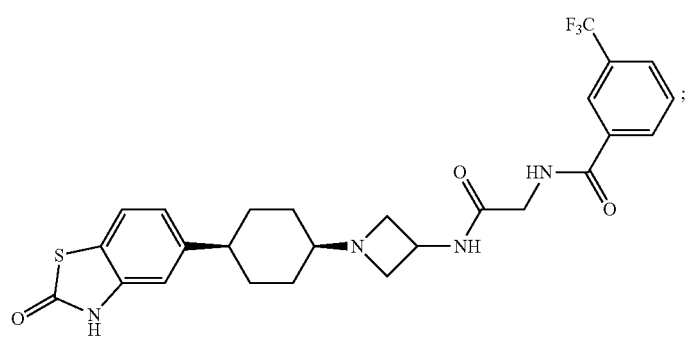
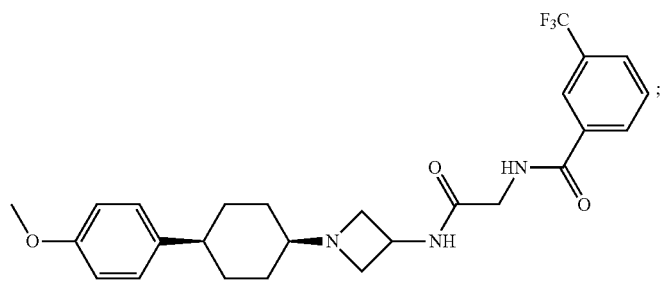
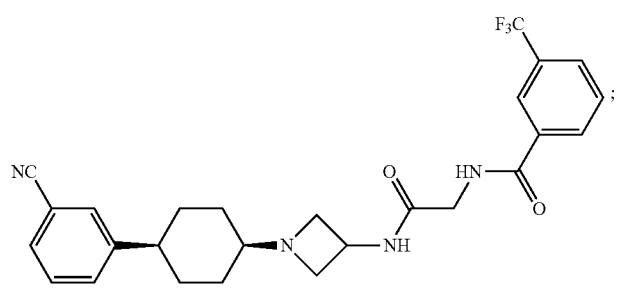
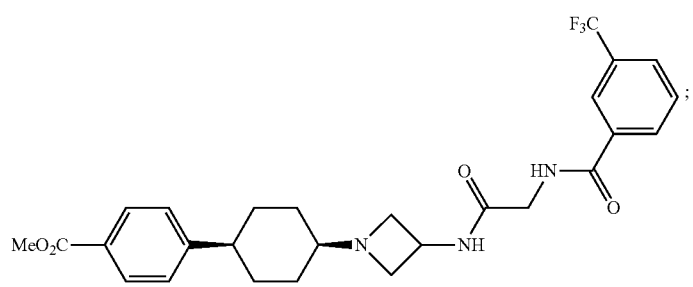

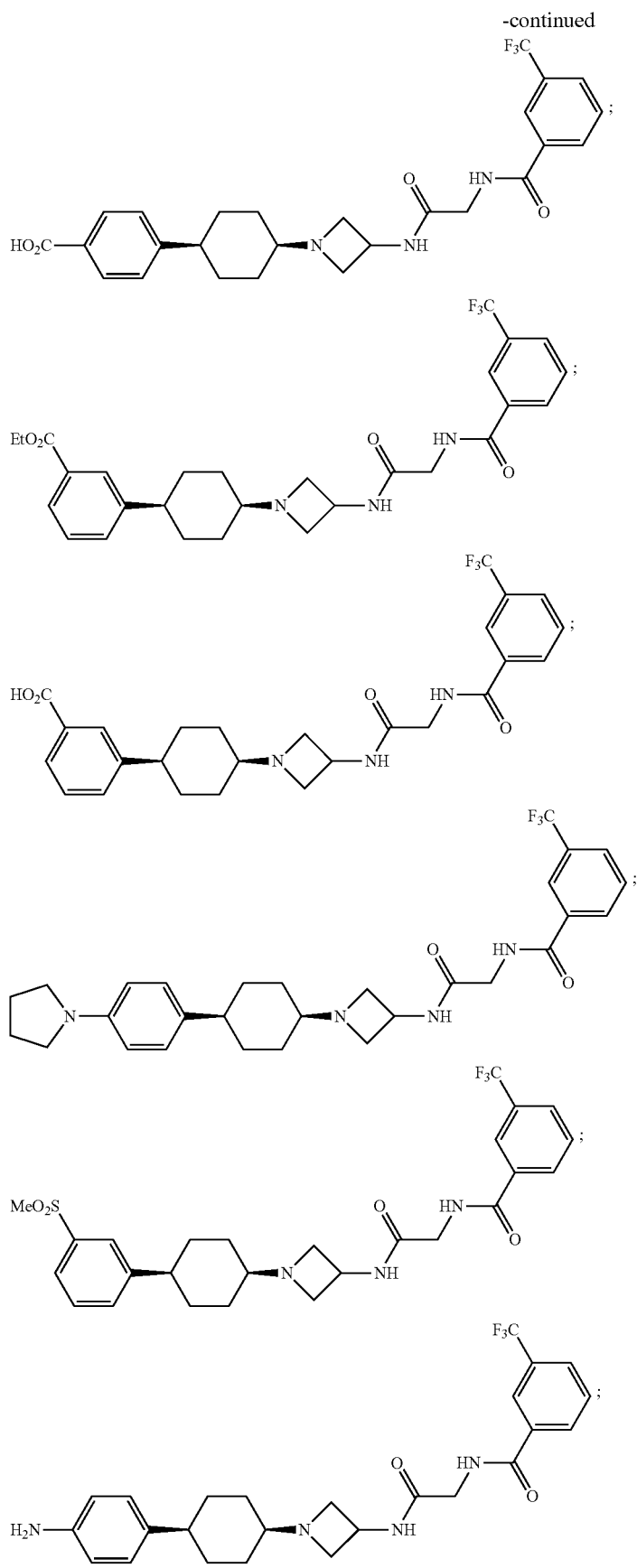

-continued
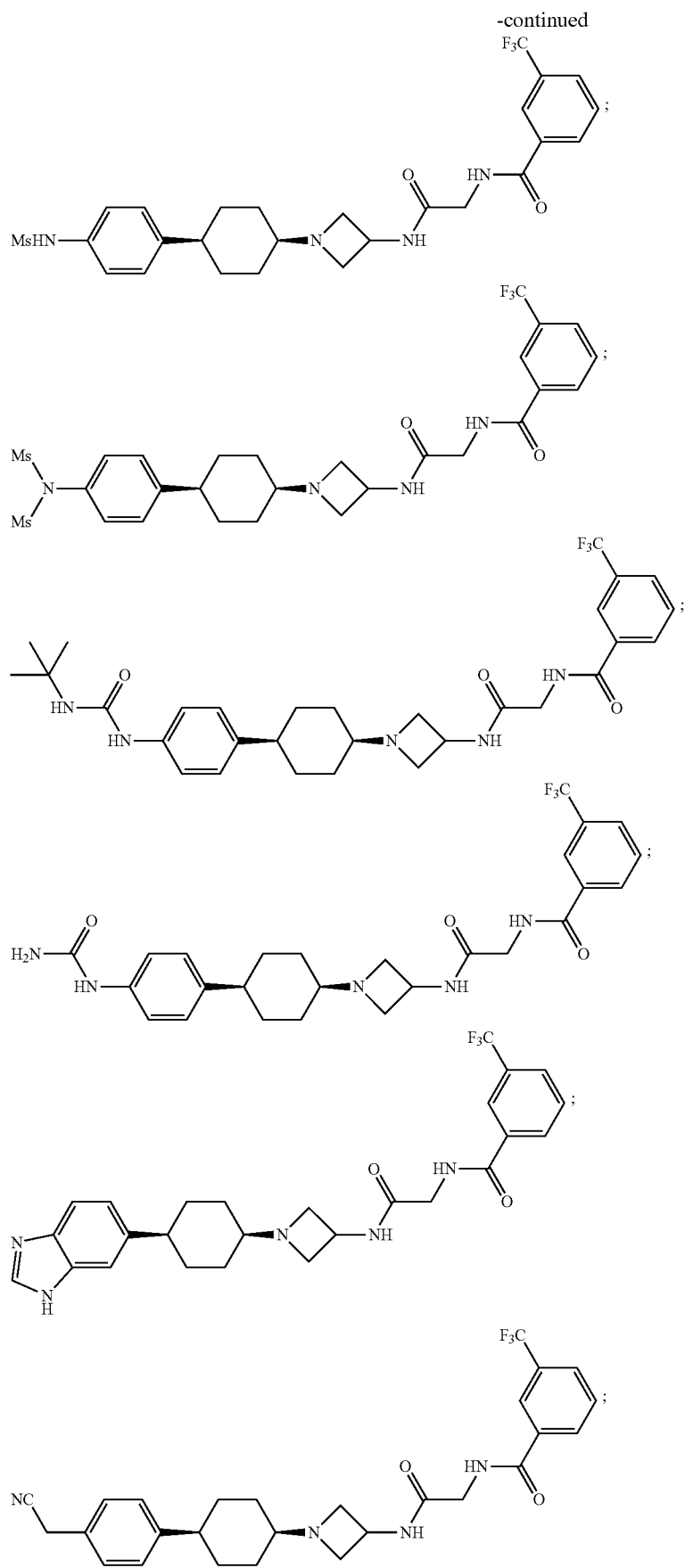

-continued
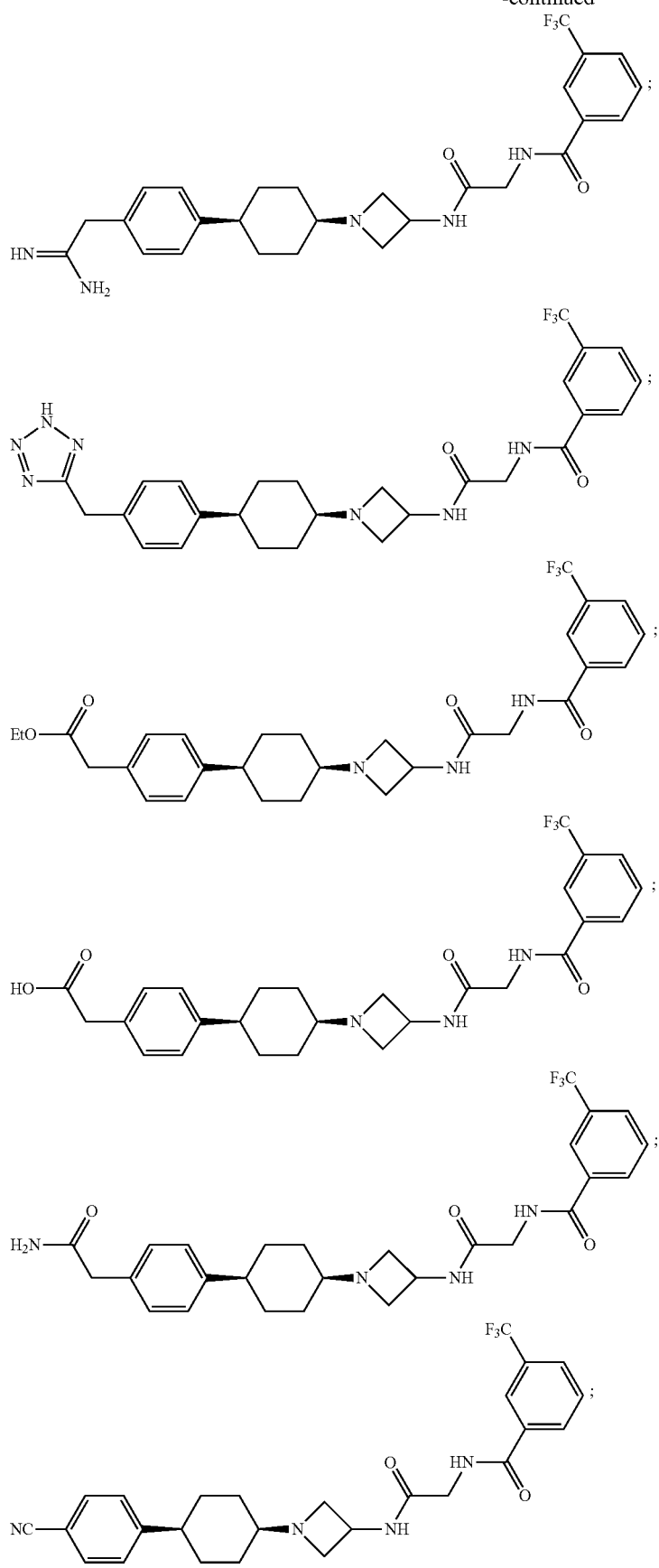

-continued
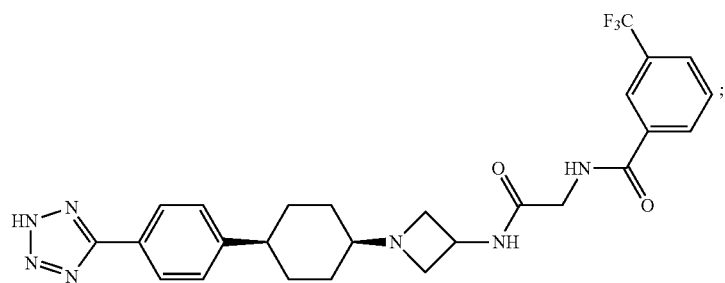
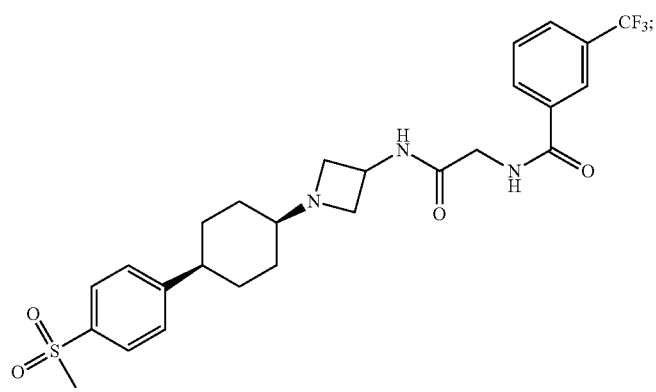
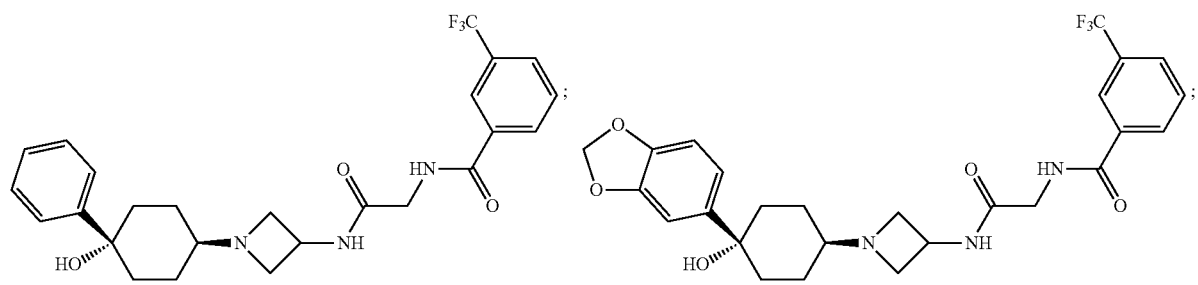
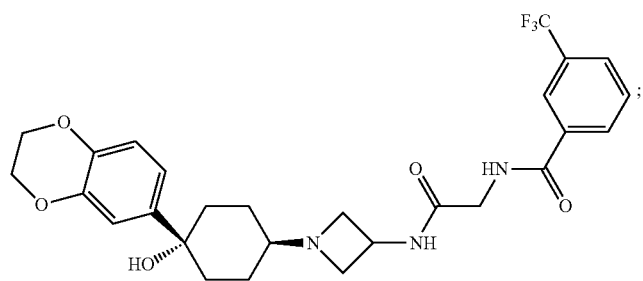 [SMILES: COc1cccc([C@]2(N)CC[C@H](N3CC(NC(=O)CNC(=O)c4cccc(C(F)(F)F)c4)C3)CC2)c1]
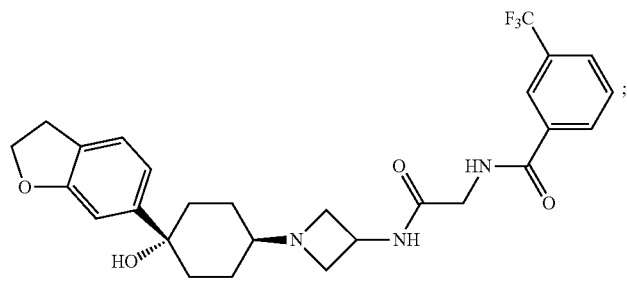

-continued
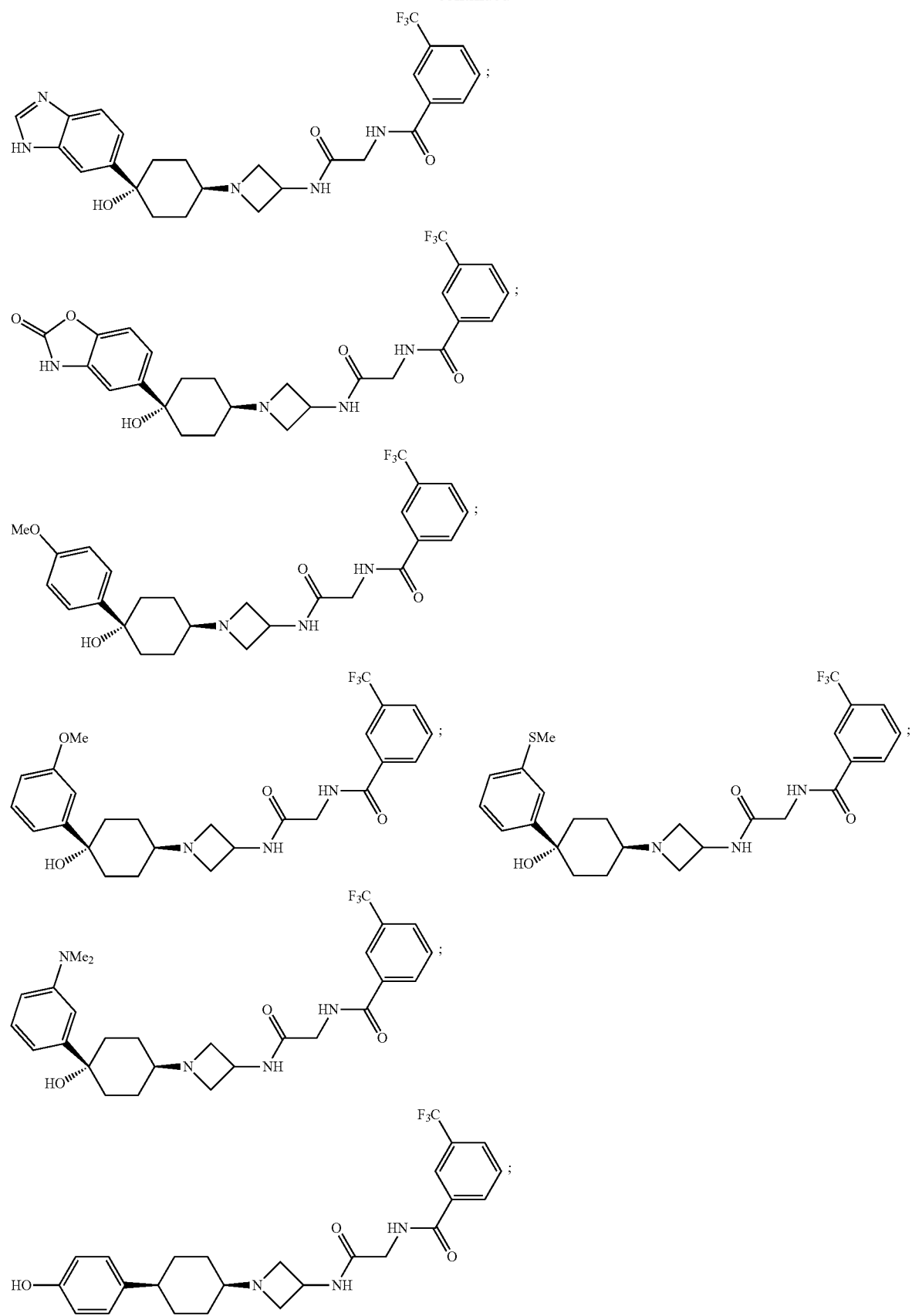

-continued
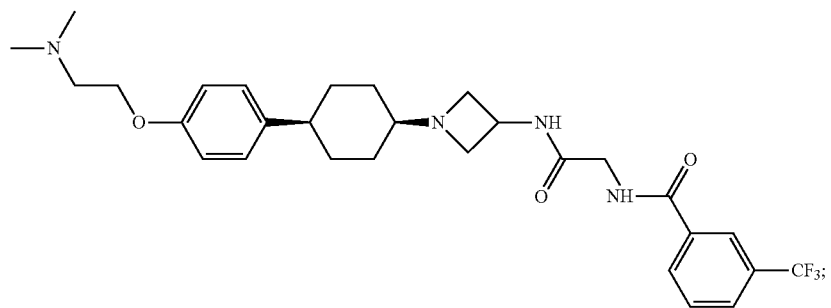
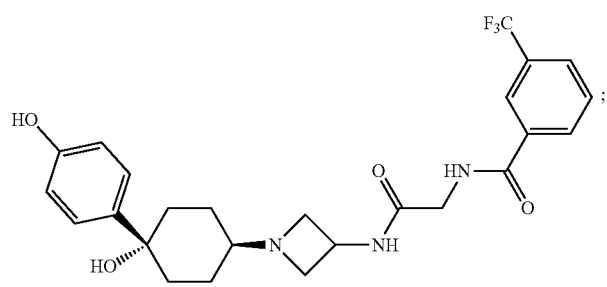
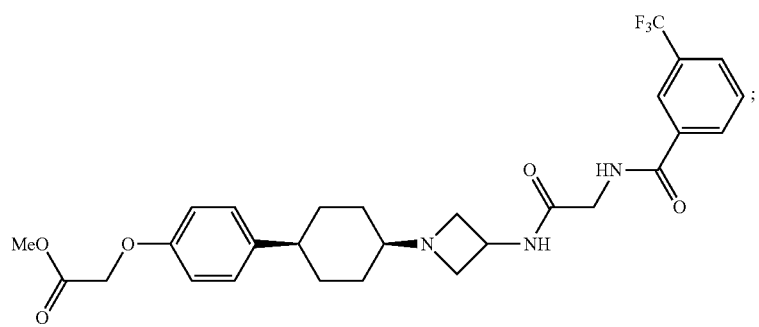
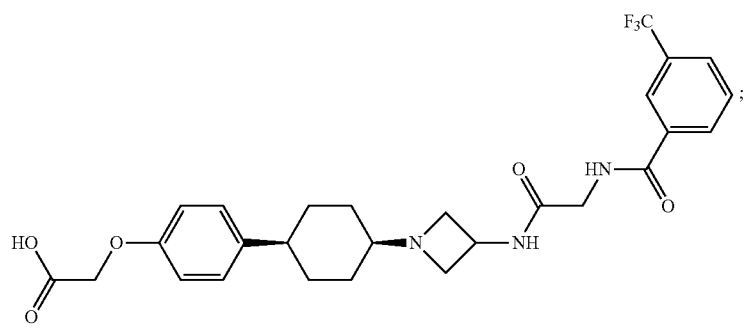
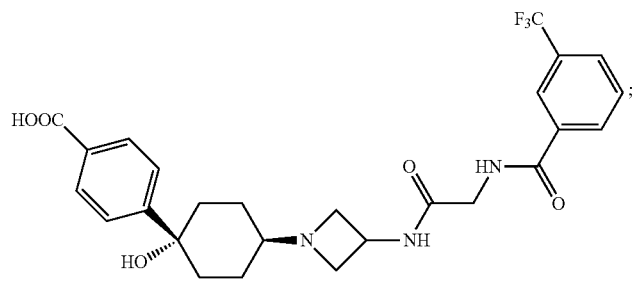

-continued
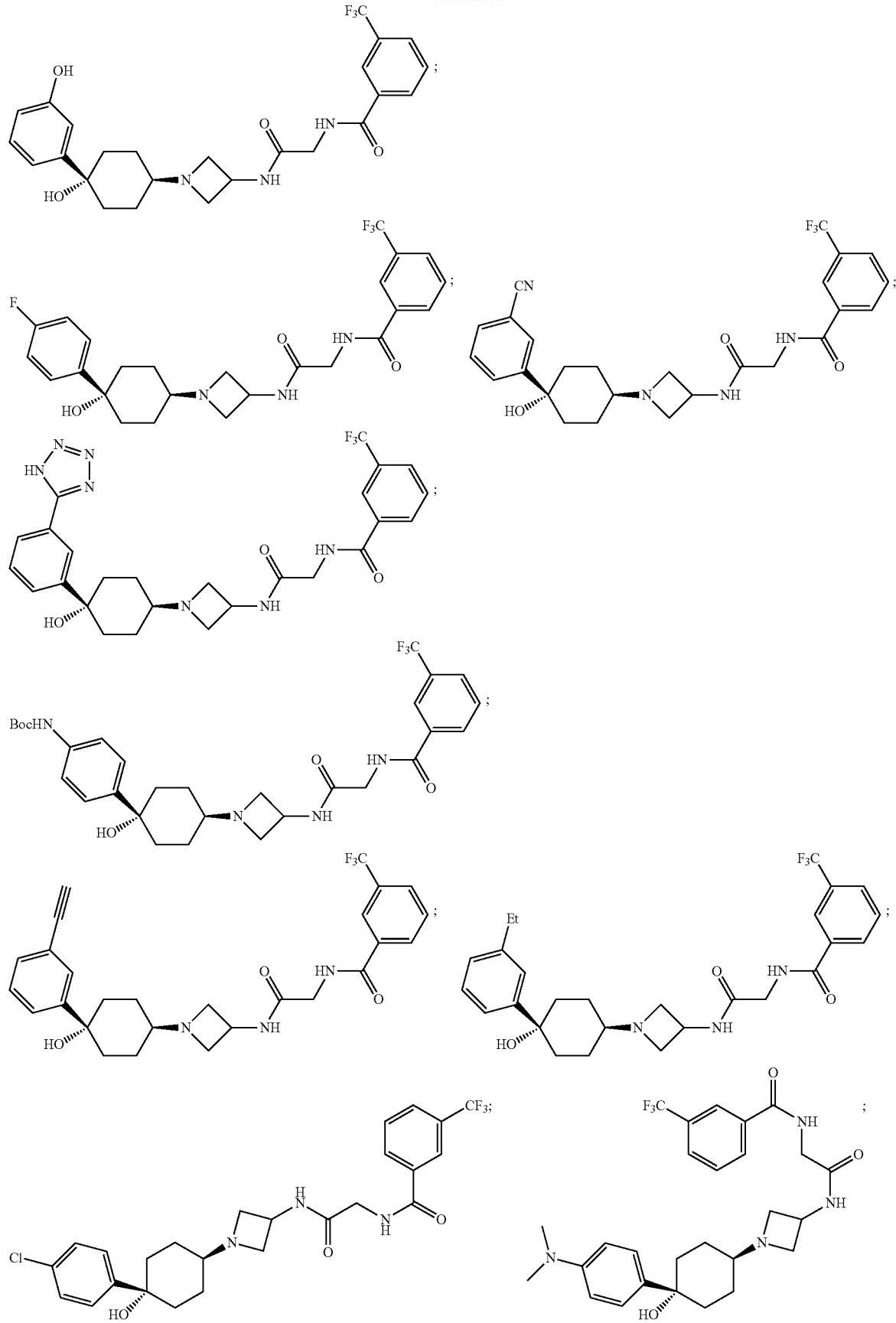

-continued
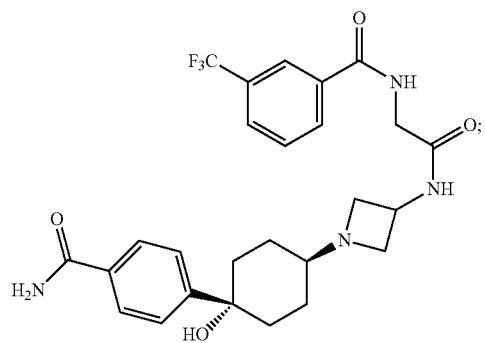
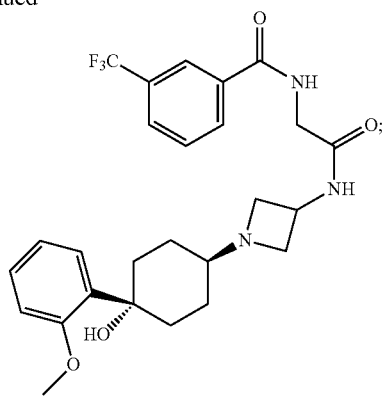
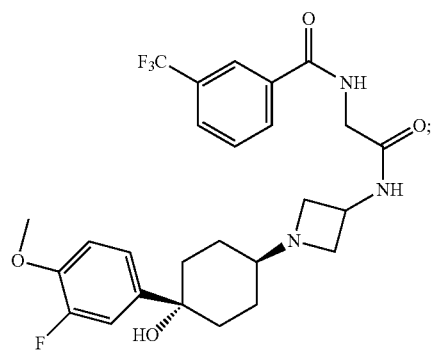
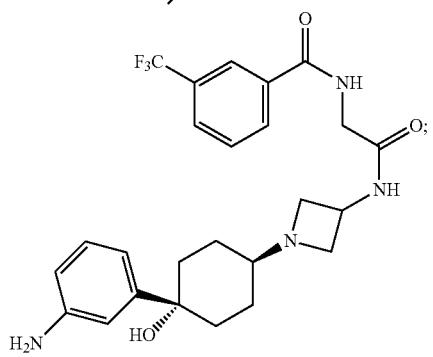
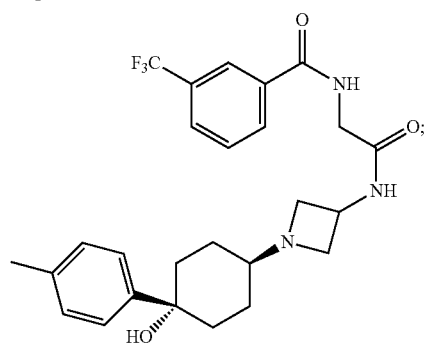
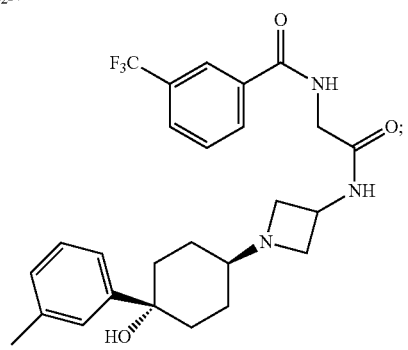
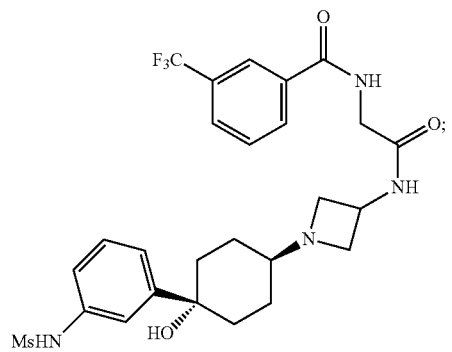
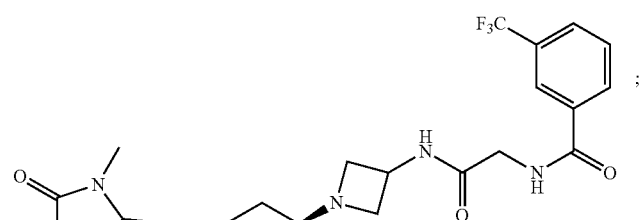
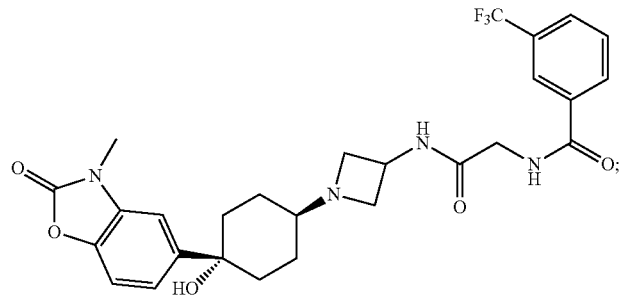

-continued
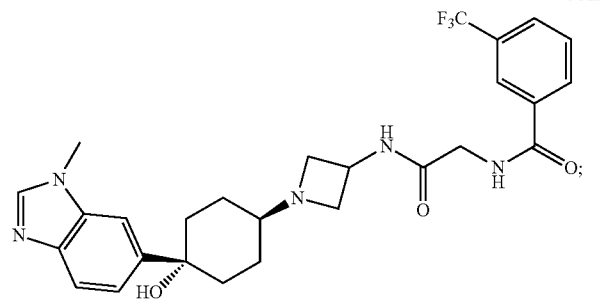
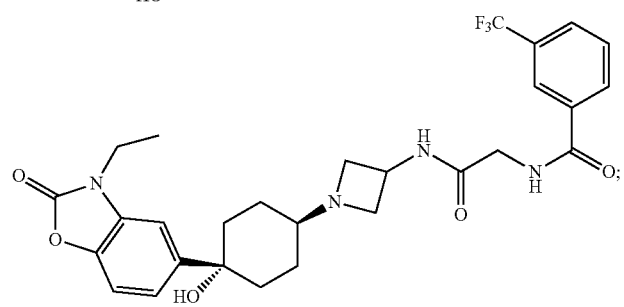
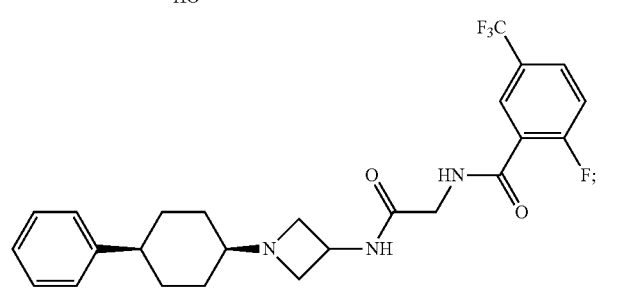
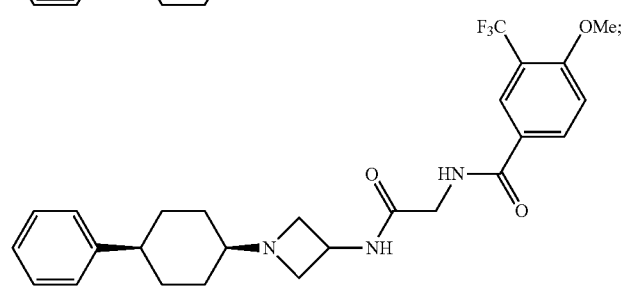
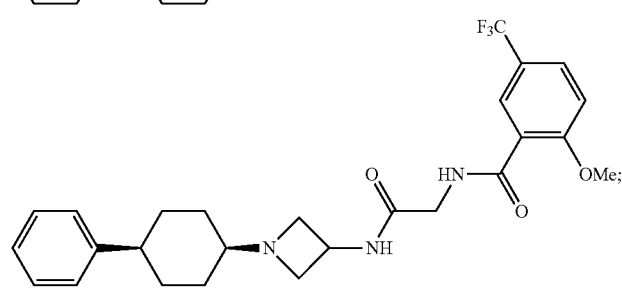
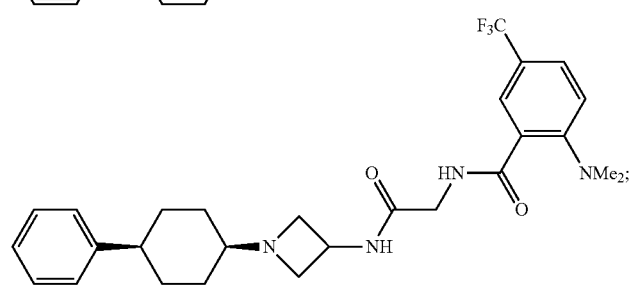

-continued
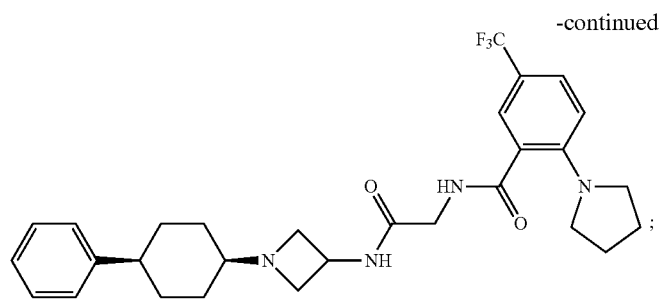
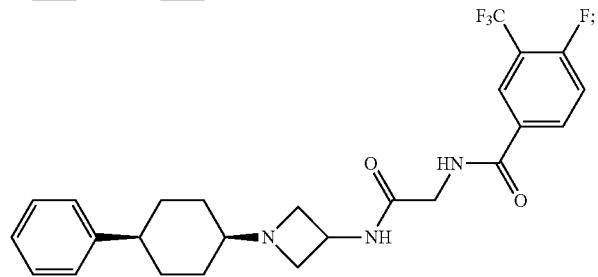
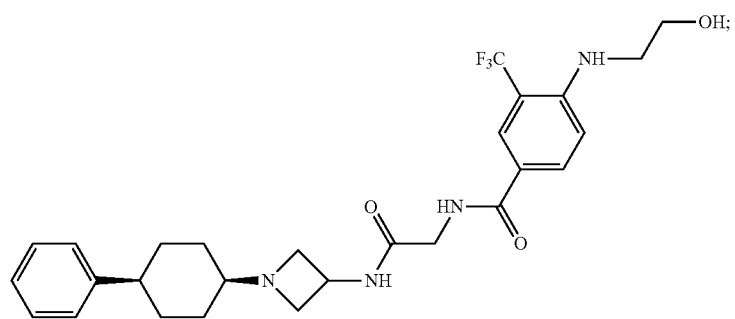
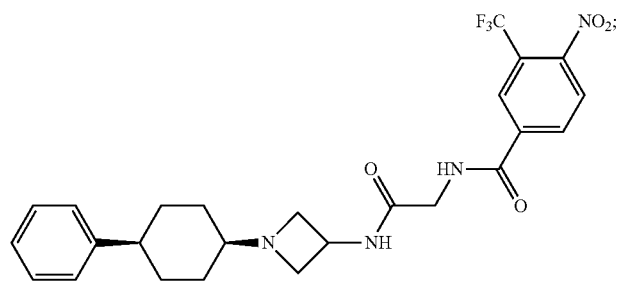
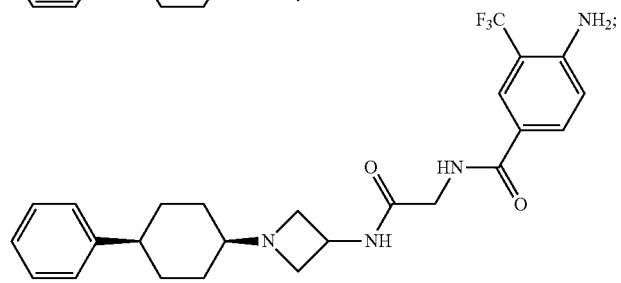
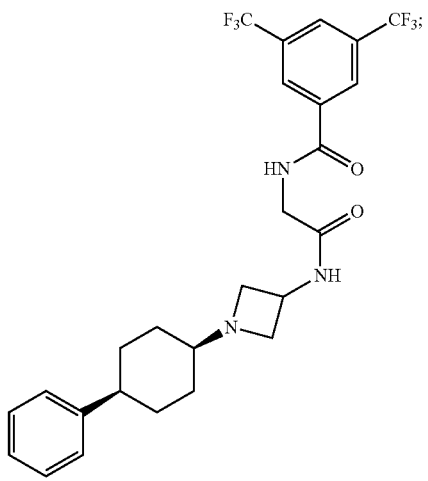

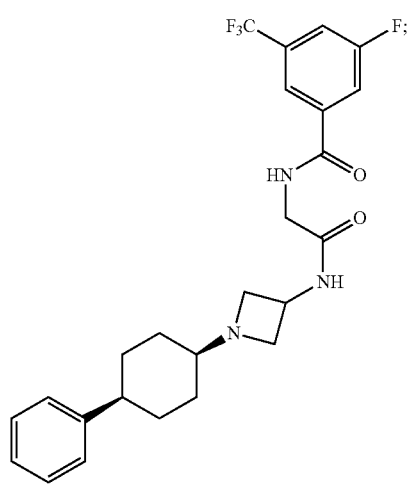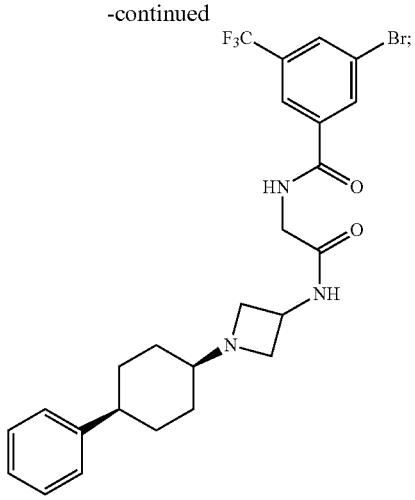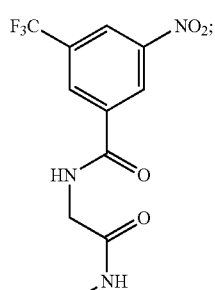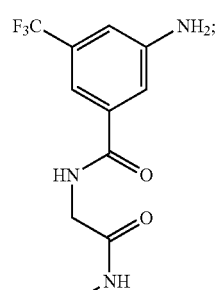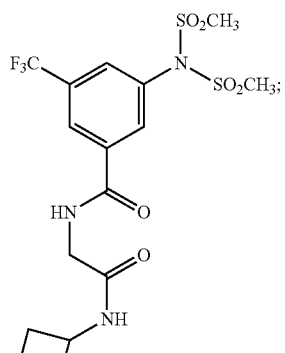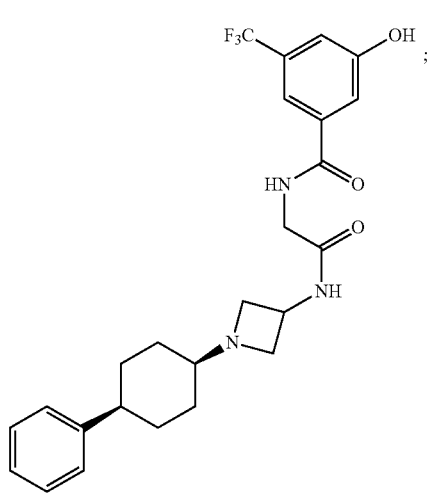

63 64
-continued
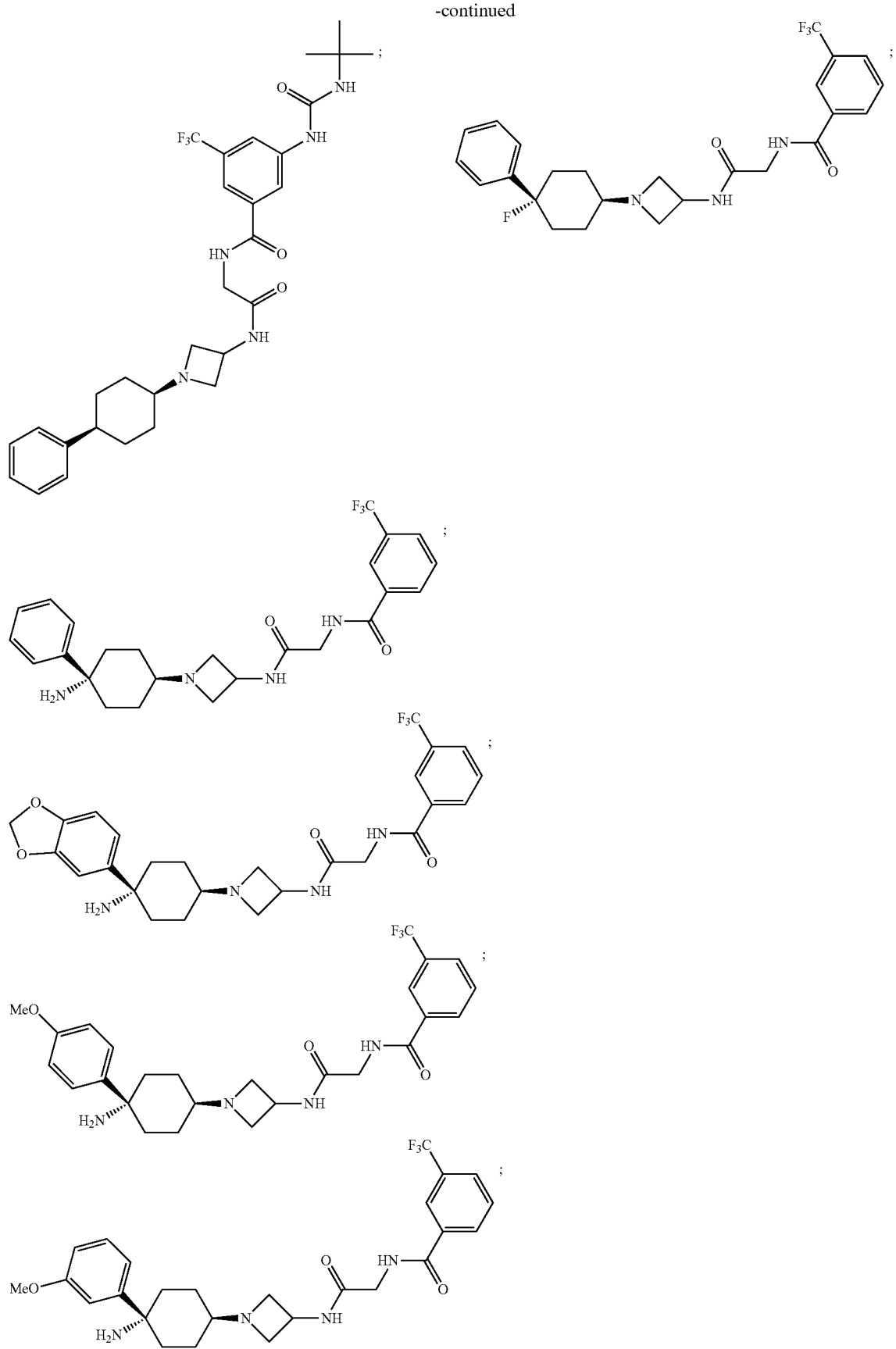

and solvates, hydrates, tautomers, prodrugs, and pharmaceutically acceptable salts thereof.

Another embodiment of the invention is the compound:

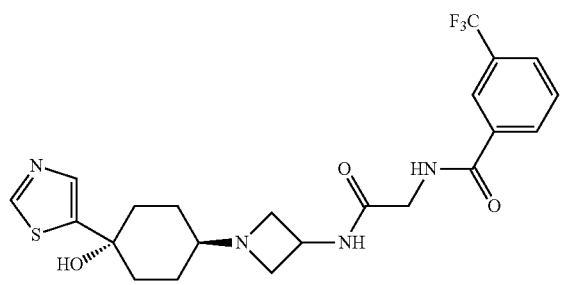 [SMILES: O=C(CNC(=O)c1cccc(C(F)(F)F)c1)NC1CN([C@H]2CC[C@@](O)(c3cncs3)CC2)C1]

and solvates, hydrates, tautomers, prodrugs, and pharmaceutically acceptable salts thereof.

Another embodiment of the invention is a pharmaceutical composition, comprising a compound of Formula (I) and/or (Ia) and a pharmaceutically acceptable carrier.

Another embodiment of the invention is a pharmaceutical composition, comprising a compound listed in the Examples section of this specification and a pharmaceutically acceptable carrier.

The present invention also provides a method for preventing, treating or ameliorating a CCR2 mediated syndrome, disorder or disease comprising administering to a subject in need thereof a therapeutically effective amount of a compound of Formula (I) and/or (Ia) or a form, composition or medicament thereof. In one embodiment of the present invention, the CCR2 mediated syndrome, disorder or disease is an inflammatory syndrome, disorder or disease.

The present invention also provides a method for preventing, treating or ameliorating a CCR2 mediated inflammatory syndrome, disorder or disease wherein the syndrome, disorder or disease is associated with elevated MCP-1 expression or MCP-1 overexpression, or is an inflammatory condition that accompanies syndromes, disorders or diseases associated with elevated MCP-1 expression or MCP-1 overexpression comprising administering to a subject in need thereof a therapeutically effective amount of a compound of Formula (I) and/or (Ia) or a form, composition or medicament thereof.

The present invention also provides a method of preventing, treating or ameliorating a syndrome, disorder or disease, wherein said syndrome, disorder or disease is selected from the group consisting of: Chronic Obstructive Pulmonary Disease (COPD), ophthalmic disorders, uveitis, atherosclerosis, rheumatoid arthritis, psoriasis, psoriatic arthritis, atopic dermatitis, multiple sclerosis, Crohn's Disease, ulcerative colitis, nephritis, organ allograft rejection, fibroid lung, renal insufficiency, type II diabetes and diabetic complications, diabetic nephropathy, obesity, weight disorders, diabetic retinopathy, diabetic retinitis, diabetic microangiopathy, tuberculosis, chronic obstructive pulmonary disease, sarcoidosis, invasive staphyloccocia, inflammation after cataract surgery, allergic rhinitis, allergic conjunctivitis, chronic urticaria, asthma, allergic asthma, periodontal diseases, periodonitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, or stomach comprising administering to a subject in need thereof a therapeutically effective amount of a compound of Formula (I) and/or (Ia) or a form, composition or medicament thereof.

In one embodiment, the present invention provides a method of treating or ameliorating a syndrome, disorder or disease, wherein said syndrome, disorder or disease is selected from the group consisting of: ophthalmic disorders, rheumatoid arthritis, psoriasis, psoriatic arthritis, atopic dermatitis, chronic obstructive pulmonary disease, allergic rhinitis, asthma, allergic asthma, and periodontal diseases comprising administering to a subject in need thereof a therapeutically effective amount of a compound of Formula (I) and/or (Ia) or a form, composition or medicament thereof.

The invention also relates to methods of inhibiting CCR2 activity in a mammal by administration of an effective amount of at least one compound of Formula (I) and/or (Ia).

In another embodiment, the invention relates to a product made by the process of any of Examples from Example 1 to Example 87.

In another embodiment, the invention relates to a compound which is the less polar isomer of any of Examples #1-87.

In another embodiment, the invention relates to a compound which is the less polar isomer of Example #30.

In another embodiment, the invention relates to a process for the preparation of a compound of Formula (I), comprising reacting a compound of Formula (V)

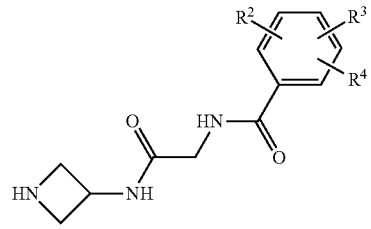

with a compound of Formula (VI)

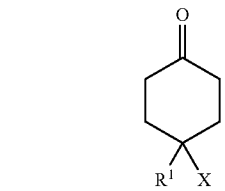

in the presence of a reducing agent to provide the compound of Formula (I).

In another embodiment, the invention relates to a product made by the above process.

In another embodiment, the invention relates to a process for the preparation of a compound of Formula (I), comprising reacting a compound of Formula (XIII)

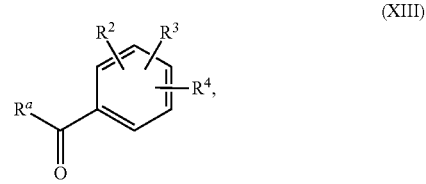

where $R_a$ is OH or Cl, with a compound of Formula (XII)

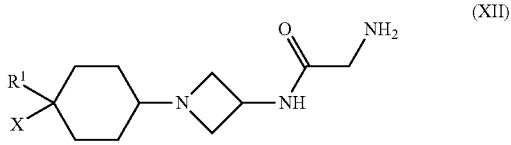

(XII)

in the presence of HOBt/EDCI or $Et_3N$ to provide the compound of Formula (I).

In another embodiment, the invention relates to a product made by the above process.

In another embodiment, the invention relates to the use of hCCR2 knock-in mice to identify antagonists of CCR2 for use in the treatment of asthma.

In another embodiment, the invention relates to the use of hCCR2 knock-in mice to identify antagonists of CCR2 for use in the treatment of obesity.

In another embodiment, the invention relates to the use of hCCR2 knock-in mice to identify antagonists of CCR2 as described in Example 93.

In another embodiment, the invention relates to the use of hCCR2 knock-in mice to identify antagonists of CCR2 as described in Example 94.

In another embodiment, the invention relates to the use of hCCR2 knock-in mice to identify antagonists of CCR2 as described in Example 95.

DEFINITIONS

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl.

The term "$C_{(a-b)}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{(1-4)}$denotes a radical containing 1, 2, 3 or 4 carbon atoms.

The term "cycloalkyl" refers to a saturated or partially unsaturated monocyclic or bicyclic hydrocarbon ring radical derived by the removal of one hydrogen atom from a single ring carbon atom. Typical cycloalkyl radicals include cyclopropyl, cyclobutyl, cyclopentyl, cyclopentenyl, cyclohexyl, cyclohexenyl, cycloheptyl and cyclooctyl. Additional examples include $C_{(3-8)}$cycloalkyl, $C_{(5-8)}$cycloalkyl, $C_{(3-12)}$cycloalkyl, $C_{(3-20)}$cycloalkyl, decahydronaphthalenyl, and 2,3,4,5,6,7-hexahydro-1H-indenyl.

The term "oxo" refers to the functional group

The term "heterocyclyl" refers to a saturated or partially unsaturated monocyclic cycloalkyl ring radical wherein from 1 to 3 ring carbon atoms have been replaced with heteroatoms selected from N, O, or S. Said heteroatoms may exist in any allowed oxidation state. The radical may be derived from the removal of a hydrogen atom from a carbon or a nitrogen atom. Typical heterocyclyl radicals include, but are not limited to, 2H-pyrrolyl, 2-pyrrolinyl, 3-pyrrolinyl, pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolyl, piperidinyl, 1,4-dioxanyl, morpholinyl, 1,4-dithianyl, thiomorpholinyl, piperazinyl, azepanyl, hexahydro-1,4-diazepinyl and the like.

The term "heteroaromatic" or "heteroaryl" refers to 5- to 7-membered mono- or 8- to 10-membered bicyclic aromatic ring systems, containing from one to four heteroatoms selected from N, O, or S where the nitrogen and sulfur atoms can exist in any allowed oxidation state. Examples include, but are not limited to, benzimidazolyl, benzothiazolyl, benzothienyl, benzoxazolyl, furyl, imidazolyl, isothiazolyl, isoxazolyl, oxazolyl, pyrazinyl, pyrazolyl, pyridyl, pyrimidinyl, pyrrolyl, quinolinyl, thiazolyl and thienyl.

The term "heteroatom" refers to a nitrogen atom, an oxygen atom or a sulfur atom wherein the nitrogen and sulfur atoms can exist in any allowed oxidation states.

For use in medicines, the salts of the compounds of this invention refer to non-toxic "pharmaceutically acceptable salts." FDA approved pharmaceutically acceptable salt forms (Ref. International J. Pharm. 1986, 33, 201-217; J. Pharm. Sci., 1977, January, 66(1), p 1) include pharmaceutically acceptable acidic/anionic or basic/cationic salts.

Throughout this specification, compounds are described as being separated, usually by silica gel column, although preparatory thin layer chromatography, or high or low pressure liquid chromatography may also be used. It is generally accepted that when eluting compounds through a silica gel-type separation medium, that the least polar compounds elute before the more polar compounds. Therefore, the term "less polar isomer", refers to the isomer that will elute first from a silica gel type separation medium.

ABBREVIATIONS

Herein and throughout this application, the following abbreviations may be used.

BOC or Boc tert-butyloxycarbonyl
Bu butyl
DAST diethylaminosulfur trifluoride
DBU 1,8-diazabicyclo[5.4.0]undec-7-ene
DCC dicyclohexylcarbodiimide
DCM dicholomethane
DMF dimethylformamide
EDCI 1-ethyl-3-(3'-dimethylaminopropyl)carbodiimide
Et ethyl
EtOAc ethyl acetate
HOBt hydroxybenzotriazole
IPA isopropyl alcohol
Me methyl
Ms mesylate
OAc acetate
OXONE registered trademark of Dupont, the active ingredient of which is potassium monopersulfate ($KHSO_5$)
$PdCl_2$(dppf) [1,1'-bis(diphenylphosphino)ferrocene]dichloropalladium(II)
$PPh_3$ triphenylphosphine
iPr isopropyl
PyBrop bromo-tris-pyrrolidinophosphonium hexafluorophosphate
TBAF tetrabutylammonium fluoride
TEA triethylamine
TFA trifluoroacetic acid
THF tetrahydrofuran Ts tosylate Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, sodium, sodium carbonate, sodium-2-ethylhexanoate (SEH), sodium hydroxide, triethanolamine or zinc.

Methods of Use

The present invention is directed to a method for preventing, treating or ameliorating a CCR2 mediated syndrome, disorder or disease comprising administering to a subject in need thereof an effective amount of a compound of Formula (I) and/or (Ia) or a form, composition or medicament thereof.

Examples of a CCR2 mediated syndrome, disorder or disease for which the compounds of Formula (I) and/or (Ia) are useful include chronic obstructive pulmonary disorder (COPD), ophthalmic disorders, uveitis, atherosclerosis, rheumatoid arthritis, psoriasis, psoriatic arthritis, atopic dermatitis, multiple sclerosis, Crohn's Disease, ulcerative colitis, nephritis, organ allograft rejection, fibroid lung, renal insufficiency, type-I diabetes, type II diabetes and diabetic complications, diabetic nephropathy, diabetic retinopathy, diabetic retinitis, diabetic microangiopathy, overweight, obesity, obesity-associated insulin resistance, tuberculosis, chronic obstructive pulmonary disease, sarcoidosis, invasive staphyloccocia, inflammation after cataract surgery, allergic rhinitis, allergic conjunctivitis, chronic urticaria, asthma, allergic asthma, periodontal diseases, periodonitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, or stomach.

The term "administering" with respect to the methods of the invention, means a method for therapeutically or prophylactically preventing, treating or ameliorating a syndrome, disorder or disease as described herein by using a compound of Formula (I) and/or (Ia) or a form, composition or medicament thereof. Such methods include administering an effective amount of said compound, compound form, composition or medicament at different times during the course of a therapy or concurrently in a combination form. The methods of the invention are to be understood as embracing all known therapeutic treatment regimens.

The term "subject" refers to a patient, which may be animal, typically a mammal, typically a human, which has been the object of treatment, observation or experiment. In one aspect of the invention, the subject is at risk of (or susceptible to) developing a syndrome, disorder or disease that is associated with elevated MCP-1 expression or MCP-1 overexpression, or a patient with an inflammatory condition that accompanies syndromes, disorders or diseases associated with elevated MCP-1 expression or MCP-1 overexpression.

The term "therapeutically effective amount" means that amount of active compound or pharmaceutical agent that elicits the biological or medicinal response in a tissue system, animal or human, that is being sought by a researcher, veterinarian, medical doctor, or other clinician, which includes preventing, treating or ameliorating the symptoms of a syndrome, disorder or disease being treated.

The term "uveitis" generically refers to any inflammatory disease involving the eye. Uveitis can be divided into clinically distinct subtypes based on the part of the eye in which the inflammation is present (percentages correspond to patients known to fit these categories): anterior (51%), intermediate (13%), posterior (20%), or panuveitis (16%) and, according to the course of the disease, as either acute (16%), recurring (26%), or chronic (58%). Those with anterior uveitis (•19%) eventually develop irreparable vision damage despite aggressive treatment such as unilateral blindness (9%), bilateral blindness (2%), or unilateral or bilateral vision impairment (8%). Most cases of uveitis are idiopathic, but known causes include infection (e.g., toxoplasmosis, cytomegalovirus, and the like) or development as a component of a systemic inflammatory and/or autoimmune disorder (e.g., juvenile RA, HLA-B27 associated spondyloarthropathies, sarcoidosis, and the like). (HLA-B27: Human Leukocyte Antigen B*27—is a class I surface antigen encoded by the B locus in the major histocompatibility complex (MHC) on chromosome 6 and presents microbial antigens to T cells. HLA-B27 is strongly associated with a certain set of autoimmune diseases referred to as the seronegative spondyloarthropathies.)

When employed as CCR2 inhibitors, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula (I) and/or (Ia) may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula (I) and/or (Ia) include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention. As used herein, the term "composition" is intended to encompass a product comprising the specified ingredients in the specified amounts, as well as any product which results, directly or indirectly, from combinations of the specified ingredients in the specified amounts.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope polymorphs and solvates of the compounds of the present invention. Thus, in the methods of treatment of the present invention, the term "administering" shall encompass the means for treating, ameliorating or preventing a syndrome, disorder or disease described herein with the compounds of the present invention or a polymorph or solvate thereof, which would obviously be included within the scope of the invention albeit not specifically disclosed.

In another embodiment, the invention relates to a compound as described in the Examples or Formula (I) and/or Formula (Ia) for use as a medicament, in particular, for use as a medicament for treating a CCR2 mediated syndrome disorder or disease.

In another embodiment, the invention relates to the use of a compound as described in the Examples of Formula (I) and/or Formula (Ia) for the preparation of a medicament for the treatment of a disease associated with an elevated or inappropriate CCR2 activity.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", Ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

General Reaction Scheme

Representative compounds of the present invention can be synthesized in accordance with the general synthetic methods described below. Compounds of Formula (I) can be prepared by methods known to those who are skilled in the art. The following reaction schemes are only meant to represent examples of the invention and are in no way meant to be a limit of the invention.

Compounds of Formula (I) may be prepared according to the processes outlined in Scheme 1.

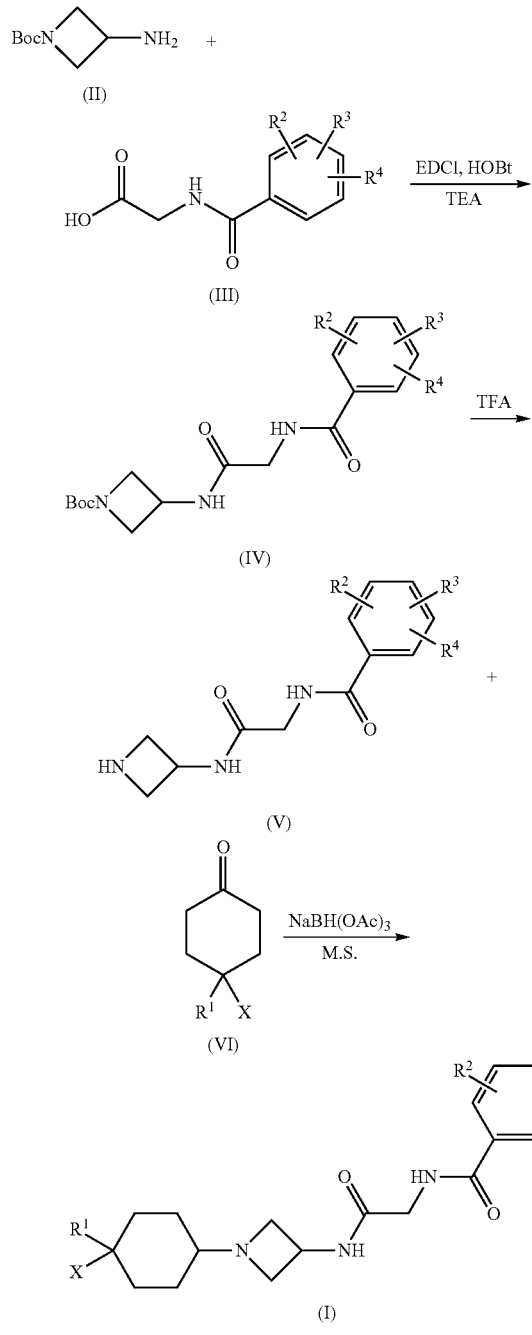

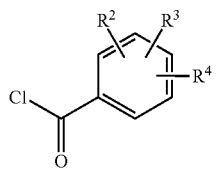

for benzoyl chloride, in the presence of a coupling reagent such as EDCI/HOBt, PyBrop, or DCC, in an organic solvent such as THF, dichloromethane or 1,2-dichloroethane, at a temperature in the range of about 0° C. to about 25° C., to yield the corresponding amide (IV).

Amide (IV) is treated with an acid such as 1N HCl, 1N $H_2SO_4$ or trifluoroacetic acid in an organic solvent such as diethyl ether, THF, dichloromethane or dioxane, at a temperature in the range of about 0° C. to about 25° C. to yield amine (V).

Amine (V) is reacted with a suitably substituted ketone (VI), in the presence of a reducing reagent such as $NaBH_4$, $NaBH(CN)_3$ or $NaBH(OAc)_3$, in an organic base such as triethylamine, diethylpropylamine or N-methylmorpholine with or without molecule sieves, in an organic solvent such as dichloromethane, 1,2-dichloroethane or THF, at a temperature in the range of 0° C. to about 25° C., to yield the corresponding azetidine (I).

Alternatively, compounds of Formula (I) may be prepared according to the processes outlined in Scheme 2.

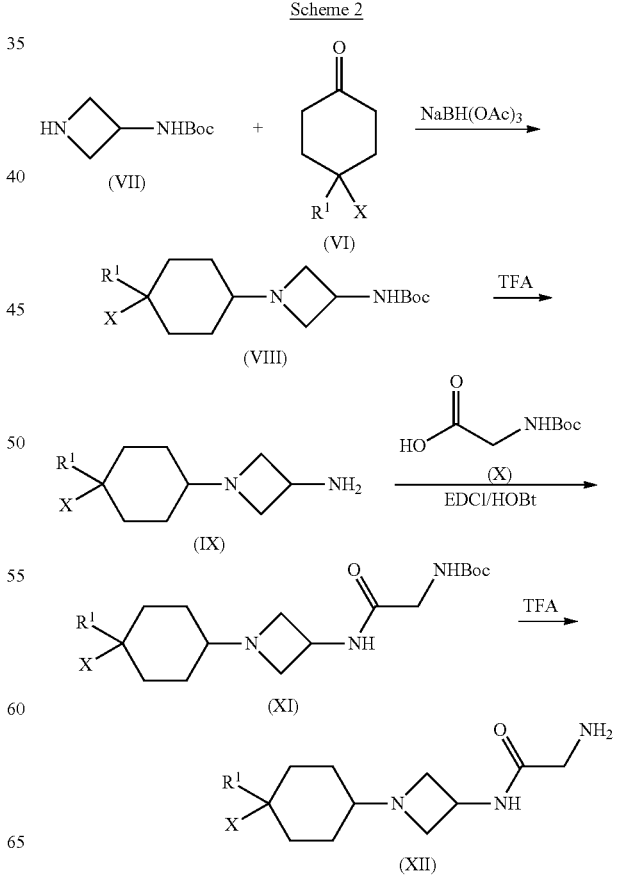

Scheme 1 illustrates a synthetic route leading to compounds of Formula (I). Commercially available azetidine (II) is reacted with acid (III), wherein (III) is prepared according to the procedure described by Ingersoll, A. W. et. al., Organic Syntheses 1932, XII, 40-2 substituting commercially available -continued

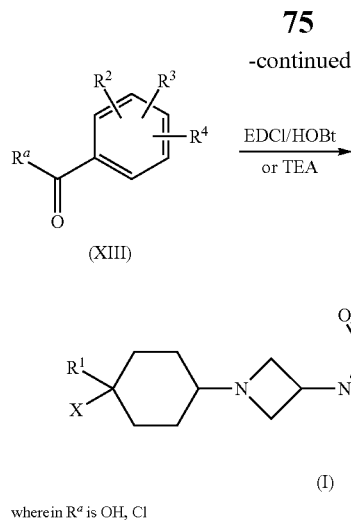

wherein $R^a$ is OH, Cl

Commercially available azetidine (VII) is reacted with a suitably substituted ketone (VI), in the presence of a reducing reagent such as $NaBH_4$, $NaBH(CN)_3$ or $NaBH(OAc)_3$, in an organic base such as triethylamine, diethylpropylamine or N-methylmorpholine, with or without molecule sieves, in an organic solvent such as dichloromethane, 1,2-dichloroethane or THF at a temperature in the range of 0° C. to about 25° C., to yield the corresponding azetidine (VIII).

Azetidine (VIII) is treated with 1N HCl, 1N $H_2SO_4$ or trifluoroacetic acid in an organic solvent such as diethyl ether, THF, dioxane or dichloromethane, at a temperature in the range of about 0° C. to about 25° C., to yield the corresponding amine (IX).

Amine (IX) is reacted with acid (X), in the presence of a coupling reagent such as EDCI/HOBt, PyBrop or DCC, in an organic solvent such as THF, dichloromethane or 1,2-dichloroethane, at a temperature in the range of about 0° C. to about 25° C., to yield the corresponding azetidine (XI).

Azetidine (XI) is treated with 1N HCl or $H_2SO_4$ or trifluoroacetic acid, in an organic solvent such as diethyl ether, THF or dioxane, at a temperature in the range of about 0° C. to about 25° C., to yield the corresponding amine (XII).

Amine (XII) is reacted with acid (XIII). When $R^a$ is OH, the reaction is performed in the presence of a coupling reagent such as EDCI/HOBt, PyBrop or DCC, in an organic solvent such as THF, dichloromethane or 1,2-dichloroethane, at a temperature in the range of about 0° C. to about 25° C. When $R^a$ is Cl, the reaction is performed in the presence of an organic base such triethylamine, diethylpropylamine or N-methylmorpholine, in an organic solvent such as THF, dichloromethane or 1,2-dichloroethane, at a temperature in the range of about 0° C. to about 25° C., to yield the corresponding azetidine (I).

Compounds of Formula (I) may be derived from ketone (VI). Preparation of (VI) is outlined in Scheme 3.

Scheme 3

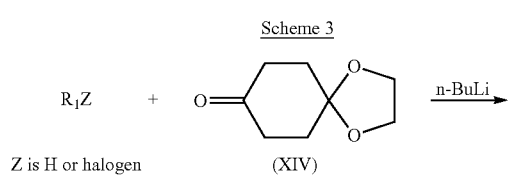

Z is H or halogen   (XIV)

-continued

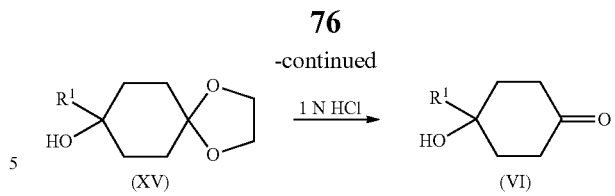

Commercially available aryl halide or aryl alkane $R^1Z$ (where $R^1$ is as defined in Formula (I)) is reacted with commercially available ketone (XIV) in the presence of organometallic agent such as n-BuLi, i-PrMgBr or i-PrMgCl, in an organic solvent such as ether, THF or dioxane, at a temperature in the range of about −78° C. to about 0° C., to yield the corresponding ketal (XV).

Ketal (XV) is treated with an acid such as 1N HCl or 1N $H_2SO_4$ in an organic solvent such as acetone, acetonitrile or THF, at a temperature in the range of about 0° C. to about 25° C., to yield the corresponding ketone (VI).

Compounds of Formula (I) may be derived from ketone (XIX). Preparation of (XIX) is outlined in Scheme 4.

Scheme 4

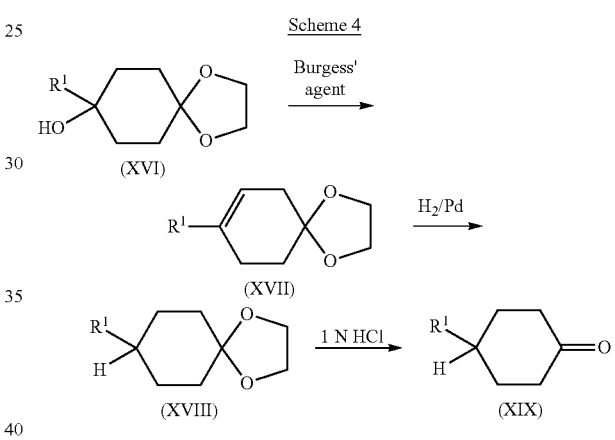

Ketal (XVI) is treated with a dehydrating agent such as Burgess' reagent, in an organic solvent such as ether, THF or dioxane, at a temperature in the range of about 0° C. to about 25° C., to yield the corresponding alkene (XVII).

Alkene (XVII) is treated with hydrogen gas under pressure from 5 to 50 psi catalyzed by 5-10% Pd/C, in an organic solvent such as methanol, at a temperature in the range of about 25° C. to about 50° C., to yield the corresponding alkane (XVIII).

Alkane (XVIII) is treated with 1N HCl or 1N $H_2SO_4$, in an organic solvent such as acetone, acetonitrile or THF, at a temperature in the range of about 0° C. to about 25° C., to yield the corresponding ketone (XIX).

Alternatively compound (XVII) may be prepared according to the processes outlined in Scheme 5.

Scheme 5

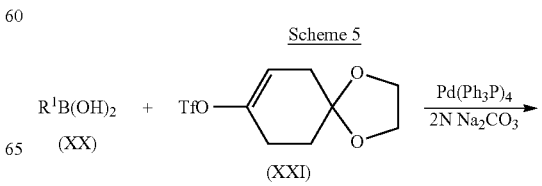

-continued

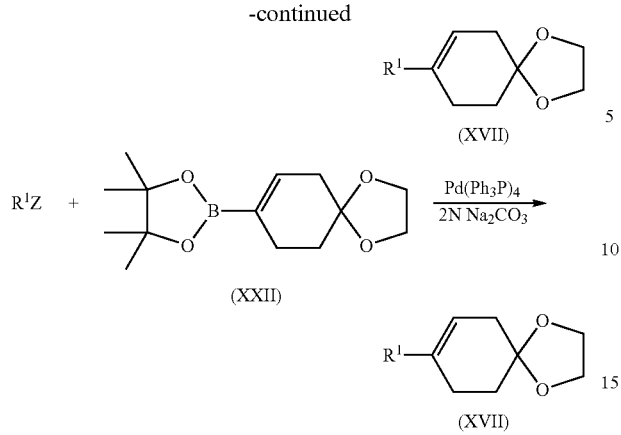

Z is halogen

Commercially available aryl boronic acid (XX), (wherein R[1] is as defined in Formula (I)) is reacted with vinyl triflate (XXI) prepared according to the procedure of Pearson, W. et. al., *J. Org. Chem.* 2004, 69, 9109-9122, in the presence of a catalyst such as $Pd(Ph_3P)_4$, $PdCl_2(Ph_3P)_2$ or $PdCl_2(dppf)$ and a base such as $2N\ Na_2CO_3$ or $K_2CO_3$, in an organic solvent such as toluene, dioxane or THF, at a temperature in the range of about 80° C. to about 120° C., to yield the corresponding alkene (XVII).

Alternatively, commercially available aryl or heteroaryl halide R[1]Z is reacted with vinyl boronic ester (XXII) prepared according to Birch, A. M. et. al., PCT Int. Appl. 2006, WO 2006064189, in the presence of a catalyst such as $Pd(Ph_3P)_4$, $PdCl_2(Ph_3P)_2$ or $PdCl_2$ (dppf) and a base such as $2N\ Na_2CO_3$ or $K_2CO_3$, in an organic solvent such as toluene, dioxane or THF, at a temperature in the range of about 80° C. to about 120° C., to yield the corresponding alkene (XVII).

Compounds of Formula (I) may be derived from ketone (XXIII). Ketone (XXIII) may be prepared according to the processes outlined in Scheme 6.

Scheme 6

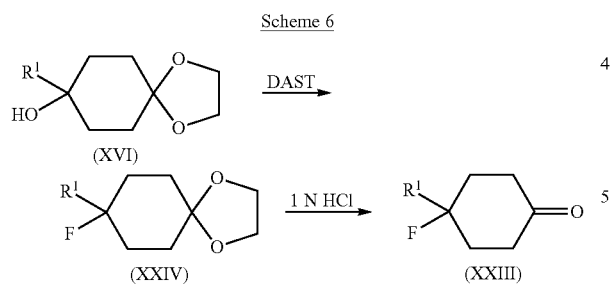

Ketal (XVI) is treated with a fluorinating agent such as DAST or trifluorosulfonyl fluoride, in an organic solvent such as dichloromethane, THF or dioxane, at a temperature in the range of about –78° C. to about 0° C., to yield the corresponding fluoride (XXIV). Fluoride (XXIV) is treated with an acid such as 1N HCl or $1N\ H_2SO_4$, in an organic solvent such as acetone, acetonitrile or THF, at a temperature in the range of about 0° C. to about 25° C., to yield the corresponding ketone (XXIII).

Compounds of Formula (I) may be derived from ketone (XXV). Ketone (XXV) may be prepared according to the processes outlined in Scheme 7.

Scheme 7

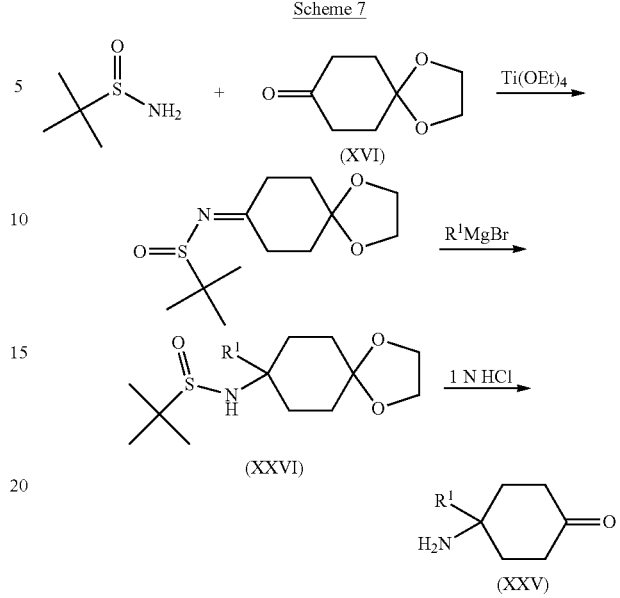

Commercially available 2-methyl-propane-2-sulfinic acid amide is reacted with commercially available 1,4-dioxa-spiro [4.5]decan-8-one in the presence of a coupling agent such as $Ti(OEt)_4$ or $CuSO_4$, in an organic solvent such as dichloromethane, THF or dioxane, at a temperature in the range of about 25° C. to about 80° C., to yield 2-methyl-propane-2-sulfinic acid (1,4-dioxa-spiro[4.5]dec-8-ylidene)-amide.

2-Methyl-propane-2-sulfinic acid (1,4-dioxa-spiro[4.5] dec-8-ylidene)-amide is treated with an organometallic agent such as R[1]MgBr or R[1]Li, in an organic solvent such as ether, THF or dioxane, at a temperature in the range of about –78° C. to about 25° C., to yield the corresponding sulfonamide (XXVI).

Sulfinamide (XXVI) is treated with an acid such as 1N HCl or $1N\ H_2SO_4$ in an organic solvent such as acetone, acetonitrile or THF, at a temperature in the range of about 0° C. to about 25° C., to yield the corresponding ketone (XXV).

Compounds of Formula (I) where R[1] is linked with the cyclohexyl ring through N or O may be prepared according to the process outlined in Scheme 8.

Scheme 8

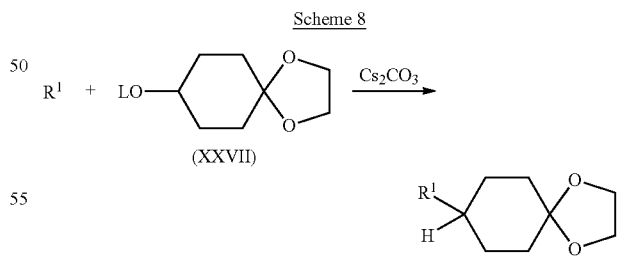

L is Ms, Ts

Commercially available OH or NH substituted R[1] is reacted with alkyl tosylate or alkyl mesylate (XXVII) in the presence of inorganic base such as $K_2CO_3$, $Cs_2CO_3$ or NaH, in an organic solvent such as DMF or THF, at a temperature in the range of about 25° C. to about 80° C., to yield the corresponding ketal (XVIII).

EXAMPLES

Representative compounds of the present invention can be synthesized in accordance with the general synthetic methods described herein. Compounds of Formula (I) can be prepared by methods known to those who are skilled in the art. The following examples are only meant to represent examples of the invention and are in no way meant to be a limit of the invention.

Example 1

N-{[1-(4-Benzo[1,3]dioxol-5-yl-cyclohexyl)-azetidin-3-ylcarbamoyl]-methyl}-3-trifluoromethyl-benzamide

Step A

8-Benzo[1,3]dioxol-5-yl-1,4-dioxa-spiro[4.5]decan-8-ol

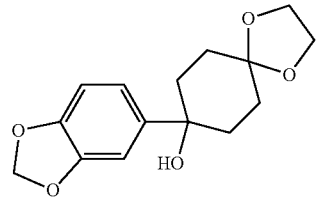 [SMILES: OC1(c2ccc3c(c2)OCO3)CCC2(CC1)OCCO2]

A solution of n-BuLi (2.5 M in hexanes, 24 mL, 60 mmol) was dropped slowly into a solution of 5-bromo-benzo[1,3]dioxole (Aldrich, 10.0 g, 50 mmol) in THF (100 mL) at −78° C. over 10 min. The reaction was stirred for additional 20 min. at −78° C. A solution of 1,4-dioxa-spiro[4.5]decan-8-one (Aldrich, 8.60 g, 55 mmol) in THF (20 mL) was slowly dropped into the reaction. After addition, the reaction was stirred for additional 2 hours at −78° C. The reaction was then quenched with diluted NH$_4$Cl solution and warmed to room temperature. The solvent was removed in vacuo and the residue was partitioned between ethyl acetate and water. The organic layer was washed with brine, dried over anhydrous Na$_2$SO$_4$, filtered and concentrated to give a yellow solid, which was then purified by silica gel column on a CombiFlash® system (Teledyne Isco, Inc, Lincoln, Nebr.) using hexanes and ethyl acetate (from 10% ethyl acetate to 100% ethyl acetate) to afford the title compound as a white solid.

$^1$H-NMR (CDCl$_3$): δ 7.03 (s, 1H), 6.96 (d, J=6.5 Hz, 1H), 6.74 (d, J=6.4 Hz, 1H), 5.91 (s, 2H), 3.96 (s, 4H), 2.17 (m, 1H), 2.10 (m, 2H), 1.99 (m, 2H), 1.86 (m, 2H), 1.64 (m, 2H).

Step B

4-Benzo[1,3]-dioxol-5-yl-4-hydroxy-cyclohexanone

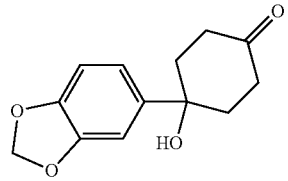 [SMILES: O=C1CCC(O)(c2ccc3c(c2)OCO3)CC1]

A solution of 8-benzo[1,3]dioxol-5-yl-1,4-dioxa-spiro[4.5]decan-8-ol (as prepared in the previous step, 4.50 g, 16.2 mmol) in acetone (40 mL) was treated with 1N HCl (~15 mL) at room temperature for 4 hours. The reaction was neutralized with saturated NaHCO$_3$ solution and the solvent was removed. The residue was partitioned between ethyl acetate and water. The organic layer was washed with brine, dried over anhydrous Na$_2$SO$_4$, filtered and concentrated to give a yellow solid, which was then purified by silica gel column on a CombiFlash® system using hexanes and ethyl acetate (from 10% ethyl acetate to 100% ethyl acetate) to afford the title compound as a white solid.

$^1$H NMR (400 MHz, CDCl$_3$) δ 7.10 (s, 1H), 6.95 (d, J=6.0 Hz, 1H), 6.75 (d, J=6.4 Hz, 1H), 5.98 (s, 2H), 2.86 (m, 2H), 2.42 (m, 2H), 2.26 (m, 4H).

Step C

4-Benzo[1,3]-dioxol-5-yl-cyclohex-3-enone

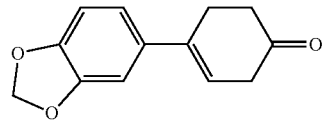

A solution of 4-benzo[1,3]dioxol-5-yl-4-hydroxy-cyclohexanone (as prepared in the previous step, 3.5 g, 15 mmol) in THF (10 mL) was treated with 6N HCl (5 mL) overnight under argon at room temperature. The resulting solution was quenched with sufficient 1N NaOH to neutralize the reaction. The solvent was removed and the residue was partitioned between DCM and water. The organic layer was washed with brine, dried over anhydrous Na$_2$SO$_4$, filtered and concentrated to give a yellow oil, which was then purified by silica gel column on a CombiFlash® system using hexanes and ethyl acetate (from 10% ethyl acetate to 100% ethyl acetate) to afford the title compound as a white solid.

$^1$H NMR (400 MHz, CDCl$_3$) δ 7.85 (s, 1H), 7.80 (d, J=7.0 Hz, 1H), 7.75 (d, J=6.8 Hz, 1H), 5.95 (m, 1H), 5.90 (s, 2H), 3.05 (s, 2H), 2.85 (t, J=6.5 Hz, 2H), 2.58 (t, J=6.8 Hz, 2H).

Step D

[1-(4-Benzo[1,3]-dioxol-5-yl-cyclohex-3-enyl)-azetidin-3-yl]-carbamic acid tert-butyl ester

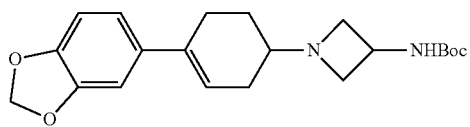 [SMILES: CC(C)(C)OC(=O)NC1CN(C2CC=C(c3ccc4c(c3)OCO4)CC2)C1]

A solution of 4-benzo[1,3]dioxol-5-yl-cyclohex-3-enone (as prepared in the previous step, 680 mg, 3.15 mmol) and azetidin-3-yl-carbamic acid tert-butyl ester (BetaPharma, 542 mg, 3.15 mmol) in DCM (10 mL) was treated with NaBH(OAc)$_3$ (Aldrich, 2.0 g, 9.45 mmol) at room temperature. The reaction was stirred for 4 hours and quenched with saturated sodium bicarbonate. The organic layer was separated and the aqueous layer was extracted 3 times with DCM. The combined organic layers were dried over anhydrous Na$_2$SO$_4$, filtered and concentrated to give the crude product, which was then purified by a CombiFlash® system using hexanes and ethyl acetate as eluent (from pure hexanes to pure ethyl acetate) to afford the title compound as a white solid.

$^1$H NMR (400 MHz, CDCl$_3$) δ 7.85 (s, 1H), 7.82 (d, J=7.0 Hz, 1H), 7.75 (d, J=6.8 Hz, 1H), 5.95 (s, 2H0, 5.90 (s, br, 1H), 4.35 (s, br, 1H), 3.76 (m, 2H), 3.18 (s, br, 2H), 2.45 (m, 1H), 2.35 (m, 4H0, 2.02 (m, 2H), 1.45 (s, 9H).

Step E 1-(4-Benzo[1,3]-dioxol-5-yl-cyclohex-3-enyl)-azetidin-3-ylamine TFA Salt

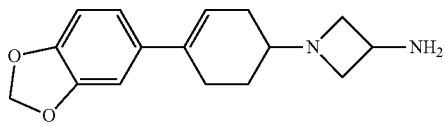 [SMILES: NC1CN(C2CC=C(c3ccc4c(c3)OCO4)CC2)C1]

A solution of [1-(4-Benzo[1,3]dioxol-5-yl-cyclohex-3-enyl)-azetidin-3-yl]-carbamic acid tert-butyl ester (as prepared in the previous step, 750 mg, 2.02 mmol) in DCM (5 mL) and TFA (5 mL) was stirred at room temperature for 2 hours. The solvent was removed under vacuum to give the title compound as colorless oil.

ESI-MS (m/z): Calcd. For $C_{16}H_{20}N_2O_2$, 272; found: 273 (M+H).

Step F

N-{[1-(4-Benzo[1,3]-dioxol-5-yl-cyclohex-3-enyl)-azetidin-3-ylcarbamoyl]-methyl}-3-trifluoromethyl-benzamide

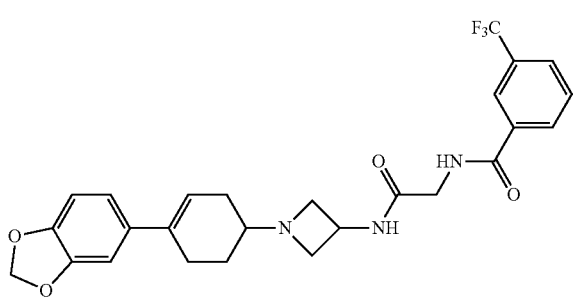 [SMILES: O=C(CNC(=O)c1cccc(C(F)(F)F)c1)NC1CN(C2CC=C(c3ccc4c(c3)OCO4)CC2)C1]

A solution of 1-(4-benzo[1,3]dioxol-5-yl-cyclohex-3-enyl)-azetidin-3-ylamine TFA salt (as prepared in the previous step, 550 mg, 1.10 mmol) and (3-trifluoromethyl-benzoylamino)-acetic acid (Bionet, 272 mg, 1.10 mmol) in DCM (10 mL) was treated with TEA (770 µL, 5.5 mmol) at room temperature. The mixture was treated with EDCI (Aldrich, 252 mg, 1.32 mmol), HOBT (Aldrich 149 mg, 1.10 mmol), and the reaction was stirred at room temperature for additional 6 hours. The reaction was partitioned between DCM and water. The organic layer was washed with brine, dried over anhydrous $Na_2SO_4$, filtered and concentrated to give the crude product, which was then purified by CombiFlash® system using ethyl acetate and 7N $NH_3$ in MeOH as eluent (from pure ethyl acetate to 5% 7N $NH_3$ in MeOH in ethyl acetate) to afford the title compound as a white solid.

$^1$H NMR (400 MHz, CDCl$_3$) δ 7.85 (d, J=6.5 Hz, 2H), 7.55 (t, J=6.5 Hz, 1H), 7.45 (d, J=7.0 Hz, 2H), 6.85 (s, 1H), 6.75 (d, J=6.5 Hz, 1H), 6.72 (d, J=6.6 Hz, 1H), 5.98 (s, 2H), 5.85 (m, 1H), 4.52 (m, 1H), 4.10 (d, J=3.5 Hz, 2H), 3.65 (t, J=7.0 Hz, 2H), 3.08 (t, J=7.0 Hz, 2H), 2.80 (m, 1H), 2.42 (m, 4H), 1.90 (m, 2H).

Step G

N-{[1-(4-Benzo[1,3]-dioxol-5-yl-cyclohexyl)-azetidin-3-ylcarbamoyl]-methyl}-3-trifluoromethyl-benzamide A solution of N-{[1-(4-Benzo[1,3]dioxol-5-yl-cyclohex-3-enyl)-azetidin-3-ylcarbamoyl]-methyl}-3-trifluoromethyl-benzamide (as prepared in the previous step, 250 mg, 0.5 mmol) in MeOH (20 mL) was driven through an H-Cube® Continuous-flow Hydrogenation reactor (ThalesNano, Budapest, Hungary) under full hydrogen mode at room temperature using a 5% Pd/C cartridge. The resulting solution was concentrated and purified by silica gel column on a CombiFlash® system using ethyl acetate and 7N $NH_3$ in MeOH as eluent (from pure ethyl acetate to 5% 7N $NH_3$ in MeOH in ethyl acetate) to afford the two title compounds as white solids.

1a: Less Polar Fraction from Silica Gel Column
$^1$H NMR (400 MHz, CDCl$_3$) δ 8.11 (s, 1H), 8.02 (d, J=6.8 Hz, 1H), 7.85 (m, 1H), 7.74 (d, J=7.0 Hz, 2H), 7.55 (t, J=6.8 Hz, 1H), 7.40 (d, J=7.0 Hz, 1H), 6.72 (d, J=6.5 Hz, 1H), 6.70 (s, 1H), 6.62 (d, J=6.2 Hz, 1H), 5.92 (s, 2H), 4.53 (m, 1H), 4.20 (d, J=3.5 Hz, 2H), 3.60 (t, J=7.0 Hz, 2H), 2.85 (t, J=7.0 Hz, 2H), 2.42 (m, 1H), 2.30 (s, br, 1H), 1.85 (m, 2H), 1.70 (m, 2H), 1.52 (m, 2H), 1.42 (m, 2H).

1b: More Polar Fraction from Silica Gel Column
$^1$H NMR (400 MHz, CDCl$_3$) δ 8.12 (s, 1H), 8.05 (d, J=6.5 Hz, 1H), 7.80 (d, J=6.6 Hz, 1H), 7.58 (t, J=6.8 Hz, 1H), 7.50 (m, 1H), 7.10 (d, J=6.2 Hz, 1H), 6.75 (d, J=6.8 Hz, 1H), 6.60 (s, 1H), 5.90 (s, 2H), 4.52 (m, 1H), 4.20 (d, J=4.6 Hz, 2H), 3.64 (t, J=7.5 Hz, 2H), 2.98 (t, J=7.5 Hz, 2H), 2.35 (m, 1H), 2.02 (m, 2H), 1.85 (m, 2H), 1.35 (m, 2H), 1.15 (m, 2H).

Example 2

N-{[1-(4-Benzo[1,3]dioxol-5-yl-cyclohexyl)-azetidin-3-ylcarbamoyl]-methyl}-benzamide The title compounds were prepared as white solids by an EDCI coupling between 1-(4-benzo[1,3]dioxol-5-yl-cyclohex-3-enyl)-azetidin-3-ylamine (as prepared in Example 1, Step E) and benzoylamino-acetic acid (Hippuric acid, Aldrich) followed by hydrogenation of the corresponding alkene using the procedures described in Steps F and G of Example 1.

2a: Less Polar Fraction from Silica Gel Column $^1$H NMR (400 MHz, CDCl$_3$) δ 7.85 (d, J=6.0 Hz, 2H), 7.51 (t, J=6.8 Hz, 1H), 7.41 (d, J=7.0 Hz, 2H), 7.25 (m, 1H), 7.10 (d, J=7.0 Hz, 1H), 6.72 (d, J=6.5 Hz, 1H), 6.70 (s, 1H), 6.62 (d, J=6.2 Hz, 1H), 5.90 (s, 2H), 4.52 (m, 1H), 4.20 (d, J=3.5 Hz, 2H), 3.60 (t, J=7.0 Hz, 2H), 2.85 (t, J=7.0 Hz, 2H), 2.42 (m, 1H), 2.30 (s, br, 1H), 1.85 (m, 2H), 1.70 (m, 2H), 1.52 (m, 2H), 1.40 (m, 2H).

2b: More Polar Fraction from Silica Gel Column $^1$H NMR (400 MHz, CDCl$_3$) δ 7.85 (d, J=6.5 Hz, 2H), 7.55 (t, J=6.6 Hz, 1H), 7.52 (t, J=6.8 Hz, 2H), 7.30 (m, 2H), 6.72 (d, J=6.8 Hz, 1H), 6.66 (s, 1H), 6.60 (d, J=5.8 Hz, 1H), 4.52 (m, 1H), 4.20 (d, J=4.6 Hz, 2H), 3.65 (t, J=7.5 Hz, 2H), 3.00 (t, J=7.5 Hz, 2H), 2.35 (m, 1H), 2.02 (m, 2H), 1.85 (m, 2H), 1.35 (m, 2H), 1.15 (m, 2H).

Example 3

N-({1-[4-(2,3-Dihydro-benzofuran-6-yl)-cyclohexyl]-azetidin-3-ylcarbamoyl}-methyl)-3-trifluoromethylbenzamide Step A 8-(2,3-Dihydro-benzofuran-6-yl)-1,4-dioxa-spiro[4.5]decan-8-ol

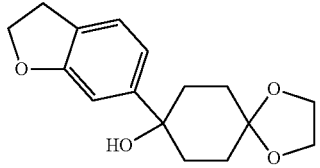 [SMILES: OC1(c2ccc3c(c2)OCC3)CCC2(CC1)OCCO2]

The title compound was prepared as a white solid from 6-bromo-2,3-dihydro-benzofuran (Milestone) and 1,4-dioxa-spiro[4.5]decan-8-one using the procedure described in Step A of Example 1.

$^1$H NMR (400 MHz, CDCl$_3$) δ 7.38 (s, 1H), 7.25 (d, J=6.0 Hz, 1H), 6.72 (d, J=6.1 Hz, 1H), 4.55 (t, J=7.5 Hz, 2H), 4.01 (s, 4H), 3.20 (t, J=7.4 Hz, 2H), 2.51 (s, 1H), 2.15 (m, 2H), 2.06 (m, 2H), 1.85 (m, 2H), 1.70 (m, 2H).

Step B 4-(2,3-Dihydro-benzofuran-6-yl)-4-hydroxy-cyclohexanone

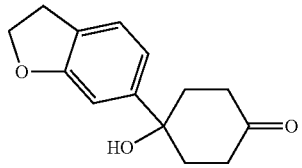 [SMILES: O=C1CCC(O)(c2ccc3c(c2)OCC3)CC1]

The title compound was prepared as a white solid from 8-(2,3-dihydro-benzofuran-6-yl)-1,4-dioxa-spiro[4.5]decan-8-ol (as prepared in the previous step) using the procedure described in Step B of Example 1.

$^1$H NMR (400 MHz, CDCl$_3$) δ 7.38 (s, 1H), 7.25 (d, J=6.0 Hz, 1H), 6.75 (d, J=6.4 Hz, 1H), 4.55 (t, J=7.0 Hz, 2H), 3.20 (d, J=7.2 Hz, 2H), 2.90 (m, 2H), 2.31 (m, 2H), 2.20 (m, 4H).

Step C 4-(2,3-Dihydro-benzofuran-6-yl)-cyclohex-3-enone

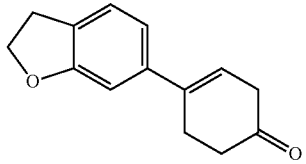 [SMILES: O=C1CC=C(c2ccc3c(c2)OCC3)CC1]

The title compound was prepared as a white solid from 4-(2,3-dihydro-benzofuran-6-yl)-4-hydroxy-cyclohexanone (as prepared in the previous step) using the procedure described in Step C of Example 1.

$^1$H NMR (400 MHz, CDCl$_3$) δ 7.25 (s, 1H), 7.16 (d, J=6.6 Hz, 1H), 6.75 (d, J=7.0 Hz, 1H), 5.95 (m, 1H), 4.55 (t, J=6.6 Hz, 2H), 3.22 (t, J=6.6 Hz, 2H), 3.08 (s, 2H), 2.88 (t, J=5.5 Hz, 2H), 2.66 (t, J=6.6 Hz, 2H).

Step D

1-[4-(2,3-Dihydro-benzofuran-6-yl)-cyclohex-3-enyl]-azetidin-3-ylamine

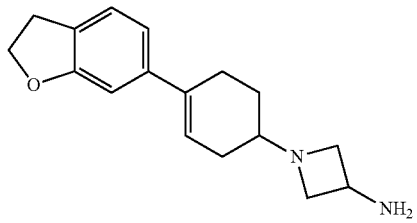 [SMILES: NC1CN(C2CC=C(c3ccc4c(c3)OCC4)CC2)C1]

The title compound was prepared as colorless oil from 4-(2,3-dihydro-benzofuran-6-yl)-cyclohex-3-enone (as prepared in the previous step) using the procedures described in Steps D and E of Example 1.

$^1$H NMR (400 MHz, CDCl$_3$) δ 7.20 (s, 1H), 7.12 (d, J=6.0 Hz, 1H), 6.70 (d, J=6.3 Hz, 1H), 4.55 (t, J=6.8 Hz, 2H), 3.72 (t, J=6.8 Hz, 2H), 3.66 (m, 1H), 3.20 (t, J=6.5 Hz, 2H), 2.65 (t, J=6.4 Hz, 2H), 2.45 (m, 1H), 2.30 (m, 2H), 1.90 (m, 2H), 1.65 (m, 2H), 1.37 (m 2H).

Step E

N-({1-[4-(2,3-Dihydro-benzofuran-6-yl)-cyclohexyl]-azetidin-3-ylcarbamoyl}-methyl)-3-trifluoromethylbenzamide

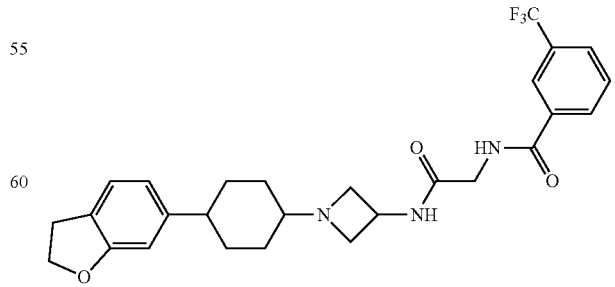

The title compounds were prepared as white solids from the EDCI coupling between the amine (from step D) and (3-trifluoromethyl-benzoylamino)-acetic acid followed by H-Cube hydrogenation using the procedures described in Steps E and F of Example 1.

3a: Less Polar Fraction from Silica Gel Column

¹H NMR (400 MHz, CDCl₃) δ 8.11 (s, 1H), 8.02 (d, J=6.8 Hz, 1H), 7.80 (d, J=6.2 Hz, 1H), 7.60 (t, J=7.0 Hz, 2H), 7.35 (m, 1H), 7.10 (s, 1H), 6.92 (d, J=6.5 Hz, 1H), 6.80 (d, J=6.5 Hz, 1H), 6.68 (d, J=6.8 Hz, 1H), 4.55 (t, J=6.2 Hz, 2H), 4.52 (m, 1H), 4.20 (s, 2H), 3.60 (t, J=6.8 Hz, 2H), 3.15 (t, J=6.6 Hz, 2H), 2.45 (m, 1H), 2.31 (m, 1H), 1.80 (m, 2H), 1.73 (m, 2H), 1.45 (m, 4H).

3b: More Polar Fraction from Silica Gel Column

¹H NMR (400 MHz, CDCl₃) δ 8.12 (s, 1H), 8.05 (d, J=6.5 Hz, 1H), 7.78 (d, J=6.6 Hz, 1H), 7.58 (t, J=6.8 Hz, 1H), 7.50 (m, 1H), 7.08 (d, J=6.2 Hz, 1H), 7.01 (s, 1H), 6.90 (d, J=6.8 Hz, 1H), 6.70 (d, J=6.6 Hz, 1H), 4.55 (t, J=6.8 Hz, 2H), 4.52 (m, 1H), 4.20 (d, J=4.6 Hz, 2H), 3.68 (t, J=7.5 Hz, 2H), 3.21 (t, J=6.7 Hz, 2H), 2.98 (t, J=7.5 Hz, 2H), 2.45 (m, 1H), 2.02 (m, 1H), 1.85 (m, 4H), 1.45 (m, 2H), 1.15 (m, 2H).

Example 4

N-{[1-(4-Phenyl-cyclohexyl)-azetidin-3-ylcarbamoyl]-methyl}-3-trifluoromethyl-benzamide

Step A

3-[2-(3-Trifluoromethyl-benzoylamino)-acetylamino]-azetidine-1-carboxylic acid tert-butyl ester

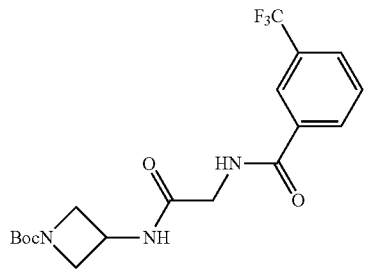 [SMILES: CC(C)(C)OC(=O)N1CC(NC(=O)CNC(=O)c2cccc(C(F)(F)F)c2)C1]

A solution of 3-amino-azetidine-1-carboxylic acid tert-butyl ester (BetaPharma, 1.2 g, 6.97 mmol) and (3-trifluoromethyl-benzoylamino)-acetic acid (Bionet, 1.57 g, 6.36 mmol) in DCM (10 mL) was treated with EDCI (Aldrich, 1.57 g, 6.36 mmol) and HOBT (Aldrich, 1.22 g, 6.36 mmol) at room temperature for 4 hours. The reaction solution was partitioned between DCM and water. The organic layer was washed with brine, dried over anhydrous Na₂SO₄, filtered and concentrated to give a yellow oil, which was then purified by silica gel column on a CombiFlash® system using hexanes and ethyl acetate (from 10% ethyl acetate to 100% ethyl acetate) to afford the title compound as a white solid.

¹H NMR (400 MHz, CDCl₃) δ 8.10 (s, 1H), 8.02 (d, J=6.6 Hz, 1H), 7.80 (d, J=6.8 Hz, 1H), 7.56 (t, J=6.5 Hz, 1H), 4.61 (m, 1H), 4.25 (t, J=7.2 Hz, 2H), 4.18 (d, J=5.5 Hz, 2H), 3.82 (t, J=7.5 Hz, 2H), 1.41 (s, 9H).

Step B

N-(Azetidin-3-ylcarbamoylmethyl)-3-trifluoromethyl-benzamide free base, HCl and TFA Salt

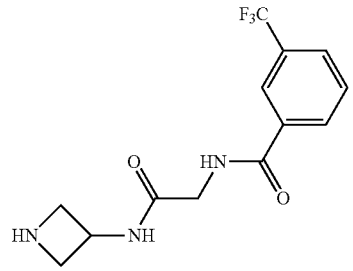 [SMILES: O=C(CNC(=O)c1cccc(C(F)(F)F)c1)NC1CNC1]

A solution of 3-[2-(3-trifluoromethyl-benzoylamino)-acetylamino]-azetidine-1-carboxylic acid tert-butyl ester (as prepared in the previous step, 7.5 g, 18.7 mmol) in dioxane (5 mL) and MeOH (20 mL) was treated with 4N HCl at room temperature. The reaction was stirred for 4 hours. The solvent was removed and the residue was dried to give the title compound as an HCl salt (yellow foam).

A solution of 3-[2-(3-trifluoromethyl-benzoylamino)-acetylamino]-azetidine-1-carboxylic acid tert-butyl ester (as prepared in Step A of this Example, 2.10 g, 5.24 mmol) in 1:1 TFA and DCM (10 mL) was stirred for 2 hours at room temperature. The solvent was removed to give the title compound as a TFA salt containing extra TFA (colorless oil).

The free base was obtained by treating the salt in MeOH with solid Na₂CO₃ overnight. The solid was filtered and residue was dried to give the title compound for analytical characterization.

¹H NMR (400 MHz, CDCl₃) δ 8.10 (s, 1H), 8.05 (d, J=6.0 Hz, 1H), 7.78 (d, J=6.2 Hz, 1H), 7.55 (m, 2H), 4.78 (m, 1H), 4.15 (d, J=3.2 Hz, 2H), 3.95 (t, J=7.0 Hz, 2H), 3.52 (t, J=7.0 Hz, 2H).

Step C

N-{[1-(4-Phenyl-cyclohexyl)-azetidin-3-ylcarbamoyl]-methyl}-3-trifluoromethyl-benzamide

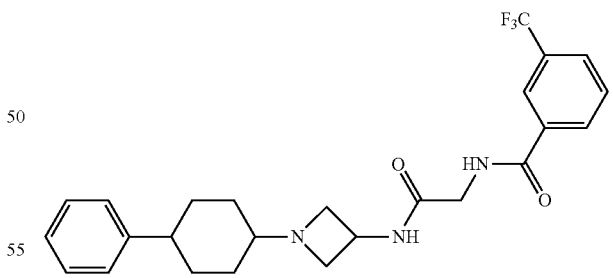

A solution of 4-phenyl-cyclohexanone (Aldrich, 1.5 g, 8.62 mmol) and N-(azetidin-3-ylcarbamoylmethyl)-3-trifluoromethyl-benzamide TFA salt (as prepared in the previous step, 3.89 g, 12.9 mmol) in DCM (20 mL) was treated with TEA (6 mL, 43 mmol) for 10 min followed by NaBH(OAc)₃ (Aldrich, 3.65 g, 17.2 mmol) for another 4 hours at room temperature. The reaction was quenched with saturated sodium bicarbonate. The organic layer was separated and the aqueous layer was extracted 3 times with a chloroform/IPA "cocktail" (~3:1, v/v). The combined organic layers were dried over anhydrous Na$_2$SO$_4$, filtered and concentrated to give the crude product, which was then purified by a CombiFlash® system using ethyl acetate and 7N NH$_3$ in MeOH as eluent (from pure ethyl acetate to 5% 7N NH$_3$ in MeOH in ethyl acetate) to afford the two title compounds as white solids.

4a: Less Polar Fraction from Silica Gel Column $^1$H NMR (400 MHz, CDCl$_3$) δ 8.11 (s, 1H), 8.02 (d, J=6.8 Hz, 1H), 7.80 (d, J=7.0 Hz, 1H), 7.55 (t, J=6.8 Hz, 1H), 7.30 (m, 2H), 7.20 (m, 4H), 6.72 (d, J=6.5 Hz, 1H), 4.33 (m, 1H), 4.30 (d, J=3.5 Hz, 2H), 3.55 (t, J=7.0 Hz, 2H), 2.85 (t, J=7.0 Hz, 2H), 2.45 (m, 1H), 2.10 (m, 1H), 1.95 (m, 2H), 1.70 (m, 2H), 1.52 (m, 2H), 1.22 (m, 2H).

4b: More Polar Fraction from Silica Gel Column $^1$H NMR (400 MHz, CDCl$_3$) δ 8.12 (s, 1H), 8.05 (d, J=6.5 Hz, 1H), 7.80 (d, J=6.6 Hz, 1H), 7.58 (t, J=6.8 Hz, 1H), 7.40 (m, 2H), 7.15 (m, 4H), 6.75 (d, J=6.8 Hz, 1H), 4.42 (m, 1H), 4.25 (d, J=4.6 Hz, 2H), 3.64 (t, J=7.5 Hz, 2H), 3.10 (t, J=7.5 Hz, 2H), 2.35 (m, 1H), 2.08 (s, 1H), 2.02 (m, 2H), 1.85 (m, 2H), 1.35 (m, 2H), 1.15 (m, 2H).

Example 5

N-({1-[4-(2-oxo-2,3-dihydro-benzooxazol-5-yl)-cyclohexyl]-azetidin-3-ylcarbamoyl}-methyl)-3-trifluoromethyl-benzamide Step A 5-(1-Hydroxy-4-oxo-cyclohexyl)-3H-benzooxazol-2-one

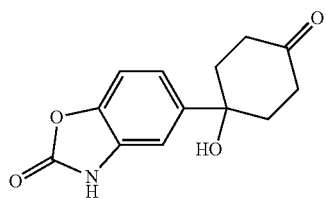 [SMILES: O=C1CCC(O)(c2ccc3oc(=O)[nH]c3c2)CC1]

The title compound was prepared as a white solid from 5-bromo-3H-benzooxazol-2-one (Aldrich) using the procedures described in Steps A and B of Example 1.

$^1$H NMR (400 MHz, d$_4$-MeOH) δ 7.35 (d, J=6.5 Hz, 1H), 7.23 (d, J=4.5 Hz, 1H), 7.12 (d, J=6.0 Hz, 1H), 2.90 (m, 2H), 2.30 (m, 4H), 2.08 (m, 2H).

Step B 5-(4-Oxo-cyclohex-1-enyl)-3H-benzooxazol-2-one

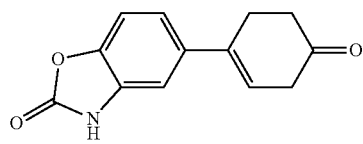 [SMILES: O=C1CC=C(c2ccc3oc(=O)[nH]c3c2)CC1]

A solution of 5-(1-hydroxy-4-oxo-cyclohexyl)-3H-benzooxazol-2-one (230 mg, 0.93 mmol) in THF (10 mL) was treated with Burgess' reagent (Aldrich, 334 mg, 1.40 mmol) at room temperature. The reaction was stirred overnight. The solvent was removed and the residue was partitioned between ethyl acetate and water. The organic layer was washed with brine, dried over anhydrous Na$_2$SO$_4$, filtered, concentrated and then purified by silica gel column on a CombiFlash® system using hexanes and ethyl acetate (from 10% ethyl acetate to 100% ethyl acetate) to afford the title compound as a white solid.

$^1$H NMR (400 MHz, d$_4$-MeOH) δ 7.25 (d, J=6.0 Hz, 1H), 7.18 (d, J=5.8 Hz, 1H), 7.05 (d, J=6.0 Hz, 1H), 5.98 (m, 1H), 2.95 (s, 1H), 2.82 (t, J=5.2 Hz, 1H), 2.49 (t, J=6.5 Hz, 2H).

Step C 5-(4-Oxo-cyclohexyl)-3H-benzooxazol-2-one

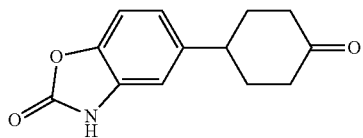 [SMILES: O=C1CCC(c2ccc3oc(=O)[nH]c3c2)CC1]

To a Parr hydrogenation flask was added a solution of 5-(4-oxo-cyclohex-1-enyl)-3H-benzooxazol-2-one (as prepared in the previous step, 180 mg, 0.79 mmol) in MeOH (10 mL) followed by 5% Pd/C (Aldrich, ~100 mg). The reaction was charged with 40 psi H$_2$ gas for 10 hours at room temperature. The catalyst was removed by passing the reaction solution through a pad of Celite. MeOH was added to washed the Celite column three times. The combined organic layers were concentrated in vacuo to give the title compound as a white solid.

$^1$H NMR (400 MHz, CDCl$_3$) δ 10.05 (s, br, 1H), 7.15 (d, J=5.8 Hz, 1H), 7.05 (m, 2H), 3.05 (m, 1H), 2.55 (m, 4H), 2.20 (m, 2H), 1.90 (m, 2H).

Step D

N-({1-[4-(2-oxo-2,3-dihydro-benzooxazol-5-yl)-cyclohexyl]-azetidin-3-ylcarbamoyl}-methyl)-3-trifluoromethyl-benzamide

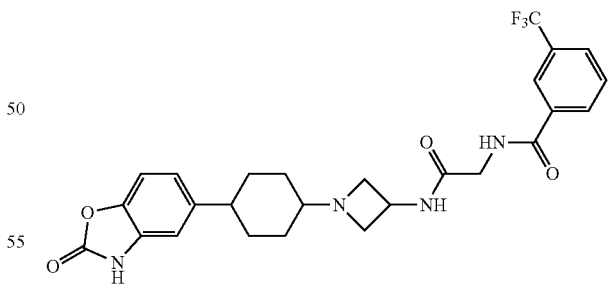

The title compounds were prepared as white solids from reductive amination of 5-(4-oxo-cyclohexyl)-3H-benzooxazol-2-one (as prepared in the previous step) and N-(azetidin-3-ylcarbamoylmethyl)-3-trifluoromethyl-benzamide (as prepared in step B of Example 4) using the procedure described in Step C of Example 4.

5a: Less Polar Fraction from Silica Gel Column $^1$H NMR (400 MHz, d$_4$-MeOH) δ 8.21 (s, 1H), 8.15 (d, J=6.3 Hz, 1H), 7.88 (d, J=6.5 Hz, 1H), 7.70 (t, J=6.6 Hz, 1H), 7.13 (d, J=6.6 Hz, 1H), 7.05 (m, 2H), 4.52 (m, 1H), 4.05 (s, 2H), 3.85 (m, 2H), 3.18 (m, 2H), 2.65 (m, 1H), 1.85 (m, 4H), 1.62 (m, 4H).

5b: More Polar Fraction from Silica Gel Column

¹H NMR (400 MHz, d₄-MeOH) δ 8.25 (s, 1H), 8.16 (d, J=5.5 Hz, 1H), 7.87 (d, J=6.0 Hz, 1H), 7.68 (t, J=6.0 Hz, 1H), 7.11 (d, J=6.6 Hz, 1H), 6.95 (m, 2H), 4.45 (m, 1H), 4.05 (s, 2H), 3.70 (t, J=6.2 Hz, 2H), 3.10 (t, J=6.5 Hz, 2H), 2.55 (m, 1H), 1.95 (m, 4H), 1.52 (m, 2H), 1.20 (m, 2H).

Example 6

N-({1-[4-(2-Oxo-2,3-dihydro-benzothiazol-5-yl)-cyclohexyl]-azetidin-3-ylcarbamoyl}-methyl)-3-trifluoromethyl-benzamide Step A 5-(1-Hydroxy-4-oxo-cyclohexyl)-3H-benzothiazol-2-one

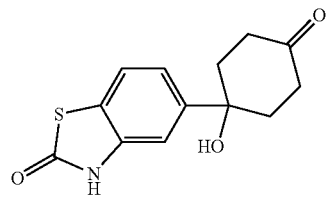 [SMILES: O=C1CCC(O)(c2ccc3sc(=O)[nH]c3c2)CC1]

The title compound was prepared as a white solid from 6-bromo-3H-benzothiazol-2-one (Aldrich) using the procedures described in Steps A and B of Example 1.

¹H NMR (400 MHz, CDCl₃) δ 7.41 (d, J=5.5 Hz, 1H), 7.20 (d, J=6.0 Hz, 1H), 7.10 (s, 1H), 2.85 (m, 2H), 2.63 (m, 2H), 2.48 (m, 2H). 2.10 (m, 2H).

Step B 5-(4-Oxo-cyclohex-1-enyl)-3H-benzothiazol-2-one

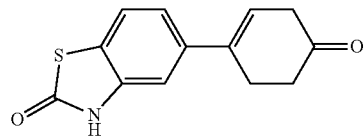 [SMILES: O=C1CC=C(c2ccc3sc(=O)[nH]c3c2)CC1]

The title compound was prepared as a white solid from 5-(1-hydroxy-4-oxo-cyclohexyl)-3H-benzothiazol-2-one (as prepared in the previous step) using the procedure described in Step B of Example 5.

¹H NMR (400 MHz, CDCl₃) δ 9.50 (s, br, 1H), 7.41 (s, 1H), 7.30 (d, J=6.0 Hz, 1H), 7.08 (d, J=6.4 Hz, 1H), 6.05 (m, 1H), 2.90 (m, 2H), 2.65 (m, 2H), 2.50 (m, 2H).

Step C

N-({1-[4-(2-oxo-2,3-dihydro-benzothiazol-5-yl)-cyclohexyl]-azetidin-3-ylcarbamoyl}-methyl)-3-trifluoromethyl-benzamide

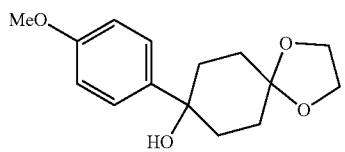 [SMILES: COc1ccc(C2(O)CCC3(CC2)OCCO3)cc1]

The title compounds were prepared as white solids from hydrogenation of 5-(4-oxo-cyclohex-1-enyl)-3H-benzothiazol-2-one (as prepared in the previous step) followed by reductive amination of the corresponding ketone with N-(azetidin-3-ylcarbamoylmethyl)-3-trifluoromethyl-benzamide (as prepared in step B of Example 4) using the procedures described in Step C of Example 5 and Step C of Example 4.

6a: Less Polar Fraction from Silica Gel Column

¹H NMR (400 MHz, d₆-DMSO) δ 8.15 (s, 1H), 8.10 (d, J=4.5 Hz, 1H), 7.95 (d, J=5.5 Hz, 1H), 7.75 (t, J=6.0 Hz, 1H), 7.35 (s, 1H), 7.10 (d, J=6.0 Hz, 1H), 7.05 (d, J=6.0 Hz, 1H), 4.38 (m, 1H), 3.95 (m, 2H), 3.56 (t, J=6.5 Hz, 2H), 2.80 (t, J=6.4 Hz, 2H), 3.02 (m, 1H), 1.80~1.65 (m, 4H), 1.45 (m, 4H).

6b: More Polar Fraction from Silica Gel Column

ESI-MS (m/z): Calcd. For C₂₆H₂₇F₃N₄O₃S, 532; found: 533 (M+H).

Example 7

N-({1-[4-(4-Methoxy-phenyl)-cyclohexyl]-azetidin-3-ylcarbamoyl}-methyl)-3-trifluoromethyl-benzamide Step A 8-(4-Methoxy-phenyl)-1,4-dioxa-spiro[4.5]decan-8-ol The title compound was prepared as a white solid from 1-bromo-4-methoxy-benzene (Aldrich) using the procedure described in Step A of Example 1.

¹H NMR (400 MHz, CDCl₃) δ 7.51 (d, J=7.0 Hz, 2H), 6.85 (d, J=7.1 Hz, 2H), 3.98 (s, 4H), 3.79 (s, 3H), 2.10 (m, 4H), 1.80 (m, 2H), 1.65 (m, 2H).

Step B

4-Hydroxy-4-(4-methoxy-phenyl)-cyclohexanone

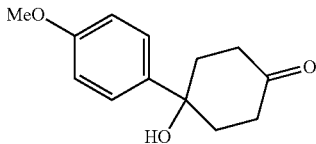 [SMILES: COc1ccc(C2(O)CCC(=O)CC2)cc1]

The title compound was prepared as a white solid from 8-(4-methoxy-phenyl)-1,4-dioxa-spiro[4.5]decan-8-ol (as prepared in the previous step) using the procedure described in Step B of Example 1.

¹H NMR (400 MHz, CDCl₃) δ 7.55 (d, J=6.8 Hz, 2H), 6.90 (d, J=6.8 Hz, 2H), 3.85 (s, 3H), 2.95 (m, 2H), 2.33 (m, 4H), 2.20 (m, 2H).

Step C 4-(4-Methoxy-phenyl)-cyclohex-3-enone

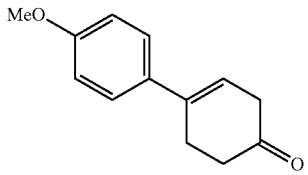

The title compound was prepared as a white solid from 4-hydroxy-4-(4-methoxy-phenyl)-cyclohexanone (as prepared in the previous step) using the procedure described in Step B of Example 5.

¹H NMR (400 MHz, CDCl₃) δ 7.35 (d, J=6.8 Hz, 2H), 6.85 (d, J=6.8 Hz, 2H), 5.98 (m, 1H), 3.80 (s, 3H), 3.05 (s, 2H), 2.85 (m, 2H), 2.65 (t, J=7.0 Hz, 2H).

Step D

N-({1-[4-(4-Methoxy-phenyl)-cyclohexyl]-azetidin-3-ylcarbamoyl}-methyl)-3-trifluoromethyl-benzamide

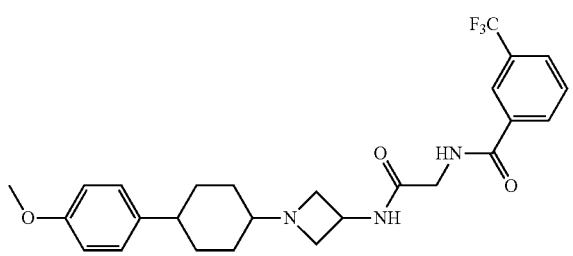

The title compounds were prepared as white solids from the hydrogenation of 4-(4-methoxy-phenyl)-cyclohex-3-enone (as prepared in the previous step) followed by reductive amination of the corresponding ketone with N-(azetidin-3-ylcarbamoylmethyl)-3-trifluoromethyl-benzamide (as prepared in step B of Example 4) using the procedures described in Step C of Example 5 and Step C of Example 4.

7a: Less Polar Fraction from Silica Gel Column

¹H NMR (400 MHz, CDCl₃) δ 8.15 (s, 1H), 8.05 (d, J=6.8 Hz, 1H), 7.80 (d, J=6.2 Hz, 1H), 7.65 (t, J=7.0 Hz, 2H), 7.45 (d, J=6.5 Hz, 1H), 6.92 (d, J=6.5 Hz, 2H), 4.52 (m, 1H), 4.18 (d, J=3.5 Hz, 2H), 3.85 (s, 3H), 3.60 (t, J=7.0 Hz, 2H), 2.90 (t, J=7.0 Hz, 2H), 2.52 (m, 1H), 2.30 (s, br, 1H), 1.95 (m, 2H), 1.75 (m, 2H), 1.50 (m, 2H), 1.35 (m, 2H).

7b: More Polar Fraction from Silica Gel Column

¹H NMR (400 MHz, CDCl₃) δ 8.12 (s, 1H), 8.05 (d, J=6.5 Hz, 1H), 7.75 (d, J=6.6 Hz, 1H), 7.68 (d, J=6.8 Hz, 2H), 7.60 (t, J=6.8 Hz, 1H), 7.50 (d, J=6.8 Hz, 2H), 4.52 (m, 1H), 4.20 (d, J=4.6 Hz, 2H), 3.82 (s, 3H), 3.64 (t, J=7.5 Hz, 2H), 2.98 (t, J=7.5 Hz, 2H), 2.55 (m, 1H), 2.40 (s, 1H), 2.02 (m, 2H), 1.85 (m, 2H), 1.35 (m, 2H), 1.15 (m, 2H).

Example 8

N-({1-[4-(3-Cyano-phenyl)-cyclohexyl]-azetidin-3-ylcarbamoyl}-methyl)-3-trifluoromethyl-benzamide Step A 3-(8-Hydroxy-1,4-dioxa-spiro[4.5]dec-8-yl)-benzonitrile

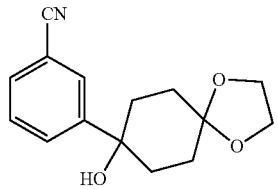 [SMILES: N#Cc1cccc(C2(O)CCC3(CC2)OCCO3)c1]

A solution of iso-propyl-magnesium bromide (Aldrich, 2.0 M in THF, 8 mL, 16 mmol) was slowly dropped into a solution of 3-iodo-benzonitrile (Aldrich, 3.25 g, 14.2 mmol) in THF (20 mL) at 0° C. After addition, the reaction was stirred for another 30 min. A solution of 1,4-dioxa-spiro[4.5]decan-8-one (2.22 g, 14.2 mmol) in THF (5 mL) was added to the reaction mixture at 0° C. The reaction was then stirred for additional 2 hours. The reaction was quenched with diluted NH₄Cl solution and warmed to room temperature. The solvent was removed in vacuo and the residue was partitioned between ethyl acetate and water. The organic layer was washed with brine, dried over anhydrous Na₂SO₄, filtered and concentrated to give a yellow solid, which was purified by silica gel column on a CombiFlash® system using hexanes and ethyl acetate (from 10% ethyl acetate to 100% ethyl acetate) to afford the title compound as a white solid.

¹H NMR (400 MHz, CDCl₃) δ 7.82 (s, 1H), 7.75 (d, J=6.8 Hz, 1H), 7.51 (d, J=6.5 Hz, 2H), 7.42 (t, J=6.6 Hz, 1H), 3.98 (m, 4H), 2.12 (m, 4H), 1.78 (m, 2H), 1.65 (m, 2H).

Step B 3-(1-Hydroxy-4-oxo-cyclohexyl)-benzonitrile

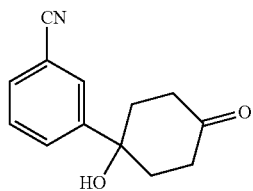 [SMILES: N#Cc1cccc(C2(O)CCC(=O)CC2)c1]

The title compound was prepared as a white solid from 3-(8-hydroxy-1,4-dioxa-spiro[4.5]dec-8-yl)-benzonitrile (as prepared in the previous step) using the procedure described in Step B of Example 1.

$^1$H NMR (400 MHz, CDCl$_3$) δ 7.80 (s, 1H), 7.68 (d, J=6.7 Hz, 1H), 7.50 (d, J=6.8 Hz, 2H), 7.41 (t, J=6.6 Hz, 1H), 2.90 (m, 2H), 2.35 (m, 2H), 2.25 (m, 2H), 2.14 (m, 2H).

Step C 3-(4-Oxo-cyclohex-1-enyl)-benzonitrile

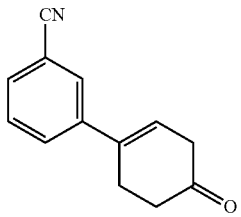 [SMILES: N#Cc1cccc(C2=CCC(=O)CC2)c1]

The title compound was prepared as a white solid from 3-(1-hydroxy-4-oxo-cyclohexyl)-benzonitrile (as prepared in the previous step) using the procedure described in Step B of Example 5.

$^1$H NMR (400 MHz, CDCl$_3$) δ 7.90 (s, 1H), 7.78 (d, J=6.5 Hz, 1H), 7.65 (m, 1H), 7.48 (t, J=−6.6 Hz, 1H), 6.20 (m, 1H), 3.10 (s, 2H), 2.85 (m, 2H), 2.68 (t, J=6.8 Hz, 2H).

Step D

N-({1-[4-(3-Cyano-phenyl)-cyclohexyl]-azetidin-3-ylcarbamoyl}-methyl)-3-trifluoromethyl-benzamide

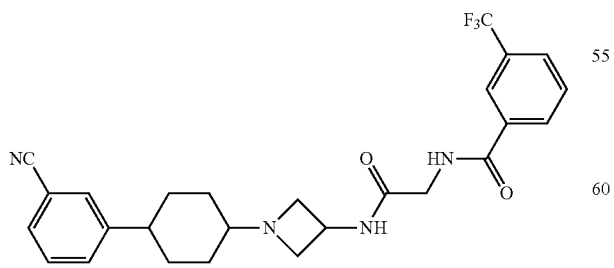

The title compounds were prepared as white solids from hydrogenation of 3-(4-oxo-cyclohex-1-enyl)-benzonitrile (as prepared in the previous step) followed by reductive amination of the corresponding ketone with N-(azetidin-3-ylcarbamoylmethyl)-3-trifluoromethyl-benzamide (as prepared in step B of Example 4) using the procedures described in Step C of Example 5 and Step C of Example 4.

8a: Less Polar Fraction from Silica Gel Column $^1$H NMR (400 MHz, CDCl$_3$) δ 8.15 (s, 1H), 8.02 (d, J=6.4 Hz, 1H), 7.85 (s, 1H), 7.78 (t, J=7.0 Hz, 2H), 7.60 (d, J=6.4 Hz, 1H), 7.58 (t, J=6.8 Hz, 1H), 7.40 (d, J=7.5 Hz, 1H), 4.60 (m, 1H), 4.18 (d, J=4.5 Hz, 2H), 3.66 (t, J=7.0 Hz, 2H), 3.10 (t, J=5.7 Hz, 2H), 2.52 (m, 1H), 2.32 (s, br, 1H), 2.20 (m, 2H), 1.95 (m, 2H), 1.60~1.45 (m, 4H).

8b: More Polar Fraction from Silica Gel Column, $^1$H NMR (400 MHz, CDCl$_3$) δ 8.11 (s, 1H), 8.02 (d, J=6.6 Hz, 1H), 7.90 (s, 1H), 7.75 (d, J=6.5 Hz, 2H), 7.60 (d, J=6.8 Hz, 1H), 7.45 (t, J=6.5 Hz, 1H), 7.35 (d, J=5.8 Hz, 1H), 4.55 (m, 1H), 4.20 (d, J=3.5 Hz, 2H), 3.65 (t, J=7.0 Hz, 2H), 2.95 (s, br, 2H), 2.55 (m, 1H), 2.30 (s, br, 1H), 2.05 (m, 2H), 1.90 (m, 2H), 1.75 (m, 4H).

Example 9

4-(4-{3-[2-(3-Trifluoromethyl-benzoylamino)-acetylamino]-azetidin-1-yl}-cyclohexyl)-benzoic acid methyl ester

Step A 4-(8-Hydroxy-1,4-dioxa-spiro[4.5]dec-8-yl)-benzoic acid methyl ester

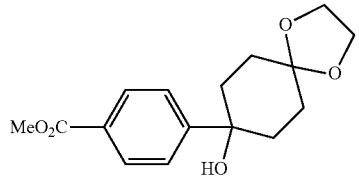 [SMILES: COC(=O)c1ccc(C2(O)CCC3(CC2)OCCO3)cc1]

The title compound was prepared as a white solid from 4-iodo-benzoic acid methyl ester (Aldrich) using the procedure described in Step A of Example 8.

$^1$H NMR (400 MHz, CDCl$_3$) δ 7.95 (d, J=7.0 Hz, 2H), 6.85 (d, J=7.3 Hz, 2H), 4.08 (s, 4H), 2.51 (t, J=6.0 Hz, 4H), 2.03 (t, J=6.0 Hz, 4H).

Step B 4-(1-Hydroxy-4-oxo-cyclohexyl)-benzoic acid methyl ester

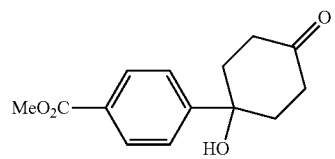 [SMILES: COC(=O)c1ccc(C2(O)CCC(=O)CC2)cc1]

The title compound was prepared as a white solid from 4-(8-hydroxy-1,4-dioxa-spiro[4.5]dec-8-yl)-benzoic acid methyl ester (as prepared in the previous step) using the procedure described in Step B of Example 1.

$^1$H NMR (400 MHz, CDCl$_3$) δ 8.05 (d, J=6.8 Hz, 2H), 7.60 (d, J=6.8 Hz, 2H), 4.01 (m, 4H), 3.90 (s, 3H), 2.95 (m, 2H), 2.38 (m, 2H), 2.30 (m, 2H), 2.20 (m, 2H).

Step C 4-(4-Oxo-cyclohex-1-enyl)-benzoic acid methyl ester

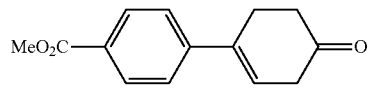

The title compound was prepared as a white solid from 4-(1-hydroxy-4-oxo-cyclohexyl)-benzoic acid methyl ester (as prepared in the previous step) using the procedure described in Step B of Example 5.

$^1$H NMR (400 MHz, CDCl$_3$) δ 8.01 (d, J=6.5 Hz, 2H), 7.46 (d, J=6.6 Hz, 2H), 6.21 (m, 1H), 3.95 (s, 3H), 3.15 (s, 2H), 2.95 (t, J=5.6 Hz, 2H), 2.70 (t, J=6.3 Hz, 2H).

Step D 4-(4-Oxo-cyclohexyl)-benzoic acid methyl ester

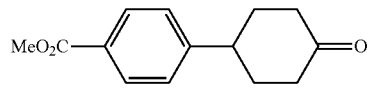

The title compound was prepared as a white solid from 4-(4-oxo-cyclohex-1-enyl)-benzoic acid methyl ester (as prepared in the previous step) using the procedure described in Step C of Example 5.

$^1$H NMR (400 MHz, CDCl$_3$) δ 8.05 (d, J=8.0 Hz, 2H), 7.58 (d, J=8.0 Hz, 2H), 3.92 (s, 3H), 2.70 (m, 1H), 2.35~2.00 (8H).

Step E 4-(4-{3-[2-(3-Trifluoromethyl-benzoylamino)-acetylamino]-azetidin-1-yl}-cyclohexyl)-benzoic acid methyl ester

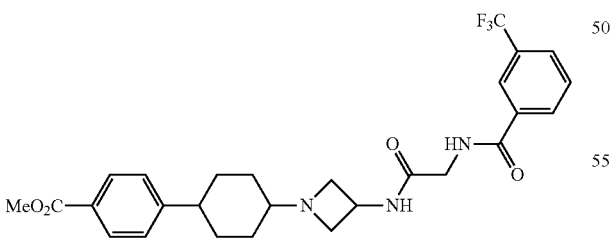

The title compound was prepared as a white solid by reductive amination of 4-(4-oxo-cyclohexyl)-benzoic acid methyl ester (as prepared in the previous step) and N-(azetidin-3-ylcarbamoylmethyl)-3-trifluoromethyl-benzamide (as prepared in step B of Example 4) using the procedure described in Step C of Example 4.

$^1$H NMR (400 MHz, CDCl$_3$) δ 8.11 (s, 1H), 8.02 (d, J=6.4 Hz, 1H), 7.95 (d, J=7.0 Hz, 2H), 7.80 (d, J=6.4 Hz, 1H), 7.58 (t, J=6.8 Hz, 1H), 7.30 (d, J=7.5 Hz, 2H), 6.56 (s, br, 1H), 4.55 (m, 1H), 4.18 (d, J=3.5 Hz, 2H), 3.62 (t, J=7.0 Hz, 2H), 2.95 (s, br, 2H), 2.62 (m, 1H), 1.95 (m, 2H), 1.80~1.55 (m, 6H).

Example 10

4-(4-{3-[2-(3-Trifluoromethyl-benzoylamino)-acetylamino]-azetidin-1-yl}-cyclohexyl)-benzoic acid

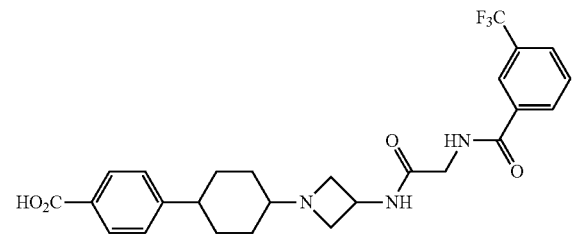 [SMILES: O=C(CNC(=O)c1cccc(C(F)(F)F)c1)NC1CN(C2CCC(c3ccc(C(=O)O)cc3)CC2)C1]

A solution of 4-(4-{3-[2-(3-trifluoromethyl-benzoylamino)-acetylamino]-azetidin-1-yl}-cyclohexyl)-benzoic acid methyl ester (less polar fraction from Example 9, 250 mg, 0.48 mmol) in THF (1 mL), MeOH (1 mL) and H$_2$O (1 mL) was treated with LiOH.H$_2$O (50 mg, 1.2 mmol) at room temperature. The reaction was then heated to 50° C. for 2 hours. The reaction was allowed to cool and solvent was removed in vacuo. 1 N HCl solution was added to adjust the solution to pH=6~7. The white precipitate was collected by filtration and washed with water. The solid was dried in vacuo, re-dissolved in ethyl acetate and re-crystallization to afford the title compound.

$^1$H NMR (400 MHz, d$_4$-MeOH) δ 8.10 (s, 1H), 8.01 (d, J=6.4 Hz, 1H), 7.72 (d, J=6.0 Hz, 1H), 7.70 (d, J=7.5 Hz, 2H), 7.55 (t, J=6.0 Hz, 1H), 7.18 (d, J=7.6 Hz, 2H), 4.56 (m, 1H), 4.15 (t, J=6.0 Hz, 2H), 4.08 (d, J=3.2 Hz, 2H), 3.81 (s, br, 2H), 2.65 (m, 1H), 1.95 (m, 2H), 1.80 (m, 2H), 1.66 (m, 4H).

Example 11

3-(4-{3-[2-(3-Trifluoromethyl-benzoylamino)-acetylamino]-azetidin-1-yl}-cyclohexyl)-benzoic acid ethyl ester Step A 3-(8-Hydroxy-1,4-dioxa-spiro[4.5]dec-8-yl)-benzoic acid ethyl ester

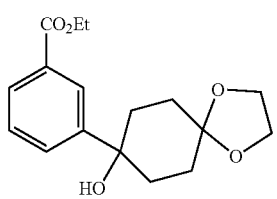 [SMILES: CCOC(=O)c1cccc(C2(O)CCC3(CC2)OCCO3)c1]

The title compound was prepared as a white solid from 3-iodo-benzoic acid ethyl ester (Aldrich) using the procedure described in Step A of Example 8.

$^1$H NMR (400 MHz, CDCl$_3$) δ 8.20 (s, 1H), 7.95 (d, J=6.8 Hz, 1H), 7.75 (d, J=6.6 Hz, 1H), 7.40 (t, J=6.4 Hz, 1H), 4.35

(q, J=6.2 Hz, 2H), 4.05 (m, 4H), 2.20 (m, 4H), 1.85 (m, 2H), 1.72 (m, 2H), 1.40 (t, J=7.8 Hz, 3H).

Step B 3-(1-Hydroxy-4-oxo-cyclohexyl)-benzoic acid ethyl ester

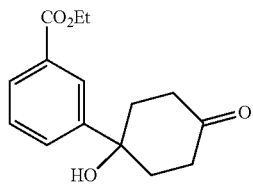 [SMILES: CCOC(=O)c1cccc(C2(O)CCC(=O)CC2)c1]

The title compound was prepared as a white solid from 3-(8-hydroxy-1,4-dioxa-spiro[4.5]dec-8-yl)-benzoic acid ethyl ester (as prepared in the previous step) using the procedure described in Step B of Example 1.

$^1$H NMR (400 MHz, CDCl$_3$) δ 8.20 (s, 1H), 8.00 (d, J=6.0 Hz, 1H), 7.78 (d, J=6.2 Hz, 1H), 7.45 (t, J=6.5 Hz, 1H), 4.35 (q, J=7.1 Hz, 2H), 2.95 (m, 2H), 2.40 (m, 4H), 2.21 (m, 2H), 1.38 (t, J=7.2 Hz, 3H).

Step C 3-(4-Oxo-cyclohex-1-enyl)-benzoic acid ethyl ester

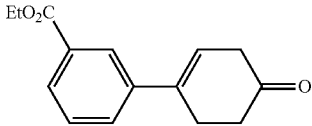

The title compound was prepared as a white solid from 3-(1-hydroxy-4-oxo-cyclohexyl)-benzoic acid ethyl ester (as prepared in the previous step) using the procedure described in Step B of Example 5.

$^1$H NMR (400 MHz, CDCl$_3$) δ 8.10 (s, 1H), 7.96 (d, J=7.2 Hz, 1H), 7.59 (d, J=6.5 Hz, 1H), 7.42 (t, J=6.5 Hz, 1H), 6.20 (m, 1H), 4.37 (q, J=7.5 Hz, 2H), 3.10 (s, 2H), 2.95 (t, J=6.8 Hz, 2H), 2.68 (t, J=7.7 Hz, 2H), 1.40 (t, J=8.2 Hz, 3H).

Step D 3-(4-Oxo-cyclohexyl)-benzoic acid ethyl ester

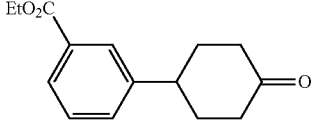

The title compound was prepared as a white solid from 3-4-oxo-cyclohex-1-enyl)-benzoic acid ethyl ester (as prepared in the previous step) using the procedure described in Step C of Example 5.

$^1$H NMR (400 MHz, CDCl$_3$) δ 8.00 (s, 1H), 7.90 (d, J=6.8 Hz, 1H), 7.48 (d, J=6.5 Hz, 1H), 7.36 (t, J=6.6 Hz, 1H), 4.35 (q, J=7.2 Hz, 2H), 2.61 (m, 1H), 2.45 (m, 2H), 2.30 (m, 2H), 2.25 (m, 2H0, 2.05 (m, 2H), 1.35 (t, J=7.9 Hz, 3H).

Step E 3-(4-{3-[2-(3-Trifluoromethyl-benzoylamino)-acetylamino]-azetidin-1-yl}-cyclohexyl)-benzoic acid ethyl ester

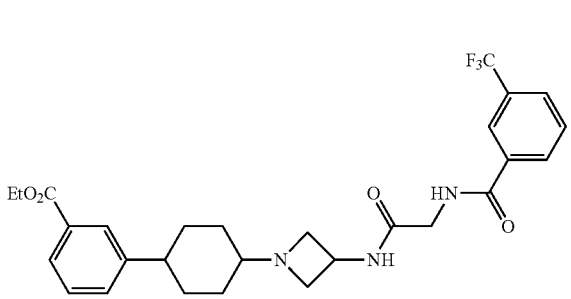 [SMILES: CCOC(=O)c1cccc(C2CCC(N3CC(NC(=O)CNC(=O)c4cccc(C(F)(F)F)c4)C3)CC2)c1]

The title compound was prepared as a white solid by the reductive amination of 3-(4-oxo-cyclohexyl)-benzoic acid ethyl ester (as prepared in the previous step) and N-(azetidin-3-ylcarbamoylmethyl)-3-trifluoromethyl-benzamide (as prepared in step B of Example 4) using the procedure described in Step C of Example 4.

11a: Less Polar Isomer $^1$H NMR (400 MHz, d$_4$-MeOH) δ 8.26 (s, 1H), 8.18 (d, J=5.6 Hz, 1H), 7.85 (m, 3H), 7.71 (t, J=6.5 Hz, 1H), 7.55 (d, J=6.0 Hz, 1H), 7.38 (t, J=6.5 Hz, 1H), 4.55 (m, 1H), 4.32 (q, J=6.8 Hz, 2H), 4.09 (s, 2H), 4.04 (t, J=6.0 Hz, 2H), 3.70 (d, J=6.0 Hz, 2H), 2.72 (m, 1H), 2.60 (m, 1H), 2.10 (m, 2H), 2.02 (m, 2H), 1.65 (m, 2H), 1.36 (t, J=6.0 Hz, 3H), 1.28 (m, 2H).

11b: More Polar Isomer $^1$H NMR (400 MHz, d$_4$-MeOH) δ 8.20 (s, 1H), 8.10 (d, J=3.6 Hz, 1H), 8.02 (d, J=6.5 Hz, 1H), 7.80 (m, 2H), 7.65 (t, J=6.0 Hz, 1H), 7.50 (d, J=6.0 Hz, 1H), 7.29 (t, J=6.5 Hz, 1H), 4.50 (m, 1H), 4.30 (q, J=6.5 Hz, 2H), 4.10 (s, 2H), 3.85 (t, J=6.0 Hz, 2H), 3.35 (d, J=6.0 Hz, 2H), 2.72 (m, 1H), 2.30 (m, 2H), 2.08 (m, 2H), 1.75 (m, 4H), 1.50 (2H), 1.35 (t, J=6.0 Hz, 3H).

Example 12

3-(4-{3-[2-(3-Trifluoromethyl-benzoylamino)-acetylamino]-azetidin-1-yl}-cyclohexyl)-benzoic acid

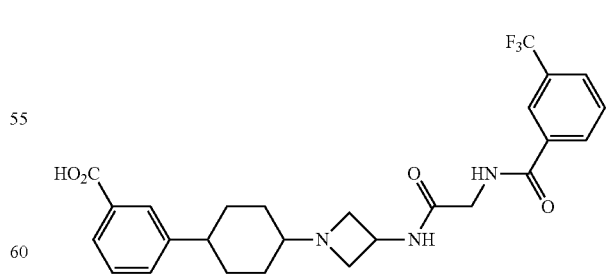

The title compound was prepared as a white solid by hydrolysis of 3-(4-{3-[2-(3-trifluoromethyl-benzoylamino)-acetylamino]-azetidin-1-yl}-cyclohexyl)-benzoic acid ethyl ester (less polar fraction, as prepared in Example 11, Step E) using the procedure described in Example 10.

$^1$H NMR (400 MHz, d$_4$-MeOH) δ 8.15 (s, 1H), 8.10 (d, J=6.0 Hz, 1H), 8.85 (s, 1H), 7.80 (d, J=6.5 Hz, 1H), 7.71 (d, J=6.0 Hz, 1H), 7.65 (t, J=6.5 Hz, 1H), 7.32 (d, J=6.4 Hz, 1H), 7.20 (t, J=6.7 Hz, 1H), 4.55 (m, 1H), 4.20 (s, 2H), 4.15 (t, J=6.0 Hz, 2H), 3.02 (s, br, 2H), 3.69 (t, J=6.0 Hz, 2H), 2.68 (m, 1H), 1.80 (m, 4H), 1.72 (m, 4H).

Example 13

N-({1-[4-(4-Pyrrolidin-1-yl-phenyl)-cyclohexyl]-azetidin-3-ylcarbamoyl}-methyl)-3-trifluoromethyl-benzamide Step A 8-(4-Pyrrolidin-1-yl-phenyl)-1,4-dioxa-spiro[4.5]decan-8-ol

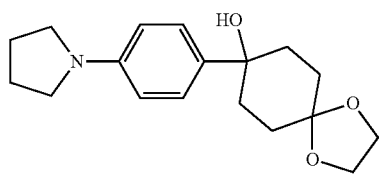 [SMILES: OC1(c2ccc(N3CCCC3)cc2)CCC2(CC1)OCCO2]

The title compound was prepared as a white solid from 1-(4-bromo-phenyl)-pyrrolidine (Ryan Scientific) using the procedure described in Step A of Example 1.

$^1$H NMR (400 MHz, CDCl$_3$) δ 7.36 (d, J=7.1 Hz, 2H), 6.51 (d, J=7.2 Hz, 2H), 4.01 (s, 4H), 3.95 (m, 2H), 3.30 (m, 2H), 2.11 (m, 2H), 2.05 (m, 6H), 1.88 (m, 2H), 1.70 (m, 2H).

Step B

1-[4-(1,4-Dioxa-spiro[4.5]dec-7-en-8-yl)-phenyl]-pyrrolidine

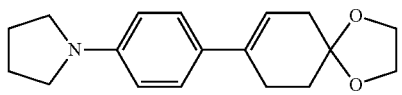 [SMILES: C1=C(c2ccc(N3CCCC3)cc2)CCC2(C1)OCCO2]

The title compound was prepared as a white solid from 8-(4-pyrrolidin-1-yl-phenyl)-1,4-dioxa-spiro[4.5]decan-8-ol (as prepared in the previous step) using the procedure described in Step B of Example 5.

$^1$H NMR (400 MHz, CDCl$_3$) δ 7.26 (d, J=7.5 Hz, 2H), 6.55 (d, J=7.6 Hz, 2H), 5.85 (m, 1H), 4.10 (s, 4H), 3.25 (t, J=5.6 Hz, 4H), 2.62 (m, 2H), 2.53 (t, J=6.4 Hz, 2H), 2.42 (s, 2H), 2.05 (t, J=5.8 Hz, 4H).

Step C

1-[4-(1,4-Dioxa-spiro[4.5]dec-8-yl)-phenyl]-pyrrolidine

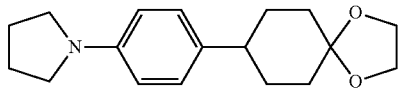 [SMILES: c1cc(N2CCCC2)ccc1C1CCC2(CC1)OCCO2]

The title compound was prepared as a white solid from 1-[4-(1,4-dioxa-spiro[4.5]dec-7-en-8-yl)-phenyl]-pyrrolidine (as prepared in the previous step) using the procedure described in Step C of Example 5.

$^1$H NMR (400 MHz, CDCl$_3$) δ 7.10 (d, J=7.5 Hz, 2H), 6.48 (d, J=7.8 Hz, 2H), 3.96 (s, 4H), 3.25 (t, J=5.6 Hz, 4H), 2.45 (m, 1H), 2.00 (t, J=6.0 Hz, 4H), 1.85 (m, 4H), 1.75~1.60 (m, 4H).

Step D 4-(4-Pyrrolidin-1-yl-phenyl)-cyclohexanone

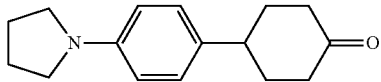 [SMILES: O=C1CCC(c2ccc(N3CCCC3)cc2)CC1]

The title compound was prepared as a white solid from 1-[4-(1,4-dioxa-spiro[4.5]dec-8-yl)-phenyl]-pyrrolidine (as prepared in the previous step) using the procedure described in Step B of Example 1.

ESI-MS (m/z): Calcd. for C$_{16}$H$_{21}$NO, 243; found: 244 (M+H).

Step E

N-({1-[4-(4-Pyrrolidin-1-yl-phenyl)-cyclohexyl]-azetidin-3-ylcarbamoyl}-methyl)-3-trifluoromethyl-benzamide

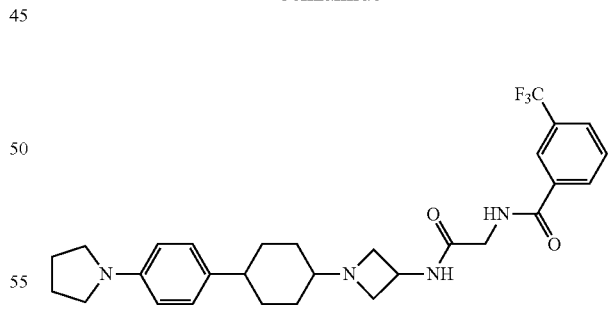

The title compound was prepared as a white solid from the reductive amination of 4-(4-pyrrolidin-1-yl-phenyl)-cyclohexanone (as prepared in the previous step) and N-(azetidin-3-ylcarbamoylmethyl)-3-trifluoromethyl-benzamide (as prepared in step B of Example 4) using the procedure described in Step C of Example 4.

$^1$H NMR (400 MHz, CDCl$_3$) δ 8.11 (s, 1H), 8.02 (d, J=6.8 Hz, 1H), 7.82 (d, J=6.0 Hz, 1H), 7.58 (t, J=6.5 Hz, 2H), 7.45 (d, J=6.5 Hz, 1H), 6.85 (d, J=6.5 Hz, 2H), 4.52 (m, 1H), 4.18 (d, J=3.5 Hz, 2H), 3.60 (t, J=6.0 Hz, 2H), 3.20 (t, J=7.0 Hz,

4H), 2.95 (t, J=6.0 Hz, 2H), 2.50 (m, 1H), 2.30 (s, br, 1H), 1.96 (t, J=7.5 Hz, 4H), 1.90 (m, 2H), 1.75 (m, 2H), 1.55 (m, 2H), 1.30 (m, 2H).

Example 14

N-({1-[4-(3-Methanesulfonyl-phenyl)-cyclohexyl]-azetidin-3-ylcarbamoyl}-methyl)-3-trifluoromethyl-benzamide

Step A 8-(3-Methylsulfanyl-phenyl)-1,4-dioxa-spiro[4.5]decan-8-ol

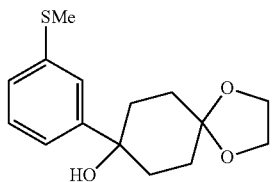 [SMILES: CSc1cccc(C2(O)CCC3(CC2)OCCO3)c1]

The title compound was prepared as a white solid from 1-bromo-3-methylsulfanyl-benzene (Aldrich) using the procedure described in Step A of Example 1.

$^1$H NMR (400 MHz, CDCl$_3$) δ 7.45 (s, 1H), 7.25 (d, J=4.5 Hz, 2H), 7.14 (t, J=5.2 Hz, 1H), 4.01 (m, 4H), 2.46 (s, 3H), 2.10 (m, 4H), 1.78 (d, J=8.2 Hz, 2H), 1.70 (d, J=8.2 Hz, 2H).

Step B

4-Hydroxy-4-(3-methylsulfanyl-phenyl)-cyclohexanone

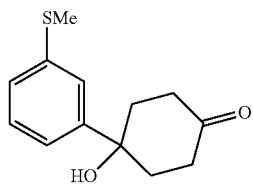 [SMILES: CSc1cccc(C2(O)CCC(=O)CC2)c1]

The title compound was prepared as a white solid from 8-(3-methylsulfanyl-phenyl)-1,4-dioxa-spiro[4.5]decan-8-ol (as prepared in the previous step) using the procedure described in Step B of Example 1.

$^1$H NMR (400 MHz, CDCl$_3$) δ 7.41 (s, 1H), 7.25 (m, 2H), 7.19 (d, J=7.0 Hz, 1H), 2.92 (m, 2H), 2.49 (s, 3H), 2.32 (m, 2H), 2.25 (m, 2H), 2.20 (m, 2H).

Step C 4-(3-Methanesulfonyl-phenyl)-cyclohex-3-enone

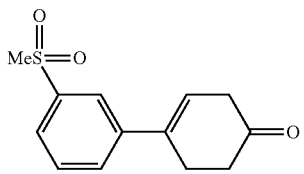

A solution of 4-hydroxy-4-(3-methylsulfanyl-phenyl)-cyclohexanone (as prepared in the previous step, 1.10 g, 4.66 mmol) in THF (10 mL) was treated with Burgess' reagent (1.20 g, 5.00 mmol) at room temperature overnight. The solvent was removed and the residue was partitioned between ethyl acetate and water. The organic layer was washed with brine, dried over anhydrous Na$_2$SO$_4$, filtered, concentrated to give a white solid. To this white solid in MeOH (5 mL) and water (5 mL) was added OXONE (Aldrich, 6.10 g, 10 mmol) at room temperature. The reaction mixture was stirred overnight and quenched with saturated NaHCO$_3$. The solvent was removed in vacuo and the residue was partitioned between ethyl acetate and water. The organic layer was washed with brine, dried over anhydrous Na$_2$SO$_4$, filtered, concentrated and purified by silica gel column on a CombiFlash® system using hexanes and ethyl acetate (from 10% ethyl acetate to 100% ethyl acetate) to afford the title compound as a white solid.

ESI-MS (m/z): Calcd. for C$_{13}$H$_{14}$O$_3$S, 250; found: 251 (M+H).

Step D

N-({1-[4-(3-Methanesulfonyl-phenyl)-cyclohex-3-enyl]-azetidin-3-ylcarbamoyl}-methyl)-3-trifluoromethyl-benzamide

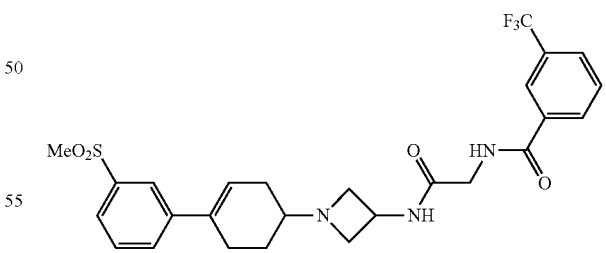

The title compound was prepared as a white solid from 4-(3-methanesulfonyl-phenyl)-cyclohex-3-enone (as prepared in the previous step) using the procedure described in Step C of Example 4.

$^1$H NMR (400 MHz, CDCl$_3$) δ 8.10 (s, 1H), 8.02 (d, J=6.0 Hz, 1H), 7.90 (s, 1H), 7.82 (d, J=6.2 Hz, 1H), 7.60 (t, J=6.2 Hz, 1H), 7.55 (d, J=6.1 Hz, 1H), 7.45 (t, J=6.2 Hz, 1H), 6.85 (d, J=6.0 Hz, 1H), 6.11 (m, 1H), 4.53 (m, 1H), 4.15 (d, J=3.5

Hz, 2H), 3.65 (t, J=6.5 Hz, 2H), 3.05 (s, 3H), 3.02 (t, J=6.5 Hz, 2H), 2.42 (m, 1H), 2.33 (m, 2H), 2.20 (m, 1H), 2.01 (m, 1H), 1.90 (m, 1H), 1.83 (m, 1H).

Step E

N-({1-[4-(3-Methanesulfonyl-phenyl)-cyclohexyl]-azetidin-3-ylcarbamoyl}-methyl)-3-trifluoromethyl-benzamide

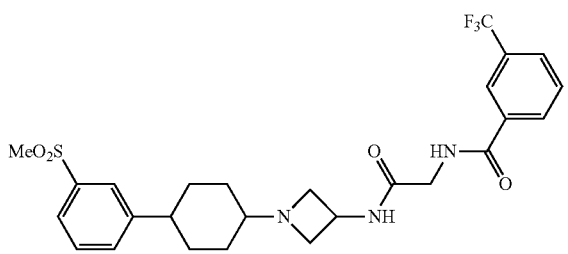 [SMILES: CS(=O)(=O)c1cccc(C2CCC(N3CC(NC(=O)CNC(=O)c4cccc(C(F)(F)F)c4)C3)CC2)c1]

The title compound was prepared as a white solid from N-({1-[4-(3-methanesulfonyl-phenyl)-cyclohex-3-enyl]-azetidin-3-ylcarbamoyl}-methyl)-3-trifluoromethyl-benzamide (as prepared in the previous step) using the procedure described in Step G of Example 1.

14a: Less Polar Fraction from Silica Gel Column $^1$H NMR (400 MHz, CDCl$_3$) δ 8.20 (s, 1H), 8.10 (d, J=6.2 Hz, 1H), 7.90 (s, 1H), 7.75 (m, 2H), 7.54 (m, 1H), 7.40 (m, 1H), 7.30 (s, 1H), 4.58 (m, 1H), 4.20 (d, J=3.5 Hz, 2H), 3.75 (s, br, 2H), 3.10 (s, 3H), 2.01 (m, 1H), 1.80 (m, 2H), 1.75~1.50 (m, 5H).

14b: More Polar Fraction from Silica Gel Column $^1$H NMR (400 MHz, CDCl$_3$) δ 8.18 (s, 1H), 8.05 (d, J=6.0 Hz, 1H), 7.85 (s, 1H), 7.76 (m, 2H), 7.55 (m, 2H), 7.42 (m, 1H), 5.51 (s, br, 1H), 4.55 (m, 1H), 4.20 (d, J=3.0 Hz, 2H), 3.68 (t, J=5.5 Hz, 2H), 3.11 (s, 3H), 3.05 (m, 2H), 1.98 (m, 4H), 1.80 (m, 2H), 1.55 (m, 2H).

Example 15

N-({1-[4-(4-Amino-phenyl)-cyclohexyl]-azetidin-3-ylcarbamoyl}-methyl)-3-trifluoromethyl-benzamide Step A

[4-(8-Hydroxy-1,4-dioxa-spiro[4.5]dec-8-yl)-phenyl]-carbamic acid tert-butyl ester

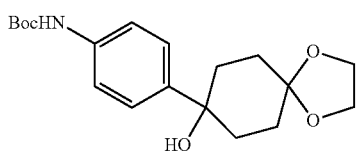 [SMILES: CC(C)(C)OC(=O)Nc1ccc(C2(O)CCC3(CC2)OCCO3)cc1]

The title compound was prepared as a white solid from (4-bromo-phenyl)-carbamic acid tert-butyl ester (Aldrich) using the procedure described in Step A of Example 1.

$^1$H NMR (400 MHz, CDCl$_3$) δ 7.42 (d, J=6.5 Hz, 2H), 7.30 (d, J=6.6 Hz, 2H), 3.98 (m, 4H), 2.12 (m, 4H), 1.80 (m, 2H), 1.65 (M, 2H), 1.51 (s, 9H).

Step B

[4-(4-Oxo-cyclohex-1-enyl)-phenyl]-carbamic acid tert-butyl ester

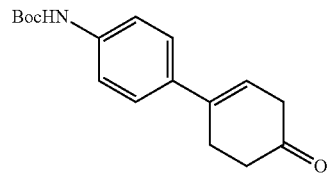 [SMILES: CC(C)(C)OC(=O)Nc1ccc(C2=CCC(=O)CC2)cc1]

The title compound was prepared as a white solid from [4-(8-hydroxy-1,4-dioxa-spiro[4.5]dec-8-yl)-phenyl]-carbamic acid tert-butyl ester (as prepared in the previous step) using the procedure described in Step B of Example 1 followed by dehydration of the alcohol using the procedure described in Step B of Example 5.

$^1$H NMR (400 MHz, CDCl$_3$) δ 7.35 (s, 4H), 6.51 (s, br, 1H), 6.03 9m, 1H), 3.08 (s, 2H), 2.90 (t, J=4.5 Hz, 2H), 2.64 (t, J=6.8 Hz, 2H), 1.48 (s, 9H).

Step C

[4-(4-Oxo-cyclohexyl)-phenyl]-carbamic acid tert-butyl ester

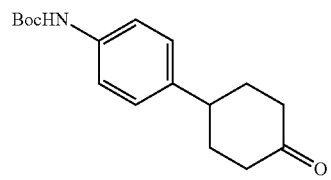 [SMILES: CC(C)(C)OC(=O)Nc1ccc(C2CCC(=O)CC2)cc1]

The title compound was prepared as a white solid from [4-(4-oxo-cyclohex-1-enyl)-phenyl]-carbamic acid tert-butyl ester (as prepared in the previous step) using the procedure described in Step C of Example 5.

ESI-MS (m/z): Calcd. for C$_{17}$H$_{23}$NO$_3$, 289; found: 290 (M+H).

Step D

{1-[4-(4-tert-Butoxycarbonylamino-phenyl)-cyclohexyl]-azetidin-3-yl}-carbamic acid tert-butyl ester

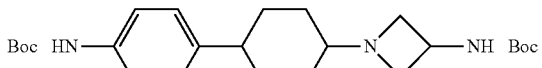

The title compound was prepared as a white solid from [4-(4-oxo-cyclohexyl)-phenyl]-carbamic acid tert-butyl ester (as prepared in the previous step) using the procedure described in Step D of Example 1.

Less polar fraction from silica gel column, ¹H NMR (400 MHz, CDCl₃) δ 7.25 (d, J=6.5 Hz, 2H), 7.14 (d, J=6.5 Hz, 2H), 6.38 (s, br, 1H), 4.88 (s, br, 1H), 4.25 (m, 1H), 3.55 (t, J=6.8 Hz, 2H), 2.72 (t, J=4.0 Hz, 2H), 2.42 (m, 1H), 1.85 (m, 4H), 1.63 (m, 4H), 1.51 (s, 9H), 1.43 (s, 9H).

More polar fraction from silica gel column, ¹H NMR (400 MHz, CDCl₃) δ 7.26 (d, J=6.8 Hz, 2H), 7.10 (d, J=6.6 Hz, 2H), 6.42 (s, br, 1H), 4.95 (s, br, 1H), 4.26 (m, 1H), 3.60 (t, J=6.5 Hz, 2H), 2.87 (s, br, 2H), 2.38 (m, 1H), 2.00 (m, 2H), 1.85 (m, 2H), 1.45 (s, 9H), 1.40 (s, 9H), 1.38 (m, 2H), 1.18 (m, 2H).

Step E

1-[4-(4-Amino-phenyl)-cyclohexyl]-azetidin-3-ylamine TFA Salt

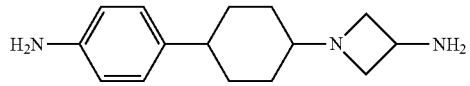 [SMILES: Nc1ccc(C2CCC(N3CC(N)C3)CC2)cc1]

The title compound was prepared as colorless oil from {1-[4-(4-tert-butoxycarbonylamino-phenyl)-cyclohexyl]-azetidin-3-yl}-carbamic acid tert-butyl ester (as prepared in the previous step, less polar fraction) using the procedure described in Step E of Example 1.

¹H NMR (400 MHz, CDCl₃) δ 7.01 (d, J=6.6 Hz, 2H), 6.60 (d, J=6.8 Hz, 2H), 3.60 (t, J=7.0 Hz, 2H), 3.55 (m, 1H), 2.50 (t, J=7.0 Hz, 2H), 2.40 (m, 1H), 1.80 (m, 2H), 1.65 (m, 2H), 1.55~1.30 (m, 4H).

Step F

N-({1-[4-(4-Amino-phenyl)-cyclohexyl]-azetidin-3-ylcarbamoyl}-methyl)-3-trifluoromethyl-benzamide

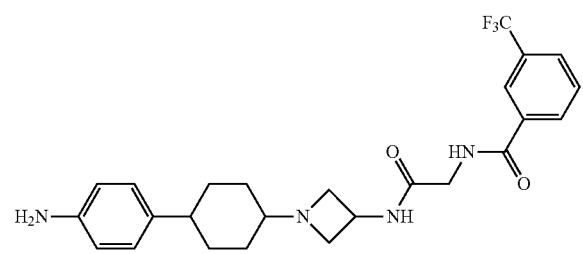 [SMILES: Nc1ccc(C2CCC(N3CC(NC(=O)CNC(=O)c4cccc(C(F)(F)F)c4)C3)CC2)cc1]

The title compound was prepared as a white solid from an EDCI coupling of 1-[4-(4-amino-phenyl)-cyclohexyl]-azetidin-3-ylamine TFA salt (as prepared in the previous step) and (3-trifluoromethyl-benzoylamino)-acetic acid using the procedure described in Step F of Example 1.

ESI-MS (m/z): Calcd. For $C_{25}H_{29}F_3N_4O_2$, 474; found: 475 (M+H).

Example 16, 17

N-({1-[4-(4-Methanesulfonylamino-phenyl)-cyclohexyl]-azetidin-3-ylcarbamoyl}-methyl)-3-trifluoromethyl-benzamide and N-({1-[4-(4,4-bis-Methanesulfonylamino-phenyl)-cyclohexyl]-azetidin-3-ylcarbamoyl}-methyl)-3-trifluoromethyl-benzamide

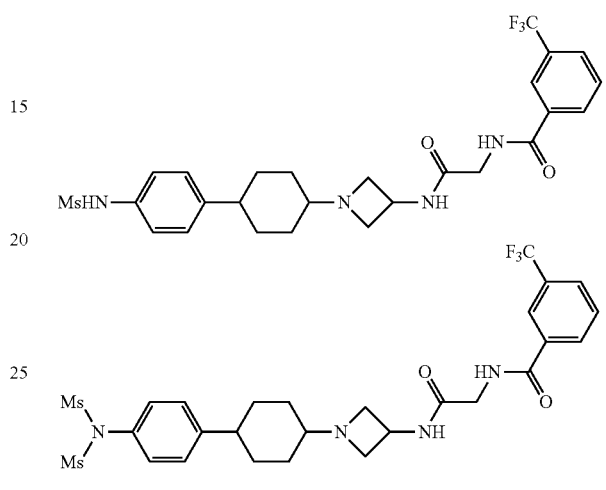

N-({1-[4-(4-Amino-phenyl)-cyclohexyl]-azetidin-3-ylcarbamoyl}-methyl)-3-trifluoromethyl-benzamide (as prepared in example 15, 450 mg, 0.95 mmol) in DCM (8 mL) was treated with TEA (200 µL, 1.42 mmol) followed by MsCl (Aldrich, 130 mg, 1.14 mmol) at 0° C. for 2 hours. The reaction was warmed to room temperature and partitioned between DCM and saturated NaHCO₃. The organic layer was separated and the aqueous layer was extracted 3 times with a chloroform/IPA "cocktail" (~3:1, v/v). The combined organic layers were dried over anhydrous Na₂SO₄, filtered and concentrated to give the crude product, which was then purified by a CombiFlash® system using ethyl acetate and 7N NH₃ in MeOH as eluent (from pure ethyl acetate to 5% 7N NH₃ in MeOH in ethyl acetate) to afford two title compounds as white solids: a less polar fraction, N-({1-[4-(4,4-bis-methanesulfonylamino-phenyl)-cyclohexyl]-azetidin-3-ylcarbamoyl}-methyl)-3-trifluoromethyl-benzamide; and a more polar isomer, N-({1-[4-(4-methane sulfonylamino-phenyl)-cyclohexyl]-azetidin-3-ylcarbamoyl}-methyl)-3-trifluoromethyl-benzamide.

16,

¹H NMR (400 MHz, CDCl₃) δ 8.25 (s, 1H), 8.10 (d, J=6.8 Hz, 1H), 7.80 (d, J=6.2 Hz, 1H), 7.65 (d, J=7.5 Hz, 1H), 7.60 (t, J=6.6 Hz, 1H), 7.36 (d, J=6.2 Hz, 1H), 7.10 (abq, J=9.5 Hz, 2H), 4.55 (m, 1H), 4.18 (d, J=3.5 Hz, 2H), 3.70 (t, J=6.8 Hz, 2H), 3.40 (s, 3H), 2.90 (t, J=6.6 Hz, 2H), 2.55 (m, 1H), 2.30 (m, 1H), 1.90~1.65 (4H), 1.50 (m, 4H).

17,

¹H NMR (400 MHz, CDCl₃) δ 8.15 (s, 1H), 8.05 (d, J=6.0 Hz, 1H), 7.75 (d, J=6.0 Hz, 1H), 7.60 (m, 1H), 7.54 (d, J=7.0 Hz, 1H), 7.25 (abq, J=9.5 Hz, 4H), 4.51 (m, 1H), 4.15 (d, J=5.0 Hz, 2H), 3.58 (t, J=6.6 Hz, 2H), 3.35 (s, 6H), 2.85 (s, br, 2H), 2.55 (m, 1H), 2.33 (s, br, 1H), 1.80 (m, 2H), 1.65 (m, 2H), 1.50 (m, 2H), 1.43 (m, 2H).

Example 18

N-[(1-{4-[4-(3-tert-Butyl-ureido)-phenyl]-cyclohexyl}-azetidin-3-ylcarbamoyl)-methyl]-3-trifluoromethyl-benzamide

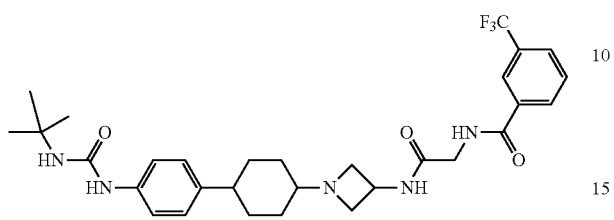

N-({1-[4-(4-Amino-phenyl)-cyclohexyl]-azetidin-3-ylcarbamoyl}-methyl)-3-trifluoromethyl-benzamide (as prepared in Example 15, 100 mg, 0.21 mmol) in DMF (2 mL) was treated with t-butyl-isocyanate (Aldrich, 25 mg, 0.25 mmol) at room temperature for 48 hours. The reaction mixture was directly purified on a silica gel column using a CombiFlash® system using ethyl acetate and 7N NH$_3$ in MeOH as eluent (from pure ethyl acetate to 5% 7N NH$_3$ in MeOH in ethyl acetate) to afford the title compound as a white solid.

$^1$H NMR (400 MHz, d$_4$-MeOH) δ 8.25 (s, 1H), 8.20 (d, J=6.8 Hz, 1H), 7.90 (d, J=6.5 Hz, 1H), 7.70 (d, J=6.8 Hz, 1H), 7.20 (abq, J=10.5 Hz, 4H), 4.48 (m, 1H), 4.05 (s, 2H), 3.65 (t, J=7.0 Hz, 2H), 2.95 (t, J=6.6 Hz, 2H), 2.55 (m, 1H), 2.40 (s, br, 1H), 1.95~1.65 (4H), 1.55 (m, 2H), 1.35 (s, 9H).

Example 19

3-Trifluoromethyl-N-({1-[4-(4-ureido-phenyl)-cyclohexyl]-azetidin-3-ylcarbamoyl}-methyl)-benzamide

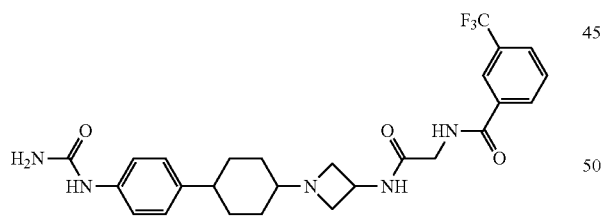

N-[(1-{4-[4-(3-tert-Butyl-ureido)-phenyl]-cyclohexyl}-azetidin-3-ylcarbamoyl)-methyl]-3-trifluoromethyl-benzamide (prepared as described in Example 18, 50 mg, 0.087 mmol) was treated with TFA (1 mL) at room temperature overnight. The reaction was quenched with saturated NaHCO$_3$. The reaction solution was extracted with a chloroform/IPA "cocktail" (~3:1, v/v). The organic layer was dried over anhydrous Na$_2$SO$_4$, filtered and concentrated to give the crude product, which was then purified by a CombiFlash® system using ethyl acetate and 7N NH$_3$ in MeOH as eluent (from pure ethyl acetate to 5% 7N NH$_3$ in MeOH in ethyl acetate) to afford two title compound as white solid.

$^1$H NMR (400 MHz, d$_4$-MeOH) δ 8.11 (s, 1H), 8.05 (d, J=6.5 Hz, 1H), 7.75 (d, J=6.0 Hz, 1H), 7.70 (d, J=7.5 Hz, 1H), 7.58 (t, J=6.5 Hz, 1H), 7.30 (d, J=6.0 Hz, 1H), 7.15 (abq, J=10.5 Hz, 2H), 4.45 (m, 1H), 3.95 (s, 2H), 3.55 (t, J=6.8 Hz, 2H), 2.85 (t, J=6.6 Hz, 2H), 2.35 (m, 1H), 1.80~1.55 (6H), 1.45 (m, 2H).

Example 20

N-({1-[4-(3H-Benzoimidazol-5-yl)-cyclohexyl]-azetidin-3-ylcarbamoyl}-methyl)-3-trifluoromethyl-benzamide

Step A 8-(3H-Benzoimidazol-5-yl)-1,4-dioxa-spiro[4.5]decan-8-ol

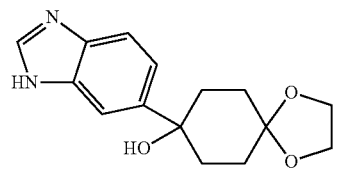 [SMILES: OC1(c2ccc3nc[nH]c3c2)CCC2(CC1)OCCO2]

The title compound was prepared as a white solid from 6-bromo-1H-benzoimidazole (Ryan Scientific) using the procedure described in Step A of Example 1.

$^1$H NMR (400 MHz, CDCl$_3$) δ 8.03 (s, 1H), 7.88 (s, 1H), 7.65 (d, J=6.8 Hz, 1H), 7.45 (d, J=6.5 Hz, 1H), 4.02 (s, 4H), 2.20 (m, 2H), 2.10 (m, 2H), 1.90 (d, J=6.8 Hz, 2H), 1.72 (m, 2H).

Step B 4-(3H-Benzoimidazol-5-yl)-4-hydroxy-cyclohexanone

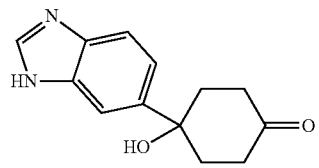 [SMILES: O=C1CCC(O)(c2ccc3nc[nH]c3c2)CC1]

The title compound was prepared as a white solid from 8-(3H-benzoimidazol-5-yl)-1,4-dioxa-spiro[4.5]decan-8-ol (as prepared in the previous step) using the procedure described in Step B of Example 1.

$^1$H NMR (400 MHz, CDCl$_3$) δ 8.05 (s, 1H), 7.80 (s, br, 1H), 7.36 (d, J=6.5 Hz, 1H), 7.25 (d, J=6.4 Hz, 1H), 7.01 (s, 1H), 2.98 (m, 2H), 2.35 (m, 2H), 2.28 (m, 2H), 2.20 (m, 2H).

Step C 4-(3H-Benzoimidazol-5-yl)-cyclohex-3-enone

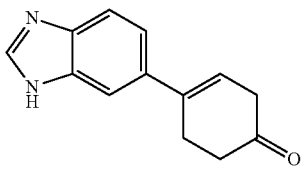 [SMILES: O=C1CC=C(c2ccc3nc[nH]c3c2)CC1]

The title compound was prepared as a white solid from 4-(3H-benzoimidazol-5-yl)-4-hydroxy-cyclohexanone (as prepared in the previous step) using the procedure described in Step C of Example 1.

$^1$H NMR (400 MHz, d$_4$-MeOH) δ 8.30 (s, 1H), 7.65 (d, J=6.8 Hz, 1H), 7.50 (d, J=6.5 Hz, 1H), 7.38 (s, 1H), 6.10 (m, 1H), 3.10 (s, br, 2H), 2.95 (d, J=6.1 Hz, 2H), 2.65 (t, J=6.5 Hz, 2H).

Step D

N-({1-[4-(3H-Benzoimidazol-5-yl)-cyclohexyl]-azetidin-3-ylcarbamoyl}-methyl)-3-trifluoromethyl-benzamide

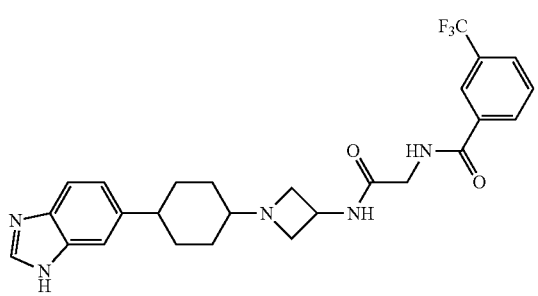 [SMILES: O=C(CNC(=O)c1cccc(C(F)(F)F)c1)NC1CN(C2CCC(c3ccc4nc[nH]c4c3)CC2)C1]

The title compound was prepared as a white solid by hydrogenation of 4-(3H-benzoimidazol-5-yl)-cyclohex-3-enone (as prepared in the previous step) using the procedure described in Step C of Example 5 followed by reductive amination of the ketone with N-(azetidin-3-ylcarbamoylmethyl)-3-trifluoromethyl-benzamide (as prepared in step B of Example 4) using the procedure described in Step C of Example 4.

20a: Less Polar Fraction from Silica Gel Column $^1$H NMR (400 MHz, d$_4$-MeOH) δ 8.15 (s, 1H), 8.10 (d, J=6.0 Hz, 1H), 7.85 (s, 1H), 7.72 (d, J=6.5 Hz, 1H), 7.63 (t, J=6.0 Hz, 1H), 7.55 (s, 1H), 7.40 (d, J=6.5 Hz, 1H), 7.12 (d, J=6.4 Hz, 1H), 4.45 (m, 1H), 3.98 (s, 2H), 3.60 (t, J=6.0 Hz, 2H), 2.95 (t, J=5.4 Hz, 2H), 2.69 (t, J=3.0 Hz, 2H), 2.48 (m, 1H), 1.85 (m, 4H), 1.48 (m, 4H).

20b: More Polar Fraction from Silica Gel Column $^1$H NMR (400 MHz, d$_4$-MeOH) δ 8.13 (s, 1H), 8.08 (d, J=6.3 Hz, 1H), 8.01 (s, 1H), 7.80 (d, J=6.5 Hz, 1H), 7.70 (s, 1H), 7.59 (d, J=6.1 Hz, 1H), 7.65 (d, J=5.5 Hz, 1H), 7.30 (d, J=6.4 Hz, 1H), 4.40 (m, 1H), 3.95 (s, 2H), 3.90 (t, J=5.0 Hz, 2H), 3.10 (t, J=4.5 Hz, 2H), 2.59 (m, 1H), 2.25 (m, 1H), 2.00 (m, 2H), 1.80 (m, 2H), 1.62 (m, 2H), 1.35 (m, 2H).

Example 21

N-({1-[4-(4-Cyanomethyl-phenyl)-cyclohexyl]-azetidin-3-ylcarbamoyl}-methyl)-3-trifluoromethyl-benzamide Step A

[4-(1,4-Dioxa-spiro[4.5]dec-7-en-8-yl)-phenyl]-acetonitrile

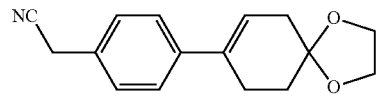

A solution of 8-(4,4,5,5-tetramethyl-[1,3,2]dioxaborolan-2-yl)-1,4-dioxa-spiro[4.5]dec-7-ene (as prepared by PCT Int. Appl. WO2006064189, 1.81 g, 6.80 mmol), 4-bromo-phenyl-acetonitrile (Aldrich, 1.40 g, 7.10 mmol), and tetrakis(triphenylphosphino)-palladium(0) (Aldrich, 350 mg, 0.34 mmol) in 1,4-dioxane (20 mL), was treated with 2M aqueous Na$_2$CO$_3$ (7 mL, 14.0 mmol), bubbled with argon for a few minutes, and heated to 100° C. under reflux condenser for 24 h. After cooling to ambient temperature, the reaction was diluted with water (30 mL) and extracted thrice with dichloromethane. The combined organic layers were washed with brine, dried over anhydrous Na$_2$SO$_4$, filtered, and the filtrate concentrated in vacuo to give a colorless oil. Purification by silica gel column, using a CombiFlash® system using hexanes and ethyl acetate as eluent (from pure hexanes to pure ethyl acetate), afforded the title compound as a white solid.

ESI-MS (m/z): Calcd. For C$_{16}$H$_{17}$NO$_2$, 255; found: 256 (M+H).

Step B

[4-(4-Oxo-cyclohex-1-enyl)-phenyl]-acetonitrile

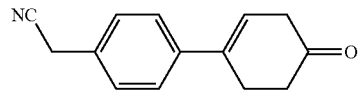

The title compound was prepared as a white solid from [4-(1,4-dioxa-spiro[4.5]dec-7-en-8-yl)-phenyl]-acetonitrile (as prepared in the previous step) using the procedure described in Step B of Example 1.

$^1$H NMR (400 MHz, CDCl$_3$) δ 7.28 (d, J=6.5 Hz, 2H), 7.12 (d, J=6.5 Hz, 2H), 5.98 (m, 1H), 3.12 (s, 2H), 2.88 (t, J=6.0 Hz, 2H), 2.64 (d, J=6.0 Hz, 2H).

Step C

[4-(4-Oxo-cyclohexyl)-phenyl]-acetonitrile

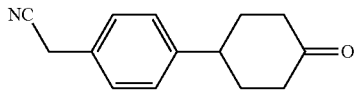

The title compound was prepared as a white solid from [4-(4-oxo-cyclohex-1-enyl)-phenyl]-acetonitrile (as prepared in the previous step) using the procedure described in Step C of Example 5.

ESI-MS (m/z): Calcd. For $C_{14}H_{15}NO$, 213; found: 214 (M+H).

Step D

N-({1-[4-(4-Cyanomethyl-phenyl)-cyclohexyl]-azetidin-3-ylcarbamoyl}-methyl)-3-trifluoromethyl-benzamide

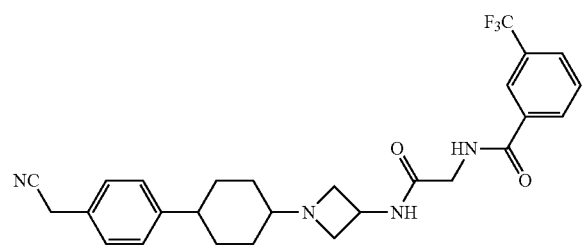 [SMILES: N#CCc1ccc(C2CCC(N3CC(NC(=O)CNC(=O)c4cccc(C(F)(F)F)c4)C3)CC2)cc1]

The title compound was prepared as a white solid by the reductive amination of [4-(4-oxo-cyclohexyl)-phenyl]-acetonitrile (as prepared in the previous step) and N-(azetidin-3-ylcarbamoylmethyl)-3-trifluoromethyl-benzamide (as prepared in step B of Example 4) using the procedure described in Step C of Example 4.

21a: Less Polar Fraction from Silica Gel Column $^{1}$H NMR (400 MHz, $d_4$-MeOH) δ 8.25 (s, 1H), 8.12 (d, J=6.5 Hz, 1H), 8.01 (s, 1H), 7.86 (d, J=6.2 Hz, 1H), 7.68 (t, J=6.8 Hz, 1H), 7.35~7.22 (m, 4H), 4.52 (m, 1H), 4.10 (s, 2H), 3.80 (s, 2H), 3.68 (t, J=6.6 Hz, 2H), 2.95 (t, J=6.9 Hz, 3H), 2.65 (m, 1H), 2.45 (s, br, 1H), 1.90 (m, 2H), 1.75 (m, 2H), 1.58 (m, 4H).

21b: More Polar Fraction from Silica Gel Column $^{1}$H NMR (400 MHz, $CDCl_3$) δ 8.15 (s, 1H), 8.05 (d, J=6.5 Hz, 1H), 7.80 (d, J=6.2 Hz, 1H), 7.71 (m, 1H), 7.61 (t, J=6.8 Hz, 1H), 7.30~7.20 (m, 4H), 4.52 (m, 1H), 4.15 (d, J=5.4 Hz, 2H), 3.71 (s, 2H), 3.68 (t, J=6.6 Hz, 2H), 3.01 (t, J=6.9 Hz, 3H), 2.45 (m, 1H), 2.30 (s, br, 1H), 2.05 (m, 2H), 1.90 (m, 2H), 1.45 (m, 2H), 1.15 (m, 2H).

Example 22

N-({1-[4-(4-Carbamimidoylmethyl-phenyl)-cyclohexyl]-azetidin-3-ylcarbamoyl}-methyl)-3-trifluoromethyl-benzamide

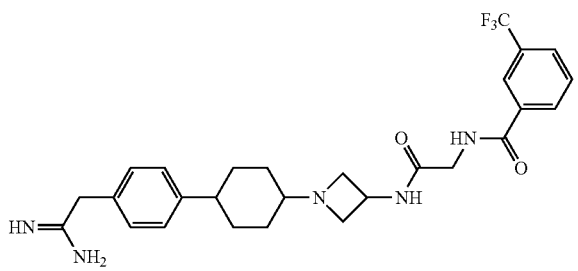 [SMILES: N=C(N)Cc1ccc(C2CCC(N3CC(NC(=O)CNC(=O)c4cccc(C(F)(F)F)c4)C3)CC2)cc1]

A solution of N-({1-[4-(4-cyanomethyl-phenyl)-cyclohexyl]-azetidin-3-ylcarbamoyl}-methyl)-3-trifluoromethyl-benzamide (as prepared in Example 21, 250 mg, 0.50 mmol) in dioxane (2 mL) and saturated $NH_4Cl$ (2 mL) was heated in a sealed tube to 120° C. overnight. The solvent was removed in vacuo and the residue was purified on a silica gel column using a CombiFlash® system using ethyl acetate and 7N $NH_3$ in MeOH as eluent (from pure ethyl acetate to 5% 7N $NH_3$ in MeOH in ethyl acetate) to afford the title compound as yellow solid.

$^{1}$H NMR (400 MHz, $d_4$-MeOH) δ 8.15 (s, 1H), 8.10 (d, J=6.5 Hz, 1H), 7.81 (d, J=6.0 Hz, 1H), 7.66 (d, J=6.5 Hz, 1H), 7.20 (m, 4H), 4.42 (m, 1H), 3.98 (s, 2H), 3.60 (t, J=6.8 Hz, 2H), 2.98 (t, J=6.6 Hz, 2H), 2.80 (m, 1H), 2.35 (m, 1H), 2.05 (m, 2H), 1.85 (m, 2H), 1.65 (m, 2H), 1.50 (m, 2H).

Example 23

N-[(1-{4-[4-(2H-Tetrazol-5-ylmethyl)-phenyl]-cyclohexyl}-azetidin-3-ylcarbamoyl)-methyl]-3-trifluoromethyl-benzamide

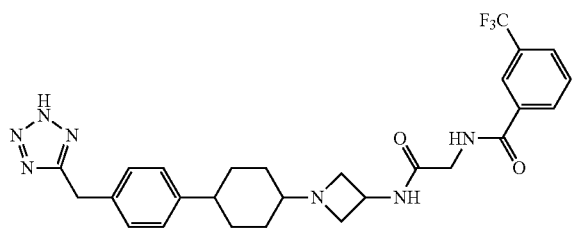 [SMILES: O=C(CNC(=O)c1cccc(C(F)(F)F)c1)NC1CN(C2CCC(c3ccc(Cc4nn[nH]n4)cc3)CC2)C1]

A solution of N-({1-[4-(4-cyanomethyl-phenyl)-cyclohexyl]-azetidin-3-ylcarbamoyl}-methyl)-3-trifluoromethyl-benzamide (as prepared in Example 21, 250 mg, 0.50 mmol), sodium azide (Aldrich, 160 mg, 2.50 mmol), and $Et_3N$ HCl salt (350 mg, 2.50 mmol) in dioxane (5 mL) was heated in a sealed tube to 120° C. overnight. The solvent was removed in vacuo and the residue was purified on a silica gel column using a CombiFlash® system using ethyl acetate and 7N $NH_3$ in MeOH as eluent (from pure ethyl acetate to 5% 7N $NH_3$ in MeOH in ethyl acetate) to afford the title compound as a white solid.

$^1$H NMR (400 MHz, d$_4$-MeOH) δ 8.11 (s, 1H), 8.02 (d, J=6.5 Hz, 1H), 7.78 (d, J=6.5 Hz, 1H), 7.55 (t, J=6.5 Hz, 1H), 7.20 (d, J=6.8 Hz, 2H), 7.08 (d, J=7.0 Hz, 2H), 4.15 (m, 1H), 3.95 (q, J=11.5 Hz, 2H), 3.75 (s, 2H), 3.42 (d, J=3.5 Hz, 2H), 2.80 (m, 1H), 2.65 (m, 2H), 2.45 (m, 1H), 1.86 (m, 4H), 1.55 (m, 4H).

Example 24

[4-(4-{3-[2-(3-Trifluoromethyl-benzoylamino)-acetylamino]-azetidin-1-yl}-cyclohexyl)-phenyl]-acetic acid ethyl ester

Step A

[4-(1,4-Dioxa-spiro[4.5]dec-7-en-8-yl)-phenyl]-acetic acid ethyl ester

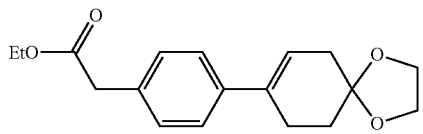 [SMILES: CCOC(=O)Cc1ccc(C2=CCC3(CC2)OCCO3)cc1]

The title compound was prepared as a white solid from (4-bromo-phenyl)-acetic acid ethyl ester (Aldrich) using the procedure described in Step A of Example 21.
ESI-MS (m/z): Calcd. for C$_{18}$H$_{22}$O$_4$, 302; found: 303 (M+H).

Step B

[4-(1,4-Dioxa-spiro[4.5]dec-8-yl)-phenyl]-acetic acid ethyl ester

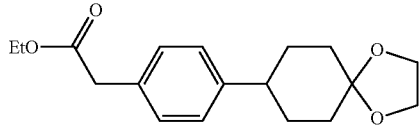

The title compound was prepared as a white solid from [4-(1,4-dioxa-spiro[4.5]dec-7-en-8-yl)-phenyl]-acetic acid ethyl ester (as prepared in the previous step) using the procedure described in Step C of Example 5.
$^1$H NMR (400 MHz, CDCl$_3$) δ 7.20 (m, 4H), 4.16 (q, J=6.5 Hz, 2H), 3.98 (s, 4H), 3.58 (s, 2H), 2.52 (m, 1H), 1.85 (m, 4H), 1.68 (m, 4H), 1.28 (t, J=7.0 Hz, 3H).

Step C

[4-(4-Oxo-cyclohexyl)-phenyl]-acetic acid ethyl ester

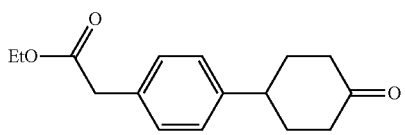

The title compound was prepared as a white solid from [4-(1,4-dioxa-spiro[4.5]dec-8-yl)-phenyl]-acetic acid ethyl ester (as prepared in the previous step) using the procedure described in Step B of Example 1.
$^1$H NMR (400 MHz, CDCl$_3$) δ 7.21 (q, J=6.5 Hz, 4H), 4.15 (q, J=6.0 Hz, 2H), 3.59 (s, 2H), 3.05 (m, 1H), 2.46 (m, 4H), 2.21 (m, 2H), 1.95 (m, 2H).

Step D

[4-(4-{3-[2-(3-Trifluoromethyl-benzoylamino)-acetylamino]-azetidin-1-yl}-cyclohexyl)-phenyl]-acetic acid ethyl ester

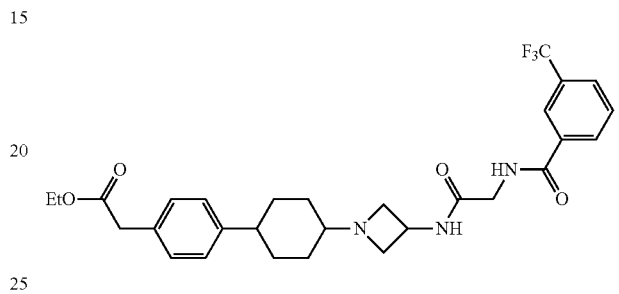

The title compound was prepared as a white solid by the reductive amination of [4-(4-oxo-cyclohexyl)-phenyl]-acetic acid ethyl ester (as prepared in the previous step) and N-(azetidin-3-ylcarbamoylmethyl)-3-trifluoromethyl-benzamide (as prepared in step B of Example 4) using the procedure described in Step C of Example 4.
24a: Less Polar Fraction from Silica Gel Column
$^1$H NMR (400 MHz, CDCl$_3$) δ 8.20 (s, 1H), 8.12 (d, J=6.5 Hz, 1H), 7.90 (m, 1H), 7.76 (d, J=6.2 Hz, 1H), 7.55 (t, J=6.8 Hz, 1H), 7.35~7.15 (abq, J=9.5, 5.0 Hz, 4H), 4.68 (m, 1H), 4.15 (m, 2H), 4.10 (q, J=7.0 Hz, 2H), 3.90 (t, J=6.6 Hz, 2H), 3.05 (t, J=4.5 Hz, 3H), 2.91 (s, 1H), 2.65 (m, 1H), 1.90 (m, 2H), 1.75 (m, 2H), 1.58 (m, 4H), 1.32 (t, J=7.5 Hz, 3H).
24b: More Polar Fraction from Silica Gel Column
$^1$H NMR (400 MHz, CDCl$_3$) δ 8.21 (s, 1H), 8.10 (d, J=6.5 Hz, 1H), 7.90 (d, J=6.2 Hz, 1H), 7.75 (m, 1H), 7.59 (t, J=6.8 Hz, 1H), 7.25~7.05 (abq, J=9.0, 4.5 Hz, 4H), 4.65 (m, 1H), 4.18 (d, J=5.4 Hz, 2H), 4.15 (q, J=6.2 Hz, 2H), 3.75 (t, J=6.6 Hz, 2H), 3.10 (t, J=6.9 Hz, 3H), 2.65 (m, 1H), 2.35 (s, br, 1H), 2.05 (m, 2H), 1.90 (m, 2H), 1.45 (m, 2H), 1.30 (t, J=6.5 Hz, 3H), 1.25 (m, 2H).

Example 25

[4-(4-{3-[2-(3-Trifluoromethyl-benzoylamino)-acetylamino]-azetidin-1-yl}-cyclohexyl)-phenyl]-acetic acid

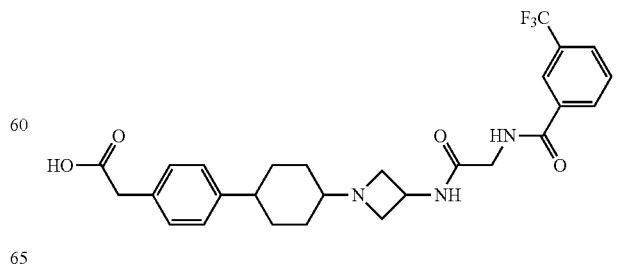

The title compound was prepared as a white solid by hydrolysis of [4-(4-{3-[2-(3-trifluoromethyl-benzoylamino)-acetylamino]-azetidin-1-yl}-cyclohexyl)-phenyl]-acetic acid ethyl ester (as prepared in Example 24, less polar fraction) using the procedure described in Example 10.

$^1$H NMR (400 MHz, d$_4$-MeOH) δ 8.25 (s, 1H), 8.15 (d, J=6.5 Hz, 1H), 7.89 (d, J=6.0 Hz, 1H), 7.72 (t, J=7.2 Hz, 1H), 7.18 (abq, J=10.5, 5.0 Hz, 4H), 4.60 (m, 1H), 4.10 (s, 2H), 3.98 (t, J=5.6 Hz, 2H), 3.55 (m, 2H), 3.50 (s, 2H), 2.85 (s, 1H), 2.55 (m, 1H), 1.80 (m, 4H), 1.65 (m, 4H).

Example 26

N-({1-[4-(4-Carbamoylmethyl-phenyl)-cyclohexyl]-azetidin-3-ylcarbamoyl}-methyl)-3-trifluoromethyl-benzamide

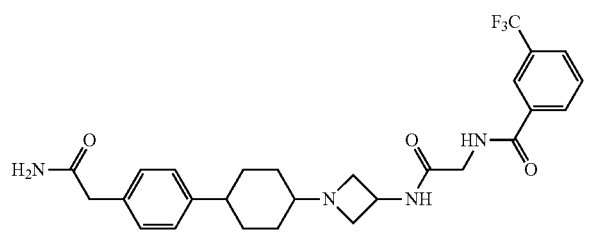 [SMILES: NC(=O)Cc1ccc(C2CCC(N3CC(NC(=O)CNC(=O)c4cccc(C(F)(F)F)c4)C3)CC2)cc1]

A solution of [4-(4-{3-[2-(3-trifluoromethyl-benzoylamino)-acetylamino]-azetidin-1-yl}-cyclohexyl)-phenyl]-acetic acid (as prepared in Example 25, 450 mg, 0.87 mmol), EDCI (240 mg, 1.25 mmol), HOBT (130 mg, 0.96 mmol) and TEA (610 μL, 4.35 mmol) in DCM (10 mL) was treated with 2N NH$_3$ in dioxane (5 mL) at room temperature overnight. The solvent was removed in vacuo and the residue was purified by a CombiFlash® system using ethyl acetate and 7N NH$_3$ in MeOH as eluent (from pure ethyl acetate to 5% 7N NH$_3$ in MeOH in ethyl acetate) to afford the two title compound as white solids.

$^1$H NMR (400 MHz, d$_4$-MeOH) δ 8.11 (s, 1H), 8.05 (d, J=6.5 Hz, 1H), 7.75 (d, J=6.0 Hz, 1H), 7.60 (d, J=6.5 Hz, 1H), 7.10 (s, 4H), 4.35 (m, 1H), 3.95 (s, 2H), 3.58 (t, J=6.8 Hz, 2H), 3.05 (t, J=6.6 Hz, 2H), 2.75 (m, 1H), 2.45 (m, 1H), 2.20 (m, 2H), 1.80 (m, 2H), 1.65 (m, 2H), 1.45 (m, 2H).

Example 27

N-({1-[4-(4-Cyano-phenyl)-cyclohexyl]-azetidin-3-ylcarbamoyl}-methyl)-3-trifluoromethyl-benzamide Step A 4-(1,4-Dioxa-spiro[4.5]dec-7-en-8-yl)-benzonitrile

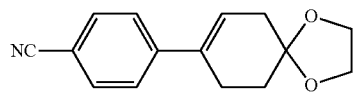

The title compound was prepared as a white solid from 4-bromophenylnitrile (Aldrich) using the procedure described in Step A of Example 21.

ESI-MS (m/z): Calcd. For C$_{15}$H$_{15}$NO$_2$, 241; found: 242 (M+H).

Step B 4-(1,4-Dioxa-spiro[4.5]dec-8-yl)-benzonitrile

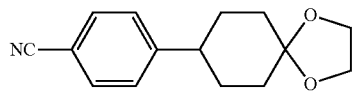

The title compound was prepared as a white solid from 4-(1,4-dioxa-spiro[4.5]dec-7-en-8-yl)-benzonitrile (as prepared in the previous step) using the procedure described in Step C of Example 5.

ESI-MS (m/z): Calcd. For C$_{15}$H$_{17}$NO$_2$, 243; found: 244 (M+H).

Step C 4-(4-Oxo-cyclohexyl)-benzonitrile

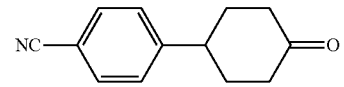 [SMILES: N#Cc1ccc(C2CCC(=O)CC2)cc1]

The title compound was prepared as a white solid from 4-(1,4-dioxa-spiro[4.5]dec-8-yl)-benzonitrile (as prepared in the previous step) using the procedure described in Step B of Example 1.

$^1$H NMR (400 MHz, CDCl$_3$) δ 7.75 (d, J=6.8 Hz, 2H), 7.34 (d, J=6.8 Hz, 2H), 3.10 (m, 1H), 2.58 (m, 4H), 2.20 (m, 2H), 1.95 (m, 2H).

Step D

N-({1-[4-(4-Cyano-phenyl)-cyclohexyl]-azetidin-3-ylcarbamoyl}-methyl)-3-trifluoromethyl-benzamide

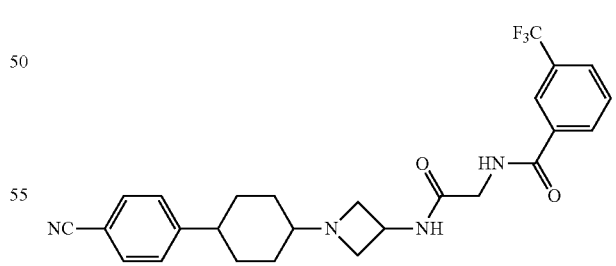

The title compound was prepared as a white solid by the reductive amination of 4-(4-oxo-cyclohexyl)-benzonitrile and N-(azetidin-3-ylcarbamoylmethyl)-3-trifluoromethyl-benzamide (as prepared in step B of Example 4) using the procedure described in Step C of Example 4.

$^1$H NMR (400 MHz, d$_4$-MeOH) δ 8.21 (s, 1H), 8.15 (d, J=6.5 Hz, 1H), 7.85 (d, J=6.0 Hz, 1H), 7.70 (t, J=7.0 Hz, 1H), 7.58 (d, J=6.5 Hz, 2H), 7.42 (d, J=6.0 Hz, 2H), 4.48 (m, 1H), 4.05 (s, 2H), 3.65 (t, J=6.8 Hz, 2H), 2.95 (t, J=6.6 Hz, 2H), 2.65 (m, 1H), 2.42 (s, 1H), 1.95 (m, 2H), 1.90 (m, 2H), 1.65 (m, 4H).

Example 28

N-[(1-{4-[4-(2H-Tetrazol-5-yl)-phenyl]-cyclohexyl}-azetidin-3-ylcarbamoyl)-methyl]-3-trifluoromethyl-benzamide

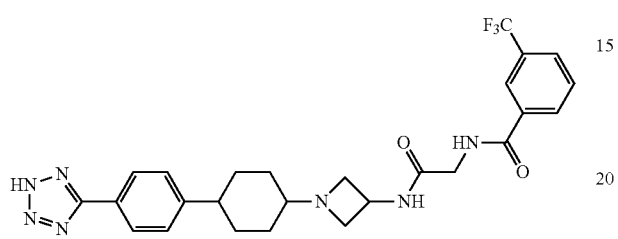

The title compound was prepared as a white solid from N-({1-[4-(4-cyano-phenyl)-cyclohexyl]-azetidin-3-ylcarbamoyl}-methyl)-3-trifluoromethyl-benzamide (as prepared in Example 27) using the procedure described in Example 23.

$^1$H NMR (400 MHz, d$_4$-MeOH) δ 8.20 (s, 1H), 8.15 (d, J=6.5 Hz, 1H), 7.75 (d, J=6.0 Hz, 1H), 7.70 (t, J=7.0 Hz, 1H), 7.58 (d, J=6.5 Hz, 2H), 7.45 (d, J=6.0 Hz, 2H), 4.24 (m, 1H), 4.05 (m, 1H), 4.06 (q, J=9.0 Hz, 2H), 3.55 (t, J=6.8 Hz, 2H), 2.90 (s, 1H), 2.80 (t, J=6.6 Hz, 2H), 2.65 (m, 2H), 1.95 (m, 4H), 1.65 (m, 4H).

Example 29

N-({1-[4-(4-Methanesulfonyl-phenyl)-cyclohexyl]-azetidin-3-ylcarbamoyl}-methyl)-3-trifluoromethyl-benzamide

Step A 8-(4-Methylsulfanyl-phenyl)-1,4-dioxa-spiro[4.5]decan-8-ol

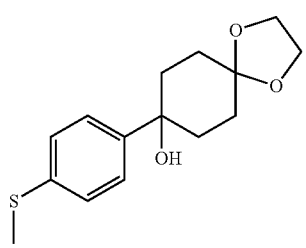 [SMILES: CSc1ccc(C2(O)CCC3(CC2)OCCO3)cc1]

The title compound was prepared as a white solid from 4-bromo-1-methylsulfanyl-benzene (Aldrich) using the procedure described in Step A of Example 1.

$^1$H NMR(CHLOROFORM-d) δ: 7.45 (d, J=8.6 Hz, 2H), 7.24-7.29 (m, 2H), 7.23 (s, 1H), 3.99 (dd, J=4.8, 3.3 Hz, 4H), 2.48 (s, 3H), 2.05-2.21 (m, 4H), 1.80 (d, J=11.6 Hz, 2H), 1.69 (d, J=11.1 Hz, 2H).

Step B 4-(4-Methylsulfanyl-phenyl)-cyclohex-3-enone

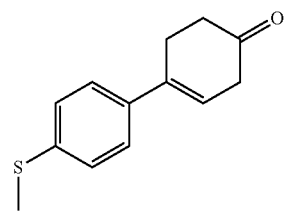

De-protection followed by dehydration occurred when 8-(4-methylsulfanyl-phenyl)-1,4-dioxa-spiro[4.5]decan-8-ol (as prepared in the previous step) was subjected to the reaction conditions described in Step B of Example 1. The title compound was prepared as a white solid.

$^1$H NMR(CHLOROFORM-d) δ: 7.32 (d, J=8.6 Hz, 2H), 7.22 (d, J=8.8 Hz, 2H), 6.02-6.09 (m, 1H), 3.00-3.09 (m, 2H), 2.81-2.91 (m, 2H), 2.59-2.69 (m, 2H), 2.48 (s, 3H).

Step C

N-({1-[4-(4-Methylsulfanyl-phenyl)-cyclohex-3-enyl]-azetidin-3-ylcarbamoyl}-methyl)-3-trifluoromethyl-benzamide

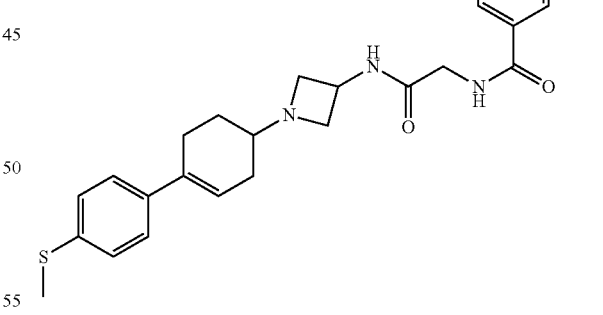

The title compound was prepared as a white solid by the reductive amination of 4-(4-methylsulfanyl-phenyl)-cyclohex-3-enone (as prepared in the previous step) and N-(azetidin-3-ylcarbamoylmethyl)-3-trifluoromethyl-benzamide (as prepared in step B of Example 4) using the procedure described in Step C of Example 4.

$^1$H NMR(CHLOROFORM-d) δ: 8.12 (s, 1H), 8.01 (d, J=7.8 Hz, 1H), 7.77 (d, J=7.6 Hz, 1H), 7.56 (t, J=7.8 Hz, 1H), 7.25-7.32 (m, 2H), 7.17-7.23 (m, 2H), 5.98 (br. s., 1H), 4.57 (t, J=6.1 Hz, 1H), 4.17 (m, 2H), 3.66 (d, J=8.1 Hz, 2H), 2.98-3.06 (m, 2H), 2.42-2.52 (m, 3H), 2.23-2.42 (m, 2H), 1.92 (br. s., 2H), 1.75-1.89 (m, 2H), 1.36-1.51 (m, 2H).

Step D

N-({1-[4-(4-Methanesulfonyl-phenyl)-cyclohex-3-enyl]-azetidin-3-ylcarbamoyl}-methyl)-3-trifluoromethyl-benzamide

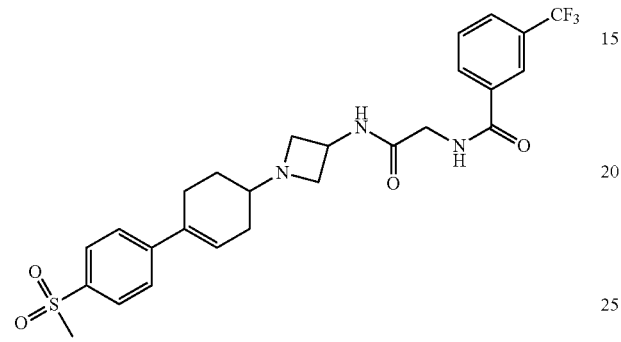

The title compound was prepared as a white solid from the OXONE oxidation of N-({1-[4-(4-methylsulfanyl-phenyl)-cyclohex-3-enyl]-azetidin-3-ylcarbamoyl}-methyl)-3-trifluoromethyl-benzamide (as prepared in the previous step) using the procedure described in Step C of Example 14.

ESI-MS (m/z): Calcd. For $C_{26}H_{28}F_3N_3O_4S$: 535.22; found: 536.2 (M+H).

Step E

N-({1-[4-(4-Methanesulfonyl-phenyl)-cyclohexyl]-azetidin-3-ylcarbamoyl}-methyl)-3-trifluoromethyl-benzamide

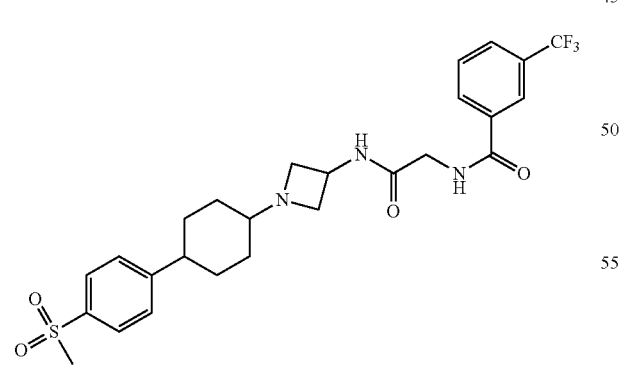

The title compound was prepared as a white solid from N-({1-[4-(4-methanesulfonyl-phenyl)-cyclohex-3-enyl]-azetidin-3-ylcarbamoyl}-methyl)-3-trifluoromethyl-benzamide (as prepared in the previous step) using the procedure described in Step G of Example 1.

$^1$H NMR(CHLOROFORM-d) δ: 8.12 (s, 1H), 8.01 (d, J=8.1 Hz, 1H), 7.82-7.89 (m, J=8.3 Hz, 1H), 7.79 (d, J=7.8 Hz, 1H), 7.59 (t, J=7.8 Hz, 1H), 7.48-7.54 (m, J=8.3 Hz, 2H), 7.42 (t, J=4.9 Hz, 1H), 4.42-4.59 (m, 1H), 4.16 (d, J=5.1 Hz, 2H), 3.95 (br. s., 1H), 3.66-3.76 (m, 2H), 3.04 (s, 1H), 3.03 (s, 3H), 2.74 (d, J=12.6 Hz, 2H), 2.67 (br. s., 2H), 1.99-2.07 (m, 2H), 1.92 (d, J=13.4 Hz, 4H).

Example 30

N-{[1-(4-Hydroxy-4-phenyl-cyclohexyl)-azetidin-3-ylcarbamoyl]-methyl}-3-trifluoromethyl-benzamide

Step A

8-Phenyl-1,4-dioxa-spiro[4.5]decan-8-ol

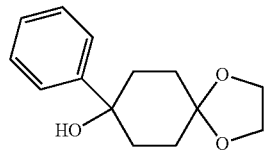 [SMILES: OC1(c2ccccc2)CCC2(CC1)OCCO2]

The title compound was prepared as a white solid from 1-bromo-benzene and 1,4-dioxa-spiro[4.5]decan-8-one using the procedure described in Step A of Example 1.

$^1$H NMR (400 MHz, CDCl$_3$) δ 7.52 (d, J=6.6 Hz, 2H), 7.35 (t, J=7.0 Hz, 2H), 7.28 (t, J=6.8 Hz, 2H), 4.02 (m, 4H), 2.10 (m, 2H), 1.80 (d, J=8.2 Hz, 2H), 1.68 (d, J=8.2 Hz, 2H), 1.56 (d, J=9.5 Hz, 2H).

Step B

4-Hydroxy-4-phenyl-cyclohexanone

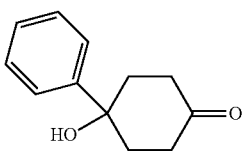 [SMILES: O=C1CCC(O)(c2ccccc2)CC1]

The title compound was prepared as a white solid from 8-phenyl-1,4-dioxa-spiro[4.5]decan-8-ol (as prepared in the previous step) using the procedure described in Step B of Example 1.

¹H NMR (400 MHz, CDCl₃) δ 7.52 (d, J=6.6 Hz, 2H), 7.42 (t, J=6.5 Hz, 2H), 7.30 (d, J=6.3 Hz, 1H), 2.34 (m, 4H), 2.18 (m, 4H).

Step C

N-{[1-(4-Hydroxy-4-phenyl-cyclohexyl)-azetidin-3-ylcarbamoyl]-methyl}-3-trifluoromethyl-benzamide

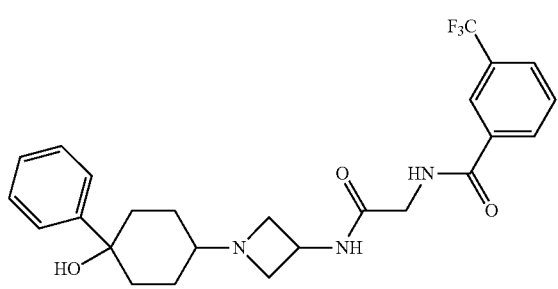

The title compound was prepared as a white solid by reductive amination of 4-hydroxy-4-phenyl-cyclohexanone (as prepared in the previous step) and N-(azetidin-3-ylcarbamoylmethyl)-3-trifluoromethyl-benzamide (as prepared in step B of Example 4) using the procedure described in Step C of Example 4.

30a: Less Polar Fraction from Silica Gel Column
¹H NMR (400 MHz, CDCl₃) δ 8.10 (s, 1H), 8.01 (d, J=6.5 Hz, 1H), 7.79 (d, J=6.4 Hz, 1H), 7.58 (t, J=6.8 Hz, 1H), 7.50 (d, J=6.0 Hz, 2H), 7.45 (m, 1H), 7.35 (m, 2H), 7.26 (d, J=5.8 Hz, 1H), 7.22 (m, 1H), 6.96 (d, J=6.8 Hz, 1H), 4.53 (m, 1H), 4.15 (d, J=3.2 Hz, 2H), 3.70 (t, J=7.2 Hz, 2H), 2.89 (t, J=7.5 Hz, 2H), 2.25 (m, 2H), 1.80 (m, 2H), 1.55 (m, 2H), 1.40 (m, 2H).

30b: More Polar Fraction from Silica Gel Column
¹H NMR (400 MHz, CDCl₃) δ 8.11 (s, 1H), 8.01 (d, J=6.6 Hz, 1H), 7.78 (d, J=6.5 Hz, 1H), 7.61 (m, 1H), 7.52 (m, 3H), 7.30 (t, J=6.0 Hz, 3H), 7.22 (m, 3H), 4.52 (m, 1H), 4.20 (d, J=3.2 Hz, 2H), 3.60 (t, J=7.0 Hz, 2H), 2.87 (t, J=7.50 Hz, 2H), 2.30 (s, 2H), 2.22 (m, 2H), 1.80 (m, 2H), 1.50 (m, 2H), 1.40 (m, 2H).

Example 31

N-{[1-(4-Benzo[1,3]dioxol-5-yl-4-hydroxy-cyclohexyl)-azetidin-3-ylcarbamoyl]-methyl}-3-trifluoromethyl-benzamide

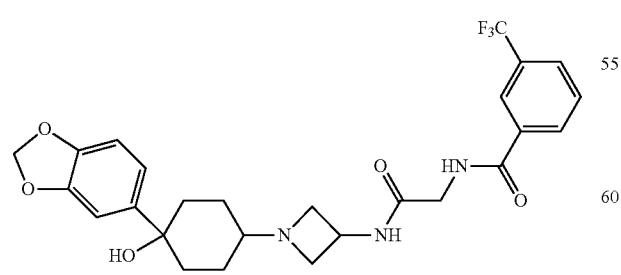

The title compound was prepared as a white solid by reductive amination of 4-benzo[1,3]dioxol-5-yl-4-hydroxy-cyclohexanone (as prepared in Example 1, Step B) and N-(azetidin-3-ylcarbamoylmethyl)-3-trifluoromethyl-benzamide (as prepared in step B of Example 4) using the procedure described in Step C of Example 4.

31a: Less Polar Fraction from Silica Gel Column
¹H NMR (400 MHz, CDCl₃) δ 8.11 (s, 1H), 8.02 (d, J=6.8 Hz, 1H), 7.80 (d, J=7.0 Hz, 2H), 7.58 (t, J=6.8 Hz, 1H), 7.45 (m, 1H), 7.01 9s, 1H), 6.92 (d, J=6.5 Hz, 1H), 6.88 (m, 1H), 6.75 (d, J=6.2 Hz, 1H), 5.92 (s, 2H), 4.53 (m, 1H), 4.18 (d, J=3.5 Hz, 2H), 3.60 (t, J=7.0 Hz, 2H), 2.95 (t, J=7.0 Hz, 2H), 2.32 (s, br, 1H), 2.20 (m, 1H), 1.85 (m, 4H), 1.60 (m, 2H), 1.42 (m, 2H).

31b: More Polar Fraction from Silica Gel Column
¹H NMR (400 MHz, CDCl₃) δ 8.30 (s, br, 1H), 8.12 (s, 1H), 8.05 (d, J=6.5 Hz, 1H), 7.80 (d, J=6.6 Hz, 1H), 7.58 (t, J=6.8 Hz, 1H), 7.50 (m, 1H), 7.02 (s, 1H), 6.95 (d, J=6.8 Hz, 1H), 6.85 (s, 1H), 5.92 (s, 2H), 4.57 (m, 1H), 4.20 (d, J=4.6 Hz, 2H), 3.75 (t, J=7.5 Hz, 2H), 3.38 (t, J=7.5 Hz, 2H), 2.38 (m, 1H), 1.95 (m, 2H), 1.75 (m, 4H), 1.60 (m, 2H).

Example 32

N-({1-[4-(2,3-Dihydro-benzo[1,4]dioxin-6-yl)-4-hydroxy-cyclohexyl]-azetidin-3-ylcarbamoyl}-methyl)-3-trifluoromethyl-benzamide Step A 8-(2,3-Dihydro-benzo[1,4]dioxin-6-yl)-1,4-dioxa-spiro[4.5]decan-8-ol

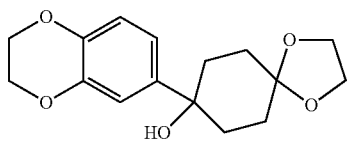 [SMILES: OC1(c2ccc3c(c2)OCCO3)CCC2(CC1)OCCO2]

The title compound was prepared as a white solid from and 1,4-dioxa-spiro[4.5]decan-8-one (Aldrich) using the procedure described in Step A of Example 1.

¹H NMR (400 MHz, CDCl₃) δ 7.05 (s, 1H), 6.95 (d, J=7.1 Hz, 1H), 6.80 (d, J=7.0 Hz, 1H), 4.22 (s, 4H), 4.00 (m, 4H), 2.10 (m, 4H), 1.80 (m, 2H), 1.65 (d, J=7.5 Hz, 2H).

Step B 4-(2,3-Dihydro-benzo[1,4]dioxin-6-yl)-4-hydroxy-cyclohexanone

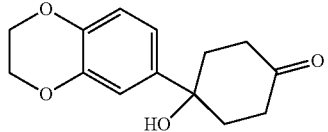 [SMILES: O=C1CCC(O)(c2ccc3c(c2)OCCO3)CC1]

The title compound was prepared as a white solid from 8-(2,3-dihydro-benzo[1,4]dioxin-6-yl)-1,4-dioxa-spiro[4.5]decan-8-ol (as prepared in the previous step) using the procedure described in Step B of Example 1.

¹H NMR (400 MHz, CDCl₃) δ 7.01 (s, 1H), 6.98 (d, J=6.8 Hz, 1H), 6.85 (d, J=6.5 Hz, 1H), 4.28 (s, 4H), 2.90 (m, 2H), 2.30 (m, 2H), 2.25 (m, 2H), 2.15 (m, 2H).

Step C

N-({1-[4-(2,3-Dihydro-benzo[1,4]dioxin-6-yl)-4-hydroxy-cyclohexyl]-azetidin-3-ylcarbamoyl}-methyl)-3-trifluoromethyl-benzamide

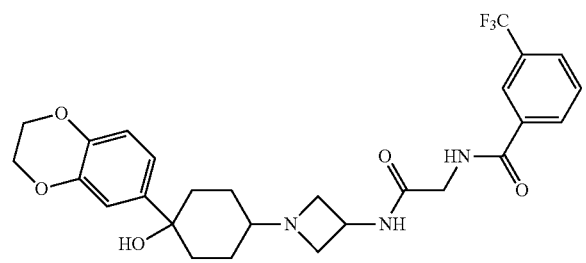 [SMILES: O=C(CNC(=O)c1cccc(C(F)(F)F)c1)NC1CN(C2CCC(O)(c3ccc4c(c3)OCCO4)CC2)C1]

The title compound was prepared as a white solid by reductive amination of 4-(2,3-dihydro-benzo[1,4]dioxin-6-yl)-4-hydroxy-cyclohexanone (as prepared in the previous step) and N-(azetidin-3-ylcarbamoylmethyl)-3-trifluoromethyl-benzamide (as prepared in step B of Example 4) using the procedure described in Step C of Example 4.

32a: Less Polar Isomer

¹H NMR (400 MHz, d₄-MeOH) δ 8.15 (s, 1H), 8.07 (d, J=6.5 Hz, 1H), 7.78 (d, J=6.4 Hz, 1H), 7.59 (t, J=6.5 Hz, 1H), 6.90 (s, 1H), 6.88 (d, J=7.0 Hz, 2H), 6.66 (d, J=7.0 Hz, 1H), 4.35 (m, 1H), 4.12 (s, 4H), 3.95 (s, 2H), 3.70 (t, J=6.0 Hz, 2H), 3.12 (d, J=6.0 Hz, 2H), 2.45 (m, 1H), 2.16 (m, 2H), 1.85 (m, 2H), 1.55 (m, 2H), 1.30 (m, 2H).

32b: More Polar Isomer

¹H NMR (400 MHz, d₄-MeOH) δ 8.25 (s, 1H), 8.16 (d, J=6.0 Hz, 1H), 7.90 (d, J=6.0 Hz, 1H), 7.72 (t, J=6.0 Hz, 1H), 6.95 (s, 1H), 6.90 (d, J=6.0 Hz, 2H), 6.76 (t, J=6.5 Hz, 1H), 4.50 (m, 1H), 4.21 (s, 4H), 4.08 (s, 2H), 4.05 (t, J=6.0 Hz, 2H), 3.65 (d, J=6.0 Hz, 2H), 2.75 (m, 1H), 1.90 (m, 4H), 1.65 (m, 2H).

Example 33

N-({1-[4-(2,3-Dihydro-benzofuran-6-yl)-4-hydroxy-cyclohexyl]-azetidin-3-ylcarbamoyl}-methyl)-3-trifluoromethyl-benzamide

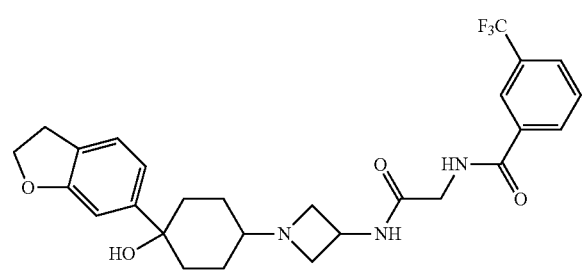 [SMILES: O=C(CNC(=O)c1cccc(C(F)(F)F)c1)NC1CN(C2CCC(O)(c3ccc4c(c3)OCC4)CC2)C1]

The title compound was prepared as a white solid by reductive amination of 4-(2,3-dihydro-benzofuran-6-yl)-4-hydroxy-cyclohexanone (as prepared in Example 3, Step B) and N-(azetidin-3-ylcarbamoylmethyl)-3-trifluoromethyl-benzamide (as prepared in step B of Example 4) using the procedure described in Step C of Example 4.

33a: Less Polar Fraction from Silica Gel Column

¹H NMR (400 MHz, CDCl₃) δ 8.11 (s, 1H), 8.02 (d, J=6.8 Hz, 1H), 7.75 (m, 2H), 7.55 (t, J=6.8 Hz, 1H), 7.35 (d, J=7.0 Hz, 1H), 7.23 (d, J=6.5 Hz, 1H), 6.72 (d, J=6.5 Hz, 1H), 4.55 (t, J=7.5 Hz, 2H), 4.53 (m, 1H), 4.20 (d, J=3.5 Hz, 2H), 3.60 (t, J=7.0 Hz, 2H), 3.22 (t, J=7.0 Hz, 2H), 2.85 (t, J=7.0 Hz, 2H), 2.25 (m, 3H), 1.85 (m, 2H), 1.60 (m, 2H), 1.35 (m, 2H).

33b: More Polar Fraction from Silica Gel Column

¹H NMR (400 MHz, CDCl₃) δ 8.12 (s, 1H), 8.05 (d, J=6.5 Hz, 1H), 7.80 (d, J=6.6 Hz, 1H), 7.58 (t, J=6.8 Hz, 1H), 7.50 (m, 1H), 7.48 (d, J=5.6 hz, 1H), 7.35 9s, 1H), 7.20 (d, J=6.2 Hz, 1H), 6.72 (d, J=6.8 Hz, 1H), 4.55 (t, J=7.0 Hz, 2H), 4.52 (m, 1H), 4.20 (d, J=4.6 Hz, 2H), 3.64 (t, J=7.5 Hz, 2H), 3.21 9t, J=7.0 Hz, 2H), 3.06 (t, J=7.5 Hz, 2H), 2.35 (m, 1H), 2.02 (m, 1H), 1.85 (m, 4H), 1.75 (m, 2H), 1.65 (m, 2H).

Example 34

N-({1-[4-(3H-Benzoimidazol-5-yl)-4-hydroxy-cyclohexyl]-azetidin-3-ylcarbamoyl}-methyl)-3-trifluoromethyl-benzamide

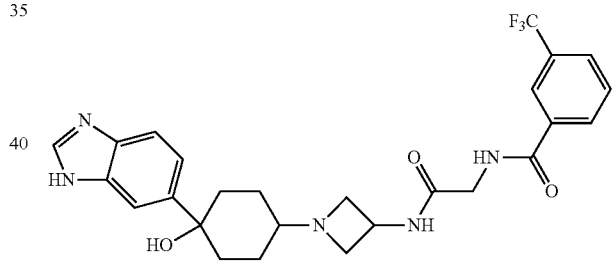

The title compound was prepared as a white solid by reductive amination of 4-(3H-benzoimidazol-5-yl)-4-hydroxy-cyclohexanone (as prepared in Example 20, Step B) and N-(azetidin-3-ylcarbamoylmethyl)-3-trifluoromethyl-benzamide (as prepared in step B of Example 4) using the procedure described in Step C of Example 4.

34a: Less Polar Fraction from Silica Gel Column

¹H NMR (400 MHz, d₄-MeOH) δ 8.21 (s, 1H), 8.12 (s, 1H), 7.88 (d, J=6.4 Hz, 1H), 7.75 (s, 1H), 7.63 (t, J=6.5 Hz, 1H), 7.42 (d, J=5.0 Hz, 1H), 7.10 (t, J=5.6 Hz, 1H), 6.88 (m, 1H), 4.47 (m, 1H), 4.05 (s, 2H), 3.65 (m, 2H), 3.08 (m, 2H), 2.85 (m, 1H), 2.30 (m, 2H), 1.95 (m, 2H), 1.68 (m, 2H), 1.32 (m, 2H).

34b: More Polar Fraction from Silica Gel Column

¹H NMR (400 MHz, d₄-MeOH) δ 8.25 (s, 1H), 8.15 (s, 1H), 7.95 (d, J=5.7 Hz, 1H), 7.82 (s, 1H), 7.75 (t, J=6.0 Hz, 1H), 7.50 (d, J=5.5 Hz, 1H), 7.18 (t, J=5.5 Hz, 1H), 6.95 (m, 1H), 4.60 (m, 1H), 4.15 (s, 2H), 3.80 (m, 2H), 3.15 (m, 2H), 2.63 (m, 1H), 2.05 (m, 4H), 1.78 (m, 4H).

Example 35

N-({1-[4-Hydroxy-4-(2-oxo-2,3-dihydro-benzooxazol-5-yl)-cyclohexyl]-azetidin-3-ylcarbamoyl}-methyl)-3-trifluoromethyl-benzamide

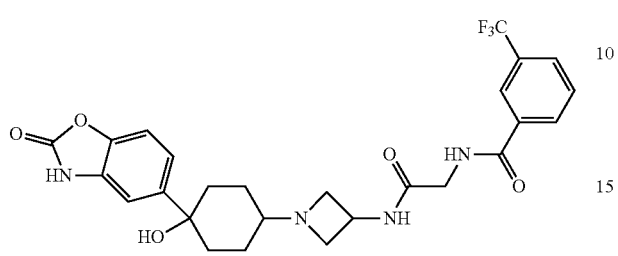

The title compound was prepared as a white solid by reductive amination of 5-(1-hydroxy-4-oxo-cyclohexyl)-3H-benzooxazol-2-one (as prepared in Example 5, Step A) and N-(azetidin-3-ylcarbamoylmethyl)-3-trifluoromethyl-benzamide (as prepared in step B of Example 4) using the procedure described in Step C of Example 4.

35a: Less Polar Fraction from Silica Gel Column $^1$H NMR (400 MHz, d$_4$-MeOH) δ 8.22 (s, 1H), 8.12 (d, J=6.5 Hz, 1H), 7.85 (d, J=6.0 Hz, 1H), 7.70 (t, J=6.6 Hz, 1H), 7.31 (d, J=7.0 Hz, 2H), 7.14 (d, J=6.6 Hz, 1H), 4.51 (m, 1H), 4.10 (s, 2H), 3.85 (t, J=6.7 Hz, 2H), 3.20 (t, J=6.8 Hz, 2H), 2.75 (s, br, 1H), 2.24 (m, 2H), 1.95 (m, 2H), 1.62 (m, 2H), 1.45 (m, 2H).

35b: More Polar Fraction from Silica Gel Column $^1$H NMR (400 MHz, d$_4$-MeOH) δ 8.15 (s, 1H), 8.20 (d, J=6.5 Hz, 1H), 7.88 (d, J=5.6 Hz, 1H), 7.75 (t, J=6.5 Hz, 1H), 7.28 (d, J=6.3 Hz, 2H), 7.17 (d, J=6.7 Hz, 1H), 4.68 (m, 1H), 4.42 (t, J=6.9 Hz, 2H), 4.25 (t, J=6.8 Hz, 2H), 4.10 (s, 2H), 3.32 (s, br, 1H), 1.98 (m, 6H), 1.85 (m, 2H).

Example 36

N-({1-[4-Hydroxy-4-(4-methoxy-phenyl)-cyclohexyl]-azetidin-3-ylcarbamoyl}-methyl)-3-trifluoromethyl-benzamide

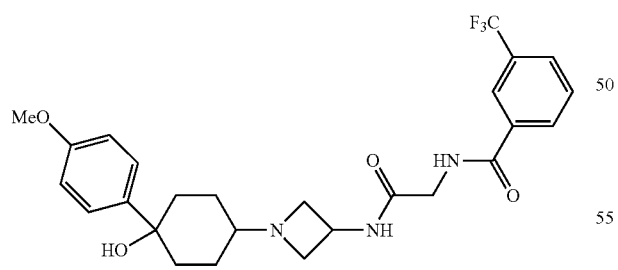

The title compound was prepared as a white solid by reductive amination of 4-hydroxy-4-(4-methoxy-phenyl)-cyclohexanone (as prepared in Example 7, Step B) and N-(azetidin-3-ylcarbamoylmethyl)-3-trifluoromethyl-benzamide (as prepared in step B of Example 4) using the procedure described in Step C of Example 4.

36a: Less Polar Fraction from Silica Gel Column $^1$H NMR (400 MHz, CDCl$_3$) δ 8.13 (s, 1H), 8.02 (d, J=6.4 Hz, 1H), 7.80 (d, J=6.7 Hz, 1H), 7.68 (m, 1H), 7.57 (t, J=6.6 Hz, 1H), 7.41 (d, J=7.5 Hz, 2H), 7.31 (d, J=6.0 Hz, 1H), 6.86 (d, J=7.5 Hz, 2H), 4.51 (m, 1H), 4.20 (d, J=3.1 Hz, 2H), 3.80 (s, 3H), 3.65 (t, J=6.5 Hz, 2H), 2.92 (t, J=6.5 Hz, 2H), 2.30 (m, 2H), 1.85 (m, 2H), 1.71 (m, 2H), 1.45 (m, 2H).

36b: More Polar Fraction from Silica Gel Column $^1$H NMR (400 MHz, CDCl$_3$) δ 8.11 (s, 1H), 8.05 (d, J=6.5 Hz, 1H), 7.78 (d, J=6.5 Hz, 1H), 7.58 (t, J=7.0 Hz, 1H), 7.52 (m, 1H), 7.40 (d, J=7.8 Hz, 2H), 7.20 (d, J=6.4 Hz, 1H), 6.85 (d, J=7.8 Hz, 2H), 4.55 (m, 1H), 4.15 (d, J=2.8 Hz, 2H), 3.75 (s, 3H), 3.62 (t, J=6.5 Hz, 2H), 3.10 (t, J=6.5 Hz, 2H), 2.05 (m, 2H), 1.80 (m, 2H), 1.72 (m, 2H), 1.55 (m, 2H).

Example 37

N-({1-[4-Hydroxy-4-(3-methoxy-phenyl)-cyclohexyl]-azetidin-3-ylcarbamoyl}-methyl)-3-trifluoromethyl-benzamide

Step A 8-(3-Methoxy-phenyl)-1,4-dioxa-spiro[4.5]decan-8-ol

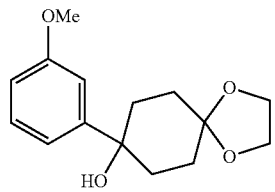 [SMILES: COc1cccc(C2(O)CCC3(CC2)OCCO3)c1]

The title compound was prepared as a white solid from 1-bromo-3-methoxy-benzene (Aldrich) and 1,4-dioxa-spiro[4.5]decan-8-one using the procedure described in Step A of Example 1.

$^1$H NMR (400 MHz, CDCl$_3$) δ 7.28 (t, J=7.1 Hz, 1H), 7.10 (m, 2H), 6.81 (d, J=6.8 Hz, 1H), 4.00 (s, 4H), 3.82 9s, 3H), 2.15 (m, 4H), 1.82 (m, 2H), 1.73 (m, 2H).

Step B

4-Hydroxy-4-(3-methoxy-phenyl)-cyclohexanone

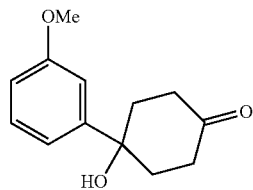 [SMILES: COc1cccc(C2(O)CCC(=O)CC2)c1]

The title compound was prepared as a white solid from 8-(3-methoxy-phenyl)-1,4-dioxa-spiro[4.5]decan-8-ol (as prepared in the previous step) using the procedure described in Step B of Example 1.

$^1$H NMR (400 MHz, CDCl$_3$) δ 7.32 (t, J=6.5 Hz, 1H), 7.10 (d, J=6.4 Hz, 1H), 7.07 (s, 1H), 6.85 (d, J=6.5 Hz, 1H), 3.85 (s, 3H), 2.92 (m, 2H), 2.35 (m, 4H), 2.20 (m, 2H).

Step C

N-({1-[4-Hydroxy-4-(3-methoxy-phenyl)-cyclohexyl]-azetidin-3-ylcarbamoyl}-methyl)-3-trifluoromethyl-benzamide

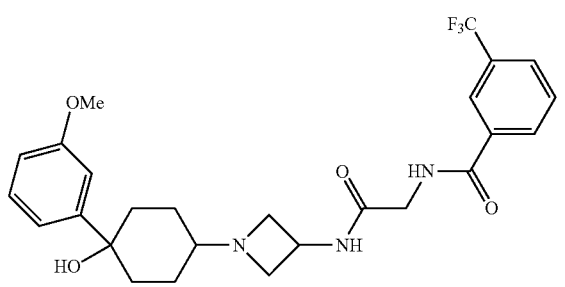 [SMILES: COc1cccc(C2(O)CCC(N3CC(NC(=O)CNC(=O)c4cccc(C(F)(F)F)c4)C3)CC2)c1]

The title compound was prepared as a white solid by reductive amination of 4-hydroxy-4-(3-methoxy-phenyl)-cyclohexanone (as prepared in the previous step) and N-(azetidin-3-ylcarbamoylmethyl)-3-trifluoromethyl-benzamide (as prepared in step B of Example 4) using the procedure described in Step C of Example 4.

37a: Less Polar Fraction from Silica Gel Column $^1$H NMR (400 MHz, CDCl$_3$) δ 8.10 (s, 1H), 8.02 (d, J=6.0 Hz, 1H), 7.80 (d, J=6.5 Hz, 1H), 7.58 (t, J=7.0 Hz, 1H), 7.25 (d, J=6.7 Hz, 1H), 7.20 (s, 1H), 7.10 (d, J=5.8 Hz, 1H), 6.82 (d, J=6.5 Hz, 1H), 4.52 (m, 1H), 4.18 (d, J=3.0 Hz, 2H), 3.62 (t, J=7.5 Hz, 2H), 2.91 (t, J=7.0 Hz, 2H), 2.32 (s, br, 1H), 2.20 (t, J=8.0 Hz, 2H), 1.85 (t, J=7.5 Hz, 2H), 1.55 (m, 2H), 1.50 (m, 2H).

37b: More Polar Fraction from Silica Gel Column $^1$H NMR (400 MHz, CDCl$_3$) δ 8.11 (s, 1H), 8.02 (d, J=6.8 Hz, 1H), 7.78 (d, J=6.8 Hz, 1H), 7.60 (t, J=6.5 Hz, 1H), 7.45 (m, 1H), 7.25 (d, J=6.6 Hz, 1H), 7.20 (d, J=6.5 Hz, 1H), 7.02 (d, J=5.8 Hz, 1H), 6.80 (d, J=6.0 Hz, 1H), 4.56 (m, 1H), 4.19 (d, J=3.0 Hz, 2H), 3.63 (t, J=6.8 Hz, 2H), 3.10 (t, J=6.8 Hz, 2H), 2.10 (m, 2H), 1.82 (m, 2H), 1.70 (m, 2H), 1.55 (m, 2H).

Example 38

N-({1-[4-Hydroxy-4-(3-methylsulfanyl-phenyl)-cyclohexyl]-azetidin-3-ylcarbamoyl}-methyl)-3-trifluoromethyl-benzamide

Step A

{1-[4-Hydroxy-4-(3-methylsulfanyl-phenyl)-cyclohexyl]-azetidin-3-yl}-carbamic acid tert-butyl ester

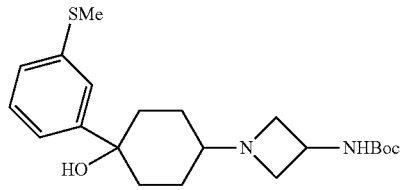 [SMILES: CSc1cccc(C2(O)CCC(N3CC(NC(=O)OC(C)(C)C)C3)CC2)c1]

The title compound was prepared as a white solid from 4-hydroxy-4-(3-methylsulfanyl-phenyl)-cyclohexanone (as prepared in Example 14, Step B) and azetidin-3-yl-carbamic acid tert-butyl ester using the procedure described in Step D of Example 1.

Less Polar Fraction from Silica Gel Column $^1$H NMR (400 MHz, CDCl$_3$) δ 7.45 (s, 1H), 7.25 (d, J=6.0 Hz, 1H), 7.20 (t, J=6.5 Hz, 1H), 7.08 (d, J=6.5 Hz, 1H), 5.05 (s, br, 1H), 4.25 (m, 1H), 3.60 (t, J=6.8 Hz, 2H), 2.88 (t, J=6.5 Hz, 2H), 2.52 (s, 3H), 2.50 (m, 1H), 2.25 (m, 2H), 2.20 (m, 2H), 1.80 (m, 2H), 1.65 (m, 2H), 1.42 (s, 9H).

More Polar Fraction from Silica Gel Column $^1$H NMR (400 MHz, CDCl$_3$) δ 7.42 (s, 1H), 7.28 (d, J=6.6 Hz, 1H), 7.25 (t, J=6.5 Hz, 1H), 7.11 (d, J=6.5 Hz, 1H), 5.05 (s, br, 1H), 4.26 (m, 1H), 3.65 (t, J=7.2 Hz, 2H), 2.92 (t, J=7.0 Hz, 2H), 2.60 (s, 3H), 2.55 (m, 1H), 1.80 (m, 4H), 1.75 (m, 2H), 1.55 (m, 2H).

Step B 4-(3-Amino-azetidin-1-yl)-1-(3-methylsulfanyl-phenyl)-cyclohexanol

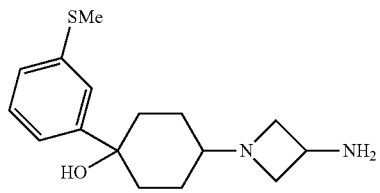 [SMILES: CSc1cccc(C2(O)CCC(N3CC(N)C3)CC2)c1]

The title compound was prepared as a white solid from {1-[4-hydroxy-4-(3-methylsulfanyl-phenyl)-cyclohexyl]-azetidin-3-yl}-carbamic acid tert-butyl ester (as prepared in the previous step, less polar fraction) using the procedure described in Step E of Example 1.

ESI-MS (m/z): Calcd. For $C_{16}H_{24}N_2OS$, 292; found: 293 (M+H).

Step C

N-({1-[4-Hydroxy-4-(3-methylsulfanyl-phenyl)-cyclohexyl]-azetidin-3-ylcarbamoyl}-methyl)-3-trifluoromethyl-benzamide

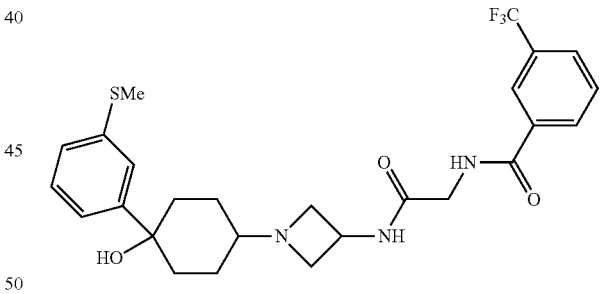

The title compound was prepared as a white solid from 4-(3-amino-azetidin-1-yl)-1-(3-methylsulfanyl-phenyl)-cyclohexanol (as prepared in the previous step) using the procedure described in Step F of Example 1.

38a: Less Polar Isomer from Silica Gel Column $^1$H NMR (400 MHz, d$_4$-MeOH) δ 8.05 (s, 1H), 7.98 (d, J=6.5 Hz, 1H), 7.70 (d, J=6.4 Hz, 1H), 7.52 (t, J=6.5 Hz, 1H), 7.28 (s, 1H), 7.15 (d, J=7.0 Hz, 2H), 7.10 (t, J=7.0 Hz, 1H), 6.88 (d, J=7.0 Hz, 1H), 4.31 (m, 1H), 3.88 (s, 2H), 3.65 (t, J=6.0 Hz, 2H), 2.91 (d, J=6.0 Hz, 2H), 2.35 (m, 1H), 2.30 (s, 3H), 2.06 (m, 2H), 1.65 (m, 2H), 1.35 (m, 2H), 1.25 (m, 2H).

38b: More Polar Isomer from Silica Gel Column $^1$H NMR (400 MHz, d$_4$-MeOH) δ 8.09 (s, 1H), 7.99 (d, J=6.0 Hz, 1H), 7.68 (d, J=6.2 Hz, 1H), 7.51 (t, J=6.5 Hz, 1H), 7.25 (s, 1H), 7.05 (m, 2H), 6.90 (d, J=7.0 Hz, 1H), 4.30 (m, 1H), 3.88 (s, 2H), 3.45 (t, J=6.0 Hz, 2H), 2.90 (d, J=6.0 Hz, 2H), 2.28 (s, 3H), 2.06 (m, 1H), 1.65 (m, 4H), 1.50 (m, 4H).

Example 39

N-({1-[4-(3-Dimethylamino-phenyl)-4-hydroxy-cyclohexyl]-azetidin-3-ylcarbamoyl}-methyl)-3-trifluoromethyl-benzamide

Step A 8-(3-Dimethylamino-phenyl)-1,4-dioxa-spiro[4.5]decan-8-ol

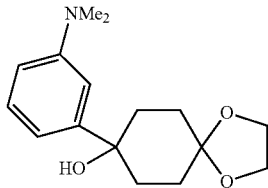 [SMILES: CN(C)c1cccc(C2(O)CCC3(CC2)OCCO3)c1]

The title compound was prepared as a white solid from 1-bromo-3-dimethylamino-benzene (Aldrich) and 1,4-dioxa-spiro[4.5]decan-8-one using the procedure described in Step A of Example 1.

$^1$H NMR (400 MHz, CDCl$_3$) δ 7.20 (t, J=7.5 Hz, 1H), 6.95 (s, 1H), 6.82 (d, J=6.5 Hz, 1H), 6.62 (d, J=6.5 Hz, 1H), 3.95 (s, 4H), 2.98 (s, 6H), 2.98 (s, 6H), 2.15 (m, 4H), 1.80 (m, 2H), 1.68 (m, 2H).

Step B 4-(3-Dimethylamino-phenyl)-4-hydroxy-cyclohexanone

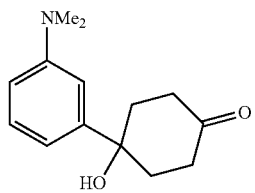 [SMILES: CN(C)c1cccc(C2(O)CCC(=O)CC2)c1]

The title compound was prepared as a white solid from 8-(3-dimethylamino-phenyl)-1,4-dioxa-spiro[4.5]decan-8-ol (as prepared in the previous step) using the procedure described in Step B of Example 1.

$^1$H NMR (400 MHz, CDCl$_3$) δ 7.23 (d, J=7.8 Hz, 1H), 6.95 (s, 1H), 6.84 (d, J=6.8 Hz, 1H), 6.69 (d, J=6.5 Hz, 1H), 2.98 (s, 6H), 2.90 (m, 2H), 2.32 (m, 4H), 2.20 (m, 2H).

Step C

N-({1-[4-(3-Dimethylamino-phenyl)-4-hydroxy-cyclohexyl]-azetidin-3-ylcarbamoyl}-methyl)-3-trifluoromethyl-benzamide The title compound was prepared as a white solid by reductive amination of 4-(3-dimethylamino-phenyl)-4-hydroxy-cyclohexanone (as prepared in the previous step) and N-(azetidin-3-ylcarbamoylmethyl)-3-trifluoromethyl-benzamide (as prepared in step B of Example 4) using the procedure described in Step C of Example 4.

39a: Less Polar Fraction from Silica Gel Column $^1$H NMR (400 MHz, CDCl$_3$) δ 8.12 (s, 1H), 8.02 (d, J=6.5 Hz, 1H), 7.88 (m, 1H), 7.75 (t, J=6.6 Hz, 1H), 7.51 (m, J=7.0 Hz, 2H), 7.20 (t, J=6.6 Hz, 1H), 6.98 (s, 1H), 6.85 (d, J=6.4 Hz, 1H), 6.62 (d, J=6.5 Hz, 1H), 4.51 (m, 1H), 4.15 (d, J=3.5 Hz, 2H), 3.58 (t, J=6.7 Hz, 2H), 2.95 (s, 6H), 2.86 (t, J=6.8 Hz, 2H), 2.40 (s, br, 1H), 2.24 (m, 2H), 1.80 (t, J=8.0 Hz, 2H), 1.52 (d, J=8.2 Hz, 2H), 1.45 (m, 2H).

39b: More Polar Fraction from Silica Gel Column $^1$H NMR (400 MHz, CDCl$_3$) δ 8.12 (s, 1H), 8.06 (d, J=6.5 Hz, 1H), 7.82 (d, J=5.6 Hz, 1H), 7.62 (t, J=6.5 Hz, 1H), 7.30 (m, 2H), 6.95 (s, 1H), 6.85 (d, J=6.7 Hz, 1H), 6.78 (d, J=6.0 Hz, 1H), 6.66 (d, J=6.5 Hz, 1H), 4.55 (m, 1H), 4.18 (d, J=4.5 Hz, 2H), 3.66 (t, J=6.9 Hz, 2H), 3.08 (t, J=6.8 Hz, 2H), 2.32 (s, br, 1H), 1.92 (m, 2H), 1.85 (m, 4H), 1.58 (m, 2H).

Example 40

N-({1-[4-(4-Hydroxy-phenyl)-cyclohexyl]-azetidin-3-ylcarbamoyl}-methyl)-3-trifluoromethyl-benzamide

Step A

8-[4-(tert-Butyl-dimethyl-silanyloxy)-phenyl]-1,4-dioxa-spiro[4.5]decan-8-ol

The title compound was prepared as a white solid from (4-bromo-phenoxy)-tert-butyl-dimethyl-silane (Aldrich) and 1,4-dioxa-spiro[4.5]decan-8-one using the procedure described in Step A of Example 1.

¹H NMR (400 MHz, CDCl₃) δ 7.18 (d, J=6.8 Hz, 2H), 6.58 (d, J=7.0 Hz, 2H), 3.79 (m, 4H), 1.98 (m, 4H), 1.65 (d, J=6.4 Hz, 2H), 1.50 (d, J=6.8 Hz, 2H), 0.80 (s, 9H), 0.05 (s, 6H).

Step B

4-[4-(tert-Butyl-dimethyl-silanyloxy)-phenyl]-4-hydroxy-cyclohexanone

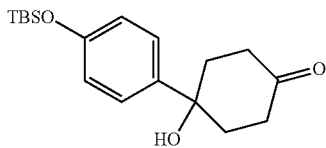 [SMILES: CC(C)(C)[Si](C)(C)Oc1ccc(C2(O)CCC(=O)CC2)cc1]

The title compound was prepared as a white solid from 8-[4-(tert-butyl-dimethyl-silanyloxy)-phenyl]-1,4-dioxa-spiro[4.5]decan-8-ol (as prepared in the previous step) using the procedure described in Step B of Example 1.

¹H NMR (400 MHz, CDCl₃) δ 7.26 (d, J=6.5 Hz, 1H), 7.10 (d, J=6.4 Hz, 1H), 7.01 (s, 1H), 6.79 (d, J=6.8 Hz, 1H), 2.95 (m, 2H), 2.38 (m, 2H), 2.25 (m, 2H), 2.20 (m, 2H), 1.02 (s, 9H), 0.21 (s, 6H).

Step C

4-[4-(tert-Butyl-dimethyl-silanyloxy)-phenyl]-cyclohex-3-enone

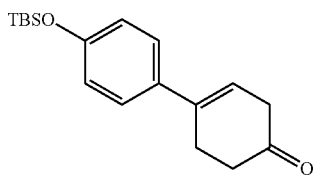 [SMILES: CC(C)(C)[Si](C)(C)Oc1ccc(C2=CCC(=O)CC2)cc1]

The title compound was prepared as a white solid from dehydration of 4-[4-(tert-butyl-dimethyl-silanyloxy)-phenyl]-4-hydroxy-cyclohexanone (as prepared in the previous step) using the procedure described in Step B of Example 5.

¹H NMR (400 MHz, CDCl₃) δ 7.01 (t, J=6.4 Hz, 1H), 6.78 (d, J=6.6 Hz, 1H), 6.65 (s, 1H), 6.54 (d, J=6.7 Hz, 1H), 5.85 (m, 1H), 2.88 (s, 2H), 2.70 (t, J=7.2 Hz, 2H), 2.42 (t, J=7.5 Hz, 2H).

Step D 4-(4-Hydroxy-phenyl)-cyclohex-3-enone

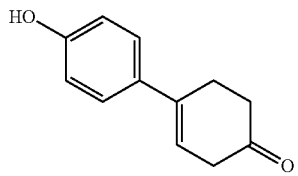 [SMILES: O=C1CC=C(c2ccc(O)cc2)CC1]

4-[4-(tert-Butyl-dimethyl-silanyloxy)-phenyl]-cyclohex-3-enone (2.0 g, 6.62 mmol) in THF was treated with TBAF (1N in THF, 10 mL, 9.93 mmol) at room temperature. After 10 min., the solvent was removed and the residue was partitioned between ethyl acetate and water. The organic layer was washed with brine, dried over anhydrous Na₂SO₄, filtered, and the filtrate concentrated in vacuo to give colorless oil, which was purified on a silica gel column by a CombiFlash® system using hexanes and ethyl acetate as eluent (from pure hexanes to pure ethyl acetate) to afford the title compound as a white solid.

¹H NMR (400 MHz, d₄-MeOH) δ 7.28 (d, J=6.5 Hz, 2H), 6.75 (d, J=6.5 Hz, 2H), 5.95 (m, 1H), 3.01 (s, 2H), 2.80 (t, J=4.2 Hz, 2H), 2.55 (t, J=6.8 Hz, 2H).

Step E 4-(4-Hydroxy-phenyl)-cyclohexanone

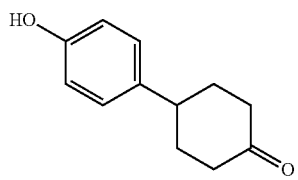 [SMILES: O=C1CCC(c2ccc(O)cc2)CC1]

The title compound was prepared as a white solid from 4-(4-hydroxy-phenyl)-cyclohex-3-enone (as prepared in the previous step) using the procedure described in Step C of Example 5.

¹H NMR (400 MHz, d₄-MeOH) δ 7.05 (t, J=6.8 Hz, 2H), 6.70 (d, J=6.8 Hz, 2H), 2.90 (m, 1H), 2.55 (m, 2H), 2.30 (m, 2H), 2.08 (m, 2H, 1.90 (m, 2H).

Step F

N-({1-[4-(4-Hydroxy-phenyl)-cyclohexyl]-azetidin-3-ylcarbamoyl}-methyl)-3-trifluoromethyl-benzamide

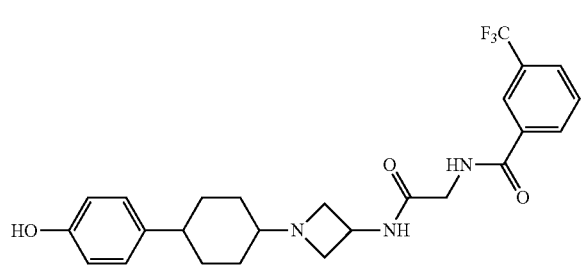

The title compound was prepared as a white solid by reductive amination of 4-(4-Hydroxy-phenyl)-cyclohexanone (as prepared in the previous step) and N-(azetidin-3-ylcarbamoylmethyl)-3-trifluoromethyl-benzamide (as prepared in step B of Example 4) using the procedure described in Step C of Example 4.

40a: Less Polar Isomer from Silica Gel Column

¹H NMR (400 MHz, d₄-MeOH) δ 8.21 (s, 1H), 8.15 (d, J=6.5 Hz, 1H), 7.88 (d, J=6.4 Hz, 1H), 7.70 (t, J=6.5 Hz, 1H), 7.15 (d, J=7.0 Hz, 2H), 6.72 (d, J=7.0 Hz, 2H), 4.47 (m, 1H), 4.05 (s, 2H), 3.65 (m, 2H), 2.95 (m, 2H), 2.45 (m, 1H), 2.40 (s, br, 1H), 1.75 (m, 4H), 1.50 (m, 4H).

40b: More Polar Isomer from Silica Gel Column

¹H NMR (400 MHz, d₄-MeOH) δ 8.11 (s, 1H), 8.08 (d, J=6.5 Hz, 1H), 7.82 (d, J=6.0 Hz, 1H), 7.60 (t, J=7.2 Hz, 1H), 6.95 (d, J=7.2 Hz, 2H), 6.62 (d, J=6.5 Hz, 1H), 4.35 (m, 1H), 3.95 (s, 2H), 3.72 (t, J=6.5 Hz, 2H), 3.15 (t, J=6.2 Hz, 2H), 3.01 (m, 1H), 2.25 (m, 1H), 1.90 (m, 4H), 1.35 (m, 2H), 1.12 (m, 2H).

Example 41

N-[(1-{4-[4-(2-Dimethylamino-ethoxy)-phenyl]-cyclohexyl}-azetidin-3-ylcarbamoyl)-methyl]-3-trifluoromethyl-benzamide

Step A

4-[4-(2-Dimethylamino-ethoxy)-phenyl]-cyclohexanone

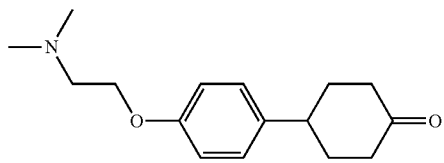 [SMILES: CN(C)CCOc1ccc(C2CCC(=O)CC2)cc1]

Into a solution of 4-(4-hydroxy-phenyl)cyclohexanone (as prepared in Example 40, Step E, 2.4 g, 12.6 mmol), N,N-dimethylethanolamine (Aldrich, 3.37 g, 37.8 mmol) and triphenylphosphine (Aldrich, 9.91 g, 37.8 mmol) in THF (100 mL) at 0° C. was added dropwise a solution of diisopropyl azodicarboxylate (7.44 mL, 37.8 mmol) in THF (15 mL) under Ar. The resulting solution was stirred at 0° C. for 1 h and at room temperature overnight. The solvent was removed and the residue was partitioned between ethyl acetate and water. The organic layer was washed with brine, dried over anhydrous $Na_2SO_4$, filtered, and the filtrate concentrated in vacuo to give a colorless oil, which was purified on a silica gel column by a CombiFlash® system using hexanes and ethyl acetate as eluent (from pure hexanes to pure ethyl acetate) to afford the title compound as a white solid.

$^1$H NMR (400 MHz, $CDCl_3$): δ 7.13-7.21 (2H, dd), 6.81-6.86 (2H, dd), 4.01-4.06 (2H, m), 3.51 (1H, m), 2.69-2.73 (2H, m), 2.47-2.50 (2H, m), 2.32-2.34 (4H, m), 2.24 (6H, s), 1.67-1.73 (2H, m).

Step B

N-[(1-{4-[4-(2-Dimethylamino-ethoxy)-phenyl]-cyclohexyl}-azetidin-3-ylcarbamoyl)-methyl]-3-trifluoromethyl-benzamide The title compound was prepared from 4-[4-(2-dimethylamino-ethoxy)-phenyl]-cyclohexanone (as prepared in the previous step) according to the general reductive amination procedure in Step C of Example 4.

A mixture of 4:1 ratio of two isomers was detected from LC. ESI-MS (m/z): Calcd. For $C_{29}H_{37}F_3N_4O_3$, 546; found: 547 [M+H].

Example 42

N-({1-[4-Hydroxy-4-(4-hydroxy-phenyl)-cyclohexyl]-azetidin-3-ylcarbamoyl}-methyl)-3-trifluoromethyl-benzamide

Step A

4-Hydroxy-4-(4-hydroxy-phenyl)-cyclohexanone

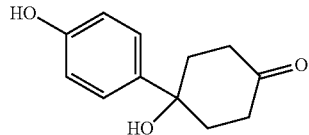

The title compound was prepared as a white solid by TBAF de-protection of 4-[4-(tert-butyl-dimethyl-silanyloxy)-phenyl]-4-hydroxy-cyclohexanone using the procedure described in Step D of Example 40.

$^1$H NMR (400 MHz, $CDCl_3$) δ 7.25 (t, J=6.5 Hz, 1H), 7.08 (s, 1H), 7.05 (d, J=6.0 Hz, 1H), 6.78 (d, J=6.4 Hz, 1H), 2.95 (m, 2H), 2.35 (m, 2H), 2.30 (m, 2H), 2.18 (m, 2H).

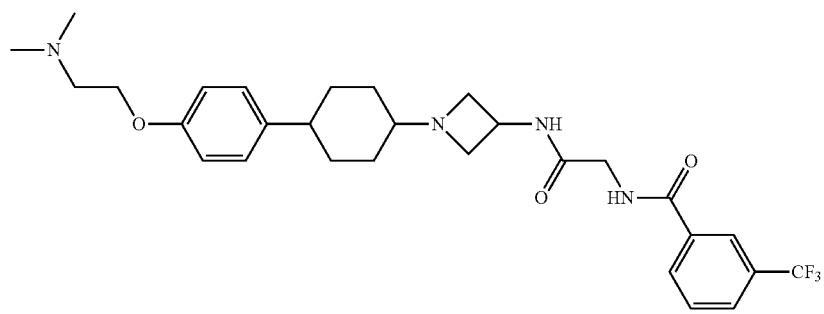 [SMILES: CN(C)CCOc1ccc(C2CCC(N3CC(NC(=O)CNC(=O)c4cccc(C(F)(F)F)c4)C3)CC2)cc1]

Step B

N-({1-[4-Hydroxy-4-(4-hydroxy-phenyl)-cyclohexyl]-azetidin-3-ylcarbamoyl}-methyl)-3-trifluoromethyl-benzamide

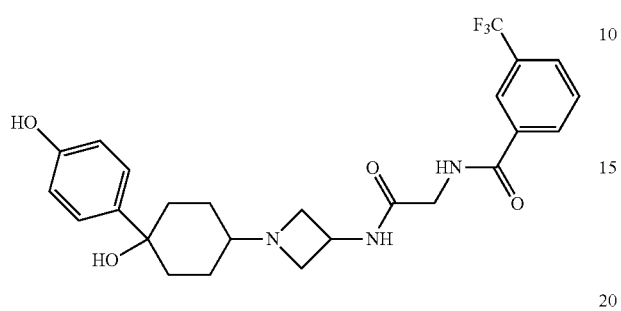

The title compound was prepared as a white solid by reductive amination of 4-hydroxy-4-(4-hydroxy-phenyl)-cyclohexanone (as prepared in the previous step) and N-(azetidin-3-ylcarbamoylmethyl)-3-trifluoromethyl-benzamide (as prepared in step B of Example 4) using the procedure described in Step C of Example 4.

$^1$H NMR (400 MHz, d$_4$-MeOH) δ 8.20 (s, 1H), 8.10 (d, J=6.5 Hz, 1H), 7.85 (d, J=6.4 Hz, 1H), 7.62 (t, J=6.5 Hz, 1H), 7.10 (t, J=6.5 Hz, 1H), 6.98 (d, J=6.5 Hz, 2H), 6.58 (d, J=7.0 Hz, 2H), 4.45 (m, 1H), 4.01 (s, 2H), 3.72 (t, J=6.0 Hz, 2H), 3.12 (d, J=6.0 Hz, 2H), 2.55 (m, 1H), 2.26 (m, 2H), 1.85 (m, 2H), 1.48 (m, 2H), 1.31 (m, 2H).

Example 43

3-[2-(3-Trifluoromethyl-benzoylamino)-acetylamino]-azetidin-1-yl}-cyclohexyl)-phenoxy]-acetic acid methyl ester

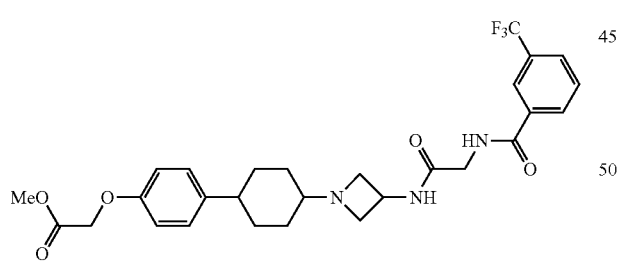

N-({1-[4-(4-Hydroxy-phenyl)-cyclohexyl]-azetidin-3-yl-carbamoyl}-methyl)-3-trifluoromethyl-benzamide (as prepared in Example 40, less polar isomer, 250 mg, 0.53 mmol) in DMF (5 mL) was treated with Cs$_2$CO$_3$ (260 mg, 0.80 mmol) followed by bromo-acetic acid methyl ester (Aldrich, 92 mg, 0.60 mmol) at room temperature. The reaction was gently heated at 60° C. for 4 hours and then allowed to cool. The solid was filtered off and DMF was removed in vacuo. The residue was partitioned between water and DCM. The aqueous layer was extracted 3 times with a chloroform/IPA "cocktail" (~3:1, v/v). The combined organic layers were dried over anhydrous Na$_2$SO$_4$, filtered and concentrated to give the crude product, which was then purified by a CombiFlash® system using ethyl acetate and 7N NH$_3$ in MeOH as eluent (from pure ethyl acetate to 5% 7N NH$_3$ in MeOH in ethyl acetate) to afford the title compound as a white solid.

$^1$H NMR (400 MHz, CDCl$_3$) δ 8.11 (s, 1H), 8.02 (d, J=6.5 Hz, 1H), 7.80 (d, J=6.5 Hz, 1H), 7.60 (t, J=6.5 Hz, 1H), 7.42 (m, 1H), 7.15 (d, J=7.0 Hz, 2H), 6.90 (d, J=5.6 Hz, 1H), 6.80 (d, J=7.0 Hz, 2H), 4.60 (s, 2H), 4.52 (m, 1H), 4.22 (d, J=3.5 Hz, 2H), 3.80 (s, 3H), 3.60 (t, J=7.0 Hz, 2H), 2.85 (t, J=7.0 Hz, 2H), 2.45 (m, 1H), 2.30 (s, br, 1H), 1.85 (2H), 1.70 (m, 2H), 1.55 (m, 2H), 1.44 (m, 2H).

Example 44

3-[2-(3-Trifluoromethyl-benzoylamino)-acetylamino]-azetidin-1-yl}-cyclohexyl)-phenoxy]-acetic acid

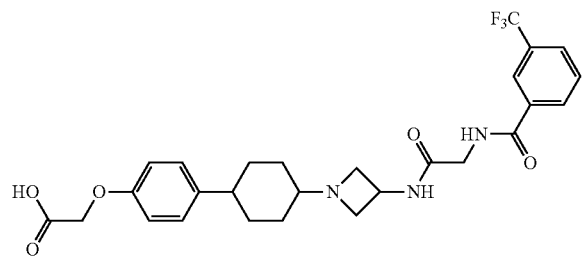 [SMILES: O=C(O)COc1ccc(C2CCC(N3CC(NC(=O)CNC(=O)c4cccc(C(F)(F)F)c4)C3)CC2)cc1]

The title compound was prepared as a white solid by hydrolysis of 3-[2-(3-trifluoromethyl-benzoylamino)-acetylamino]-azetidin-1-yl}-cyclohexyl)-phenoxy]-acetic acid methyl ester (as prepared in Example 43) using the procedure described in Example 10.

$^1$H NMR (400 MHz, d$_4$-MeOH) δ 8.15 (s, 1H), 8.02 (d, J=6.5 Hz, 1H), 7.78 (d, J=6.4 Hz, 1H), 7.60 (t, J=6.5 Hz, 1H), 7.05 (d, J=7.0 Hz, 2H), 6.72 (d, J=7.0 Hz, 2H), 4.41 (m, 1H), 4.25 (s, 2H), 4.00 (s, 2H), 3.60 (m, 2H), 2.98 (m, 2H), 2.45 (m, 1H), 1.65 (m, 4H), 1.50 (m, 4H).

Example 45

4-(1-Hydroxy-4-{3-[2-(3-trifluoromethyl-benzoylamino)-acetylamino]-azetidin-1-yl}-cyclohexyl)-benzoic acid

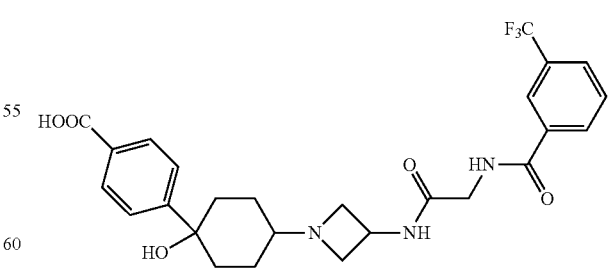

The title compound was prepared as a white solid by reductive amination of 4-(1-hydroxy-4-oxo-cyclohexyl)-benzoic acid methyl ester (as prepared in Example 9, Step B) and N-(azetidin-3-ylcarbamoylmethyl)-3-trifluoromethyl-benzamide (as prepared in step B of Example 4) using the procedure described in Step C of Example 4 followed by base catalyzed hydrolysis of the ester using the procedure described in Example 10.

¹H NMR (400 MHz, d₄-MeOH) δ 8.20 (s, 1H), 8.08 (d, J=6.5 Hz, 1H), 7.85 (d, J=6.4 Hz, 2H), 7.80 (d, J=6.3 Hz, 1H), 7.65 (t, J=6.5 Hz, 1H), 7.40 (d, J=7.0 Hz, 2H), 4.51 (m, 1H), 4.20 (s, 2H), 4.00 (s, 3H), 3.85 (m, 2H), 3.20 (m, 2H), 2.85 (m, 1H), 2.20 (m, 2H), 1.98 (m, 2H), 1.65 (m, 2H), 1.50 (m, 2H).

Example 46

N-({1-[4-Hydroxy-4-(3-hydroxy-phenyl)-cyclohexyl]-azetidin-3-ylcarbamoyl}-methyl)-3-trifluoromethyl-benzamide Step A tert-Butyl-dimethyl-silanyloxy)-phenyl]-1,4-dioxa-spiro[4.5]decan-8-ol

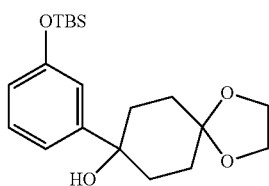 [SMILES: CC(C)(C)[Si](C)(C)Oc1cccc(C2(O)CCC3(CC2)OCCO3)c1]

The title compound was prepared as a white solid from and 1,4-dioxa-spiro[4.5]decan-8-one (Aldrich) using the procedure described in Step A of Example 1.

¹H NMR (400 MHz, CDCl₃) δ 7.20 (t, J=6.6 Hz, 1H), 7.11 (d, J=6.0 Hz, 1H), 7.04 (s, 1H), 6.76 (d, J=6.0 Hz, 1H), 3.00 (m, 4H), 2.10 (t, J=8.5 Hz, 4H), 1.80 (d, J=6.8 Hz, 2H), 1.72 (d, J=6.6 Hz, 2H), 0.98 (s, 9H), 0.21 (s, 6H).

Step B

4-[3-(tert-Butyl-dimethyl-silanyloxy)-phenyl]-4-hydroxy-cyclohexanone

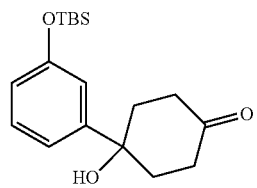 [SMILES: CC(C)(C)[Si](C)(C)Oc1cccc(C2(O)CCC(=O)CC2)c1]

The title compound was prepared as a white solid from using the procedure described in Step B of Example 1.

¹H NMR (400 MHz, CDCl₃) δ 7.25 (t, J=6.6 Hz, 1H), 7.08 (d, J=6.3 Hz, 1H), 7.05 (d, J=2.2 Hz, 1H), 6.75 (d, J=6.0 Hz, 1H0, 2.90 (m, 2H), 2.35 (m, 2H), 2.30 (m, 2H), 2.12 (m, 2H), 1.05 (s, 9H), 0.20 (s, 6H).

Step C

4-Hydroxy-4-(3-hydroxy-phenyl)-cyclohexanone

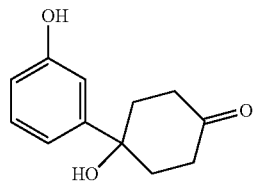 [SMILES: O=C1CCC(O)(c2cccc(O)c2)CC1]

The title compound was prepared as a white solid by TBAF de-protection of 4-[3-(tert-butyl-dimethyl-silanyloxy)-phenyl]-4-hydroxy-cyclohexanone (as prepared in the previous step) using the procedure described in Step D of Example 40.

ESI-MS (m/z): Calcd. For C₁₂H₁₄O₃, 206; found: 207 (M+H).

Step D

N-({1-[4-Hydroxy-4-(3-hydroxy-phenyl)-cyclohexyl]-azetidin-3-ylcarbamoyl}-methyl)-3-trifluoromethyl-benzamide

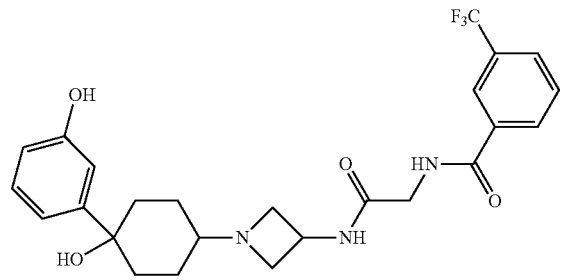

The title compound was prepared as a white solid by reductive amination of 4-hydroxy-4-(3-hydroxy-phenyl)-cyclohexanone (as prepared in the previous step) and N-(azetidin-3-ylcarbamoylmethyl)-3-trifluoromethyl-benzamide (as prepared in step B of Example 4) using the procedure described in Step C of Example 4.

46a: Less Polar Isomer from Silica Gel Column

¹H NMR (400 MHz, d₄-MeOH) δ 8.15 (s, 1H), 8.08 (d, J=6.5 Hz, 1H), 7.78 (d, J=6.4 Hz, 1H), 7.60 (t, J=6.5 Hz, 1H), 7.10 (t, J=7.0 Hz, 1H), 6.92 (d, J=4.0 Hz, 2H), 6.59 (d, J=5.2 Hz, 1H), 4.41 (m, 1H), 4.00 (s, 2H), 3.60 (t, J=6.5 Hz, 2H), 2.98 (t, J=6.5 Hz, 2H), 2.35 (m, 1H), 2.17 (m, 2H), 1.85 (m, 2H), 1.50 (m, 2H), 1.32 (m, 2H).

46b: More Polar Isomer from Silica Gel Column

¹H NMR (400 MHz, d₄-MeOH) δ 8.17 (s, 1H), 8.09 (d, J=6.6 Hz, 1H), 7.80 (d, J=6.8 Hz, 1H), 7.65 (t, J=6.5 Hz, 1H), 7.05 (t, J=6.8 Hz, 1H), 6.88 (s, 1H), 6.72 (s, 1H), 6.55 (d,

J=6.0 Hz, 1H), 4.45 (m, 1H), 4.05 (s, 2H), 3.68 (t, J=7.0 Hz, 2H), 3.10 (t, J=7.0 Hz, 2H), 2.25 (m, 1H), 1.75 (m, 4H), 1.64 (m, 2H), 1.54 (m, 2H).

Example 47

N-({1-[4-(4-Fluoro-phenyl)-4-hydroxy-cyclohexyl]-azetidin-3-ylcarbamoyl}-methyl)-3-trifluoromethyl-benzamide Step A 8-(4-Fluoro-phenyl)-1,4-dioxa-spiro[4.5]decan-8-ol

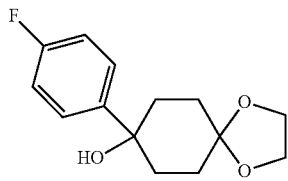 [SMILES: OC1(c2ccc(F)cc2)CCC2(CC1)OCCO2]

The title compound was prepared as a white solid from 4-fluoro-phenyl-bromide (Aldrich) and 1,4-dioxa-spiro[4.5]decan-8-one using the procedure described in Step A of Example 1.

¹H NMR (400 MHz, CDCl₃) δ 7.45 (dd, J=8.5, 6.0 Hz, 2H), 6.98 (dd, J=8.8, 6.2 Hz, 2H), 4.00 (m, 4H), 2.10 (m, 4H), 1.82 (m, 2H), 1.65 (m, 2H).

Step B 4-(4-Fluoro-phenyl)-4-hydroxy-cyclohexanone

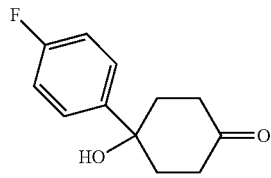 [SMILES: O=C1CCC(O)(c2ccc(F)cc2)CC1]

The title compound was prepared as a white solid from 8-(4-fluoro-phenyl)-1,4-dioxa-spiro[4.5]decan-8-ol (as prepared in the previous step) using the procedure described in Step B of Example 1.

¹H NMR (400 MHz, CDCl₃) δ 7.50 (dd, J=8.0, 6.2 Hz, 2H), 7.05 (dd, J=8.5, 6.2 Hz, 2H), 2.95 (m, 2H), 2.35 (m, 2H), 2.20 (m, 2H), 2.03 (m, 2H).

Step C

N-({1-[4-(4-Fluoro-phenyl)-4-hydroxy-cyclohexyl]-azetidin-3-ylcarbamoyl}-methyl)-3-trifluoromethyl-benzamide

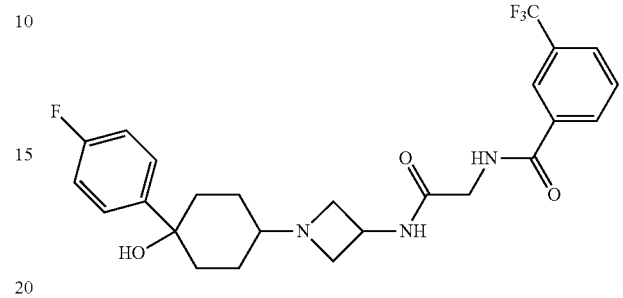

The title compound was prepared as a white solid by reductive amination of 4-(4-fluoro-phenyl)-4-hydroxy-cyclohexanone (as prepared in the previous step) and N-(azetidin-3-ylcarbamoylmethyl)-3-trifluoromethyl-benzamide (as prepared in step B of Example 4) using the procedure described in Step C of Example 4.

47a: Less Polar Isomer from Silica Gel Column

¹H NMR (400 MHz, CDCl₃) δ 8.15 (s, 1H), 8.05 (d, J=6.8 Hz, 1H), 7.80 (t, J=5.6 Hz, 1H), 7.77 (d, J=6.8 Hz, 1H), 7.51 (t, J=7.7 Hz, 2H), 7.92 (t, J=7.8 Hz, 2H), 4.51 (m, 1H), 4.15 (d, J=3.5 Hz, 2H), 3.60 (t, J=6.8 Hz, 2H), 2.96 (t, J=6.8 Hz, 2H), 2.30 (s, 1H), 2.24 (t, J=8.5 Hz, 2H), 1.85 (t, J=8.0 Hz, 2H), 1.52 (d, J=8.2 Hz, 2H), 1.42 (m, 2H).

47b: More Polar Isomer from Silica Gel Column

¹H NMR (400 MHz, CDCl₃) δ 8.11 (s, 1H), 8.02 (d, J=6.0 Hz, 1H), 7.85 (t, J=4.3 Hz, 1H), 7.72 (m, 1H), 7.53 (d, J=7.0 Hz, 1H), 7.50 (m, J=8.5, 6.5 Hz, 2H), 7.01 (t, J=6.8 Hz, 2H), 4.44 (m, 1H), 4.18 (d, J=3.2 Hz, 2H), 3.55 (t, J=7.4 Hz, 2H), 3.10 (t, J=7.0 Hz, 2H), 2.10 (m, 2H), 1.85-1.48 (m, 6H).

Example 48

N-({1-[4-(3-Cyano-phenyl)-4-hydroxy-cyclohexyl]-azetidin-3-ylcarbamoyl}-methyl)-3-trifluoromethyl-benzamide

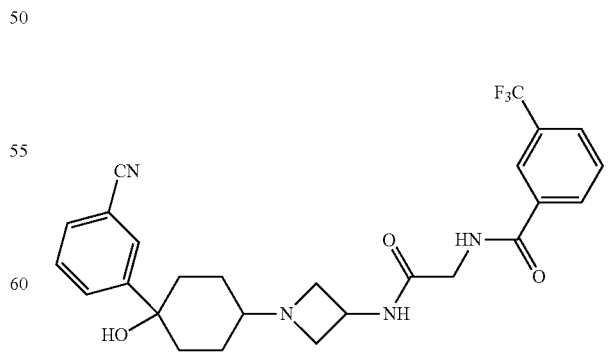

The title compounds were prepared as white solids by reductive amination of 3-(1-hydroxy-4-oxo-cyclohexyl)-benzonitrile (as prepared Example 8, Step B) and N-(azetidin-3-ylcarbamoylmethyl)-3-trifluoromethyl-benzamide (as prepared in step B of Example 4) using the procedure described in Step C of Example 4.

48a: Less Polar Isomer from Silica Gel Column

¹H NMR (400 MHz, CDCl₃) δ 8.15 (s, 1H), 8.05 (d, J=6.8 Hz, 1H), 7.85 (s, 1H), 7.80 (t, J=6.6 Hz, 1H), 7.58 (t, J=6.2 Hz, 1H), 7.51 (d, J=6.7 Hz, 1H), 7.42 (t, J=6.8 Hz, 1H), 7.30 (s, br, 1H), 6.85 (s, br, 1H), 4.55 (m, 1H), 4.21 (d, J=3.5 Hz, 2H), 3.65 (t, J=6.8 Hz, 2H), 2.90 (m, 2H), 2.45 (m, 1H), 2.20 (t, J=8.5 Hz, 2H), 1.85 (t, J=8.0 Hz, 2H), 1.48 (m, 4H).

48b: More Polar Isomer from Silica Gel Column

¹H NMR (400 MHz, CDCl₃) δ 8.15 (s, 1H), 8.05 (d, J=6.0 Hz, 1H), 7.85 (t, J=5.8 Hz, 1H), 7.75 (d, J=6.6 Hz, 1H), 7.56 (d, J=7.0 Hz, 1H), 7.50 (m, J=7.5, 6.0 Hz, 2H), 7.42 (t, J=6.2 Hz, 1H), 7.21 (s, 1H), 4.54 (m, 1H), 4.18 (d, J=3.2 Hz, 2H), 3.68 (t, J=7.4 Hz, 2H), 3.10 (t, J=7.0 Hz, 2H), 2.20 (m, 2H), 1.85-1.66 (m, 4H), 1.55 (m, 2H).

Example 49

N-[(1-{4-Hydroxy-4-[3-(1H-tetrazol-5-yl)-phenyl]-cyclohexyl}-azetidin-3-ylcarbamoyl)-methyl]-3-trifluoromethyl-benzamide

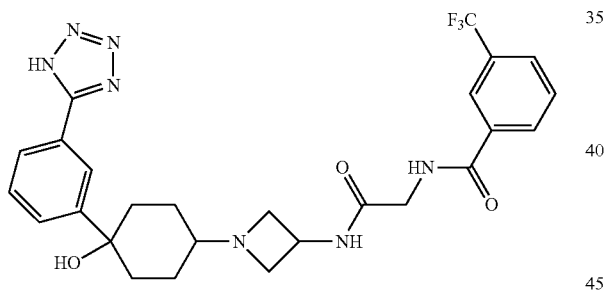

TMSN₃ (Fluka, 50 mg, 0.42 mmol), TBAF (Aldrich, 1.0 N in THF, 0.5 mL, 0.5 mmol) and N-({1-[4-(3-cyano-phenyl)-4-hydroxy-cyclohexyl]-azetidin-3-ylcarbamoyl}-methyl)-3-trifluoromethyl-benzamide (as prepared in Example 48, less polar isomer, 70 mg, 0.14 mmol) were dissolved in THF (2 mL) and water (0.5 mL) mixed solvent. The reaction mixture was subjected to microwave irradiation at 120° C. for 20 min. The crude reaction mixture was loaded on a silica gel column using a CombiFlash® system using ethyl acetate and 7N NH₃ in MeOH as eluent (from pure ethyl acetate to 5% 7N NH₃ in MeOH in ethyl acetate) to afford the title compound as a white solid.

¹H NMR (400 MHz, CDCl₃) δ 8.08 (s, 1H), 8.02 (d, J=6.5 Hz, 1H), 7.85 (s, 1H), 7.80 (t, J=6.0 Hz, 1H), 7.52 (m, 2H), 7.41 (t, J=6.2 Hz, 1H), 7.01 (d, J=6.0 Hz, 1H), 4.52 (m, 1H), 4.18 (d, J=2.8 Hz, 2H), 3.55 (t, J=6.8 Hz, 2H), 2.90 (t, J=6.5 Hz, 2H), 2.65 (m, 2H), 2.20 (m, 2H), 2.00 (m, 2H), 1.65 (m, 2H).

Example 50

[4-(1-Hydroxy-4-{3-[2-(3-trifluoromethyl-benzoylamino)-acetylamino]-azetidin-1-yl}-cyclohexyl)-phenyl]-carbamic acid tert-butyl ester

Step A

[4-(1-Hydroxy-4-oxo-cyclohexyl)-phenyl]-carbamic acid tert-butyl ester

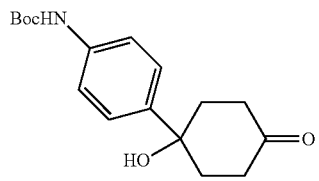 [SMILES: CC(C)(C)OC(=O)Nc1ccc(C2(O)CCC(=O)CC2)cc1]

The title compound was prepared as a white solid from [4-(8-hydroxy-1,4-dioxa-spiro[4.5]dec-8-yl)-phenyl]-carbamic acid tert-butyl ester using the procedure described in Step B of Example 1.

ESI-MS (m/z): Calcd. For C₁₇H₂₃NO₄, 305; found: 306 (M+H).

Step B

[4-(1-Hydroxy-4-{3-[2-(3-trifluoromethyl-benzoylamino)-acetylamino]-azetidin-1-yl}-cyclohexyl)-phenyl]-carbamic acid tert-butyl ester

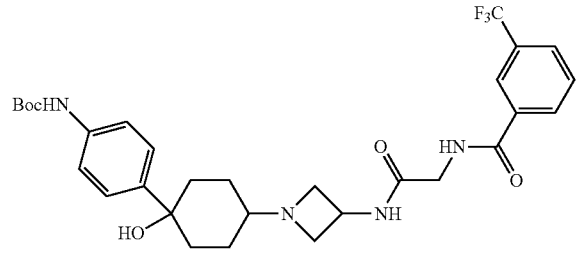 [SMILES: CC(C)(C)OC(=O)Nc1ccc(C2(O)CCC(N3CC(NC(=O)CNC(=O)c4cccc(C(F)(F)F)c4)C3)CC2)cc1]

The title compound was prepared as a white solid by reductive amination of [4-(1-hydroxy-4-oxo-cyclohexyl)-phenyl]-carbamic acid tert-butyl ester (as prepared in the previous step) and N-(azetidin-3-ylcarbamoylmethyl)-3-trifluoromethyl-benzamide (as prepared in step B of Example 4) using the procedure described in Step C of Example 4.

¹H NMR (400 MHz, d₄-MeOH) δ 8.24 (s, 1H), 8.15 (d, J=6.5 Hz, 1H), 7.88 (d, J=6.0 Hz, 1H), 7.70 (t, J=7.2 Hz, 1H), 7.45 (d, J=6.2 Hz, 2H), 7.30 (d, J=7.0 Hz, 2H), 4.45 (m, 1H), 4.05 (s, 2H), 3.65 (t, J=7.5 Hz, 2H), 2.98 (t, J=7.2 Hz, 2H), 2.45 (m, 1H), 2.25 (m, 2H), 1.87 (m, 2H), 1.52 (m, 2H), 1.64 (m, 2H), 1.58 (s, 9H), 1.32 (m, 2H).

Example 51

N-({1-[4-(3-Ethynyl-phenyl)-4-hydroxy-cyclohexyl]-azetidin-3-ylcarbamoyl}-methyl)-3-trifluoromethyl-benzamide

Step A 8-(3-Trimethylsilanylethynyl-phenyl)-1,4-dioxaspiro[4.5]decan-8-ol

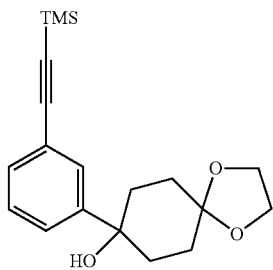 [SMILES: C[Si](C)(C)C#Cc1cccc(C2(O)CCC3(CC2)OCCO3)c1]

The title compound was prepared as a white solid from (4-bromo-phenylethynyl)-trimethyl-silane (Aldrich) and 1,4-dioxa-spiro[4.5]decan-8-one using the procedure described in Step A of Example 1.

$^1$H NMR (400 MHz, CDCl$_3$) δ 7.65 (s, 1H), 7.50 (d, J=6.1 Hz, 1H), 7.35 (d, J=6.0 Hz, 1H), 7.28 (t, J=6.4 Hz, 1H), 4.05 (s, 4H), 2.20 (m, 4H), 1.85 (m, 2H), 1.71 (m, 2H).

Step B

4-Hydroxy-4-(3-trimethylsilanylethynyl-phenyl)-cyclohexanone

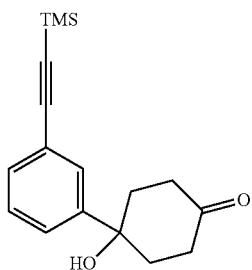 [SMILES: C[Si](C)(C)C#Cc1cccc(C2(O)CCC(=O)CC2)c1]

The title compound was prepared as a white solid from 8-(3-trimethylsilanylethynyl-phenyl)-1,4-dioxa-spiro[4.5]decan-8-ol (as prepared in the previous step) using the procedure described in Step B of Example 1.

$^1$H NMR (400 MHz, CDCl$_3$) δ 7.65 (s, 1H), 7.46 (d, J=6.0 Hz, 1H), 7.40 (d, J=5.8 Hz, 1H), 7.31 (t, J=6.1 Hz, 1H), 2.98 (m, 2H), 2.35 (m, 2H), 2.30 (m, 2H), 2.20 (m, 2H), 2.10 (s, 1H).

Step C

N-({1-[4-(3-Ethynyl-phenyl)-4-hydroxy-cyclohexyl]-azetidin-3-ylcarbamoyl}-methyl)-3-trifluoromethyl-benzamide

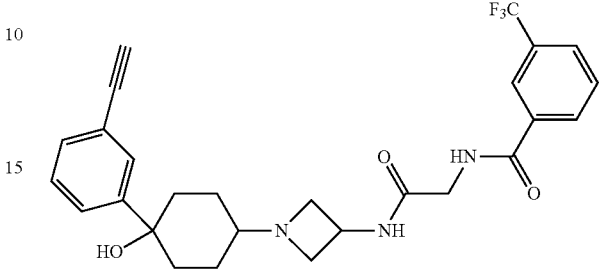

The title compound was prepared as a white solid by reductive amination of 4-hydroxy-4-(3-trimethylsilanylethynyl-phenyl)-cyclohexanone (as prepared in the previous step) and N-(azetidin-3-ylcarbamoylmethyl)-3-trifluoromethyl-benzamide (as prepared in step B of Example 4) using the procedure described in Step C of Example 4 followed by a TBAF work-up using the procedure described in Step D of Example 40.

51a: Less Polar Isomer from Silica Gel Column $^1$H NMR (400 MHz, CDCl$_3$) δ 8.15 (s, 1H), 8.02 (d, J=6.7 Hz, 1H), 7.78 (m, 2H), 7.34 (m, 2H), 7.25 (d, J=6.8 Hz, 1H), 7.10 (d, J=6.5 Hz, 1H), 4.52 (m, 1H), 4.20 (d, J=3.0 Hz, 2H), 3.60 (t, J=7.8 Hz, 2H), 2.90 (t, J=7.5 Hz, 2H), 2.30 (m, 2H), 2.25 (s, br, 1H), 1.80 (m, 2H), 1.55 (m, 2H), 1.40 (m, 2H).

51b: More Polar Isomer from Silica Gel Column $^1$H NMR (400 MHz, CDCl$_3$) δ 8.11 (s, 1H), 8.00 (d, J=6.4 Hz, 1H), 7.77 (d, J=6.5 Hz, 1H), 7.55 (m, 1H), 7.45 (d, J=6.3 Hz, 1H), 7.31 (d, J=6.6 Hz, 1H), 7.20 (d, J=6.4 Hz, 1H), 4.55 (m, 1H), 4.20 (d, J=3.2 Hz, 2H), 3.62 (t, J=7.5 Hz, 2H), 3.02 (t, J=7.5 Hz, 2H), 1.85 (m, 3H), 1.70 (s, br, 3H), 1.80 (m, 1H), 1.50 (m, 2H).

Example 52

N-({1-[4-(3-Ethyl-phenyl)-4-hydroxy-cyclohexyl]-azetidin-3-ylcarbamoyl}-methyl)-3-trifluoromethyl-benzamide

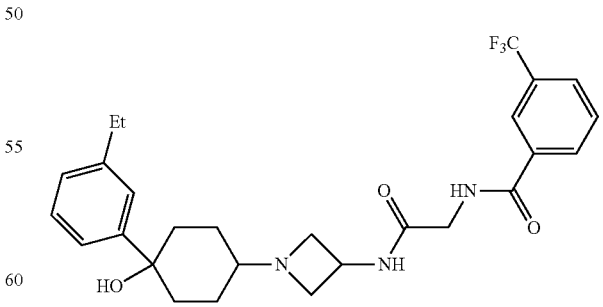

The title compound was prepared as a white solid by hydrogenation of N-({1-[4-(3-ethynyl-phenyl)-4-hydroxy-cyclohexyl]-azetidin-3-ylcarbamoyl}-methyl)-3-trifluoromethyl-benzamide (as prepared in Example 51, less polar isomer) using the procedure described in Step G of Example 1.

$^1$H NMR (400 MHz, d$_4$-MeOH) δ 8.21 (s, 1H), 8.15 (d, J=6.5 Hz, 1H), 7.86 (d, J=6.0 Hz, 1H), 7.70 (t, J=7.2 Hz, 1H), 7.35 (s, 1H), 7.30 (d, J=6.2 Hz, 1H), 7.20 (t, J=7.0 Hz, 1H), 7.05 (d, J=5.6 Hz, 1H), 4.45 (m, 1H), 4.05 (s, 2H), 3.65 (t, J=7.5 Hz, 2H), 2.98 (t, J=7.2 Hz, 2H), 2.65 (q, J=7.2 Hz, 2H), 2.45 (m, 1H), 2.25 (m, 2H), 1.87 (m, 2H), 1.52 (m, 2H), 1.34 (m, 2H), 1.20 (t, J=7.2 Hz, 3H).

Example 53

N-({1-[4-(4-Chloro-phenyl)-4-hydroxy-cyclohexyl]-azetidin-3-ylcarbamoyl}-methyl)-3-trifluoromethyl-benzamide Step A 8-(4-Chloro-phenyl)-1,4-dioxa-spiro[4.5]decan-8-ol

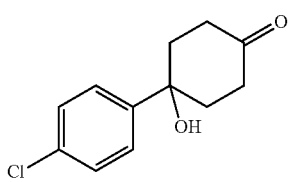 [SMILES: O=C1CCC(O)(c2ccc(Cl)cc2)CC1]

The title compound was prepared as a white solid from 4-bromochlorobenzene (Aldrich) and 1,4-dioxa-spiro[4.5]decan-8-one using the procedure described in Step A of Example 1.

$^1$H NMR(CHLOROFORM-d) δ: 7.46 (d, J=8.6 Hz, 2H), 7.30 (d, J=8.3 Hz, 2H), 3.98 (t, J=4.3 Hz, 4H), 2.51 (t, J=7.1 Hz, 1H), 2.07-2.22 (m, 2H), 1.97-2.07 (m, 2H), 1.78 (d, J=14.7 Hz, 2H), 1.69 (d, J=10.6 Hz, 2H).

Step B 4-(4-Chloro-phenyl)-4-hydroxy-cyclohexanone

The title compound was prepared as a white solid from the de-portection of 8-(4-chloro-phenyl)-1,4-dioxa-spiro[4.5]decan-8-ol (as prepared in the previous step) using the procedure described in Step B of Example 1.

$^1$H NMR(CHLOROFORM-d) δ: 7.42-7.50 (m, 2H), 7.31-7.40 (m, 2H), 2.38 (br. s., 2H), 2.28 (s, 2H), 2.18 (d, J=2.3 Hz, 2H).

Step C

N-({1-[4-(4-Chloro-phenyl)-4-hydroxy-cyclohexyl]-azetidin-3-ylcarbamoyl}-methyl)-3-trifluoromethyl-benzamide

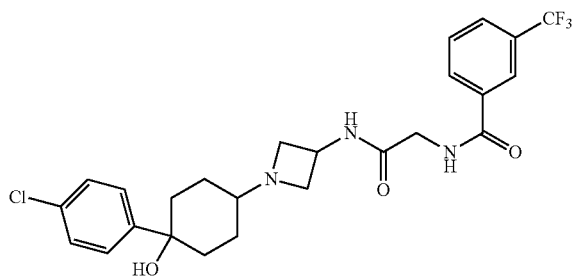 [SMILES: O=C(CNC(=O)c1cccc(C(F)(F)F)c1)NC1CN(C2CCC(O)(c3ccc(Cl)cc3)CC2)C1]

The title compound was prepared as a white solid by reductive amination of 4-(4-chloro-phenyl)-4-hydroxy-cyclohexanone (as prepared in the previous step) and N-(azetidin-3-ylcarbamoylmethyl)-3-trifluoromethyl-benzamide (as prepared in step B of Example 4) using the procedure described in Step C of Example 4.

$^1$H NMR(CHLOROFORM-d) δ: 8.12 (s, 1H), 8.00 (d, J=7.8 Hz, 1H), 7.89 (t, J=5.1 Hz, 1H), 7.75 (d, J=7.8 Hz, 1H), 7.45-7.57 (m, 2H), 7.43 (d, J=8.6 Hz, 1H), 7.27 (d, J=8.6 Hz, 1H), 4.43-4.55 (m, 1H), 4.16 (d, J=5.1 Hz, 2H), 3.58 (t, J=7.3 Hz, 2H), 2.51 (br s., 1H), 2.09-2.20 (m, 2H), 1.73-1.84 (m, 4H), 1.32-1.51 (m, 4H).

Example 54

N-({1-[4-(4-Dimethylamino-phenyl)-4-hydroxy-cyclohexyl]-azetidin-3-ylcarbamoyl}-methyl)-3-trifluoromethyl-benzamide Step A 8-(4-Dimethylamino-phenyl)-1,4-dioxa-spiro[4.5]decan-8-ol

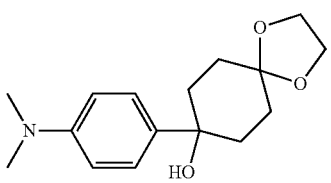 [SMILES: CN(C)c1ccc(C2(O)CCC3(CC2)OCCO3)cc1]

The title compound was prepared as a white solid from 4-bromodimethylamine (Aldrich) and 1,4-dioxa-spiro[4.5]decan-8-one using the procedure described in Step A of Example 1.

¹H NMR(CHLOROFORM-d) δ: 7.38 (d, J=8.6 Hz, 2H), 7.18-7.26 (m, 2H), 2.82-2.90 (m, 4H), 2.63 (s, 2H), 2.42-2.52 (m, 6H), 2.24 (s, 2H), 2.14-2.19 (m, 2H), 2.01 (s, 2H).

Step B 4-(4-Dimethylamino-phenyl)-4-hydroxy-cyclohexanone

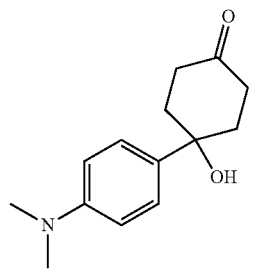 [SMILES: CN(C)c1ccc(C2(O)CCC(=O)CC2)cc1]

The title compound was prepared as a white solid from the de-protection of 8-(4-dimethylamino-phenyl)-1,4-dioxa-spiro[4.5]decan-8-ol (as prepared in the previous step) using the procedure described in Step B of Example 1.

¹H NMR(CHLOROFORM-d) δ: 7.31-7.44 (m, J=9.1 Hz, 2H), 6.67-6.77 (m, J=8.8 Hz, 2H), 2.95 (s, 6H), 2.83-2.92 (m, 2H), 2.28-2.36 (m, 2H), 2.25 (d, J=4.5 Hz, 2H), 2.14-2.22 (m, 2H).

Step C

N-({1-[4-(4-Dimethylamino-phenyl)-4-hydroxy-cyclohexyl]-azetidin-3-ylcarbamoyl}-methyl)-3-trifluoromethyl-benzamide

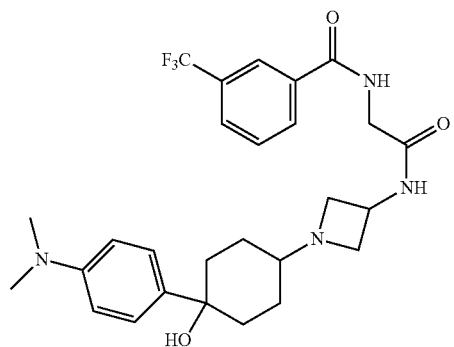 [SMILES: CN(C)c1ccc(C2(O)CCC(N3CC(NC(=O)CNC(=O)c4cccc(C(F)(F)F)c4)C3)CC2)cc1]

The title compound was prepared as a white solid by reductive amination of 4-(4-dimethylamino-phenyl)-4-hydroxy-cyclohexanone (as prepared in the previous step) and N-(azetidin-3-ylcarbamoylmethyl)-3-trifluoromethyl-benzamide (as prepared in step B of Example 4) using the procedure described in Step C of Example 4.

54a: Less Polar Isomer from Silica Gel Column

¹H NMR(CHLOROFORM-d) δ: 8.12 (d, J=4.3 Hz, 1H), 8.01 (t, J=6.9 Hz, 1H), 7.77 (d, J=7.6 Hz, 1H), 7.57 (td, J=7.8, 3.3 Hz, 1H), 7.34 (d, J=8.8 Hz, 1H), 7.37 (d, J=8.8 Hz, 1H), 6.84-6.95 (m, 1H), 6.70 (s, 1H), 4.44 (br s., 1H), 3.57 (t, J=7.3 Hz, 2H), 2.93 (d, J=2.8 Hz, 2H), 2.55 (br s., 2H), 2.16-2.30 (m, 6H), 1.72-1.87 (m, 4H), 1.53-1.61 (m, 2H), 1.29-1.42 (m, 2H).

54b: More Polar Isomer from Silica Gel Column

¹H NMR(CHLOROFORM-d) δ: 8.20 (s, 1H), 8.10 (d, J=7.6 Hz, 1H), 7.81 (d, J=7.6 Hz, 1H), 7.63 (t, J=7.8 Hz, 1H), 7.43 (s, 2H), 7.25-7.38 (m, J=8.8 Hz, 1H), 6.64-6.82 (m, J=8.8 Hz, 1H), 4.49 (t, J=6.4 Hz, 2H), 4.06 (s, 1H), 3.66 (t, J=7.7 Hz, 2H), 3.01-3.13 (m, 2H), 2.86-2.95 (m, 6H), 2.55 (br s, 1H), 1.63-1.90 (m, 4H), 1.48-1.61 (m, 4H).

Example 55

N-({1-[4-(4-benzamide)-4-hydroxy-cyclohexyl]-azetidin-3-ylcarbamoyl}-methyl)-3-trifluoromethyl-benzamide Step A 4-(8-Hydroxy-1,4-dioxa-spiro[4.5]dec-8-yl)-benzamide

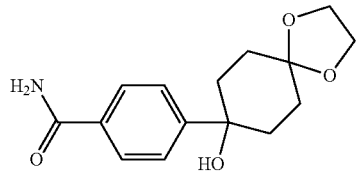 [SMILES: NC(=O)c1ccc(C2(O)CCC3(CC2)OCCO3)cc1]

The title compound was prepared as a white solid from 4-bromobenzamide (Aldrich) and 1,4-dioxa-spiro[4.5]decan-8-one using the procedure described in Step A of Example 1.

¹H NMR (MeOH) δ: 7.77-7.90 (m, J=8.3 Hz, 2H), 7.50-7.63 (m, J=8.3 Hz, 2H), 4.01 (s, 4H), 2.05-2.23 (m, 4H), 1.77-1.88 (m, 2H), 1.63-1.73 (m, 2H).

Step B 4-(1-Hydroxy-4-oxo-cyclohexyl)-benzamide

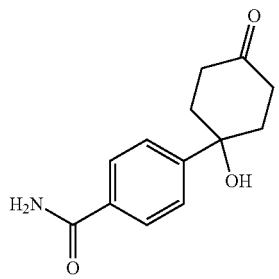 [SMILES: NC(=O)c1ccc(C2(O)CCC(=O)CC2)cc1]

The title compound was prepared as a white solid from the de-protection of 4-(8-hydroxy-1,4-dioxa-spiro[4.5]dec-8-yl)-benzamide (as prepared in the previous step) using the procedure described in Step B of Example 1.

¹H NMR (MeOH) δ: 7.79-7.95 (m, 2H), 7.58-7.68 (m, 2H), 2.94 (td, J=15.3, 6.6 Hz, 2H), 2.31 (s, 4H), 2.12 (s, 2H).

Step C

N-({1-[4-(4-benzamide)-4-hydroxy-cyclohexyl]-azetidin-3-ylcarbamoyl}-methyl)-3-trifluoromethyl-benzamide

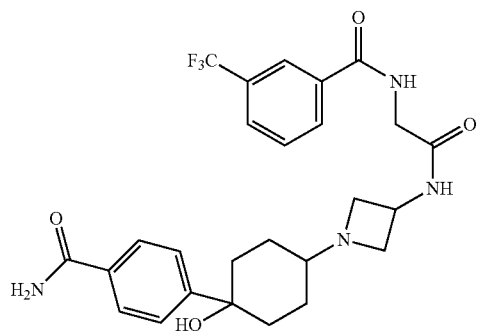 [SMILES: NC(=O)c1ccc(C2(O)CCC(N3CC(NC(=O)CNC(=O)c4cccc(C(F)(F)F)c4)C3)CC2)cc1]

The title compounds were prepared as white solids by reductive amination of 4-(1-hydroxy-4-oxo-cyclohexyl)-benzamide (as prepared in the previous step) and N-(azetidin-3-ylcarbamoylmethyl)-3-trifluoromethyl-benzamide (as prepared in step B of Example 4) using the procedure described in Step C of Example 4.

55a: Less Polar Isomer from Silica Gel Column $^1$H NMR(CHLOROFORM-d) δ: 8.18 (d, J=9.9 Hz, 1H), 8.10 (d, J=7.8 Hz, 1H), 7.71-7.81 (m, 2H), 7.47-7.66 (m, 2H), 6.89-7.09 (m, 2H), 4.29 (dd, J=16.7, 5.8 Hz, 1H), 4.12 (q, J=7.1 Hz, 2H), 3.99 (d, J=6.3 Hz, 2H), 3.66 (d, J=4.3 Hz, 2H), 2.62-2.78 (m, 1H), 2.07-2.25 (m, 2H), 1.99-2.06 (m, 2H), 1.81 (br. s., 2H), 1.70 (d, J=11.1 Hz, 2H).

55b: More Polar Isomer from Silica Gel Column $^1$H NMR(CHLOROFORM-d) δ: 8.08-8.17 (m, 1H), 7.93-8.07 (m, 1H), 7.77 (d, J=5.8 Hz, 2H), 7.55-7.65 (m, 2H), 7.40 (br. s., 1H), 6.78-6.91 (m, 1H), 4.44 (br s, 1H), 4.06-4.15 (m, 2H), 3.58 (t, J=7.7 Hz, 2H), 2.26-2.38 (m, 1H), 2.10-2.24 (m, 2H), 1.73 (t, J=4.9 Hz, 2H), 1.63 (d, J=3.5 Hz, 2H), 1.26-1.33 (m, 4H).

Example 56

N-({1-[4-Hydroxy-4-(2-methoxy-phenyl)-cyclohexyl]-azetidin-3-ylcarbamoyl}-methyl)-3-trifluoromethyl-benzamide

Step A 8-(2-Methoxy-phenyl)-1,4-dioxa-spiro[4.5]decan-8-ol

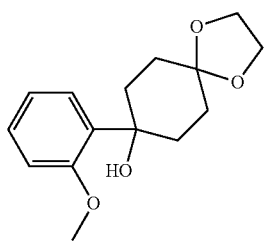 [SMILES: COc1ccccc1C1(O)CCC2(CC1)OCCO2]

The title compound was prepared as a white solid from 2-bromoanisole (Aldrich) and 1,4-dioxa-spiro[4.5]decan-8-one using the procedure described in Step A of Example 1.

$^1$H NMR(CHLOROFORM-d) δ: 7.31 (dd, J=7.7, 1.6 Hz, 1H), 7.19-7.26 (m, 1H), 6.89-6.98 (m, 2H), 3.96 (dd, J=6.7, 4.2 Hz, 4H), 3.89 (s, 3H), 2.50 (t, J=7.1 Hz, 2H), 2.13-2.26 (m, 2H), 2.05-2.12 (m, 4H), 2.00 (t, J=7.1 Hz, 2H).

Step B

4-Hydroxy-4-(2-methoxy-phenyl)-cyclohexanone

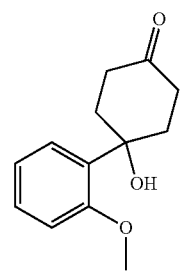 [SMILES: COc1ccccc1C1(O)CCC(=O)CC1]

The title compound was prepared as a white solid from the de-portection of 8-(2-methoxy-phenyl)-1,4-dioxa-spiro[4.5]decan-8-ol (as prepared in the previous step) using the procedure described in Step B of Example 1.

$^1$H NMR(CHLOROFORM-d) δ: 7.32 (dd, J=8.0, 1.6 Hz, 1H), 7.26 (td, J=7.8, 1.5 Hz, 1H), 6.91-7.00 (m, 2H), 3.89 (s, 3H), 2.80-3.02 (m, 2H), 2.19-2.39 (m, 6H).

Step C

N-({1-[4-Hydroxy-4-(2-methoxy-phenyl)-cyclohexyl]-azetidin-3-ylcarbamoyl}-methyl)-3-trifluoromethyl-benzamide

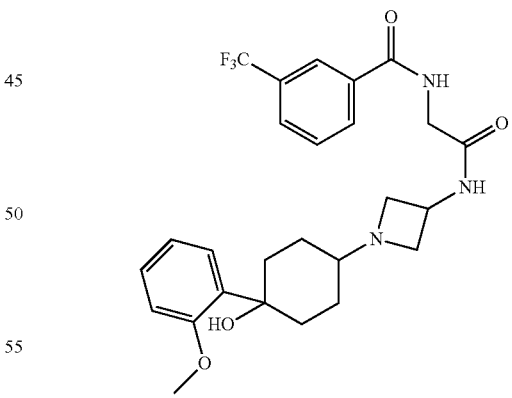

The title compound was prepared as a white solid by reductive amination of 4-hydroxy-4-(2-methoxy-phenyl)-cyclohexanone (as prepared in the previous step) and N-(azetidin-3-ylcarbamoylmethyl)-3-trifluoromethyl-benzamide (as prepared in step B of Example 4) using the procedure described in Step C of Example 4.

56a: Less Polar Isomer from Silica Gel Column $^1$H NMR(CHLOROFORM-d) δ: 8.11 (s, 1H), 8.00 (d, J=7.8 Hz, 1H), 7.76 (d, J=7.8 Hz, 1H), 7.60 (t, J=4.8 Hz, 1H), 7.55 (t, J=7.8 Hz, 1H), 7.31 (d, J=7.6 Hz, 1H), 7.14-7.26 (m, 1H), 6.82-7.01 (m, 1H), 4.38-4.62 (m, 1H), 4.12-4.25 (m, 4H), 2.85 (t, J=6.9 Hz, 3H), 2.25 (t, J=3.7 Hz, 1H), 2.08-2.22 (m, 2H), 1.81-1.96 (m, 4H), 1.75 (d, J=13.1 Hz, 2H), 1.34-1.49 (m, 2H).

56b: More Polar Isomer from Silica Gel Column

¹H NMR(CHLOROFORM-d) δ: 8.13 (s, 1H), 8.03 (d, J=7.8 Hz, 1H), 7.77 (d, J=7.6 Hz, 1H), 7.58 (t, J=7.8 Hz, 1H), 7.36 (t, J=5.1 Hz, 1H), 7.17-7.31 (m, 2H), 6.90-7.01 (m, 1H), 4.26 (d, J=5.8 Hz, 1H), 4.20 (dd, J=12.1, 5.1 Hz, 2H), 3.78 (dd, J=11.1, 4.0 Hz, 2H), 3.06 (dd, J=12.6, 5.6 Hz, 1H), 2.86-2.80 (m, 3H), 2.41-2.57 (m, 2H), 2.10 (d, J=12.9 Hz, 2H), 1.91 (d, J=11.1 Hz, 2H), 1.81 (d, J=11.4 Hz, 2H), 1.74 (d, J=19.2 Hz, 2H).

Example 57

N-({1-[4-(3-Fluoro-4-methoxy-phenyl)-4-hydroxy-cyclohexyl]-azetidin-3-ylcarbamoyl}-methyl)-3-trifluoromethyl-benzamide

Step A 8-(3-Fluoro-4-methoxy-phenyl)-1,4-dioxa-spiro[4.5]decan-8-ol

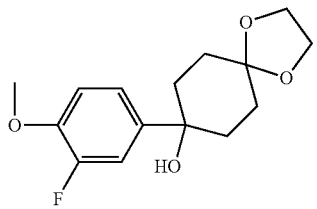 [SMILES: COc1ccc(C2(O)CCC3(CC2)OCCO3)cc1F]

The title compound was prepared as a white solid from 4-bromo-2-fluoro-anisole (Aldrich) and 1,4-dioxa-spiro[4.5]decan-8-one using the procedure described in Step A of Example 1.

¹H NMR (MeOH) δ: 7.05-7.11 (m, 2H), 6.86-6.98 (m, 1H), 3.86 (s, 4H), 3.74 (s, 3H), 1.86-2.01 (m, 4H), 1.60-1.68 (m, 2H), 1.47-1.57 (m, 2H).

Step B 4-(3-Fluoro-4-methoxy-phenyl)-4-hydroxy-cyclohexanone

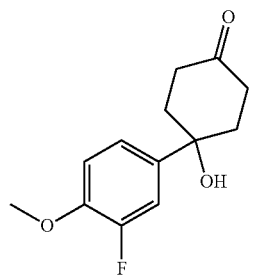 [SMILES: COc1ccc(C2(O)CCC(=O)CC2)cc1F]

The title compound was prepared as a white solid from the de-protection of 8-(3-fluoro-4-methoxy-phenyl)-1,4-dioxa-spiro[4.5]decan-8-ol (as prepared in the previous step) using the procedure described in Step B of Example 1.

¹H NMR (MeOH) δ: 7.21 (d, J=2.3 Hz, 1H), 7.12-7.19 (m, 1H), 6.94 (t, J=8.6 Hz, 1H), 3.21 (s, 3H), 2.76 (d, J=6.3 Hz, 2H), 2.06-2.23 (m, 4H), 1.98 (d, J=6.6 Hz, 2H).

Step C

N-({1-[4-(3-Fluoro-4-methoxy-phenyl)-4-hydroxy-cyclohexyl]-azetidin-3-ylcarbamoyl}-methyl)-3-trifluoromethyl-benzamide

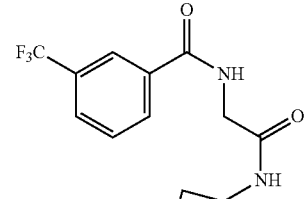

The title compound was prepared as a white solid by reductive amination of 4-hydroxy-4-(4-hydroxy-phenyl)-cyclohexanone (as prepared in the previous step) and N-(azetidin-3-ylcarbamoylmethyl)-3-trifluoromethyl-benzamide (as prepared in step B of Example 4) using the procedure described in Step C of Example 4.

57a: Less Polar Isomer from Silica Gel Column

¹H NMR (MeOH) δ: 8.12 (s, 1H), 7.97-8.09 (m, 1H), 7.77 (d, J=7.1 Hz, 1H), 7.53-7.65 (m, 1H), 7.11-7.22 (m, 2H), 6.86-6.98 (m, 1H), 4.53 (br s, 1H), 4.38 (t, J=7.1 Hz, 2H), 3.75 (s, 3H), 3.57 (t, J=7.7 Hz, 2H), 2.88 (t, J=7.6 Hz, 2H), 2.27 (br. s., 1H), 1.98-2.17 (m, 2H), 1.66-1.82 (m, 2H), 1.41 (d, J=17.9 Hz, 2H), 1.21-1.34 (m, 2H).

57b: More Polar Isomer from Silica Gel Column

¹H NMR (MeOH) δ: 8.13 (s, 1H), 8.06 (d, J=7.8 Hz, 1H), 7.77 (d, J=7.8 Hz, 1H), 7.60 (t, J=7.8 Hz, 1H), 7.03-7.21 (m, 2H), 6.85-7.00 (m, 1H), 4.30 (s, 1H), 3.89-4.07 (m, 4H), 3.74 (s, 3H), 3.60 (d, J=6.1 Hz, 2H), 2.92 (dd, J=12.9, 4.5 Hz, 1H), 2.71-2.85 (m, 2H), 2.61 (br. s., 2H), 1.57-1.82 (m, 2H), 1.18-1.37 (m, 2H).

Example 58

N-({1-[4-(3-Amino-phenyl)-4-hydroxy-cyclohexyl]-azetidin-3-ylcarbamoyl}-methyl)-3-trifluoromethyl-benzamide

Step A

[3-(8-Hydroxy-1,4-dioxa-spiro[4.5]dec-8-yl)-phenyl]-carbamic acid tert-butyl ester

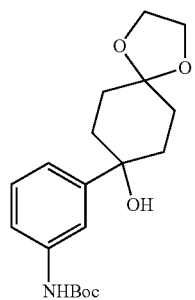 [SMILES: CC(C)(C)OC(=O)Nc1cccc(C2(O)CCC3(CC2)OCCO3)c1]

The title compound was prepared as a white solid from N-Boc-3-bromoanaline (Aldrich) and 1,4-dioxa-spiro[4.5]decan-8-one using the procedure described in Step A of Example 1.

¹H NMR (MeOH) δ: 7.54 (s, 1H), 7.26-7.32 (m, 1H), 7.23 (t, J=7.8 Hz, 1H), 7.10-7.19 (m, 1H), 3.99 (s, 4H), 2.00-2.21 (m, 4H), 1.78 (d, J=11.4 Hz, 2H), 1.66 (d, J=10.9 Hz, 2H), 1.54 (s, 9H).

Step B

[3-(1-Hydroxy-4-oxo-cyclohexyl)-phenyl]-carbamic acid tert-butyl ester

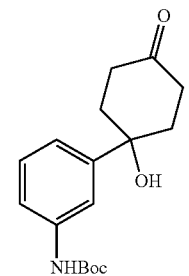 [SMILES: CC(C)(C)OC(=O)Nc1cccc(C2(O)CCC(=O)CC2)c1]

The title compound was prepared as a white solid from the de-portection of [3-(8-hydroxy-1,4-dioxa-spiro[4.5]dec-8-yl)-phenyl]-carbamic acid tert-butyl ester (as prepared in the previous step) using the procedure described in Step B of Example 1.

¹H NMR (MeOH) δ: 7.61 (s, 1H), 7.14-7.41 (m, 3H), 2.88 (d, J=8.8 Hz, 2H), 2.22-2.32 (m, 2H), 2.17 (s, 2H), 2.06-2.15 (m, 2H), 1.54 (s, 9H).

Step C

[3-(1-Hydroxy-4-{3-[2-(3-trifluoromethyl-benzoylamino)-acetylamino]-azetidin-1-yl}-cyclohexyl)-phenyl]-carbamic acid tert-butyl ester

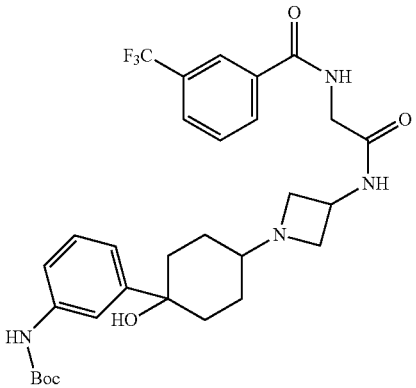 [SMILES: CC(C)(C)OC(=O)Nc1cccc(C2(O)CCC(N3CC(NC(=O)CNC(=O)c4cccc(C(F)(F)F)c4)C3)CC2)c1]

The title compound was prepared as a white solid by reductive amination of [3-(1-hydroxy-4-oxo-cyclohexyl)-phenyl]-carbamic acid tert-butyl ester (as prepared in the previous step) and N-(azetidin-3-ylcarbamoylmethyl)-3-trifluoromethyl-benzamide (as prepared in step B of Example 4) using the procedure described in Step C of Example 4.

Less Polar Isomer from Silica Gel Column

¹H NMR (MeOH) δ: 8.24 (s, 1H), 8.16 (d, J=8.3 Hz, 1H), 7.89 (d, J=8.6 Hz, 1H), 7.68-7.77 (m, 1H), 7.53-7.63 (m, 1H), 7.16-7.36 (m, 3H), 4.66 (br s., 1H), 4.48 (t, J=7.1 Hz, 2H), 3.67 (t, J=7.6 Hz, 2H), 2.99 (t, J=7.7 Hz, 2H), 2.37 (br. s., 1H), 2.23-2.32 (m, 2H), 1.80-1.93 (m, 2H), 1.58-1.67 (m, 2H), 1.52 (s, 9H), 1.32-1.46 (m, 2H).

More Polar Isomer from Silica Gel Column

¹H NMR (MeOH) δ: 8.13 (s, 1H), 8.05 (d, J=7.8 Hz, 1H), 7.78 (d, J=8.1 Hz, 1H), 7.60 (t, J=7.8 Hz, 1H), 7.44 (s, 1H), 6.99-7.18 (m, 3H), 4.66 (br s, 1H), 4.42 (t, J=7.2 Hz, 2H), 3.75 (t, J=8.2 Hz, 2H), 2.32-2.44 (m, 1H), 2.22 (br s, 2H), 1.79-1.85 (m, 2H), 1.60-1.68 (m, 4H), 1.45-1.59 (m, 2H), 1.42 (s, 9H).

Step D

N-({1-[4-(3-Amino-phenyl)-4-hydroxy-cyclohexyl]-azetidin-3-ylcarbamoyl}-methyl)-3-trifluoromethyl-benzamide

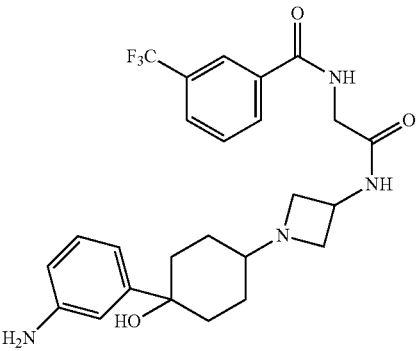 [SMILES: Nc1cccc(C2(O)CCC(N3CC(NC(=O)CNC(=O)c4cccc(C(F)(F)F)c4)C3)CC2)c1]

To a solution of [3-(1-Hydroxy-4-{3-[2-(3-trifluoromethyl-benzoylamino)-acetylamino]-azetidin-1-yl}-cyclohexyl)-phenyl]-carbamic acid tert-butyl ester (as prepared in the previous step, 25 mg) in DCM (1 mL) was added 4N HCl (200 μL). The reaction was stirred at RT and concentrated in vacuo resulting in the title compound.

58a: From Less Polar Isomer of Step C

¹H NMR (MeOH) δ: 8.16 (s, 1H), 8.09 (d, J=7.8 Hz, 1H), 7.81 (d, J=7.8 Hz, 1H), 7.64 (t, J=7.8 Hz, 1H), 6.97-7.05 (m, 1H), 6.88 (t, J=1.9 Hz, 1H), 6.78-6.86 (m, 1H), 6.55 (d, J=10.1 Hz, 1H), 3.95-4.00 (m, 1H), 3.56-3.64 (m, 4H), 2.92 (t, J=7.7 Hz, 2H), 2.30 (d, J=3.8 Hz, 1H), 2.12-2.25 (m, 2H), 1.73-1.84 (m, 2H), 1.40-1.53 (m, 2H), 1.26-1.40 (m, 2H).

58b: From More Polar Isomer of Step C

¹H NMR (MeOH) δ: 8.14 (s, 1H), 8.08 (d, J=7.8 Hz, 1H), 7.79 (d, J=7.8 Hz, 1H), 7.62 (t, J=7.7 Hz, 1H), 7.49-7.57 (m, 2H), 7.38-7.48 (m, 1H), 7.18 (d, J=7.8 Hz, 1H), 4.20 (br s, 1H), 3.39 (br. s., 4H), 2.92 (t, J=7.7 Hz, 2H), 2.30 (d, J=3.8 Hz, 1H), 1.65-1.95 (m, 8H).

Example 59

N-{[1-(4-Hydroxy-4-p-tolyl-cyclohexyl)-azetidin-3-ylcarbamoyl]-methyl}-3-trifluoromethyl-benzamide Step A 8-p-Tolyl-1,4-dioxa-spiro[4.5]decan-8-ol

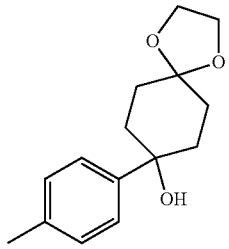 [SMILES: Cc1ccc(C2(O)CCC3(CC2)OCCO3)cc1]

The title compound was prepared as a white solid from 4-bromotoluene (Aldrich) and 1,4-dioxa-spiro[4.5]decan-8-one using the procedure described in Step A of Example 1.

¹H NMR (MeOH) δ: 7.31-7.45 (m, J=8.3 Hz, 2H), 7.09-7.21 (m, J=8.1 Hz, 2H), 3.99 (s, 4H), 2.32 (s, 3H), 1.96-2.18 (m, 4H), 1.77 (d, J=11.4 Hz, 2H), 1.59-1.71 (m, 2H).

Step B

4-Hydroxy-4-p-tolyl-cyclohexanone

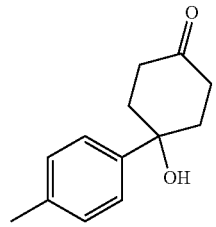

The title compound was prepared as a white solid from the de-protection of 8-p-tolyl-1,4-dioxa-spiro[4.5]decan-8-ol (as prepared in the previous step) using the procedure described in Step B of Example 1.

¹H NMR (MeOH) δ: 7.44 (d, J=8.1 Hz, 2H), 7.17 (d, J=7.8 Hz, 2H), 2.81-2.97 (m, 3H), 2.22-2.38 (m, 4H), 2.11 (dd, J=14.3, 3.2 Hz, 2H).

Step C

N-{[1-(4-Hydroxy-4-p-tolyl-cyclohexyl)-azetidin-3-ylcarbamoyl]-methyl}-3-trifluoromethyl-benzamide

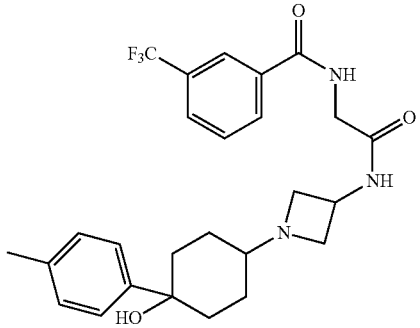 [SMILES: Cc1ccc(C2(O)CCC(N3CC(NC(=O)CNC(=O)c4cccc(C(F)(F)F)c4)C3)CC2)cc1]

The title compound was prepared as a white solid by reductive amination of 4-hydroxy-4-p-tolyl-cyclohexanone (as prepared in the previous step) and N-(azetidin-3-ylcarbamoylmethyl)-3-trifluoromethyl-benzamide (as prepared in step B of Example 4) using the procedure described in Step C of Example 4.

¹H NMR (MeOH) δ: 8.19-8.29 (m, 1H), 8.09-8.17 (m, 1H), 7.82-7.93 (m, 1H), 7.71 (t, J=7.2 Hz, 1H), 7.38-7.51 (m, 2H), 7.11-7.25 (m, 2H), 4.08-4.14 (m, 1H), 4.01-4.08 (m, 2H), 3.67 (t, J=7.7 Hz, 2H), 2.89-3.06 (m, 2H), 2.35 (d, J=8.1 Hz, 1H), 2.32 (s, 3H), 2.14-2.30 (m, 2H), 2.03 (s, 2H), 1.76-1.93 (m, 2H), 1.43-1.65 (m, 2H).

Example 60

N-{[1-(4-Hydroxy-4-m-tolyl-cyclohexyl)-azetidin-3-ylcarbamoyl]-methyl}-3-trifluoromethyl-benzamide Step A 8-m-Tolyl-1,4-dioxa-spiro[4.5]decan-8-ol

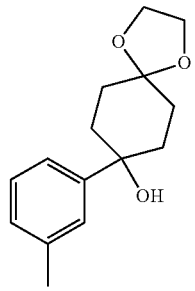

The title compound was prepared as a white solid from 3-bromotoluene (Aldrich) and 1,4-dioxa-spiro[4.5]decan-8-one using the procedure described in Step A of Example 1.

$^1$H NMR (MeOH) δ: 7.33 (s, 1H), 7.28 (d, J=7.8 Hz, 1H), 7.20 (t, J=7.7 Hz, 1H), 7.04 (d, J=7.3 Hz, 1H), 3.98 (s, 4H), 2.06-2.20 (m, 4H), 1.97-2.06 (m, 3H), 1.76 (d, J=11.4 Hz, 2H), 1.66 (d, J=10.6 Hz, 2H).

Step B

4-Hydroxy-4-m-tolyl-cyclohexanone

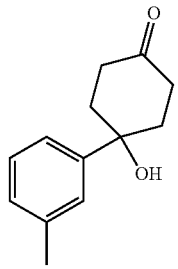

The title compound was prepared as a white solid from the de-protection of 8-m-tolyl-1,4-dioxa-spiro[4.5]decan-8-ol (as prepared in the previous step) using the procedure described in Step B of Example 1.

$^1$H NMR (MeOH) δ: 7.39 (s, 1H), 7.33 (s, 1H), 7.23 (t, J=7.6 Hz, 1H), 7.07 (d, J=7.6 Hz, 1H), 2.90 (d, J=6.3 Hz, 2H), 2.70 (s, 3H), 2.34-2.39 (m, 4H), 2.24-2.33 (m, 2H), 2.06-2.16 (m, 2H).

Step C

N-{[1-(4-Hydroxy-4-m-tolyl-cyclohexyl)-azetidin-3-ylcarbamoyl]-methyl}-3-trifluoromethyl-benzamide

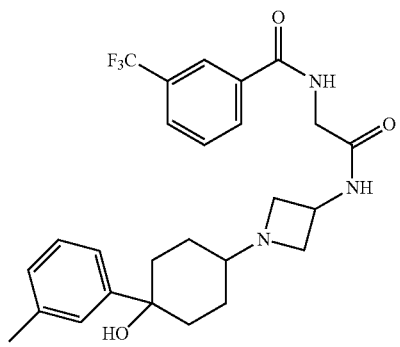 [SMILES: Cc1cccc(C2(O)CCC(N3CC(NC(=O)CNC(=O)c4cccc(C(F)(F)F)c4)C3)CC2)c1]

The title compound was prepared as a white solid by reductive amination of 4-hydroxy-4-m-tolyl-cyclohexanone (as prepared in the previous step) and N-(azetidin-3-ylcarbamoylmethyl)-3-trifluoromethyl-benzamide (as prepared in step B of Example 4) using the procedure described in Step C of Example 4.

$^1$H NMR (MeOH) δ: 8.25 (s, 1H), 8.18 (d, J=7.8 Hz, 1H), 7.89 (d, J=8.3 Hz, 1H), 7.69-7.78 (m, 1H), 7.32 (s, 1H), 7.27 (d, J=7.8 Hz, 1H), 7.19 (t, J=7.6 Hz, 1H), 7.03 (d, J=7.3 Hz, 1H), 4.21 (br s, 1H), 3.72 (d, J=6.8 Hz, 4H), 2.96-3.05 (m, 2H), 2.77-2.94 (m, 1H), 2.35 (s, 3H), 1.87 (d, J=13.6 Hz, 4H), 1.67-1.83 (m, 4H).

Example 61

N-({1-[4-Hydroxy-4-(3-methanesulfonylamino-phenyl)-cyclohexyl]-azetidin-3-ylcarbamoyl}-methyl)-3-trifluoromethyl-benzamide

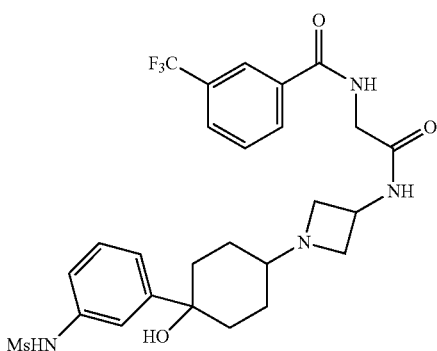

The title compound was prepared as a white solid by mesylation of N-({1-[4-(3-amino-phenyl)-4-hydroxy-cyclohexyl]-azetidin-3-ylcarbamoyl}-methyl)-3-trifluoromethyl-benzamide (as prepared in Example 58) using the procedure described in Example 16.

ESI-MS (m/z): Calcd. For $C_{26}H_{31}F_3N_4O_5S$, 568; found: 569 (M+H).

Example 62

N-({1-[4-(1,3-Dimethyl-2-oxo-2,3-dihydro-1H-benzoimidazol-5-yl)-4-hydroxy-cyclohexyl]-azetidin-3-ylcarbamoyl}-methyl)-3-trifluoromethyl-benzamide Step A 5-(8-Hydroxy-1,4-dioxa-spiro[4.5]dec-8-yl)-1,3-dimethyl-1,3-dihydro-benzoimidazol-2-one

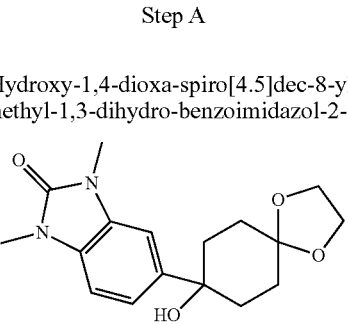

The title compound was prepared as a white solid from 5-bromo-1,3-dimethyl-1,3-dihydro-benzoimidazol-2-one (prepared by methylation of 5-bromo-1,3-dihydro-benzoimidazol-2-one from Pharmlab) and 1,4-dioxa-spiro[4.5]decan-8-one using the procedure described in Step A of Example 1.

¹H NMR (MeOH) δ: 7.21-7.36 (m, 2H), 7.03 (d, J=8.1 Hz, 1H), 4.02 (br s, 4H), 3.43 (d, J=9.1 Hz, 6H), 2.08-2.33 (m, 4H), 1.83 (d, J=10.1 Hz, 2H), 1.70 (d, J=9.6 Hz, 2H)

Step B 5-(1-Hydroxy-4-oxo-cyclohexyl)-1,3-dimethyl-1,3-dihydro-benzoimidazol-2-one

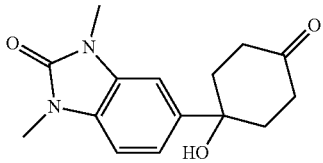

The title compound was prepared as a white solid from the de-portection of 5-(8-hydroxy-1,4-dioxa-spiro[4.5]dec-8-yl)-1,3-dimethyl-1,3-dihydro-benzoimidazol-2-one (as prepared in the previous step) using the procedure described in Step B of Example 1.

¹H NMR(CHLOROFORM-d) δ: 7.21 (dd, J=8.1, 1.8 Hz, 1H), 7.16 (d, J=1.5 Hz, 1H), 6.88 (d, J=8.1 Hz, 1H), 3.42 (d, J=3.5 Hz, 3H), 3.34 (d, J=5.8 Hz, 3H), 2.89-3.05 (m, 2H), 2.38 (d, J=16.7 Hz, 2H), 2.27 (d, J=3.5 Hz, 4H)

Step C

N-({1-[4-(1,3-Dimethyl-2-oxo-2,3-dihydro-1H-benzoimidazol-5-yl)-4-hydroxy-cyclohexyl]-azetidin-3-ylcarbamoyl}-methyl)-3-trifluoromethyl-benzamide

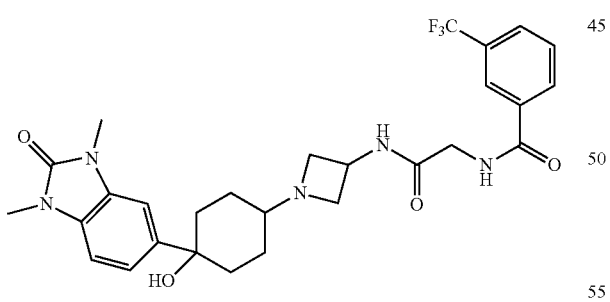

The title compound was prepared as a white solid by reductive amination of 5-(1-hydroxy-4-oxo-cyclohexyl)-1,3-dimethyl-1,3-dihydro-benzoimidazol-2-one (as prepared in the previous step) and N-(azetidin-3-ylcarbamoylmethyl)-3-trifluoromethyl-benzamide (as prepared in step B of Example 4) using the procedure described in Step C of Example 4.

¹H NMR (MeOH) δ: 8.12 (s, 1H), 8.04 (d, J=7.8 Hz, 1H), 7.77 (d, J=7.8 Hz, 1H), 7.59 (t, J=7.8 Hz, 1H), 7.25 (s, 1H), 7.04-7.14 (m, 1H), 6.95-7.02 (m, 1H), 4.40 (t, J=7.1 Hz, 1H), 3.89-3.95 (m, 2H), 3.59 (t, J=7.8 Hz, 2H), 3.30 (s, 6H), 2.88 (t, J=7.7 Hz, 2H), 2.26-2.36 (m, 1H), 2.08-2.22 (m, 2H), 1.74-1.83 (m, 2H), 1.42-1.52 (m, 2H), 1.33 (dd, J=13.5, 4.9 Hz, 2H).

Example 63

N-({1-[4-Hydroxy-4-(3-methyl-2-oxo-2,3-dihydro-benzooxazol-5-yl)-cyclohexyl]-azetidin-3-ylcarbamoyl}-methyl)-3-trifluoromethyl-benzamide Step A 5-(8-Hydroxy-1,4-dioxa-spiro[4.5]dec-8-yl)-3-methyl-3H-benzooxazol-2-one

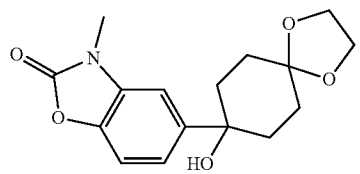

The title compound was prepared as a white solid from 5-bromo-3-methyl-3H-benzooxazol-2-one (prepared by methylation of 5-bromo-3H-benzooxazol-2-one from Aldrich) and 1,4-dioxa-spiro[4.5]decan-8-one using the procedure described in Step A of Example 1.

¹H NMR(CHLOROFORM-d) δ: 7.23-7.31 (m, 1H), 7.18 (s, 1H), 7.07-7.14 (m, 1H), 3.99 (s, 4H), 3.43 (s, 3H), 2.04-2.22 (m, 4H), 1.83 (d, J=10.1 Hz, 2H), 1.70 (d, J=9.3 Hz, 2H)

Step B 5-(1-Hydroxy-4-oxo-cyclohexyl)-3-methyl-3H-benzooxazol-2-one

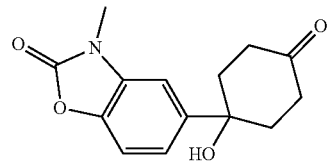 [SMILES: Cn1c(=O)n(C)c2cc(C3(O)CCC(=O)CC3)ccc21]

The title compound was prepared as a white solid from the de-protection of 5-(8-hydroxy-1,4-dioxa-spiro[4.5]dec-8-yl)-3-methyl-3H-benzooxazol-2-one (as prepared in the previous step) using the procedure described in Step B of Example 1.

¹H NMR (MeOH) δ: 7.31-7.38 (m, 2H), 7.20 (d, J=8.3 Hz, 1H), 3.43 (s, 3H), 2.84-3.01 (m, 2H), 2.24-2.44 (m, 4H), 2.15 (d, J=11.9 Hz, 2H)

Step C

N-({1-[4-Hydroxy-4-(3-methyl-2-oxo-2,3-dihydro-benzooxazol-5-yl)-cyclohexyl]-azetidin-3-ylcarbamoyl}-methyl)-3-trifluoromethyl-benzamide

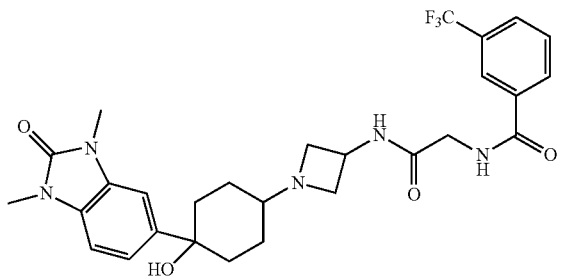 [SMILES: Cn1c(=O)n(C)c2cc(C3(O)CCC(N4CC(NC(=O)CNC(=O)c5cccc(C(F)(F)F)c5)C4)CC3)ccc21]

The title compound was prepared as a white solid by reductive amination of 5-(1-hydroxy-4-oxo-cyclohexyl)-3-methyl-3H-benzooxazol-2-one (as prepared in the previous step) and N-(azetidin-3-ylcarbamoylmethyl)-3-trifluoromethyl-benzamide (as prepared in step B of Example 4) using the procedure described in Step C of Example 4.

63a: Less Polar Isomer from Silica Gel Column $^1$H NMR (MeOH) δ: 8.23 (s, 1H), 8.16 (d, J=7.8 Hz, 1H), 7.87 (d, J=7.8 Hz, 1H), 7.70 (t, J=7.8 Hz, 1H), 7.38 (s, 2H), 7.18 (d, J=9.1 Hz, 1H), 4.52 (quin, J=7.1 Hz, 1H), 4.00-4.07 (m, 2H), 3.71 (t, J=7.7 Hz, 2H), 3.42 (s, 3H), 2.98 (t, J=7.8 Hz, 2H), 2.22 (t, J=10.6 Hz, 1H), 1.99-2.06 (m, 2H), 1.84-1.94 (m, 2H), 1.43-1.57 (m, 4H).

63b: More Polar Isomer from Silica Gel Column $^1$H NMR (MeOH) δ: 8.24 (s, 1H), 8.17 (d, J=7.8 Hz, 1H), 7.88 (d, J=8.1 Hz, 1H), 7.71 (t, J=7.8 Hz, 1H), 7.24-7.35 (m, 2H), 7.18 (d, J=8.6 Hz, 1H), 4.50 (t, J=7.1 Hz, 1H), 4.07 (s, 2H), 3.71 (t, J=7.8 Hz, 2H), 3.41 (s, 3H), 3.10 (t, J=7.8 Hz, 2H), 2.19-2.34 (m, 1H), 1.78-1.93 (m, 4H), 1.67-1.76 (m, 2H), 1.50-1.67 (m, 2H)

Example 64

N-({1-[4-Hydroxy-4-(3-methyl-3H-benzoimidazol-5-yl)-cyclohexyl]-azetidin-3-ylcarbamoyl}-methyl)-3-trifluoromethyl-benzamide

Step A 8-(3-Methyl-3H-benzoimidazol-5-yl)-1,4-dioxa-spiro[4.5]decan-8-ol

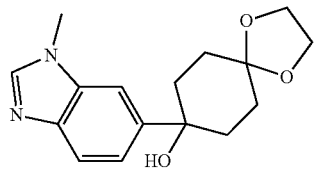 [SMILES: Cn1cnc2ccc(C3(O)CCC4(CC3)OCCO4)cc21]

The title compound was prepared as a white solid from 5-bromo-1-methyl-1H-benzoimidazole (prepared by methylation of 5-bromo-1H-benzoimidazole) and 1,4-dioxa-spiro[4.5]decan-8-one using the procedure described in Step A of Example 1.

$^1$H NMR (MeOH) δ: 7.85 (s, 1H), 7.70 (s, 1H), 7.62 (d, J=8.6 Hz, 1H), 7.45 (d, J=8.6 Hz, 1H), 3.91 (d, J=5.3 Hz, 4H), 3.33 (d, J=5.1 Hz, 3H), 2.17-2.32 (m, 2H), 2.07-2.17 (m, 2H), 1.85 (d, J=12.1 Hz, 2H), 1.69 (d, J=15.7 Hz, 2H)

Step B

4-Hydroxy-4-(3-methyl-3H-benzoimidazol-5-yl)-cyclohexanone

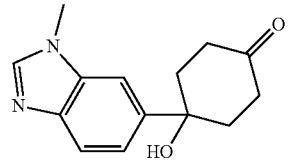 [SMILES: Cn1cnc2ccc(C3(O)CCC(=O)CC3)cc21]

The title compound was prepared as a white solid from the de-protection of 8-(3-methyl-3H-benzoimidazol-5-yl)-1,4-dioxa-spiro[4.5]decan-8-ol (as prepared in the previous step) using the procedure described in Step B of Example 1.

$^1$H NMR (MeOH) δ: 7.66 (s, 1H), 7.53 (d, J=8.6 Hz, 1H), 7.37-7.47 (m, 2H), 3.80 (d, J=6.6 Hz, 4H), 3.20 (s, 3H), 2.76-2.90 (m, 2H), 2.25-2.40 (m, 2H), 2.21 (d, J=17.4 Hz, 2H), 2.07 (d, J=12.6 Hz, 2H).

Step C

N-({1-[4-Hydroxy-4-(3-methyl-3H-benzoimidazol-5-yl)-cyclohexyl]-azetidin-3-ylcarbamoyl}-methyl)-3-trifluoromethyl-benzamide The title compound was prepared as a white solid by reductive amination of 4-hydroxy-4-(3-methyl-3H-benzoimidazol-5-yl)-cyclohexanone (as prepared in the previous step) and N-(azetidin-3-ylcarbamoylmethyl)-3-trifluoromethyl-benzamide (as prepared in step B of Example 4) using the procedure described in Step C of Example 4.

$^1$H NMR (MeOH) δ: 8.24 (s, 1H), 8.16 (d, J=7.8 Hz, 1H), 8.10 (s, 1H), 7.83-7.94 (m, 1H), 7.67-7.79 (m, 1H), 7.49-7.67 (m, 2H), 4.50 (t, J=8.6 Hz, 1H), 4.03-4.09 (m, 2H), 3.85-3.95 (m, 2H), 3.33 (s, 3H), 2.96-3.04 (m, 1H), 2.40 (d, J=7.3 Hz, 2H), 2.28-2.37 (m, 2H), 1.89-1.98 (m, 2H), 1.57-1.71 (m, 2H), 1.36-1.53 (m, 2H).

Example 65

N-({1-[4-(3-Ethyl-2-oxo-2,3-dihydro-benzooxazol-5-yl)-4-hydroxy-cyclohexyl]-azetidin-3-ylcarbamoyl}-methyl)-3-trifluoromethyl-benzamide

Step A

3-Ethyl-5-(8-hydroxy-1,4-dioxa-spiro[4.5]dec-8-yl)-3H-benzooxazol-2-one

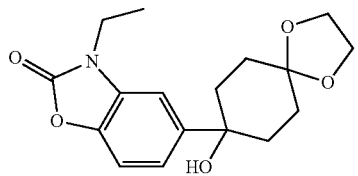 [SMILES: CCn1c(=O)oc2ccc(C3(O)CCC4(CC3)OCCO4)cc21]

The title compound was prepared as a white solid from 5-bromo-3-ethyl-3H-benzooxazol-2-one (prepared by ethylation of 5-bromo-3H-benzooxazol-2-one) and 1,4-dioxa-spiro[4.5]decan-8-one using the procedure described in Step A of Example 1.

¹H NMR (MeOH) δ: 7.37 (s, 1H), 7.31 (dd, J=8.3, 1.8 Hz, 1H), 7.21 (d, J=8.3 Hz, 1H), 3.99-4.04 (m, 3H), 3.94 (q, J=7.3 Hz, 2H), 3.33 (dt, J=3.1, 1.6 Hz, 4H), 2.04-2.24 (m, 4H), 1.79 (d, J=11.9 Hz, 2H), 1.68 (d, J=11.4 Hz, 2H)

Step B

3-Ethyl-5-(1-hydroxy-4-oxo-cyclohexyl)-3H-benzooxazol-2-one

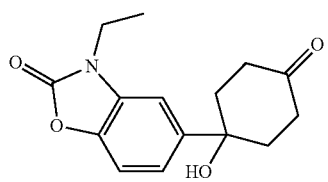 [SMILES: CCn1c(=O)oc2ccc(C3(O)CCC(=O)CC3)cc21]

The title compound was prepared as a white solid from the de-protection of 3-ethyl-5-(8-hydroxy-1,4-dioxa-spiro[4.5]dec-8-yl)-3H-benzooxazol-2-one using the procedure described in Step B of Example 1.

ESI-MS (m/z): Calcd. For C₁₅H₁₇NO₄: 275.1; found: 276.2 (M+H).

Step C

N-({1-[4-(3-Ethyl-2-oxo-2,3-dihydro-benzooxazol-5-yl)-4-hydroxy-cyclohexyl]-azetidin-3-ylcarbamoyl}-methyl)-3-trifluoromethyl-benzamide

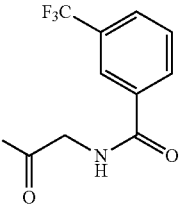

The title compound was prepared as a white solid by reductive amination of 3-ethyl-5-(1-hydroxy-4-oxo-cyclohexyl)-3H-benzooxazol-2-one (as prepared in the previous step) and N-(azetidin-3-ylcarbamoylmethyl)-3-trifluoromethyl-benzamide (as prepared in step B of Example 4) using the procedure described in Step C of Example 4.

65a: Less Polar Isomer from Silica Gel Column

¹H NMR (MeOH) δ: 8.24 (s, 1H), 8.16 (d, J=7.8 Hz, 1H), 7.87 (d, J=7.8 Hz, 1H), 7.70 (t, J=8.0 Hz, 1H), 7.42 (s, 1H), 7.38 (d, J=6.6 Hz, 1H), 7.19 (d, J=8.6 Hz, 1H), 4.47-4.60 (m, 1H), 4.07 (br s, 2H), 3.93 (q, J=7.2 Hz, 2H), 3.71 (t, J=7.7 Hz, 2H), 2.98 (t, J=7.8 Hz, 2H), 2.40-2.49 (m, 1H), 2.15-2.31 (m, 2H), 1.80-1.94 (m, 2H), 1.44-1.59 (m, 4H), 1.37 (t, J=7.2 Hz, 3H).

65b: More Polar Isomer from Silica Gel Column

¹H NMR (MeOH) δ: 8.25 (s, 1H), 8.17 (d, J=7.8 Hz, 1H), 7.89 (d, J=7.8 Hz, 1H), 7.72 (t, J=7.8 Hz, 1H), 7.36 (d, J=1.5 Hz, 1H), 7.28 (dd, J=8.3, 1.8 Hz, 1H), 7.20 (d, J=8.6 Hz, 1H), 4.50 (quin, J=7.1 Hz, 1H), 4.07 (s, 2H), 3.93 (q, J=7.3 Hz, 2H), 3.72 (t, J=7.8 Hz, 2H), 3.10 (t, J=7.8 Hz, 2H), 2.23-2.35 (m, 1H), 1.78-1.92 (m, 4H), 1.70-1.78 (m, 2H), 1.55-1.68 (m, 2H), 1.37 (t, J=7.2 Hz, 3H).

Example 66

2-Fluoro-N-{[1-(4-phenyl-cyclohexyl)-azetidin-3-ylcarbamoyl]-methyl}-5-trifluoromethyl-benzamide

Step A

[1-(4-Phenyl-cyclohexyl)-azetidin-3-yl]-carbamic acid tert-butyl ester

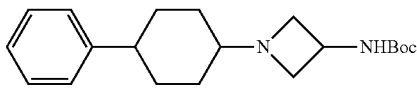 [SMILES: CC(C)(C)OC(=O)NC1CN(C2CCC(c3ccccc3)CC2)C1]

The title compound was prepared as a white solid by reductive amination of 4-phenyl-cyclohexanone and azetidin-3-yl-carbamic acid tert-butyl ester using the procedure described in Step D of Example 1.

Less Polar Fraction from Silica Gel Column Collected

¹H NMR (400 MHz, CDCl₃) δ 7.23 (m, 4H), 7.15 (t, J=6.5 Hz, 1H), 4.90 (s, br, 1H), 4.28 (s, br, 1H), 3.55 (t, J=6.4 Hz,

2H), 2.75 (s, br, 1H), 2.43 (m, 1H), 1.85 (m 2H), 1.71 (d, J=7.5 Hz, 2H), 1.64 (d, J=7.4 Hz, 2H), 1.55 (m, 2H), 1.53 (s, 9H).

Step B (4-Phenyl-cyclohexyl)-azetidin-3-ylamine TFA Salt

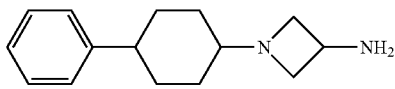 [SMILES: NC1CN(C2CCC(c3ccccc3)CC2)C1]

The title compound was prepared as colorless oil from the TFA de-protection of [1-(4-phenyl-cyclohexyl)-azetidin-3-yl]-carbamic acid tert-butyl ester (as prepared in the previous step) using the procedure described in Step E of Example 1.

$^1$H NMR (400 MHz, CDCl$_3$) δ 7.23 (m, 4H), 7.15 (m, 1H), 3.60 (t, J=6.5 Hz, 2H), 3.15 (m, 1H), 2.55 (t, J=6.5 Hz, 2H), 2.35 (m, 1H), 2.21 (m, 1H), 1.85 (m, 2H), 1.70 (m, 2H), 1.65 (m, 2H), 1.48 (m, 2H).

Step C

{[1-(4-Phenyl-cyclohexyl)-azetidin-3-ylcarbamoyl]-methyl}-carbamic acid tert-butyl ester

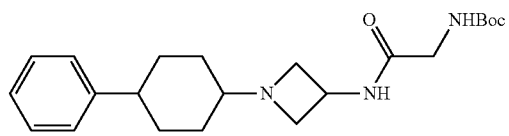 [SMILES: CC(C)(C)OC(=O)NCC(=O)NC1CN(C2CCC(c3ccccc3)CC2)C1]

The title compound was prepared as a white solid from the EDCI coupling of (4-phenyl-cyclohexyl)-azetidin-3-ylamine TFA salt (as prepared in the previous step) and tert-butoxycarbonylamino-acetic acid (Aldrich) using the procedure described in Step F of Example 1.

$^1$H NMR (400 MHz, CDCl$_3$) δ 7.25 (m, 4H), 7.18 (m, 1H), 5.21 (s, br, 1H), 4.52 (m, 1H), 4.05 (t, J=4.2 Hz, 2H), 3.58 (t, J=6.5 Hz, 2H), 2.80 (t, J=6.5 Hz, 2H), 2.60 (m, 1H), 2.33 (m 1H), 1.92 (m, 2H), 1.72 (m, 2H), 1.58 (m, 2H), 1.50 (m, 2H), 1.47 (s, 9H).

Step D

2-Amino-N-[1-(4-phenyl-cyclohexyl)-azetidin-3-yl]-acetamide TFA salt

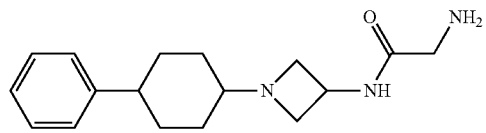 [SMILES: NCC(=O)NC1CN(C2CCC(c3ccccc3)CC2)C1]

The title compound was prepared as colorless oil from the TFA de-protection of {[1-(4-phenyl-cyclohexyl)-azetidin-3-ylcarbamoyl]-methyl}-carbamic acid tert-butyl ester (as prepared in the previous step) using the procedure described in step E of Example 1.

$^1$H NMR (400 MHz, CDCl$_3$) δ: 7.00-7.29 (m, 5H), 4.51 (br. s., 1H), 4.27 (br. s., 2H), 4.03 (br. s., 2H), 3.84 (br. s., 2H), 3.31-3.57 (m, 1H), 2.53 (br. s., 1H), 1.84 (br. s., 4H), 1.71 (br. s., 4H)

Step E

2-Fluoro-N-{[1-(4-phenyl-cyclohexyl)-azetidin-3-ylcarbamoyl]-methyl}-5-trifluoromethyl-benzamide

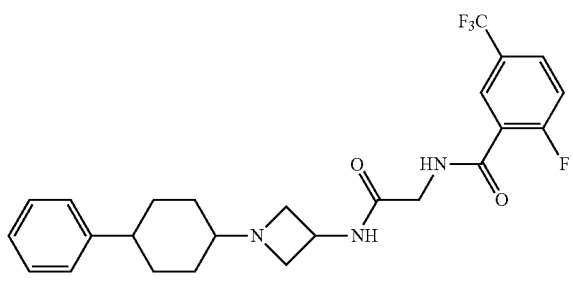 [SMILES: O=C(CNC(=O)c1cc(C(F)(F)F)ccc1F)NC1CN(C2CCC(c3ccccc3)CC2)C1]

The title compound was prepared as a white solid from the EDCI coupling of 2-amino-N-[1-(4-phenyl-cyclohexyl)-azetidin-3-yl]-acetamide TFA salt (as prepared in the previous step) and 2-fluoro-5-trifluoromethyl-benzoic acid (Aldrich) using the procedure described in Step F of Example 1.

ESI-MS (m/z): Calcd. for C$_{25}$H$_{27}$F$_4$N$_3$O$_2$, 477; found: 478 (M+H).

Example 67

4-Methoxy-N-{[1-(4-phenyl-cyclohexyl)-azetidin-3-ylcarbamoyl]-methyl}-3-trifluoromethyl-benzamide

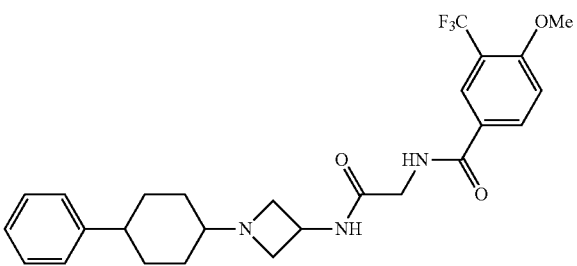 [SMILES: COc1ccc(C(=O)NCC(=O)NC2CN(C3CCC(c4ccccc4)CC3)C2)cc1C(F)(F)F]

The title compound was prepared as a white solid from EDCI coupling of 2-amino-N-[1-(4-phenyl-cyclohexyl)-azetidin-3-yl]-acetamide TFA salt (as prepared in Step D of Example 66) and 4-methoxy-3-trifluoromethyl-benzoic acid (Aldrich) using the procedure described in Step F of Example 1.

$^1$H NMR (400 MHz, CDCl$_3$) δ 8.11 (s, 1H), 8.02 (d, J=6.5 Hz, 1H), 7.25 (m, 4H), 7.16 (t, J=5.3 Hz, 1H), 7.01 (d, J=6.0 Hz, 1H), 4.55 (m, 1H), 4.15 (d, J=3.5 Hz, 2H), 3.95 (s, 3H), 3.65 (t, J=3.1 Hz, 2H), 2.90 (t, J=3.6 Hz, 2H), 2.65 (m, 1H), 2.45 (m, 1H), 1.90 (m, 2H), 1.75 (m, 2H), 1.50 (m, 4H).

Example 68

2-Methoxy-N-{[1-(4-phenyl-cyclohexyl)-azetidin-3-ylcarbamoyl]-methyl}-5-trifluoromethyl-benzamide

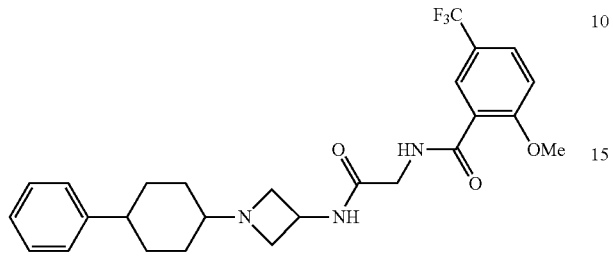

2-Fluoro-N-{[1-(4-phenyl-cyclohexyl)-azetidin-3-ylcarbamoyl]-methyl}-5-trifluoromethyl-benzamide (as prepared in Example 66, 50 mg, 0.11 mmol) was treated with NaOMe (0.5 M in MeOH, 600 µL, 0.30 mmol) in MeOH (1 mL) at room temperature overnight. The solvent was removed and the residue was purified on a silica gel column using a CombiFlash® system using ethyl acetate and 7N $NH_3$ in MeOH as eluent (from pure ethyl acetate to 5% 7N $NH_3$ in MeOH in ethyl acetate) to afford the title compound as a white solid.

$^1$H NMR (400 MHz, CDCl$_3$) δ 8.40 (s, 1H), 8.3 (d, J=5.2 Hz, 1H), 7.30 (m, 4H), 7.20 (m, 1H), 7.08 (d, J=6.2 Hz, 1H), 4.55 (m, 1H), 4.15 (d, J=4.5 Hz, 2H), 4.01 (s, 3H), 3.68 (m, 2H), 2.50 (m, 1H), 2.21 (s, 1H), 1.90 (m, 2H), 1.78 (m, 2H), 1.66 (m, 2H), 1.55 (m, 4H).

Example 69

2-Dimethylamino-N-{[1-(4-phenyl-cyclohexyl)-azetidin-3-ylcarbamoyl]-methyl}-5-trifluoromethyl-benzamide

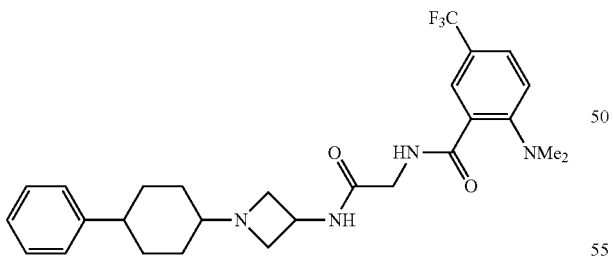

2-Fluoro-N-{[1-(4-phenyl-cyclohexyl)-azetidin-3-ylcarbamoyl]-methyl}-5-trifluoromethyl-benzamide (as prepared in Example 66, 50 mg, 0.11 mmol) was treated with dimethyl amine (Aldrich, 40 wt. % in water, ~2 mL) in a sealed tube under microwave irradiation at 120° C. for 20 min. The solvent was removed and the residue was purified on a silica gel column using a CombiFlash® system using ethyl acetate and 7N $NH_3$ in MeOH as eluent (from pure ethyl acetate to 5% 7N $NH_3$ in MeOH in ethyl acetate) to afford the title compound as a white solid.

ESI-MS (m/z): Calcd. for $C_{27}H_{33}F_3N_4O_2$, 502; found: 503 (M+H).

Example 70

N-{[1-(4-Phenyl-cyclohexyl)-azetidin-3-ylcarbamoyl]-methyl}-2-pyrrolidin-1-yl-5-trifluoromethyl-benzamide

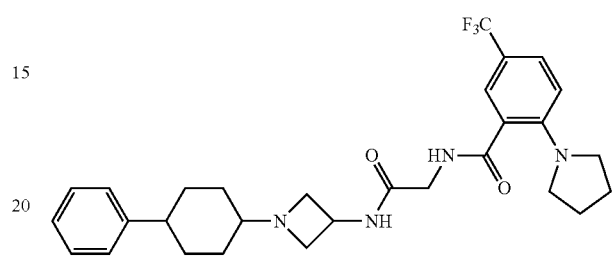

The title compound was prepared as a white solid from coupling of 2-fluoro-N-{[1-(4-phenyl-cyclohexyl)-azetidin-3-ylcarbamoyl]-methyl}-5-trifluoromethyl-benzamide (as prepared in Example 66) and pyrrolidine (Aldrich) using the procedure described in Example 69.

ESI-MS (m/z): Calcd. for $C_{29}H_{35}F_3N_4O_2$, 528; found: 529 (M+H).

Example 71

4-Fluoro-N-{[1-(4-phenyl-cyclohexyl)-azetidin-3-ylcarbamoyl]-methyl}-3-trifluoromethyl-benzamide Step A 3-[2-(4-Fluoro-3-trifluoromethyl-benzoylamino)-acetylamino]-azetidine-1-carboxylic acid tert-butylester

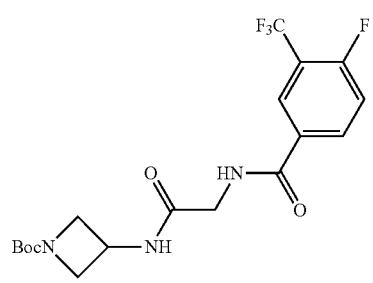 [SMILES: CC(C)(C)OC(=O)N1CC(NC(=O)CNC(=O)c2ccc(F)c(C(F)(F)F)c2)C1]

The title compounds were prepared as white solids from the EDCI coupling of 3-amino-azetidine-1-carboxylic acid tert-butyl ester (BetaPharma) and (4-fluoro-3-trifluoromethyl-benzoylamino)-acetic acid (analog synthesis by the procedure described in Organic Synthesis XII, 40-2, 1932) using the procedure described in Step F of Example 1.

¹H NMR (400 MHz, CDCl₃) δ 8.15 (d, J=4.5 Hz, 1H), 8.05 (m, 1H), 7.28 (d, J=5.5 Hz, 1H), 4.62 (m, 1H), 4.25 (t, J=7.0 Hz, 2H), 4.15 (s, 2H), 3.82 (t, J=6.8 Hz, 2H), 1.35 (s, 9H).

Step B

N-(Azetidin-3-ylcarbamoylmethyl)-4-fluoro-3-trifluoromethyl-benzamide TFA Salt

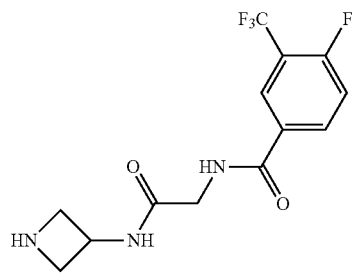 [SMILES: O=C(CNC(=O)c1ccc(F)c(C(F)(F)F)c1)NC1CNC1]

The title compound was prepared as colorless oil from the TFA de-protection of 3-[2-(4-fluoro-3-trifluoromethyl-benzoylamino)-acetylamino]-azetidine-1-carboxylic acid tert-butylester (as prepared in the previous step) using the procedure described in Step E of Example 1.

¹H NMR (400 MHz, CDCl₃) δ: 8.12-8.29 (m, 1H), 7.54-7.72 (m, 1H), 7.11-7.30 (m, 1H), 4.55 (br s., 1H), 4.06-4.13 (m, 2H), 3.75-4.02 (m, 2H), 3.03-3.15 (m, 2H).

Step C

4-Fluoro-N-{[1-(4-phenyl-cyclohexyl)-azetidin-3-ylcarbamoyl]-methyl}-3-trifluoromethyl-benzamide

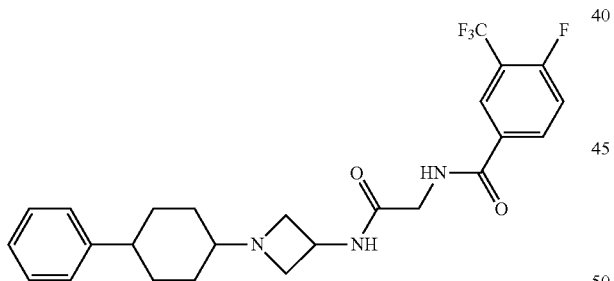

The title compound was prepared as a white solid by reductive amination of 4-phenyl-cyclohexanone (as prepared in the previous step) and N-(azetidin-3-ylcarbamoylmethyl)-4-fluoro-3-trifluoromethyl-benzamide using the procedure described in Step C of Example 4.

71a: Less Polar Isomer from Silica Gel Column

¹H NMR (400 MHz, d₄-MeOH) δ 8.28 (d, J=5.8 Hz, 1H), 8.21 (m, 1H), 7.45 (t, J=6.5 Hz, 1H), 7.25 (s, 4H), 7.12 (m, 1H), 4.51 (m, 1H), 4.05 (s, 2H), 3.72 (t, J=6.5 Hz, 2H), 2.98 (t, J=6.0 Hz, 2H), 2.55 (t, J=4.5 Hz, 1H), 2.40 (s, br, 1H), 1.96 (m, 2H), 1.75 (m, 2H), 1.52 (m, 4H).

71b: More Polar Isomer from Silica Gel Column

¹H NMR (400 MHz, d₄-MeOH) δ 8.30 (d, J=5.0 Hz, 1H), 8.20 (m, 1H), 7.46 (d, J=6.5 Hz, 1H), 7.28 (m, 4H), 7.10 (m, 1H), 4.46 (m, 1H), 4.05 (s, 2H), 3.68 (t, J=6.5 Hz, 2H), 3.05 (t, J=6.0 Hz, 2H), 2.46 (t, J=4.5 Hz, 1H), 2.22 (t, J=4.0 Hz, 1H), 1.96 (m, 4H), 1.55 (m, 2H), 1.18 (m, 2H).

Example 72

4-(2-Hydroxy-ethylamino)-N-{[1-(4-phenyl-cyclohexyl)-azetidin-3-ylcarbamoyl]-methyl}-3-trifluoromethyl-benzamide

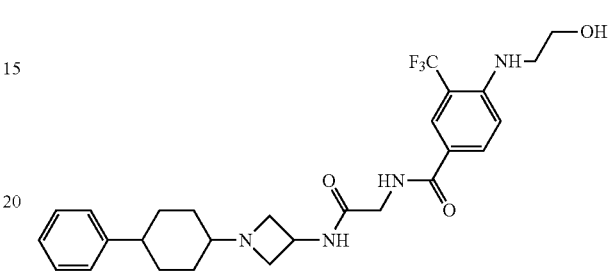

The title compound was prepared as a white solid from the coupling of 4-fluoro-N-{[1-(4-phenyl-cyclohexyl)-azetidin-3-ylcarbamoyl]-methyl}-3-trifluoromethyl-benzamide (as prepared in Example 71) and 2-amino-ethanol (Aldrich) using the procedure described in Example 65.

¹H NMR (400 MHz, d₄-MeOH) δ 8.11 (s, 1H), 7.98 (d, J=6.5 Hz, 1H), 7.38 (d, J=6.5 Hz, 1H), 7.20 (m, 4H), 7.10 (m, 1H), 6.95 (d, J=6.5 Hz, 1H), 4.58 (m, 1H), 4.10 (t, J=7.5 Hz, 2H), 4.05 (s, 2H), 3.85 (t, J=7.2 Hz, 2H), 3.78 (t, J=5.2 Hz, 2H), 3.40 (t, J=6.5 Hz, 2H), 3.22 (t, J=6.0 Hz, 1H), 2.55 (m, 1H), 2.35 (s, br, 1H), 1.86 (m, 4H), 1.62 (m, 4H).

Example 73

4-Nitro-N-{[1-(4-phenyl-cyclohexyl)-azetidin-3-ylcarbamoyl]-methyl}-3-trifluoromethyl-benzamide

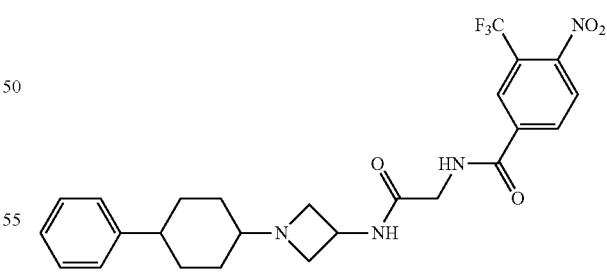

The title compound was prepared as a white solid from EDCI coupling of 2-amino-N-[1-(4-phenyl-cyclohexyl)-azetidin-3-yl]-acetamide TFA salt (as prepared in Step D of Example 66) and 4-nitro-3-trifluoromethyl-benzoic acid (Aldrich) using the procedure described in Step F of Example 1.

¹H NMR (400 MHz, CDCl₃) δ 8.01 (s, 1H), 7.78 (d, J=6.6 Hz, 1H), 7.30 (m, 5H), 7.18 (t, J=6.5 Hz, 1H), 6.80 (s, 1H), 6.71 (d, J=6.5 Hz, 1H), 6.55 (s, 1H), 4.52 (m, 1H), 4.10 (s,

2H), 3.60 (t, J=5.1 Hz, 2H), 2.90 (s, br, 2H), 2.55 (m, 1H), 2.30 (s, br, 1H), 1.90 (m, 2H), 1.70 (m, 2H), 1.55 (m, 4H).

Example 74

4-Amino-N-{[1-(4-phenyl-cyclohexyl)-azetidin-3-ylcarbamoyl]-methyl}-3-trifluoromethyl-benzamide

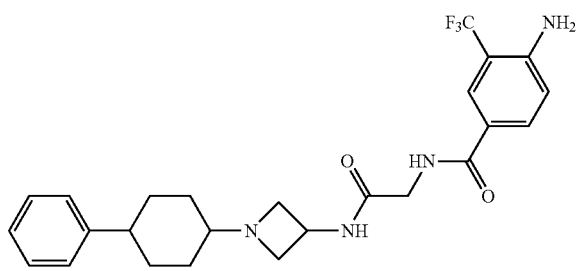 [SMILES: O=C(CNC(=O)c1ccc([N+](=O)[O-])c(C(F)(F)F)c1)NC1CN(C2CCC(c3ccccc3)CC2)C1]

The title compound was prepared as a white solid from hydrogenation of 4-nitro-N-{[1-(4-phenyl-cyclohexyl)-azetidin-3-ylcarbamoyl]-methyl}-3-trifluoromethyl-benzamide (as prepared in Example 73) using the procedure described in Step G of Example 1.

$^1$H NMR (400 MHz, d$_4$-MeOH) δ 7.90 (s, 1H), 7.68 (d, J=6.5 Hz, 1H), 7.45 (d, J=6.5 Hz, 1H), 7.20 (m, 5H), 4.58 (m, 1H), 4.05 (s, 2H), 3.75 (t, J=6.5 Hz, 2H), 3.02 (t, J=6.0 Hz, 2H), 2.55 (m, 1H), 2.35 (s, br, 1H), 1.96 (m, 2H), 1.65 (m, 2H), 1.40 (m, 4H).

Example 75

N-{[1-(4-Phenyl-cyclohexyl)-azetidin-3-ylcarbamoyl]-methyl}-3,5-bis-trifluoromethyl-benzamide

Step A

3-[2-(3,5-Bis-trifluoromethyl-benzoylamino)-acetylamino]-azetidine-1-carboxylic acid tert-butyl ester

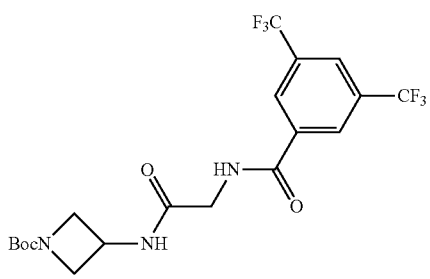 [SMILES: CC(C)(C)OC(=O)N1CC(NC(=O)CNC(=O)c2cc(C(F)(F)F)cc(C(F)(F)F)c2)C1]

The title compounds were prepared as white solids from the EDCI coupling between 3-amino-azetidine-1-carboxylic acid tert-butyl ester and (3,5-bistrifluoromethyl-benzoylamino)-acetic acid (analog synthesis by following the procedure on Organic Synthesis XII, 40-2, 1932) using the procedure described in Step F of Example 1.

ESI-MS (m/z): Calcd. For C$_{19}$H$_{21}$F$_6$N$_3$O$_4$, 469; found: 470 (M+H).

Step B

N-(Azetidin-3-ylcarbamoylmethyl)-3,5-bis-trifluoromethyl-benzamide TFA Salt

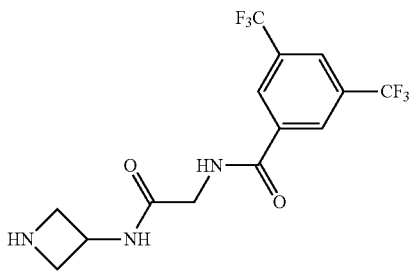 [SMILES: O=C(CNC(=O)c1cc(C(F)(F)F)cc(C(F)(F)F)c1)NC1CNC1]

The title compound was prepared as colorless oil from TFA de-protection of 3-[2-(3,5-bis-trifluoromethyl-benzoylamino)-acetylamino]-azetidine-1-carboxylic acid tert-butylester (as prepared in the previous step) using the procedure described in Step E of Example 1.

$^1$H NMR (400 MHz, CDCl$_3$) δ 8.28 (s, 2H), 8.05 (s, 1H), 4.63 (m, 1H), 4.40 (m, 2H), 4.15 (m, 2H), 3.88 (m, 2H).

Step C

N-{[1-(4-Phenyl-cyclohexyl)-azetidin-3-ylcarbamoyl]-methyl}-3,5-bis-trifluoromethyl-benzamide

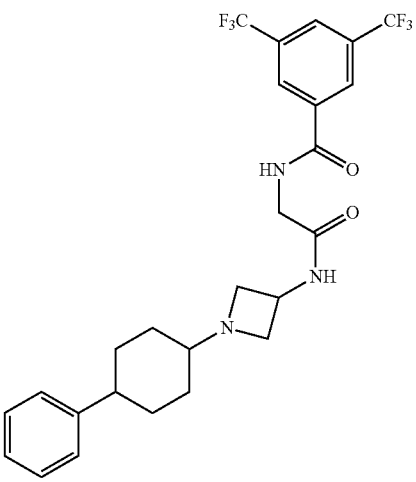 [SMILES: O=C(CNC(=O)c1cc(C(F)(F)F)cc(C(F)(F)F)c1)NC1CN(C2CCC(c3ccccc3)CC2)C1]

The title compound was prepared as a white solid by reductive amination of 4-phenyl-cyclohexanone (Aldrich) and N-(azetidin-3-ylcarbamoylmethyl)-3,5-bistrifluoromethyl-benzamide (as prepared in the previous step) using the procedure described in Step C of Example 4.

75a: Less Polar Isomer from Silica Gel Column $^1$H NMR (MeOH) δ: 8.51 (s, 2H), 8.20 (s, 1H), 7.26 (d, J=4.3 Hz, 4H), 7.05-7.19 (m, 1H), 4.53 (t, J=7.1 Hz, 1H), 4.08 (s, 2H), 3.77 (t, J=7.8 Hz, 2H), 3.09 (t, J=7.7 Hz, 2H), 2.45-2.66 (m, 2H), 1.87 (d, J=14.4 Hz, 2H), 1.75-1.82 (m, 2H), 1.41-1.67 (m, 4H).

75b: More Polar Isomer from Silica Gel Column $^1$H NMR (MeOH) δ: 8.52 (s, 2H), 8.20 (s, 1H), 7.11-7.33 (m, 5H), 4.51 (t, J=7.1 Hz, 1H), 4.08 (s, 2H), 3.73 (t, J=7.8 Hz, 2H), 3.04-3.20 (m, 2H), 2.17-2.35 (m, 2H), 1.82-2.00 (m, 4H), 1.38-1.62 (m, 2H), 1.08-1.19 (m, 2H).

Example 76

3-Fluoro-N-{[1-(4-phenyl-cyclohexyl)-azetidin-3-ylcarbamoyl]-methyl}-5-trifluoromethyl-benzamide

Step A

3-[2-(3-trifluoromethyl-5-fluoro-benzoylamino)-acetylamino]-azetidine-1-carboxylic acid tert-butyl ester

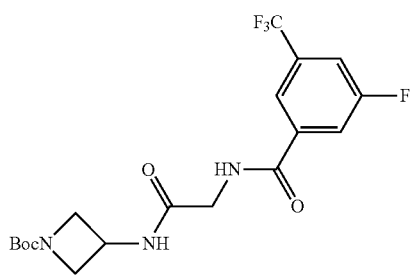 [SMILES: CC(C)(C)OC(=O)N1CC(NC(=O)CNC(=O)c2cc(F)cc(C(F)(F)F)c2)C1]

The title compounds were prepared as white solids from the EDCI coupling of 3-amino-azetidine-1-carboxylic acid tert-butyl ester (BetaPharma) and (5-fluoro-3-trifluoromethyl-benzoylamino)-acetic acid (analog synthesis by the procedure described in Organic Synthesis XII, 40-2, 1932) using the procedure described in Step F of Example 1.

$^1$H NMR (400 MHz, CDCl$_3$) δ 8.05 (s, 1H), 7.89 (d, J=7.5 Hz, 1H), 7.41 (d, J=7.2 Hz, 1H), 4.55 (m, 1H), 4.28 (t, J=7.2 Hz, 2H), 4.15 (d, J=3.0 Hz, 2H), 3.80 (t, J=4.5 Hz, 2H), 1.45 (s, 9H).

Step B

N-(Azetidin-3-ylcarbamoylmethyl)-3-trifluoromethyl-5-fluoro-benzamide TFA Salt

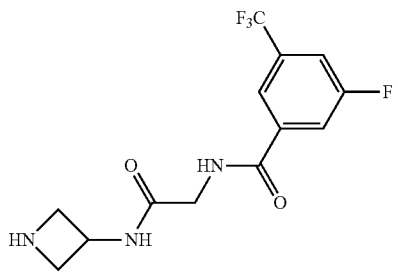 [SMILES: O=C(CNC(=O)c1cc(F)cc(C(F)(F)F)c1)NC1CNC1]

The title compound was prepared as colorless oil from the TFA de-protection of 3-[2-(5-fluoro-3-trifluoromethyl-benzoylamino)-acetylamino]-azetidine-1-carboxylic acid tert-butylester (as prepared in the previous step) using the procedure described in Step E of Example 1.

$^1$H NMR (MeOH) δ: 8.06 (s, 1H), 7.91 (d, J=9.1 Hz, 1H), 7.65 (d, J=8.3 Hz, 1H), 4.52-4.71 (m, 1H), 4.21 (t, J=8.5 Hz, 2H), 4.08 (s, 2H), 3.86 (dd, J=9.1, 5.3 Hz, 2H)

Step C

3-Fluoro-N-{[1-(4-phenyl-cyclohexyl)-azetidin-3-ylcarbamoyl]methyl}-5-trifluoromethyl-benzamide

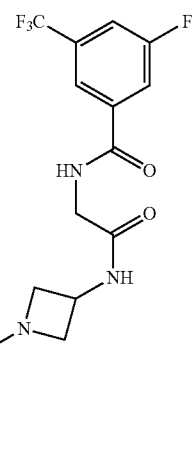

The title compound was prepared as a white solid by reductive amination of 4-phenyl-cyclohexanone (Aldrich) and N-(azetidin-3-ylcarbamoylmethyl)-5-fluoro-3-trifluoromethyl-benzamide (as prepared in the previous step) using the procedure described in Step C of Example 4.

76a: Less Polar Isomer from Silica Gel Column
$^1$H NMR (MeOH) δ: 8.09 (s, 1H), 7.93 (d, J=9.1 Hz, 1H), 7.69 (d, J=8.3 Hz, 1H), 7.26 (d, J=4.5 Hz, 4H), 7.06-7.19 (m, 1H), 4.51 (quin, J=7.0 Hz, 1H), 4.06 (s, 2H), 3.69 (t, J=7.7 Hz, 2H), 2.96 (t, J=7.7 Hz, 2H), 2.48-2.63 (m, 1H), 2.42 (t, J=3.4 Hz, 1H), 1.80-1.99 (m, 2H), 1.69-1.80 (m, 2H), 1.48-1.64 (m, 4H)

76b: Less Polar Isomer from Silica Gel Column
$^1$H NMR (MeOH) δ: 8.09 (s, 1H), 7.93 (d, J=9.3 Hz, 1H), 7.70 (d, J=8.3 Hz, 1H), 7.26 (d, J=4.5 Hz, 4H), 7.08-7.21 (m, 1H), 4.51 (quin, J=7.0 Hz, 1H), 4.06 (s, 2H), 3.62-3.76 (m, 2H), 2.96 (t, J=7.6 Hz, 2H), 2.50-2.66 (m, 1H), 2.42 (t, J=3.4 Hz, 1H), 1.80-1.94 (m, 2H), 1.62-1.80 (m, 2H), 1.57 (d, J=12.1 Hz, 4H)

Example 77

3-Bromo-N-{[1-(4-phenyl-cyclohexyl)-azetidin-3-ylcarbamoyl]-methyl}-5-trifluoromethyl-benzamide

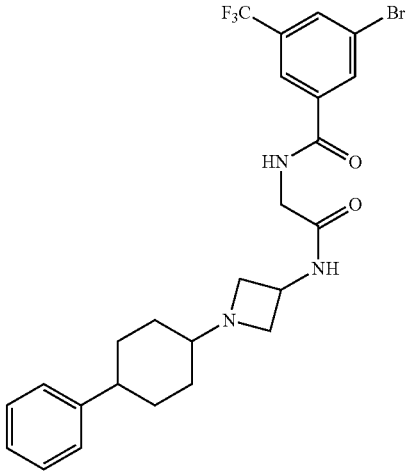 [SMILES: O=C(CNC(=O)c1cc(Br)cc(C(F)(F)F)c1)NC1CN(C2CCC(c3ccccc3)CC2)C1]

The title compound was prepared as a white solid from the EDCI coupling of 2-amino-N-[1-(4-phenyl-cyclohexyl)-azetidin-3-yl]-acetamide TFA salt (as prepared in Step D of Example 66) and 5-bromo-3-trifluoromethyl-benzoic acid (Aldrich) using the procedure described in Step F of Example 1.

$^1$H NMR (MeOH) δ: 8.35 (s, 1H), 8.21 (s, 1H), 8.07 (s, 1H), 7.27 (s, 4H), 7.13 (s, 1H), 4.41-4.61 (m, 1H), 4.05 (s, 2H), 3.70 (t, J=7.7 Hz, 2H), 2.90-3.06 (m, 2H), 2.51-2.64 (m, 1H), 2.37-2.47 (m, 1H), 1.81-1.95 (m, 2H), 1.75 (dd, J=13.4, 3.0 Hz, 2H), 1.49-1.64 (m, 4H), 0.80-1.06 (m, 1H).

Example 78

3-Nitro-N-{[1-(4-phenyl-cyclohexyl)-azetidin-3-ylcarbamoyl]-methyl}-5-trifluoromethyl-benzamide

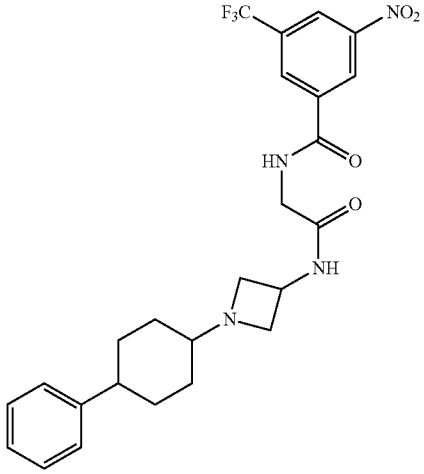 [SMILES: O=C(CNC(=O)c1cc([N+](=O)[O-])cc(C(F)(F)F)c1)NC1CN(C2CCC(c3ccccc3)CC2)C1]

The title compound was prepared as a white solid from the EDCI coupling of 2-amino-N-[1-(4-phenyl-cyclohexyl)-azetidin-3-yl]-acetamide TFA salt (as prepared in Step D of Example 66) and 5-nitro-3-trifluoromethyl-benzoic acid (Aldrich) using the procedure described in Step F of Example 1.

$^1$H NMR (MeOH) δ: 9.02 (s, 1H), 8.71 (s, 1H), 8.63 (s, 1H), 7.26 (d, J=4.3 Hz, 4H), 7.07-7.20 (m, 1H), 4.55 (t, J=7.2 Hz, 1H), 4.01-4.16 (m, 2H), 3.80 (t, J=7.7 Hz, 2H), 3.13 (t, J=5.9 Hz, 2H), 2.47-2.64 (m, 2H), 1.86 (d, J=8.1 Hz, 2H), 1.73-1.83 (m, 2H), 1.52-1.71 (m, 4H), 0.83-1.07 (m, 1H)

Example 79

3-Amino-N-{[1-(4-phenyl-cyclohexyl)-azetidin-3-ylcarbamoyl]-methyl}-5-trifluoromethyl-benzamide

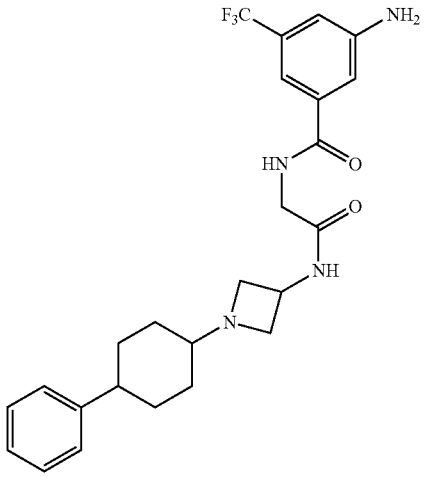 [SMILES: Nc1cc(C(=O)NCC(=O)NC2CN(C3CCC(c4ccccc4)CC3)C2)cc(C(F)(F)F)c1]

The title compound was prepared as a white solid from the hydrogenation of 5-nitro-N-{[1-(4-phenyl-cyclohexyl)-aze-tidin-3-ylcarbamoyl]-methyl}-3-trifluoromethyl-benzamide (as prepared in Example 78) using the procedure described in Step G of Example 1.

$^1$H NMR (MeOH) δ: 7.23 (s, 1H), 7.26 (s, 1H), 7.14 (d, J=4.3 Hz, 5H), 7.01-7.09 (m, 1H), 6.97 (s, 1H), 4.40 (quin, J=7.1 Hz, 1H), 3.90 (s, 2H), 3.62 (t, J=7.6 Hz, 2H), 2.92 (t, J=7.1 Hz, 2H), 2.41-2.52 (m, 1H), 2.38 (br. s., 1H), 1.68-1.84 (m, 2H), 1.64 (d, J=10.6 Hz, 2H), 1.45 (s, 4H), 1.49 (s, 2H).

Example 80

3-Bis methanesulfonyl-N-{[1-(4-phenyl-cyclohexyl)-azetidin-3-ylcarbamoyl]-methyl}-5-trifluoromethyl-benzamide

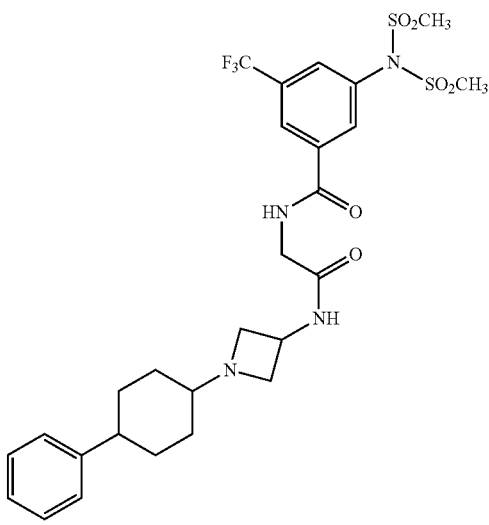 [SMILES: CS(=O)(=O)N(c1cc(C(=O)NCC(=O)NC2CN(C3CCC(c4ccccc4)CC3)C2)cc(C(F)(F)F)c1)S(C)(=O)=O]

The title compound was prepared as a white solid from mesylation of 3-amino-N-{[1-(4-phenyl-cyclohexyl)-azetidin-3-ylcarbamoyl]-methyl}-5-trifluoromethyl-benzamide (as prepared in Example 79) using the procedure described in Examples 16 and 17.

$^1$H NMR (MeOH) δ: 8.39 (s, 1H), 8.25 (s, 1H), 8.04 (s, 1H), 7.27 (s, 4H), 7.07-7.22 (m, 1H), 4.55 (s, 1H), 4.08 (s, 2H), 3.78 (t, J=7.6 Hz, 2H), 3.44-3.58 (m, 6H), 3.05-3.21 (m, 2H), 2.49-2.68 (m, 2H), 1.76-1.92 (m, 4H), 1.52-1.67 (m, 4H).

Example 81

3-Hydroxy-N-{[1-(4-phenyl-cyclohexyl)-azetidin-3-ylcarbamoyl]-methyl}-5-trifluoromethyl-benzamide

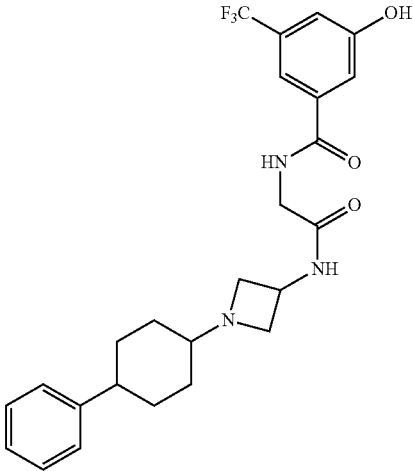 [SMILES: O=C(CNC(=O)c1cc(O)cc(C(F)(F)F)c1)NC1CN(C2CCC(c3ccccc3)CC2)C1]

The title compound was prepared as a white solid from the EDCI coupling of 2-amino-N-[1-(4-phenyl-cyclohexyl)-azetidin-3-yl]-acetamide TFA salt (as prepared in Step D of Example 66) and 5-hydroxy-3-trifluoromethyl-benzoic acid (Alfa Aesar) using the procedure described in Step F of Example 1.

¹H NMR (MeOH) δ: 8.11 (d, J=8.8 Hz, 1H), 7.98 (d, J=9.3 Hz, 1H), 7.67-7.80 (m, 1H), 7.49-7.62 (m, 1H), 7.22-7.37 (m, 4H), 4.61 (s, 1H), 4.09-4.24 (m, 2H), 3.51 (br. s., 2H), 3.16 (s, 2H), 1.54-1.72 (m, 2H), 1.22-1.44 (m, 8H)

Example 82

3-(3-tert-Butyl-ureido)-N-{[1-(4-phenyl-cyclohexyl)-azetidin-3-ylcarbamoyl]-methyl}-5-trifluoromethyl-benzamide

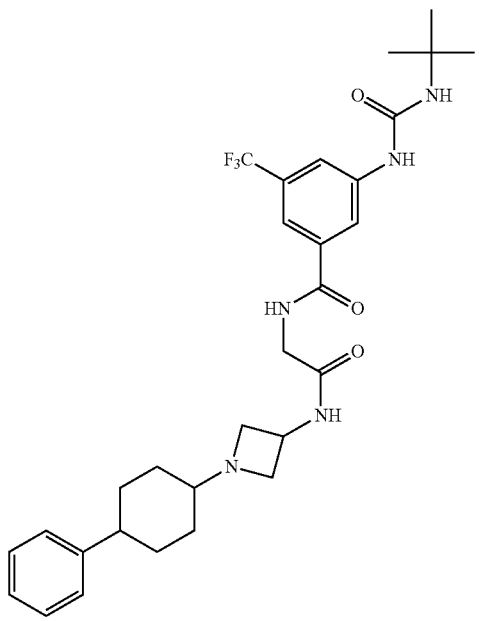 [SMILES: CC(C)(C)NC(=O)Nc1cc(C(=O)NCC(=O)NC2CN(C3CCC(c4ccccc4)CC3)C2)cc(C(F)(F)F)c1]

The title compound was prepared as a white solid from coupling of 3-amino-N-{[1-(4-phenyl-cyclohexyl)-azetidin-3-ylcarbamoyl]-methyl}-5-trifluoromethyl-benzamide (as prepared in Example 79) with t-butyl-isocyanate (Aldrich) using the procedure described in Example 18.

¹H NMR (MeOH) δ: 7.78 (d, J=11.1 Hz, 1H), 7.55 (s, 1H), 7.15 (d, J=14.9 Hz, 1H), 7.05 (d, J=4.5 Hz, 4H), 6.88-6.99 (m, 1H), 4.22-4.38 (m, 1H), 3.82 (s, 2H), 3.52 (t, J=7.1 Hz, 2H), 2.71-2.90 (m, 2H), 2.32-2.44 (m, 1H), 2.27 (br. s., 1H), 1.66 (d, J=11.4 Hz, 2H), 1.55 (d, J=12.6 Hz, 2H), 1.28-1.43 (m, 4H), 1.10-1.20 (m, 9H).

Example 83

N-{[1-(4-Fluoro-4-phenyl-cyclohexyl)-azetidin-3-ylcarbamoyl]-methyl}-3-trifluoromethyl-benzamide

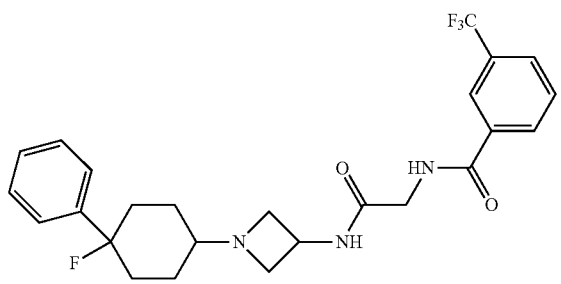 [SMILES: O=C(CNC(=O)c1cccc(C(F)(F)F)c1)NC1CN(C2CCC(F)(c3ccccc3)CC2)C1]

N-{[1-(4-Hydroxy-4-phenyl-cyclohexyl)-azetidin-3-ylcarbamoyl]-methyl}-3-trifluoromethyl-benzamide (as prepared in Example 30, 680 mg, 1.43 mmol) in DCM (5 mL) was treated with DAST (Aldrich, 418 μL, 4.29 mmol) dropwise at −78° C. for 4 hours. The reaction was quenched with MeOH, warmed to room temperature and partitioned between DCM and water. The organic layer was washed with brine, dried over anhydrous Na₂SO₄, filtered, concentrated and the residue was purified by a CombiFlash® system using ethyl acetate and 7N NH₃ in MeOH as eluent (from pure ethyl acetate to 5% 7N NH₃ in MeOH in ethyl acetate) to afford two title compound as white solid: less polar isomer.

83a: Less Polar Fraction from Silica Gel Column

¹H NMR (400 MHz, CDCl₃) δ 8.12 (s, 1H), 8.05 (d, J=6.5 Hz, 1H), 7.80 (d, J=6.2 Hz, 1H), 7.60 (t, J=6.8 Hz, 1H), 7.50 (d, J=6.5 Hz, 1H), 7.35~7.22 (m, 4H), 6.85 (s, br, 1H), 4.58 (m, 1H), 4.20 (d, J=3.1 Hz, 2H), 3.68 (m, br, 2H), 2.95 (s, br, 3H), 2.15 (m, 2H), 1.90 (m, 2H), 1.75 (m, 2H), 1.58 (m, 2H).

83b: More Polar Fraction from Silica Gel Column

¹H NMR (400 MHz, CDCl₃) δ 8.10 (s, 1H), 8.02 (d, J=6.0 Hz, 1H), 7.75 (d, J=6.0 Hz, 1H), 7.62 (m, 2H), 7.45~7.20 (m, 4H), 4.60 (m, 1H), 4.20 (d, J=3.0 Hz, 2H), 3.70 (m, br, 2H), 3.08 (s, br, 3H), 1.90~1.68 (m, 6H), 1.55 (m, 2H).

Example 84

N-{[1-(4-Amino-4-phenyl-cyclohexyl)-azetidin-3-ylcarbamoyl]-methyl}-3-trifluoromethyl-benzamide Step A 2-Methyl-propane-2-sulfinic acid (1,4-dioxa-spiro[4.5]dec-8-ylidene)-amide

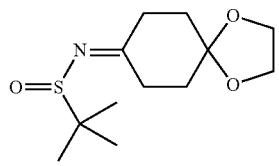 [SMILES: CC(C)(C)S(=O)N=C1CCC2(CC1)OCCO2]

To a solution of 1,4-dioxa-spiro[4.5]decan-8-one (Aldrich, 4.07 g, 26.1 mmol) and 2-methyl-propane-2-sulfinic acid amide (Aldrich, 3.16 g, 26.1 mmol) in THF (20 mL) was added Ti(OEt)₄ (Aldrich, 10.8 mL, 52.2 mmol) at room temperature. The reaction was stirred overnight and quenched with ~5 mL water until precipitation completed. The solid was filtered off and washed with additional ethyl acetate. The combined filtrate was dried over anhydrous Na₂SO₄, filtered, concentrated and the residue was purified by a CombiFlash® system using hexanes and ethyl acetate as eluent (from pure hexanes to pure ethyl acetate) to afford the title compound as colorless oil.

¹H NMR (400 MHz, CDCl₃) δ 4.01 (s, 4H), 3.10 (m, 1H), 2.93 (m, 1H), 2.65 (t, J=6.0 Hz, 2H), 1.95 (m, 4H), 1.21 (s, 9H).

Step B

4-Amino-4-phenyl-cyclohexanone

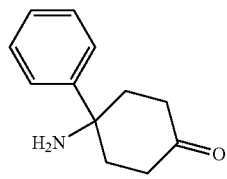 [SMILES: NC1(c2ccccc2)CCC(=O)CC1]

A solution of phenyl magnesium bromide (Aldrich, 1.0 N in THF, 5.7 mL, 5.70 mmol) was added into the solution of 2-methyl-propane-2-sulfinic acid (1,4-dioxa-spiro[4.5]dec-8-ylidene)-amide (as prepared in the previous step, 1.23 g, 4.75 mmol) in THF (10 mL) at 0° C. After addition, the reaction was slowly warmed to room temperature over 2 hours. 1N HCl (5 mL) was added, and the reaction was stirred overnight. The reaction was quenched with saturated sodium bicarbonate. The solvent was removed in vacuo and the residue was partitioned between DCM and water. The organic layer was washed with brine, dried over anhydrous $Na_2SO_4$, filtered and concentrated to afford the title compound as colorless oil.

$^1$H NMR (400 MHz, $CDCl_3$) δ 7.50~7.25 (m, 5H), 2.90 (m, 2H), 2.35 (m, 4H), 2.10 (m, 2H), 1.82 (s, br, 2H).

Step C

N-{[1-(4-Amino-4-phenyl-cyclohexyl)-azetidin-3-ylcarbamoyl]-methyl}-3-trifluoromethyl-benzamide

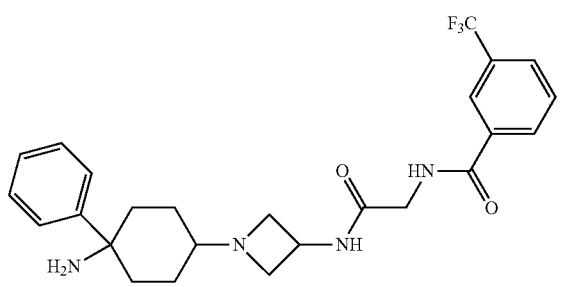

The title compound was prepared as a white solid by reductive amination of 4-amino-4-phenyl-cyclohexanone (as prepared in the previous step) and N-(azetidin-3-ylcarbamoylmethyl)-3-trifluoromethyl-benzamide (as prepared in step B of Example 4) using the procedure described in Step C of Example 4.

84a: Less Polar Isomer from Silica Gel Column $^1$H NMR (400 MHz, $d_4$-MeOH) δ 8.18 (s, 1H), 8.10 (d, J=6.5 Hz, 1H), 7.85 (d, J=7.0 Hz, 1H), 7.72 (t, J=6.0 Hz, 2H), 7.65 (d, J=6.0 Hz, 2H), 7.38 (t, J=6.0 Hz, 2H), 7.25 (m, 1H), 4.37 (m, 1H), 3.98 (s, 2H), 3.62 (m, 2H), 3.04 (m, 2H), 2.70 (m, br, 1H), 2.30 (m, 2H), 1.85 (m, 2H), 1.65 (m, 2H), 1.50 (m, 2H).

84b: More Polar Isomer from Silica Gel Column $^1$H NMR (400 MHz, $d_4$-MeOH) δ 8.22 (s, 1H), 8.15 (d, J=6.2 Hz, 1H), 7.88 (d, J=7.0 Hz, 1H), 7.70 (t, J=6.5 Hz, 2H), 7.62 (d, J=7.0 Hz, 2H), 7.48 (t, J=7.0 Hz, 2H), 7.32 (m, 1H), 4.34 (m, 1H), 4.02 (s, 2H), 3.69 (t, J=7.0 Hz, 2H), 3.11 (t, J=7.2 Hz, 2H), 2.75 (m, br, 1H), 2.35 (m, 1H), 1.90 (m, 6H), 1.18 (m, 2H).

Example 85

N-{[1-(4-Amino-4-benzo[1,3]dioxol-5-yl-cyclohexyl)-azetidin-3-ylcarbamoyl]-methyl}-3-trifluoromethyl-benzamide Step A 4-Amino-4-benzo[1,3]-dioxol-5-yl-cyclohexanone

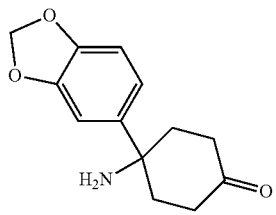 [SMILES: NC1(c2ccc3c(c2)OCO3)CCC(=O)CC1]

The title compound was prepared as a white solid from addition of 3,4-methylenedioxophenyl magnesium bromide (Aldrich) to 2-methyl-propane-2-sulfinic acid (1,4-dioxa-spiro[4.5]dec-8-ylidene)-amide (as prepared in Example 84, Step A) followed by hydrolysis using the procedure described in Step B of Example 84.

ESI-MS (m/z): Calcd. For $C_{13}H_{15}NO_3$, 233; found: 234 (M+H).

Step B

N-{[1-(4-Amino-4-benzo[1,3]-dioxol-5-yl-cyclohexyl)-azetidin-3-ylcarbamoyl]-methyl}-3-trifluoromethyl-benzamide

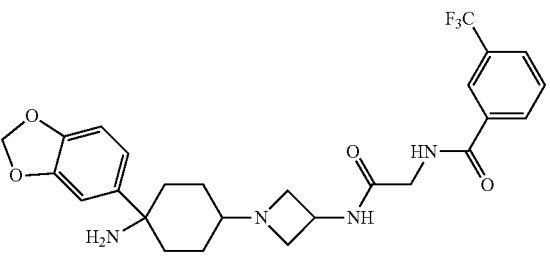 [SMILES: NC1(c2ccc3c(c2)OCO3)CCC(N2CC(NC(=O)CNC(=O)c3cccc(C(F)(F)F)c3)C2)CC1]

The title compound was prepared as a white solid by reductive amination of 4-amino-4-benzo[1,3]dioxol-5-yl-cyclohexanone (as prepared in the previous step) and N-(azetidin-3-ylcarbamoylmethyl)-3-trifluoromethyl-benzamide (as prepared in step B of Example 4) using the procedure described in Step C of Example 4.

85a: Less Polar Isomer from Silica Gel Column $^1$H NMR (400 MHz, $d_4$-MeOH) δ 8.21 (s, 1H), 8.15 (d, J=5.6 Hz, 1H), 7.88 (d, J=5.0 Hz, 1H), 7.71 (t, J=6.5 Hz, 1H), 7.15 (s, 1H), 7.12 (d, J=6.0 Hz, 1H), 6.91 (d, J=6.5 Hz, 1H), 6.02 (s, 2H), 4.35 (m, 1H), 4.02 (s, 2H), 3.70 (t, J=6.0 Hz, 2H), 3.15 (d, J=6.0 Hz, 2H), 2.72 (m, 2H), 2.35 (m, 1H), 1.90 (m, 4H), 1.25 (m, 2H).

85b: More Polar Isomer from Silica Gel Column $^1$H NMR (400 MHz, $d_4$-MeOH) δ 8.22 (s, 1H), 8.18 (d, J=6.0 Hz, 1H), 7.90 (d, J=6.0 Hz, 1H), 7.70 (t, J=6.8 Hz, 1H), 7.13 (s, 1H), 7.10 (d, J=6.0 Hz, 1H), 6.88 (d, J=6.6 Hz, 1H), 6.01 (s, 2H), 4.50 (m, 1H), 4.10 (s, 2H), 3.88 (t, J=7.0 Hz, 2H), 3.29 (d, J=7.0 Hz, 2H), 2.45 (m, 1H), 2.25 (m, 2H), 2.10 (m, 2H), 1.85 (m, 2H), 1.55 (m, 2H).

Example 86

N-({1-[4-Amino-4-(4-methoxy-phenyl)-cyclohexyl]-azetidin-3-ylcarbamoyl}-methyl)-3-trifluoromethyl-benzamide

Step A

4-Amino-4-(4-methoxy-phenyl)-cyclohexanone

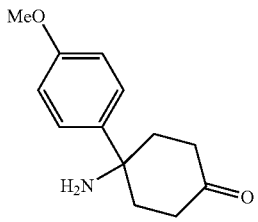 [SMILES: COc1ccc(C2(N)CCC(=O)CC2)cc1]

The title compound was prepared as a white solid from addition of 4-methoxy-phenyl magnesium bromide (Aldrich) to 2-methyl-propane-2-sulfinic acid (1,4-dioxa-spiro[4.5]dec-8-ylidene)-amide (as prepared in Example 84, Step A) followed by the hydrolysis using the procedure described in Step B of Example 84.

ESI-MS (m/z): Calcd. For $C_{13}H_{17}NO_2$, 219; found: 220 (M+H).

Step B

N-({1-[4-Amino-4-(4-methoxy-phenyl)-cyclohexyl]-azetidin-3-ylcarbamoyl}-methyl)-3-trifluoromethyl-benzamide

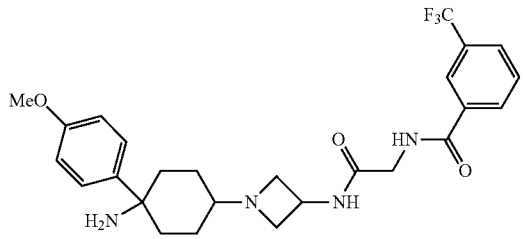

The title compound was prepared as a white solid by reductive amination of 4-amino-4-(4-methoxy-phenyl)-cyclohexanone (as prepared in the previous step) and N-(azetidin-3-ylcarbamoylmethyl)-3-trifluoromethyl-benzamide (as prepared in step B of Example 4) using the procedure described in Step C of Example 4.

$^1$H NMR (400 MHz, $d_4$-MeOH) δ 8.22 (s, 1H), 8.11 (d, J=6.2 Hz, 1H), 7.85 (d, J=7.0 Hz, 1H), 7.70 (t, J=6.5 Hz, 1H), 7.54 (d, J=7.0 Hz, 2H), 7.02 (d, J=7.0 Hz, 2H), 4.52 (m, 1H), 4.08 (s, 2H), 3.95 (s, 3H), 3.69 (t, J=7.0 Hz, 2H), 3.15 (t, J=7.2 Hz, 2H), 2.62 (m, 1H), 1.80 (m, 2H), 1.75 (m, 2H), 1.55 (m, 4H).

Example 87

N-({1-[4-Amino-4-(3-methoxy-phenyl)-cyclohexyl]-azetidin-3-ylcarbamoyl}-methyl)-3-trifluoromethyl-benzamide

Step A

4-Amino-4-(3-methoxy-phenyl)-cyclohexanone

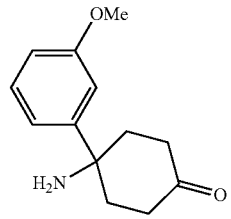 [SMILES: COc1cccc(C2(N)CCC(=O)CC2)c1]

The title compound was prepared as a white solid from addition of 3-methoxy-phenyl magnesium bromide (Aldrich) to 2-methyl-propane-2-sulfinic acid (1,4-dioxa-spiro[4.5]dec-8-ylidene)-amide (as prepared in Example 84, Step A) followed by hydrolysis using the procedure described in Step B of Example 84.

$^1$H NMR (400 MHz, $d_4$-MeOH) δ 7.20 (t, J=5.6 Hz, 1H), 7.05 (s, 1H), 6.98 (m, 1H), 6.71 (d, J=6.5 Hz, 1H), 3.65 (s, 3H), 2.60 (m, 2H), 2.35 (m, 2H), 2.21 (m, 2H), 1.95 (m, 2H).

Step B

N-({1-[4-Amino-4-(3-methoxyphenyl)-cyclohexyl]-azetidin-3-ylcarbamoyl}-methyl)-3-trifluoromethyl-benzamide

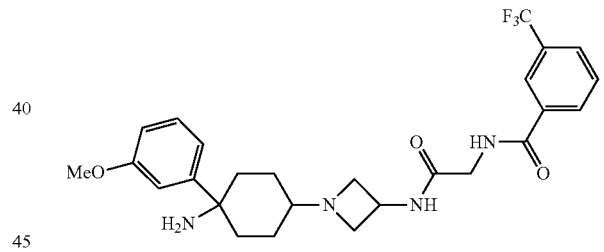

The title compound was prepared as a white solid by reductive amination of 4-amino-4-(3-methoxy-phenyl)-cyclohexanone (as prepared in the previous step) and N-(azetidin-3-ylcarbamoylmethyl)-3-trifluoromethyl-benzamide (as prepared in step B of Example 4) using the procedure described in Step C of Example 4.

86a: Less Polar Isomer from Silica Gel Column $^1$H NMR (400 MHz, $d_4$-MeOH) δ 8.25 (s, 1H), 8.18 (d, J=5.6 Hz, 1H), 7.88 (d, J=5.0 Hz, 1H), 7.71 (t, J=6.5 Hz, 1H), 7.28 (t, J=6.0 Hz, 1H), 7.12 (d, J=6.0 Hz, 1H), 7.10 (s, 1H), 6.81 (d, J=6.5 Hz, 1H), 4.35 (m, 1H), 4.02 (s, 2H), 3.81 (s, 3H), 3.60 (t, J=6.0 Hz, 2H), 3.02 (d, J=6.0 Hz, 2H), 2.45 (m, 2H), 2.30 (m, 1H), 1.83 (m, 2H), 1.65 (m, 2H), 1.12 (m, 2H).

86b: More Polar Isomer from Silica Gel Column $^1$H NMR (400 MHz, $d_4$-MeOH) δ 8.15 (s, 1H), 8.05 (d, J=6.6 Hz, 1H), 7.80 (d, J=6.0 Hz, 1H), 7.62 (t, J=6.5 Hz, 1H), 7.30 (t, J=6.2 Hz, 1H), 7.08 (d, J=6.5 Hz, 1H), 7.05 (s, 1H), 6.91 (d, J=6.5 Hz, 1H), 4.55 (m, 1H), 4.23 (t, J=7.0 Hz, 2H), 4.02 (s, 2H), 3.85 (t, J=7.0 Hz, 2H), 3.75 (s, 3H), 3.10 (m, 1H), 2.28 (m, 2H), 2.15 (m, 2H), 1.98 (m, 2H), 1.65 (m, 2H).

Example 88

In Vitro Biological Data

Compounds of the invention were subjected to various representative biological tests. The results of these tests are intended to illustrate the invention in a non-limiting fashion.
MCP-1 Receptor Binding Assay in THP-1 Cells Human monocytic cell line THP-1 cells were obtained from American Type Culture Collection (Manassas, Va., USA). The THP-1 cells were grown in RPMI-1640 (RPMI: Roswell Park Memorial Institute Medium-cell culture growth media) supplemented with 10% fetal bovine serum in a humidified 5% $CO_2$ atmosphere at 37° C. The cell density was maintained between $0.5 \times 10^6$ cells/mL.

THP-1 (cells were incubated with 0.5 nM $^{125}$I labeled MCP-1 (Perkin-Elmer Life Sciences, Inc. Boston, Mass.) in the presence of varying concentrations of either unlabeled MCP-1 (R & D Systems, Minneapolis, Minn.) or test compound for 2 hours at 30° C. in a 96 well plate. Cells were then harvested onto a filter plate, dried, and 20 μL of Microscint 20 was added to each well. Plates were counted in a TopCount NXT, Microplate Scintillation & Luminescence Counter (Perkin-Elmer Life Sciences, Inc. Boston, Mass.). Blank values (buffer only) were subtracted from all values and drug treated values were compared to vehicle treated values. 1 μM cold MCP-1 was used for nonspecific binding.

Table 1 lists $IC_{50}$ values for inhibition of MCP-1 binding to CCR2 obtained for test compounds of the invention. Where an $IC_{50}$ value was not obtained for a particular compound, the percent inhibition is provided at a test concentration of 25 μM.

TABLE 1

Inhibition of MCP-1 Binding $IC_{50}$

| Example | CCR2 Binding (nM) |
|---|---|
| 1a | 1.2 |
| 2a | 390 |
| 3a | 45 |
| 4a | 33 |
| 5a | 9 |
| 6a | 200 |
| 7a | 50 |
| 8a | 85 |
| 9 | 80 |
| 10 | 70 |
| 11a | 135 |
| 12 | 220 |
| 13 | 61 |
| 14a | 440 |
| 15 | 337 |
| 16 | 100 |
| 17 | 27 |
| 18 | >25,000 |
| 19 | 130 |
| 20a | 27 |
| 21a | 30 |
| 22 | 8,600 |
| 23 | 260 |
| 24a | 340 |
| 25 | 320 |
| 26 | 70 |
| 27 | 86 |
| 28 | 200 |
| 29 | 280 |
| 30a | 36 |
| 31a | 46 |
| 32a | 63 |
| 33a | 25 |
| 34a | 310 |
| 35a | 190 |
| 36a | 21 |
| 37a | 69 |
| 38a | 190 |
| 39a | 15 |
| 40a | 21 |
| 41 | 160 |
| 42 | 130 |
| 43 | 38 |
| 44 | 124 |
| 45 | 6,900 |
| 46a | 110 |
| 47a | 206 |
| 48a | 413 |
| 49 | 810 |
| 50 | 230 |
| 51a | 228 |
| 52 | 160 |
| 53 | 240 |
| 54a | 62 |
| 55a | 5,300 |
| 56a | 5,200 |
| 57a | 33 |
| 58a | 52 |
| 59 | 100 |
| 60 | 100 |
| 61 | 130 |
| 62 | 82 |
| 63a | 150 |
| 64 | 110 |
| 65a | 150 |
| 66 | 620 |
| 67 | 600 |
| 68 | 740 |
| 69 | 240 |
| 70 | 1,700 |
| 71a | 200 |
| 72 | 400 |
| 73 | 490 |
| 74 | 46 |
| 75a | 4,700 |
| 76a | 220 |
| 77 | 380 |
| 78 | 1,000 |
| 79 | 23 |
| 80 | 420 |
| 81 | 11,000 |
| 82 | 50 |
| 83a | 120 |
| 84a | 240 |
| 85a | 280 |
| 86 | 320 |
| 87a | 330 |

Example 90

Animals

Mouse CCR2 knock-out/human CCR2 knock-in mice were generated using targeted 129Sv/Evbrd embryonic stem cell clones injected into C57BL/6 mice. Expression of the hCCR2 transcript was confirmed by quantitative reverse transcription-polymerase chain reaction performed on spleen and blood total RNA from homozygous hCCR2 knock-in mice. Backcrossing into C57BL/6 genetic background continued to the eighth generation. Transgenic mice were housed in a specific-pathogen-free, temperature-controlled facility that maintained a 12-hour light/12-hour dark cycle. Mice had free access to water and food. Experimental procedures were carried out in accordance with institutional standards for animal care and were approved by the institute's animal care and use committee.

Example 91

Murine In vivo Cell Migration Assay

Animals were orally dosed with vehicle or CCR2 antagonists at 3, 10 and 30 mg/kg bid. Animals underwent anesthesia and laparotomy. A distal loop of small bowel (5 cm in length) was gently eventrated onto moist sterile gauze. Synthetic human MCP-1 (1 mg/100 ml sterile PBS) or PBS alone was administered drop-wise onto the serosa of the eventrated loop. A suture knot was placed into the mesentery to mark the terminus of the treated area. Twenty-four hours later, the animal was sacrificed and the segment of bowel plus the adjacent region was removed. The tissue was opened along the mesenteric border, pinned flat and the mucosa removed. The remaining muscle layer was fixed briefly in 100% EtOH and then stained using Hanker-Yates reagent to detect myeloperoxidase-containing immune cells. At 30 mpk, P.O. bid, a compound is deemed efficacious if the inhibition of cell migration reaches 30% compared with vehicle-treated animals. The compounds of Example #1 and Example #30 were found to be efficacious in blocking cell migration.

Example 92

Thiolycollate-Induced Peritonitis in Mice

Animals were orally dosed with vehicle or CCR2 antagonists at 30 mg/kg bid). One hour later, the animals were intraperiponeally injected with sterile thioglycollate (25 mL/kg, ip, Sigma) for induction of peritonitis. Animals were orally treated twice daily with vehicle or CCR2 antagonists. At 72-hour time point, perinoteal cavities were lavaged with 10 mL of sterile saline. Total cell counts in the peritoneal lavage fluid were performed using a microscope and cell differentiation was performed using cytospin analysis after Giemsa staining (Hema Tek 2000). Percent inhibition of the thioglycollate-induced peritonitis was calculated by comparing the change in number of leukocytes of CCR2 antagonist treated mice to the vehicle-treated mice. At 30 mpk, p.o. bid, the compounds of Example #1 and Example #30 were shown to have >50% inhibition of thioglycollate-induced peritonitis.

Example 93

MCP-1-Induced Monocyte Recruitment to Airway of Mice

Animals are orally treated with vehicle or CCR2 antagonists at 3, 10, and 30 mg/kg po bid). One hour later, the animals are intranasally dosed with 4 μg of MCP-1 in sterile saline. The animals are orally treated twice daily with vehicle or CCR2 antagonists. After 48 h, mice are euthanized by intraperitoneal injection of anesthesia solution (Sleepaway-Sodium pentobarbital). Whole bronchoalveolar lavage (BAL) is performed using 1.4 ml of ice-cold PBS containing 3 mM EDTA. Total cell counts in the BAL lavage fluid are performed using a microscope and cell differentiation is performed using cytospin analysis after Giemsa staining (Hema Tek 2000). Percent inhibition is calculated by comparing the change in number of total leukocyte counts (including monocytes/macrophages and lymphocytes) of compound-treated mice to the vehicle-treated mice. Compounds are deemed efficacious if percent inhibition reaches 30%.

Example 94

High-Fat Diet Induced Obesity and Insulin Resistance in Mice

Obesity was induced by a high-fat diet that derived approximately 60% calories from lipids (D-12492; Research Diets Inc.) in animals for 10-24 weeks at age of 7 weeks. Prior to age 7 weeks, animals were fed a standard pellet diet, in which 5% of calories were provided as fat. Obese animals were randomized by body weight and fat mass. The obese animals were orally treated with vehicle or CCR2 antagonists at 30 mg/kg, po bid. Body weight and food intake and fasting blood glucose levels were monitored. Body mass was determined by a NMR analyzer (Burker MiniSpec). Insulin tolerance test was carried out in animals that were fasted for 3 hours. After an intraperitoneal bolus injection of recombinant human insulin (1.5 U/kg), blood glucose concentrations were measured using a Glucometer before and 15, 30, 45, 60, 90 and 120 minutes after injection. Glucose tolerance tests were performed after an overnight (17-hour) fast. Blood glucose concentrations were measured before and after 15, 30, 60, 90, 120 minutes after an oral dose of glucose dissolved in water (1 g/kg). Energy expenditure analysis was monitored by a complete laboratory animal monitor system. After 40 days treatment with vehicle or CCR2 antagonists, the animals were sacrificed by $CO_2$ asphyxiation. Percent of weight loss was calculated by comparing the body weight changes of the compound-treated mice with the vehicle-treated mice. At 30 mpk, p.o. bid, the compound of Example #30 was shown to reduce body weight >8%.

Example 95

Mouse Model of Allergic Asthma

Animals were sensitized by intraperitoneal injection of 10 μg chicken egg albumin (OVA) absorbed to 1 mg Imject® in 100 μL phosphate-buffered saline (PBS) on days 0 and 5. Control animals received PBS ip. OVA-immunized animals were challenged by inhalation of 0.5% OVA aerosol for 10 minutes by an ultrasonic nebulizer on days 12, 16 and 20. Control animals were challenged with PBS in similar fashion. The OVA-sensitized animals received vehicle (0.5% Methocel) or CCR2 antagonists orally at 3, 10, 30 mg/kg twice daily from days 9-20 and once daily on day 21, 2 hours before sacrifice. Dexamethason (5 mg/kg) and Montelukast (1 mg/kg) were given orally once a day. On day 21, 2 hours post the last dose of CCR2 compounds, bronchial reactivity to aerosolized methacholine was measured using a Buxco whole body plethysmograpgh. On day 21, the animals were sacrificed. Bronchoalveolar lavage fluid was collected (1 mL) and total cells counted. The numbers of eosinophils, lymphocytes, monocytes and neutrophils were determined using cytospin analysis after Giemsa staining (Hema Tek 2000). Percent inhibition of total BAL leukocyte count (and eosinophil count) was calculated by comparing the compound-treated mice with vehicle-treated mice. Compounds are deemed efficacious if the inhibition reaches 30%. At 10 mpk, p.o. bid, the compound of Example #30 was shown to be efficacious in reduction of cell count.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of Formula (I)

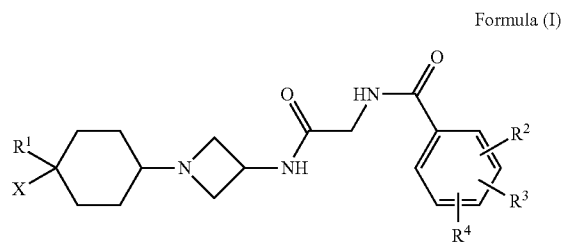

wherein:
X is $NH_2$, F, H, SH, $S(O)CH_3$, $SCH_3$, $SO_2CH_3$, or OH;
$R^1$ is phenyl optionally substituted with one or two substituents, one of which is selected from the group consisting of: $OC_{(1-4)}$alkyl, $SC_{(1-4)}$alkyl, $SOC_{(1-4)}$alkyl, $SO_2C_{(1-4)}$alkyl, $-OSO_2NH_2$, $-SO_2NHC_{(1-4)}$alkyl, $-OSO_2NH_2$, $-SO_2NH_2$, $N(C_{(1-4)}$alkyl$)_2$, $NH_2$, $NHC_{(1-4)}$alkyl, $NHSO_2C_{(1-4)}$alkyl, $N(SO_2CH_3)_2$, OH, $OC_{(1-4)}$alkyl$CO_2C_{(1-4)}$alkyl, $OC_{(1-4)}$alkyl$CO_2H$, $OCH_2CH_2N(C_{(1-4)}$alkyl$)_2$, F, Cl, $CH_2CN$, CN, $C_{(1-4)}$alkyl, $NHCO_2H$, $NHCO_2C_{(1-4)}$alkyl, $NHCOC_{(1-4)}$alkyl, $-C\equiv CH$, $CONH_2$, $NHCONH_2$, $NHCONHC_{(1-4)}$alkyl, $CONHC_{(1-4)}$alkyl, $CH_2CONHC_{(1-4)}$alkyl, $C_{(1-4)}$alkyl-$CONH_2$, $C_{(1-4)}$alkyl$CO_2C_{(1-4)}$alkyl, $C_{(1-4)}$alkyl$CO_2H$, $CO_2H$, $CH_2C(NH)NH_2$, $CO_2C_{(1-4)}$alkyl, $CF_3$, $OCHF_2$, $CHF_2$, $OCF_3$, $OCH_2CF_3$, cycloalkyl, heterocyclyl, phenoxy, phenyl, $CH_2$-phenyl, $CH_2$heteroaryl, and heteroaryl; and the second substituent, if present, is selected from the group consisting of F, $C_{(2-4)}$alkyl and $OCH_3$, or said phenyl may be substituted on two adjacent carbon atoms to form a fused bicyclic system, selected from the group consisting of benzothiazolyl, benzooxazolyl, benzofuranyl, indolyl, quinolinyl, isoquinolinyl, benzo[b]thiophenyl, 3H-benzothiazol-2-onyl, 3H-benzooxazol-2-onyl, 1,3-dihydro-benzoimidazol-2-onyl, 1-methyl-1H-benzoimidazolyl, benzo[1,3]dioxolyl, 2,3-dihydro-benzofuranyl, 2,3-dihydro-benzo[1,4]dioxinyl, wherein said 3H-benzooxazol-2-onyl, 1,3-dihydro-benzoimidazol-2-onyl, and 1-methyl-1H-benzoimidazolyl, are optionally substituted on any nitrogen atom with $C_{(1-4)}$alkyl;
$R^2$ is H, $C_{(1-4)}$alkyl, $NH_2$, $NO_2$, $NHCH_2CH_2OH$, $N(C_{(1-4)}$alkyl$)_2$, $N(SO_2CH_3)_2$, $NHCONHC_{(1-4)}$alkyl, CN, F, Cl, Br, $CF_3$, cycloalkyl, heterocyclyl, $OCF_3$, $OCF_2H$, $CF_2H$, or $OC_{(1-4)}$alkyl;
$R^3$ is F, Cl, $CF_3$, or $OC_{(1-4)}$alkyl; alternatively, $R^2$ and $R^3$ may be taken together with their attached phenyl to form a benzo[1,3]dioxolyl, 2,3-dihydro-benzofuranyl, or 2,3-dihydro-benzo[1,4]dioxinyl group;
$R^4$ is H, $OC_{(1-4)}$alkyl, or F;
and a hydrate, tautomer or pharmaceutically acceptable salt thereof.

2. A compound of claim 1 wherein:
X is $NH_2$, F, H, or OH;
$R^1$ is phenyl optionally substituted with one or two substituents, one of which is selected from the group consisting of: $OC_{(1-4)}$alkyl, $SC_{(1-4)}$alkyl, $SOC_{(1-4)}$alkyl, $SO_2C_{(1-4)}$alkyl, $-OSO_2NH_2$, $-SO_2NHC_{(1-4)}$alkyl, $-OSO_2NH_2$, $-SO_2NH_2$, $N(C_{(1-4)}$alkyl$)_2$, $NH_2$, $NHC_{(1-4)}$alkyl, $NHSO_2C_{(1-4)}$alkyl, $N(SO_2CH_3)_2$, OH, $OCH_2CO_2C_{(1-4)}$alkyl, $OCH_2CO_2H$, $OCH_2CH_2N(CH_3)_2$, F, Cl, $CH_2CN$, CN, $C_{(1-4)}$alkyl, $NHCO_2H$, $NHCO_2C_{(1-4)}$alkyl, $NHCOC_{(1-4)}$alkyl, $-C\equiv CH$, $CONH_2$, $NHCONH_2$, $NHCONHC_{(1-4)}$alkyl, $CONH C_{(1-4)}$alkyl, $CH_2CONHC_{(1-4)}$alkyl, $CH_2CONH_2$, $CH_2CO_2C_{(1-4)}$alkyl, $CH_2CO_2H$, $CO_2H$, $CH_2C(NH)NH_2$, $CO_2C_{(1-4)}$alkyl, $CF_3$, $OCHF_2$, $CHF_2$, $OCF_3$, cyclopentyl, cyclohexyl, morpholinyl, piperazinyl, piperidinyl, phenoxy, $CH_2$phenyl, phenyl, $CH_2$pyridyl, pyridyl, pyrrolidinyl, $CH_2$tetrazolyl, and tetrazolyl; and the second substituent, if present, is selected from the group consisting of F, $CH_2CH_3$ and $OCH_3$, or said phenyl may be substituted on two adjacent carbon atoms to form a fused bicyclic system, selected from the group consisting of 3H-benzothiazol-2-onyl, 3H-benzooxazol-2-onyl, 1,3-dihydro-benzoimidazol-2-onyl, 1-methyl-1H-benzoimidazolyl, benzo[1,3]dioxolyl, 2,3-dihydro-benzofuranyl, 2,3-dihydro-benzo[1,4]dioxinyl, wherein said 3H-benzooxazol-2-onyl, 1,3-dihydro-benzoimidazol-2-onyl, and 1-methyl-1H-benzoimidazolyl, are optionally substituted on any nitrogen atom with $C_{(1-4)}$alkyl;
$R^2$ is H, $C_{(1-4)}$alkyl, $NH_2$, $NO_2$, $NHCH_2CH_2OH$, $N(C_{(1-4)}$alkyl$)_2$, $N(SO_2CH_3)_2$, $NHCONHC_{(1-4)}$alkyl, CN, F, Cl, Br, $CF_3$, pyridinyl, pyrrolidinyl, $OCF_3$, $OCF_2H$, $CF_2H$, or $OC_{(1-4)}$alkyl;
$R^3$ is F, Cl, $CF_3$, or $OC_{(1-4)}$alkyl; alternatively, $R^2$ and $R^3$ may be taken together with their attached phenyl to form a benzo[1,3]dioxolyl group;
$R^4$ is H, $OCH_3$, or F;
and a hydrate, tautomer or pharmaceutically acceptable salt thereof.

3. A compound of claim 2 wherein:
$R^1$ is phenyl optionally substituted with one or two substituents, one of which is selected from the group consisting of: $OC_{(1-4)}$alkyl, $SC_{(1-4)}$alkyl, $SO_2CH_3$, $N(C_{(1-4)}$alkyl$)_2$, $NH_2$, $NHSO_2C_{(1-4)}$alkyl, $N(SO_2CH_3)_2$, OH, F, Cl, $CH_2CN$, CN, $C_{(1-4)}$alkyl, $NHCO_2C(CH_3)_3$, $OCH_2CO_2C_{(1-4)}$alkyl, $OCH_2CO_2H$, $OCH_2CH_2N(CH_3)_2$, $-C\equiv CH$, $CONH_2$, $CO_2H$, $CO_2C_{(1-4)}$alkyl, $CH_2CO_2H$, $CH_2CO_2C_{(1-4)}$alkyl, $CH_2C(NH)NH_2$, $CH_2CONH_2$, pyrrolidinyl, $CH_2$tetrazolyl, and tetrazolyl; and the second substituent, if present, is selected from the group consisting of F, $CH_2CH_3$ and $OCH_3$, or said phenyl may be substituted on two adjacent carbon atoms to form a fused bicyclic system, selected from the group consisting of 3H-benzooxazol-2-onyl, 1,3-dihydro-benzoimidazol-2-onyl, 1-methyl-1H-benzoimidazolyl, benzo[1,3]dioxolyl, 2,3-dihydro-benzofuranyl, 2,3-dihydro-benzo[1,4]dioxinyl, wherein said 3H-benzothiazol-2-onyl, 3H-benzooxazol-2-onyl, 1,3-dihydro-benzoimidazol-2-onyl, and 1-methyl-1H-benzoimidazolyl, are optionally substituted on any nitrogen atom with $C_{(1-4)}$alkyl;
$R^2$ is H, $NH_2$, $NO_2$, $NHCH_2CH_2OH$, $N(CH_3)_2$, $N(SO_2CH_3)_2$, $NHCONHC_{(1-4)}$alkyl, CN, F, Cl, Br, $CF_3$, pyridinyl, pyrrolidinyl, or $OCH_3$;
$R^3$ is F, Cl, $CF_3$, or $OCH_3$; alternatively, $R^2$ and $R^3$ may be taken together with their attached phenyl to form a benzo[1,3]dioxolyl group;
$R^4$ is H, or F;
and a hydrate, tautomer or pharmaceutically acceptable salt thereof.

4. A compound of claim 3 wherein:
$R^1$ is phenyl optionally substituted with one substituent selected from the group consisting of: $OC_{(1-4)}$alkyl, SC$_{(1-4)}$alkyl, SO$_2$CH$_3$, N(C$_{(1-4)}$alkyl)$_2$, NH$_2$, NHSO$_2$C$_{(1-4)}$alkyl, N(SO$_2$CH$_3$)$_2$, OH, F, Cl, CH$_2$CN, CN, C$_{(1-4)}$alkyl, NHCO$_2$C(CH$_3$)$_3$, OCH$_2$CO$_2$C$_{(1-4)}$alkyl, OCH$_2$CO$_2$H, OCH$_2$CH$_2$N(CH$_3$)$_2$, —C≡CH, CONH$_2$, CO$_2$H, CO$_2$C$_{(1-4)}$alkyl, CH$_2$CO$_2$H, CH$_2$CO$_2$C$_{(1-4)}$alkyl, CH$_2$C(NH)NH$_2$, CH$_2$CONH$_2$, pyrrolidinyl, CH$_2$tetrazolyl, and tetrazolyl; or said phenyl may be substituted with one OCH$_3$ group and one F, or said phenyl may be substituted on two adjacent carbon atoms to form a fused bicyclic system, selected from the group consisting of 3H-benzothiazol-2-onyl, 3H-benzooxazol-2-onyl, 1,3-dihydro-benzoimidazol-2-onyl, 1-methyl-1H-benzoimidazolyl, benzo[1,3]dioxolyl, 2,3-dihydro-benzofuranyl, 2,3-dihydro-benzo[1,4]dioxinyl, wherein said 3H-benzooxazol-2-onyl, 1,3-dihydro-benzoimidazol-2-onyl, and 1-methyl-1H-benzoimidazolyl, are optionally substituted on any nitrogen atom with C$_{(1-4)}$alkyl; and a hydrate, tautomer or pharmaceutically acceptable salt thereof.

5. A compound of claim 4 wherein:
R$^1$ is phenyl,

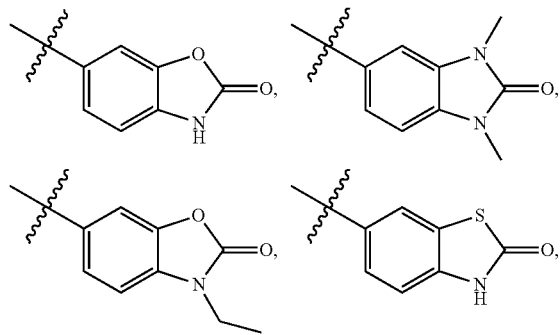

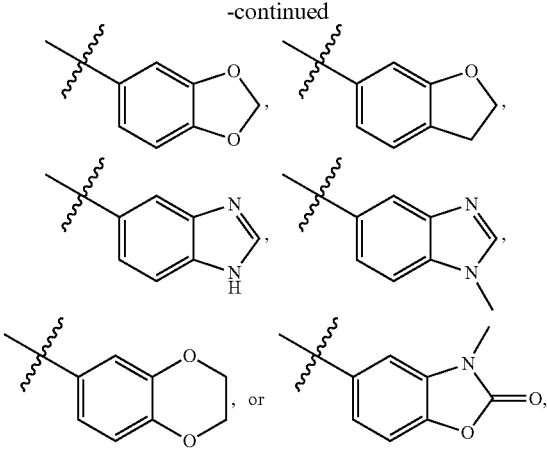

wherein said phenyl is optionally substituted with one substituent selected from the group consisting of: OCH$_3$, SCH$_3$, SO$_2$CH$_3$, N(CH$_3$)$_2$, NH$_2$, NHSO$_2$CH$_3$, N(SO$_2$CH$_3$)$_2$, OH, F, Cl, CH$_2$CN, CN, CH$_3$, NHCO$_2$C(CH$_3$)$_3$, OCH$_2$CO$_2$CH$_3$, OCH$_2$CO$_2$H, OCH$_2$CH$_2$N(CH$_3$)$_2$, —C≡CH, CH$_2$CH$_3$, CONH$_2$, CO$_2$H, CO$_2$CH$_3$, CO$_2$CH$_2$CH$_3$, CH$_2$CO$_2$H, CH$_2$CO$_2$CH$_2$CH$_3$, CH$_2$C(NH)NH$_2$, CH$_2$CONH$_2$, pyrrolidinyl, CH$_2$tetrazolyl and tetrazolyl; or said phenyl may be substituted with one OCH$_3$ group and one F;

R$^2$ is H, F, Br, CF$_3$, NO$_2$, NH$_2$, NHCH$_2$CH$_2$OH, N(CH$_3$)$_2$, N(SO$_2$CH$_3$)$_2$, NHCONHC$_{(1-4)}$alkyl, pyrrolidinyl, pyridinyl, OCH$_3$;

R$^3$ is CF$_3$;

R$^4$ is H;

and a hydrate, tautomer or pharmaceutically acceptable salt thereof.

6. A compound selected from the group consisting of:

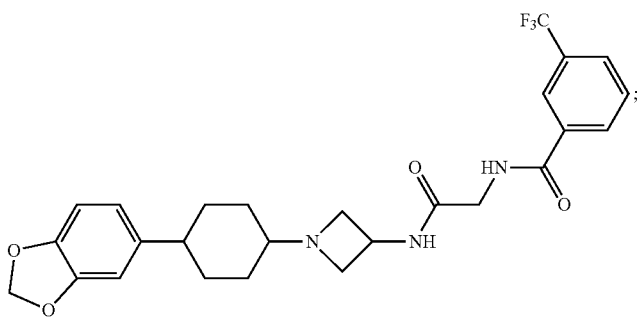

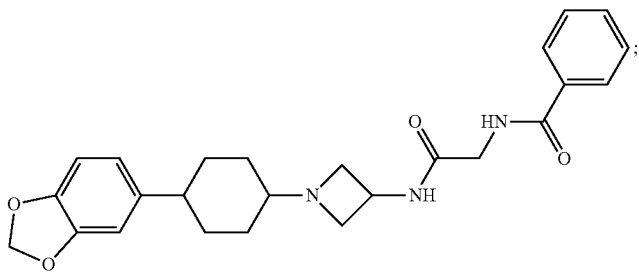

-continued
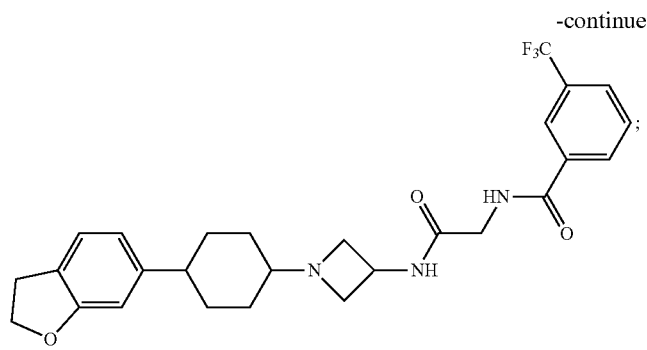
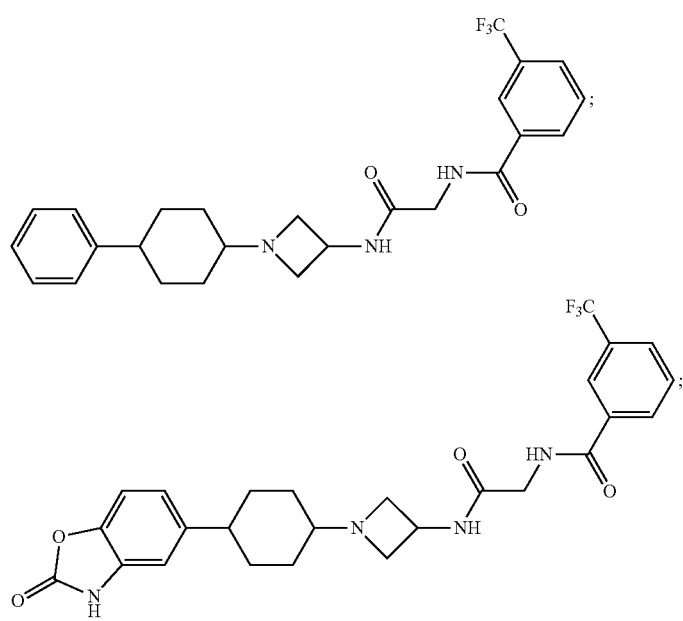
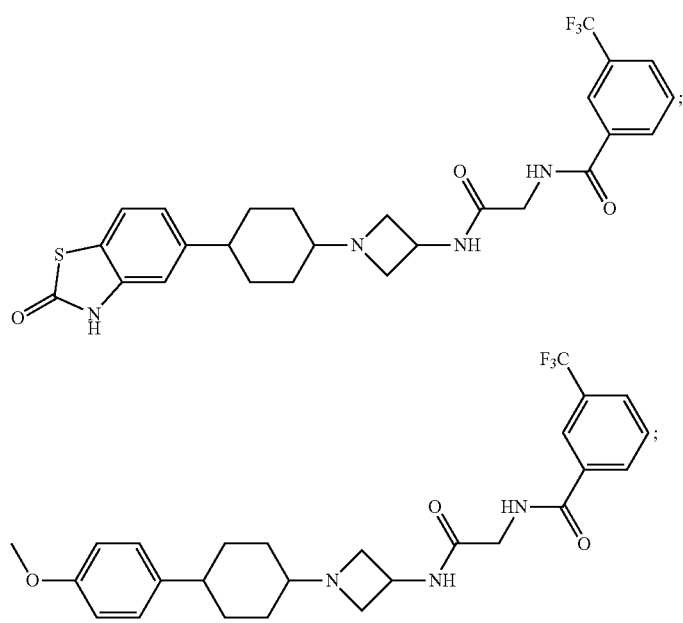

-continued
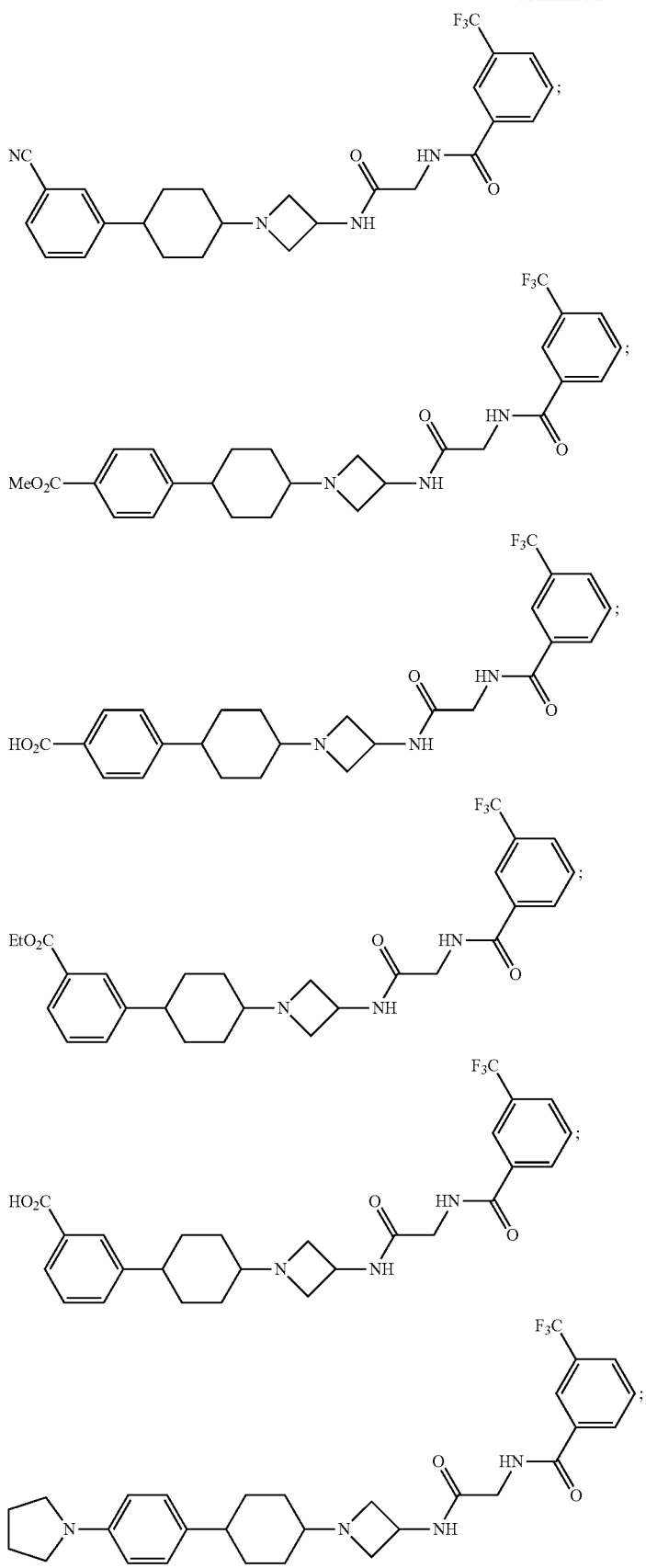

-continued
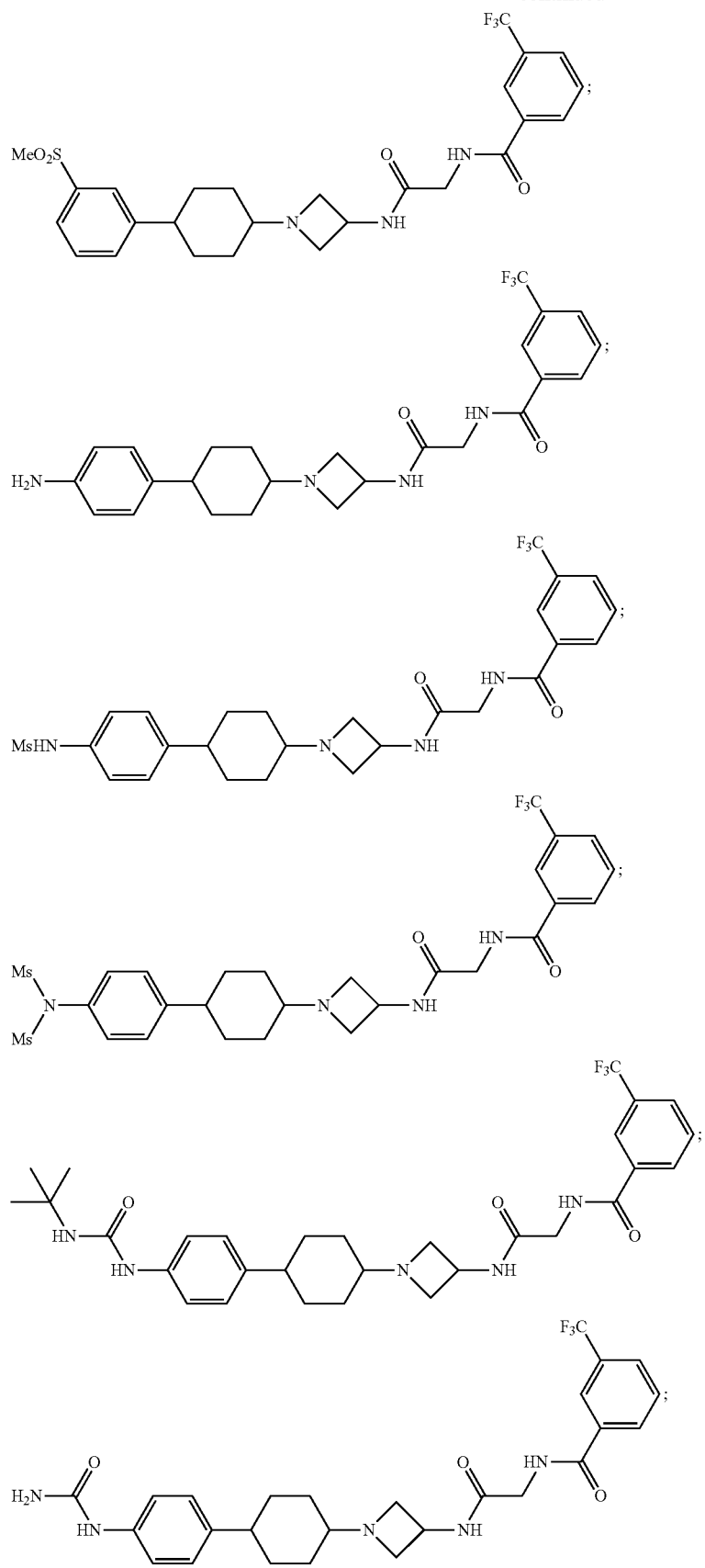

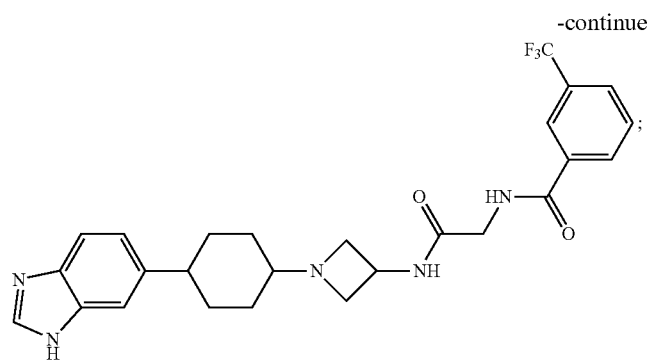
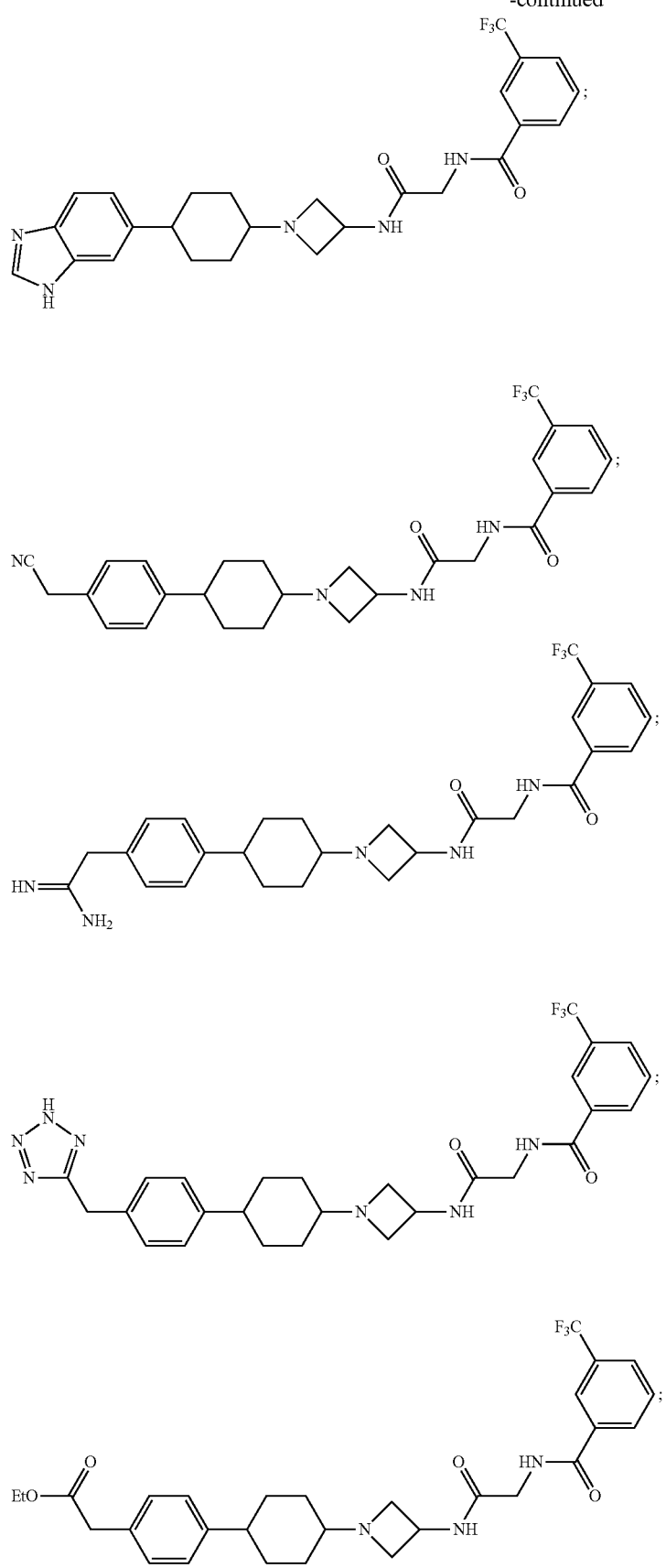

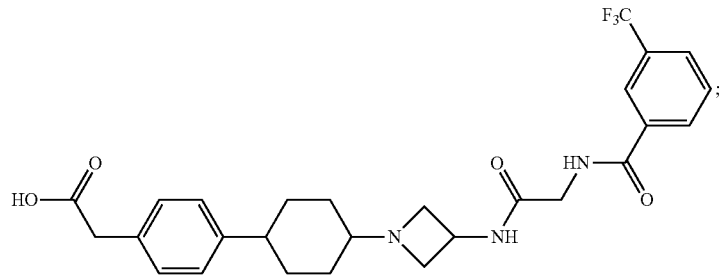
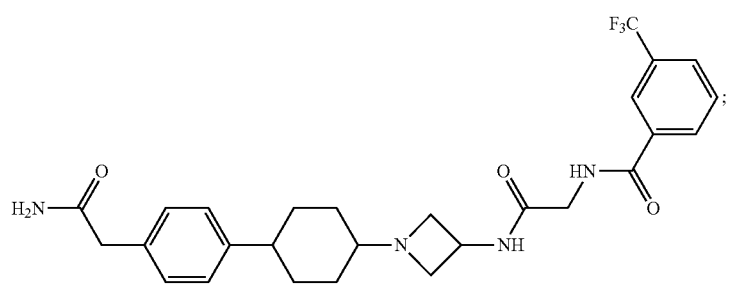
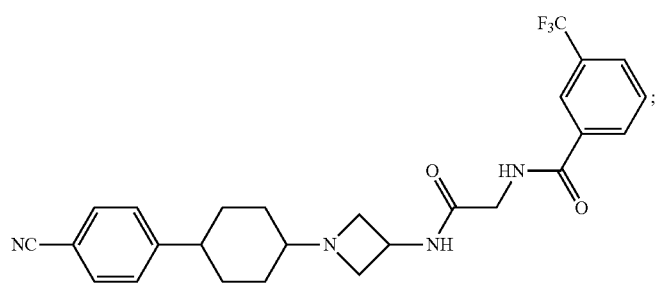
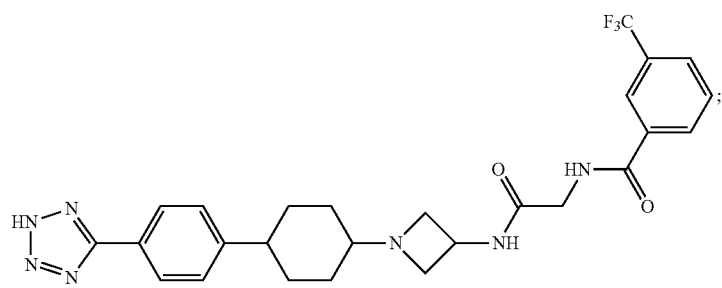
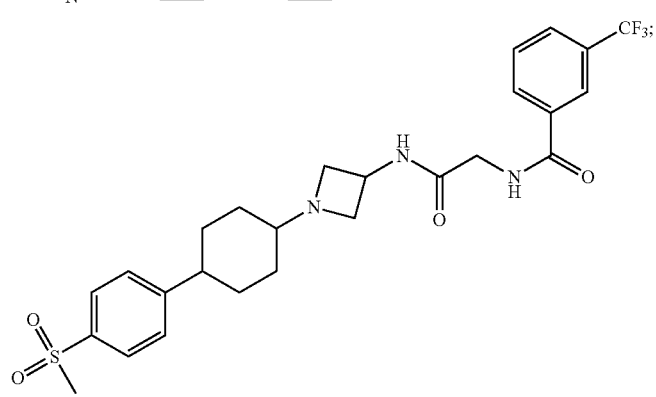

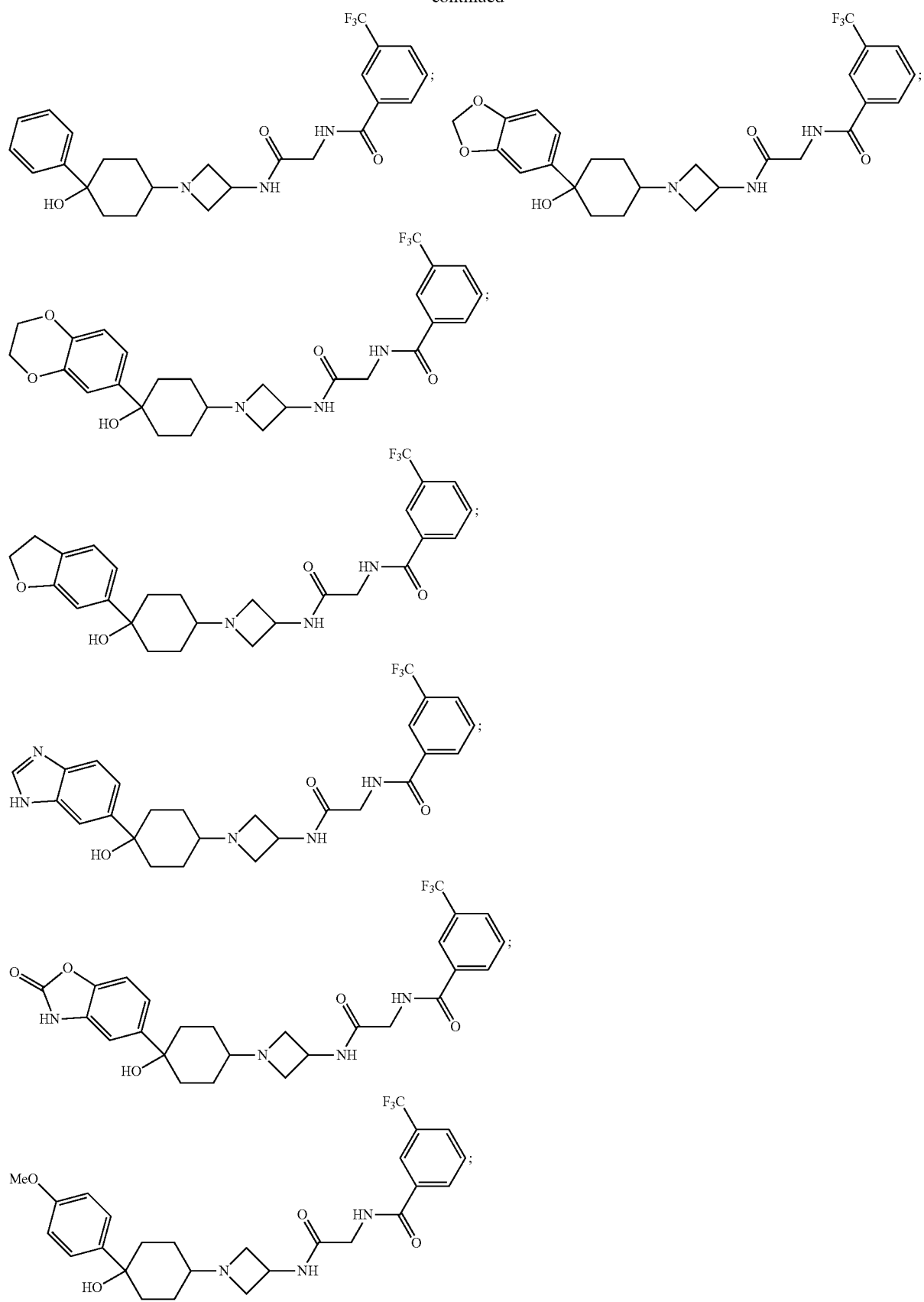

-continued
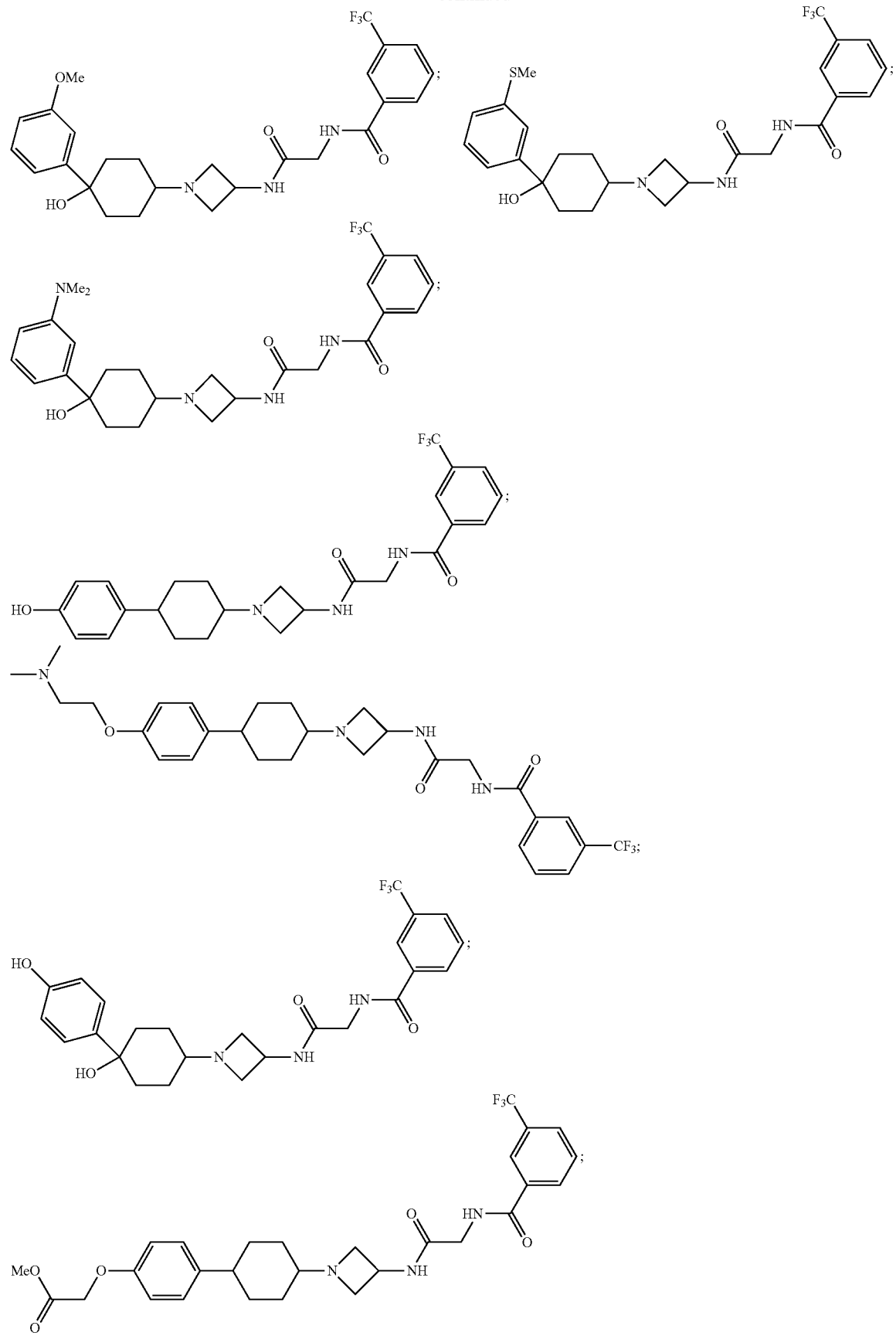

-continued
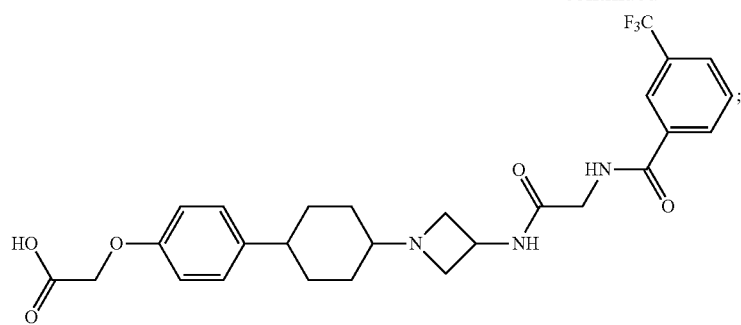
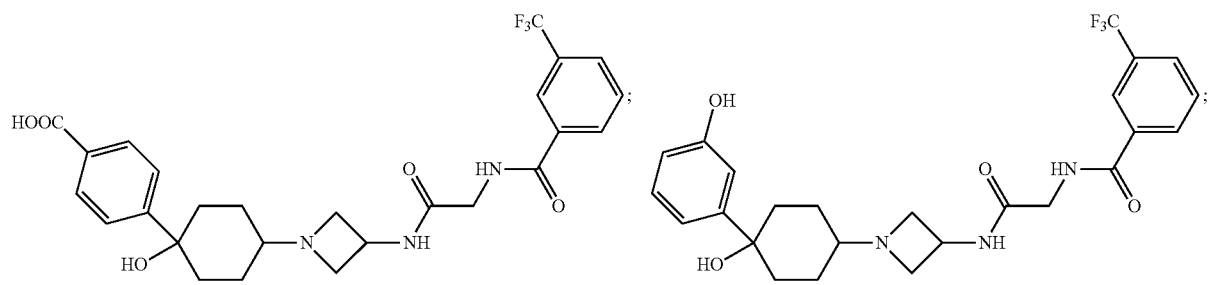
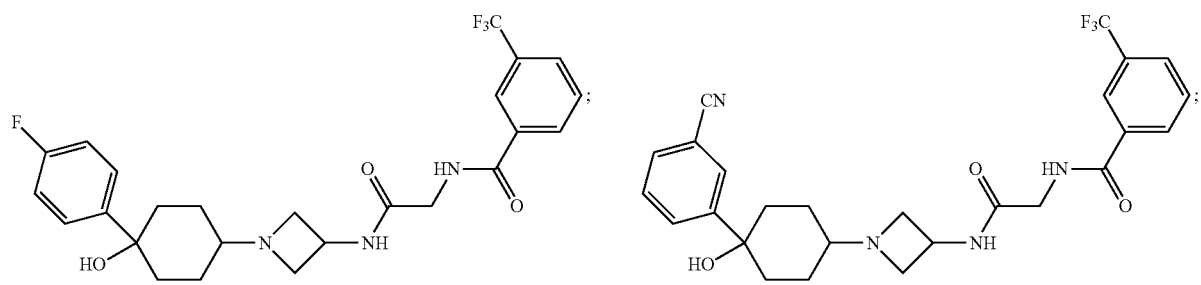
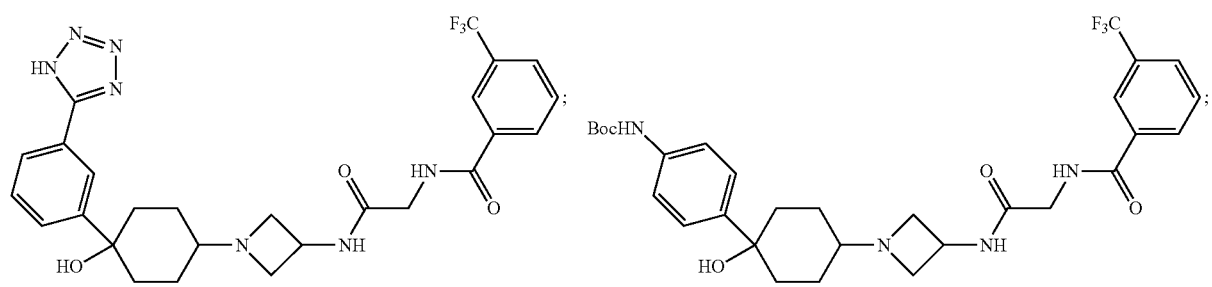
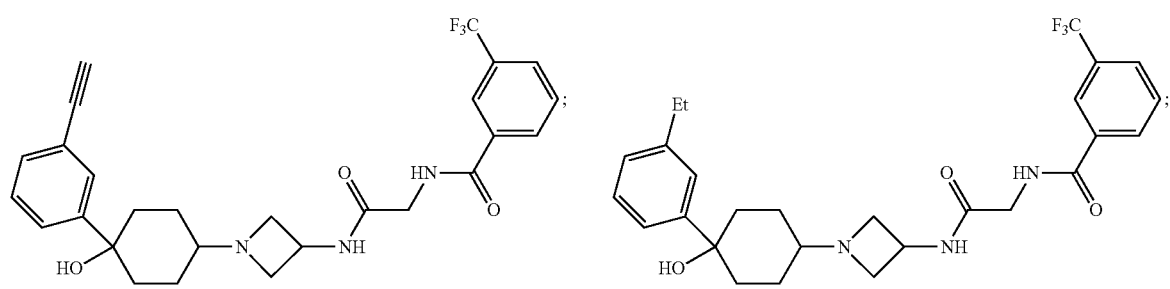

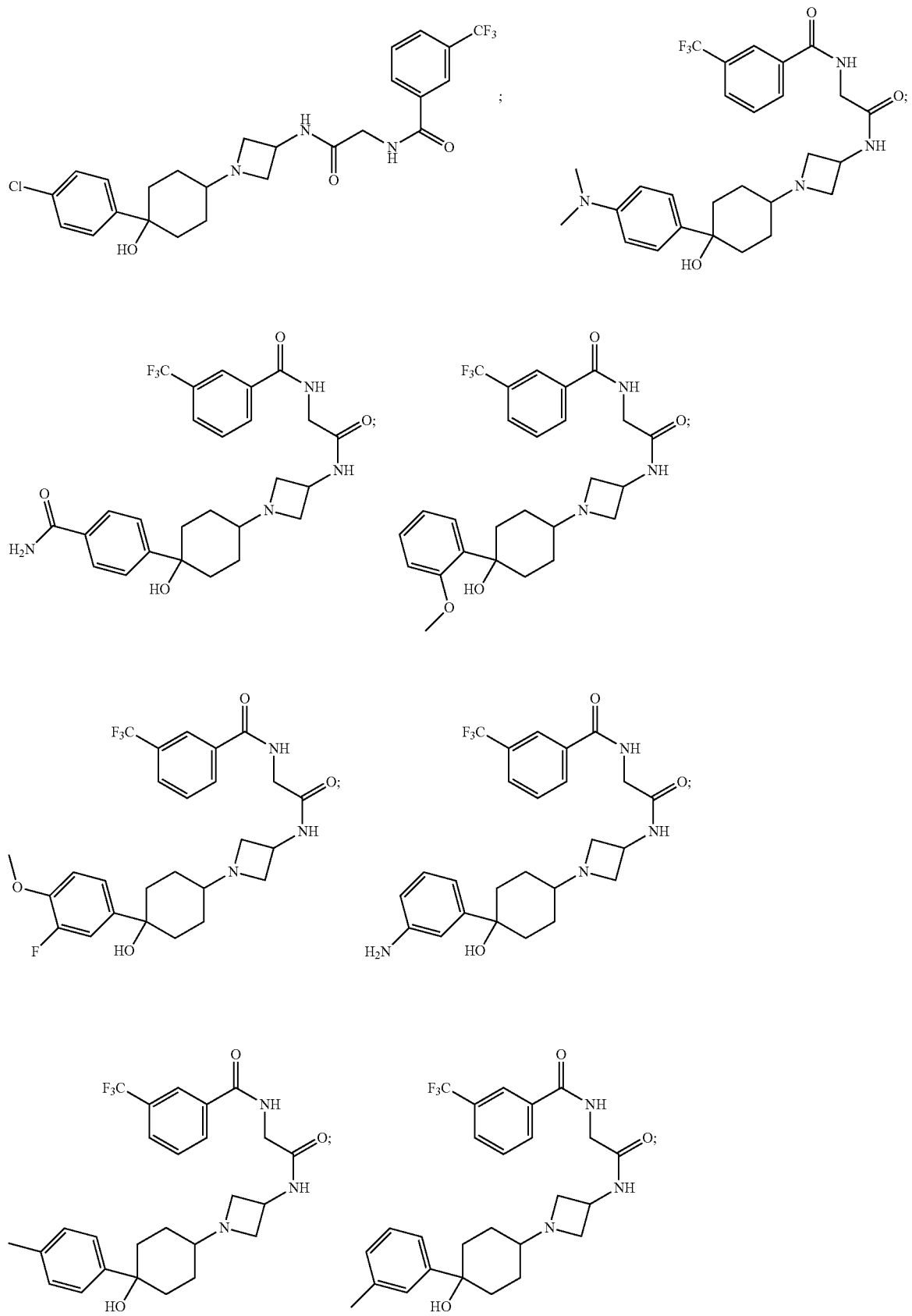

-continued
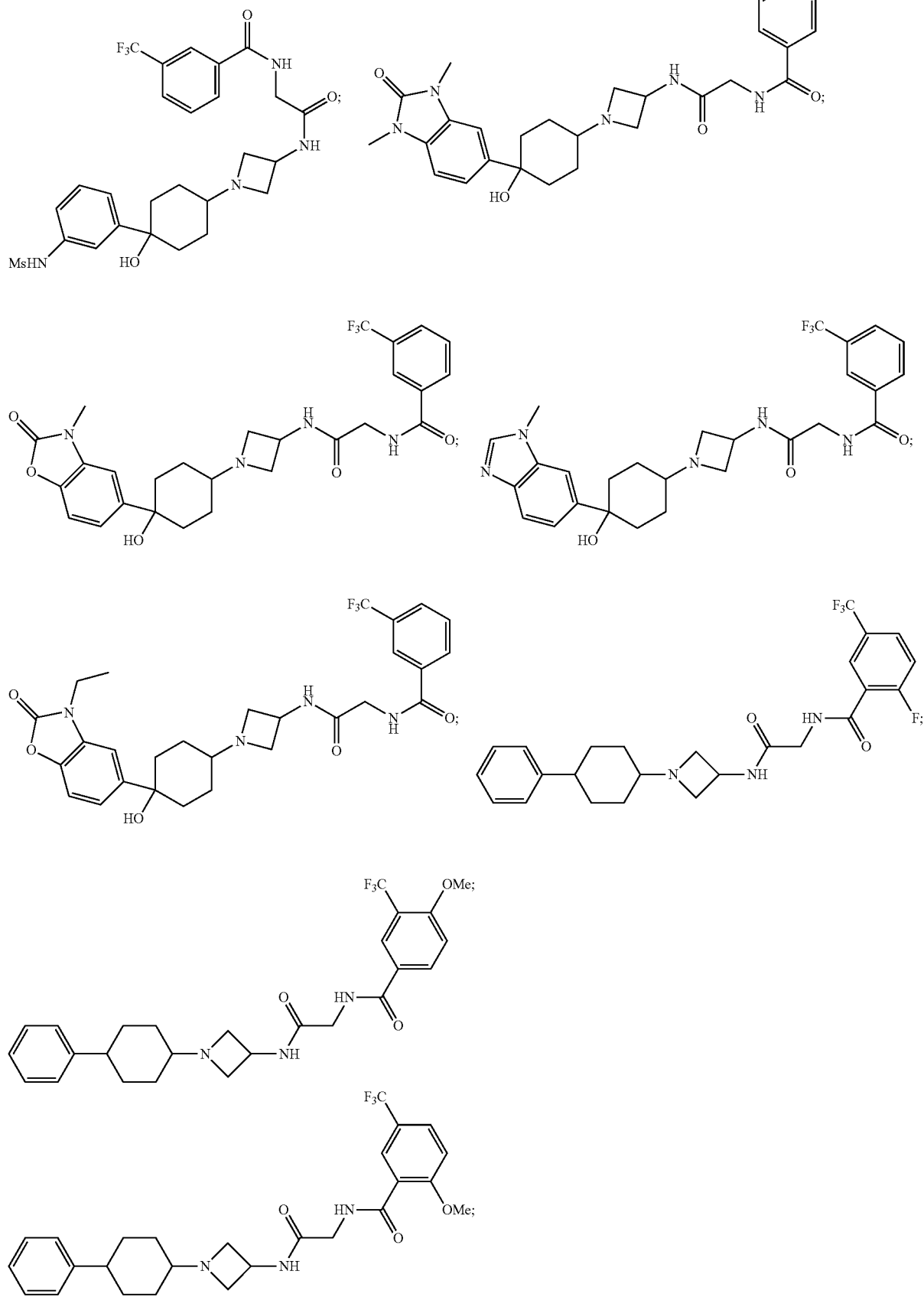

-continued
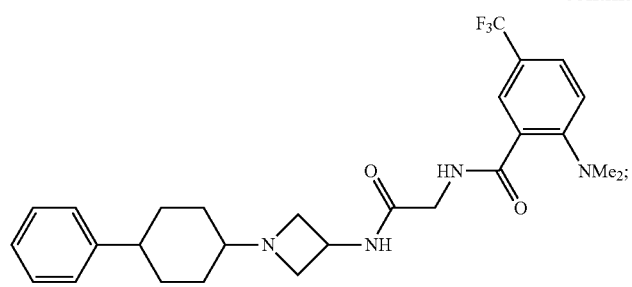
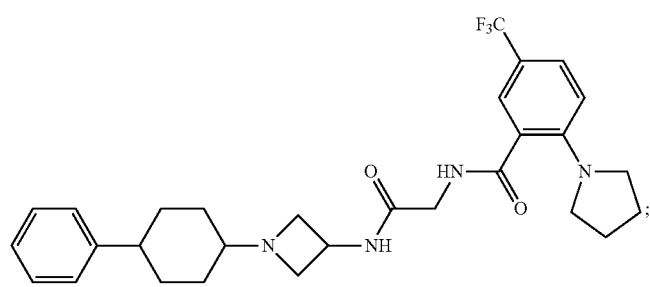
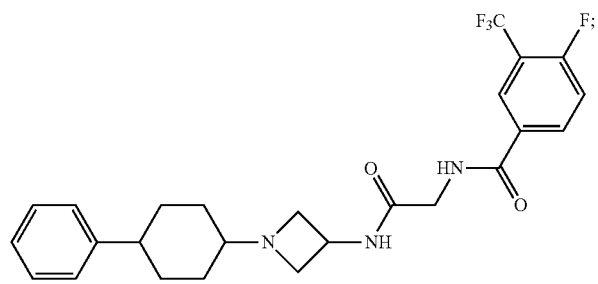
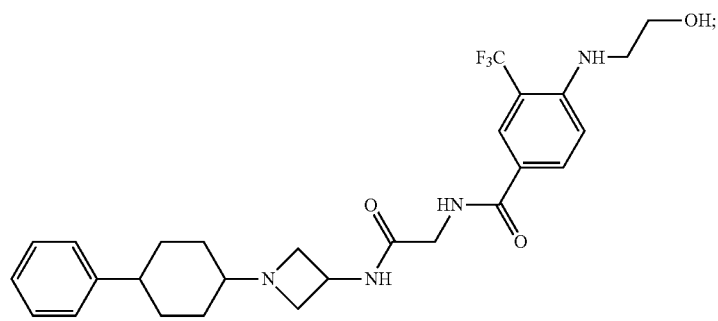
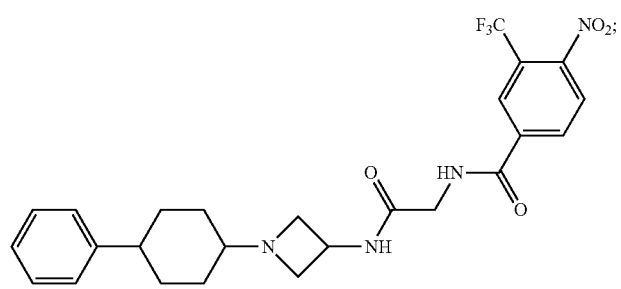

-continued
213
214
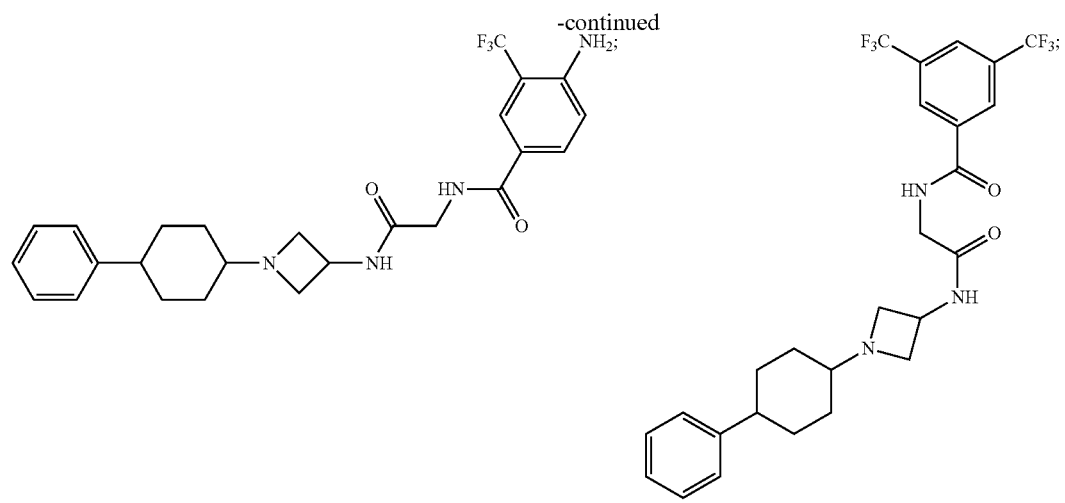
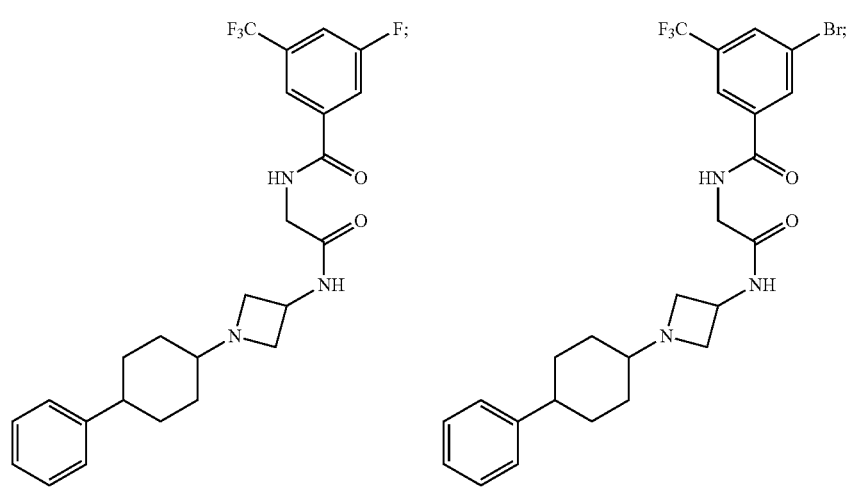
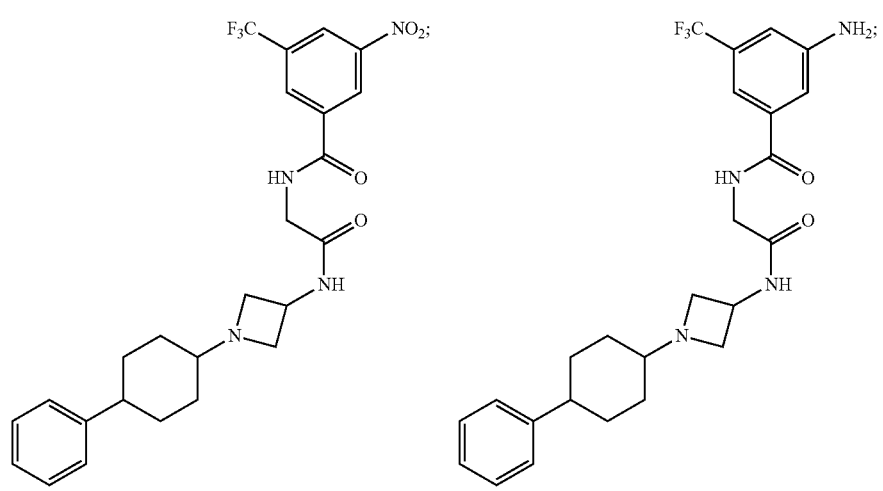

-continued
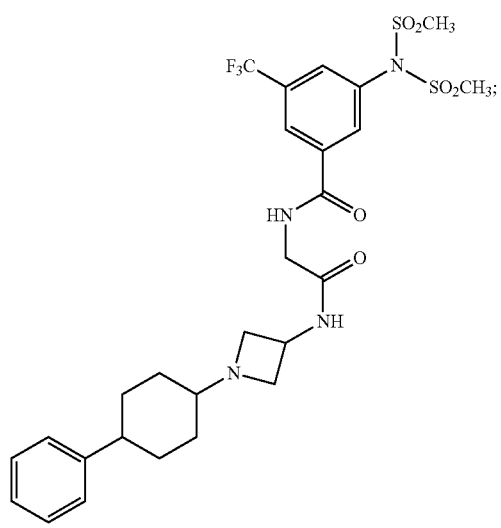
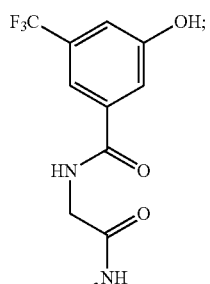
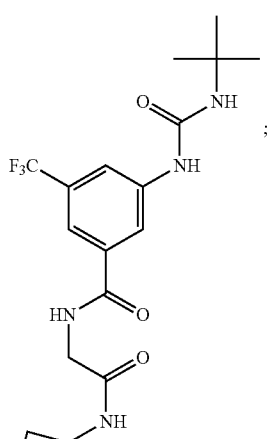
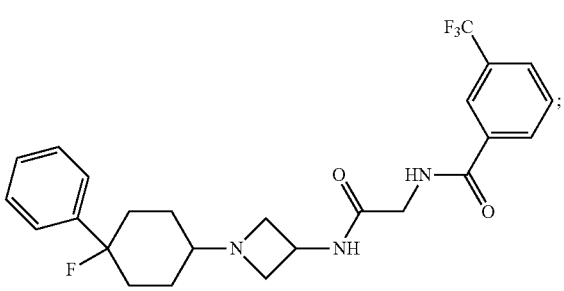
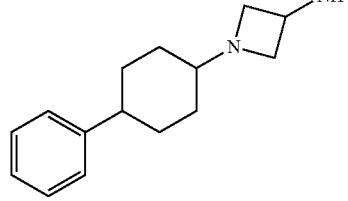
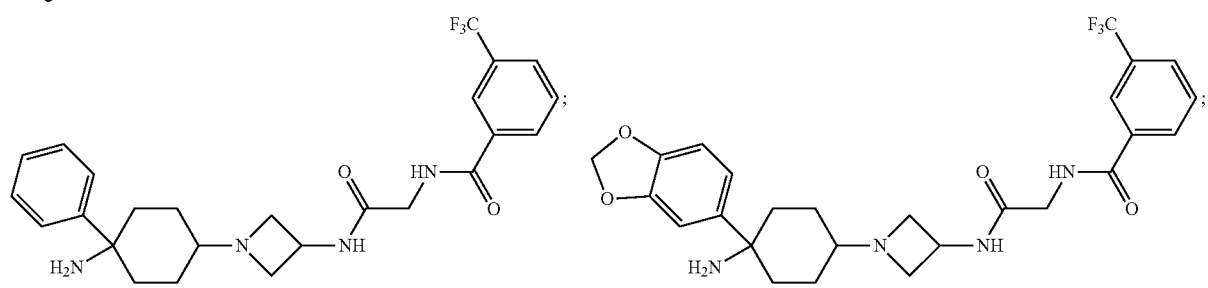
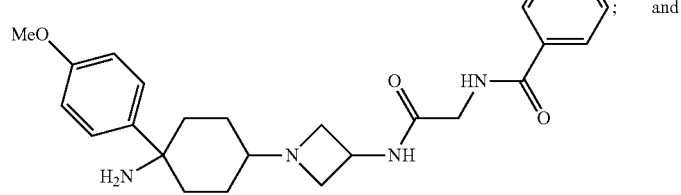

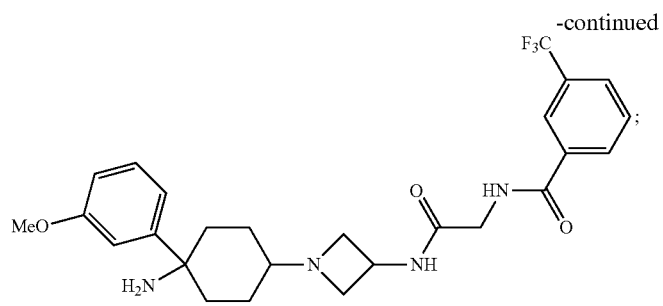
and a hydrate, tautomer or pharmaceutically acceptable salt thereof.
7. A compound of claim 6 selected from the group consisting of:
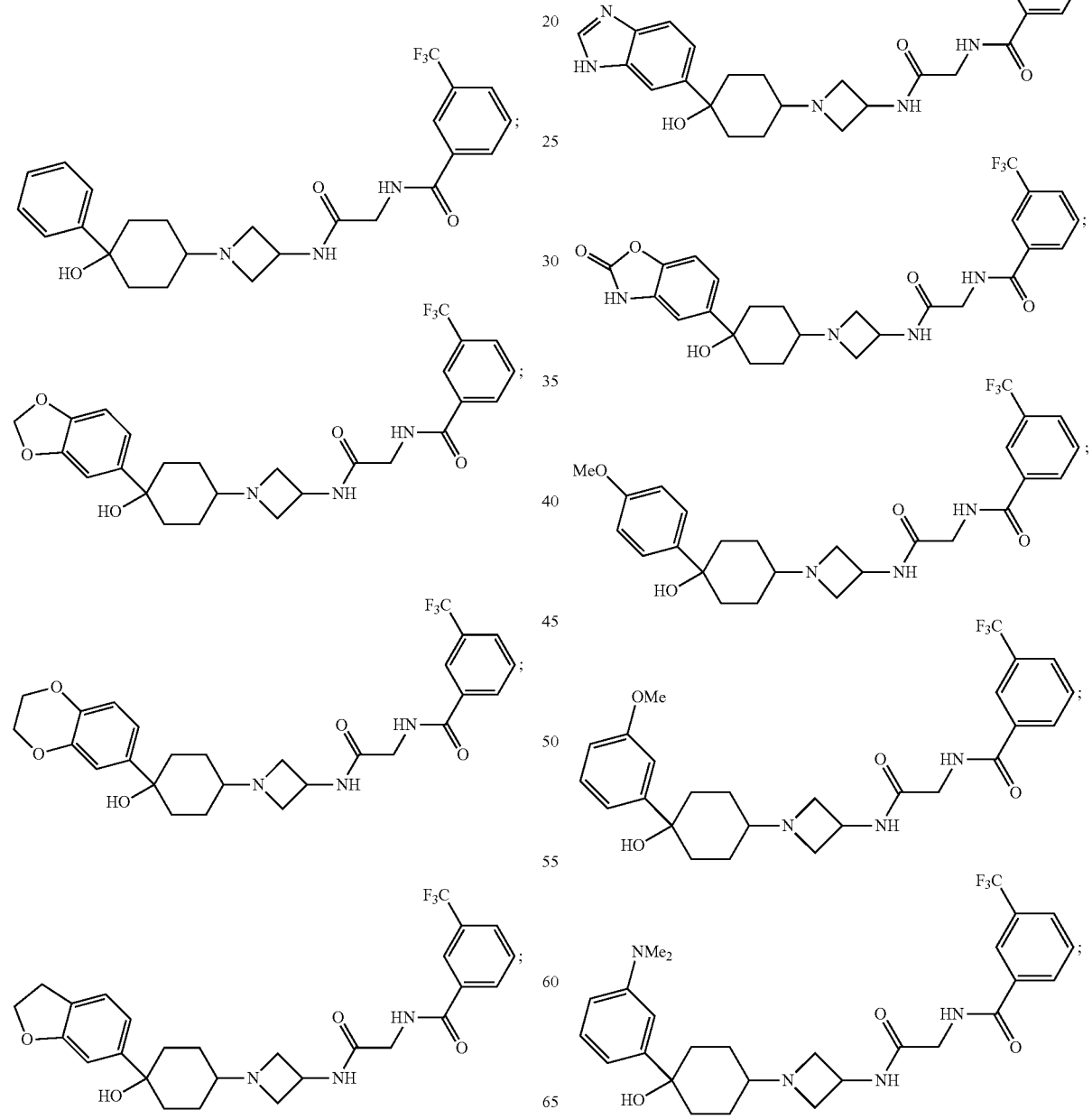

-continued

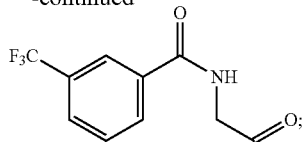

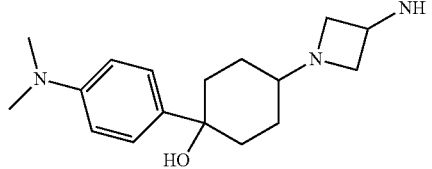

and

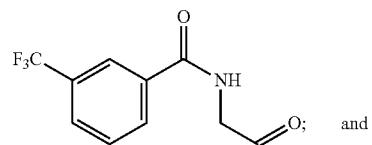

and a hydrate, tautomer or -pharmaceutically acceptable salt thereof.

8. A compound of claim 7, which is

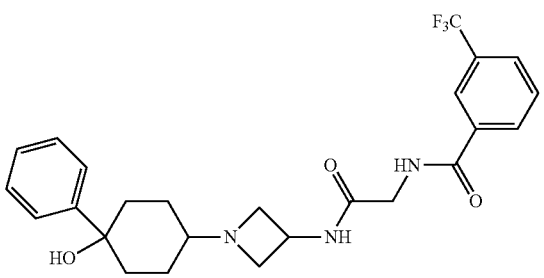 [SMILES: O=C(CNC(=O)c1cccc(C(F)(F)F)c1)NC1CN(C2CCC(O)(c3ccccc3)CC2)C1]

and a hydrate, tautomer or-pharmaceutically acceptable-salt thereof.

9. A pharmaceutical composition, comprising a compound of claim 1 and a pharmaceutically acceptable carrier.

10. A process for making a pharmaceutical composition comprising mixing a compound of claim 1 and a pharmaceutically acceptable carrier.

11. A process for the preparation of a compound of Formula (I) of claim 1, comprising reacting a compound of Formula (V)

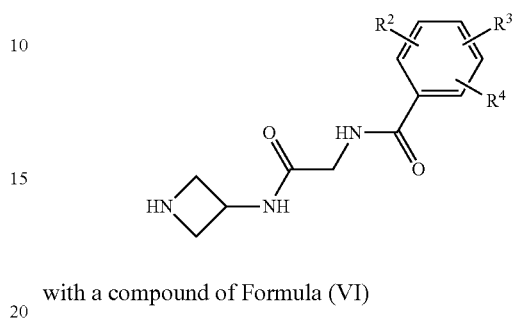

with a compound of Formula (VI)

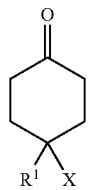

in the presence of a reducing agent to provide the compound of Formula (I).

12. A process for the preparation of a compound of Formula (I) of claim 1, comprising reacting a compound of Formula (XIII)

(XIII)

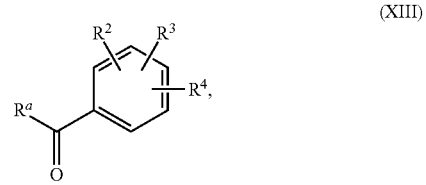

where $R_a$ is OH or Cl, with

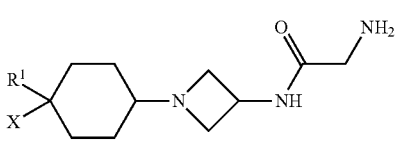

in the presence of HOBt/EDCI or $Et_3N$ to provide the compound of Formula (I).

13. A method of treating a disorder selected from the group consisting of type II diabetes, and obesity comprising administering to a subject in need thereof a therapeutically effective amount of a compound of claim 7.

* * * * *